US008940784B2

(12) United States Patent
Beusker et al.

(10) Patent No.: US 8,940,784 B2
(45) Date of Patent: Jan. 27, 2015

(54) WATER-SOLUBLE CC-1065 ANALOGS AND THEIR CONJUGATES

(75) Inventors: Patrick Henry Beusker, Nijmegen (NL); Franciscus Marinus Hendrikus de Groot, Nijmegen (NL); Lutz F. Tietze, Göttingen (DE); Felix Major, Mannheim (DE); Johannes Albertus Frederikus Joosten, Nijmegen (NL); Henri Johannes Spijker, Nijmegen (NL)

(73) Assignee: Syntarga B.V., Nijmegen (NL)

( * ) Notice: Subject to any disclaimer, the term of this patent is extended or adjusted under 35 U.S.C. 154(b) by 799 days.

(21) Appl. No.: 12/223,682

(22) PCT Filed: Feb. 2, 2007

(86) PCT No.: PCT/NL2007/050043
§ 371 (c)(1),
(2), (4) Date: Dec. 11, 2008

(87) PCT Pub. No.: WO2007/089149
PCT Pub. Date: Aug. 9, 2007

(65) Prior Publication Data
US 2009/0318668 A1 Dec. 24, 2009

(30) Foreign Application Priority Data
Feb. 2, 2006 (WO) ............... PCT/NL2006/050020

(51) Int. Cl.
*A61K 31/5377* (2006.01)
*A61K 31/545* (2006.01)
*A61K 31/404* (2006.01)
*C07D 413/14* (2006.01)
*C07D 401/14* (2006.01)
*C07D 403/06* (2006.01)
*C07D 209/60* (2006.01)
*A61K 31/454* (2006.01)
*C07D 403/14* (2006.01)
*C07H 17/02* (2006.01)

(52) U.S. Cl.
CPC ............ *C07D 209/60* (2013.01); *C07D 413/14* (2013.01); *A61K 31/454* (2013.01); *A61K 31/5377* (2013.01); *A61K 31/404* (2013.01); *C07D 401/14* (2013.01); *C07D 403/06* (2013.01); *C07D 403/14* (2013.01); *C07H 17/02* (2013.01)
USPC ........ 514/411; 514/235.2; 514/323; 544/144; 546/201; 548/427

(58) Field of Classification Search
CPC ............ A61K 31/5377; A61K 31/454; A61K 31/404; C07D 413/14; C07D 401/14; C07D 403/06
USPC ........ 514/235.2, 323, 411; 544/144; 546/201; 548/427
See application file for complete search history.

(56) References Cited

U.S. PATENT DOCUMENTS

| 5,739,350 | A | 4/1998 | Kelly et al. ............... 548/421 |
| 7,214,685 | B2 * | 5/2007 | Tietze et al. ............ 514/298 |
| 2004/0033962 | A1 * | 2/2004 | Tietze et al. ............ 514/23 |

FOREIGN PATENT DOCUMENTS

| WO | 00/64864 | 11/2000 |
| WO | 01/83448 | 11/2001 |
| WO | 02/067937 | 9/2002 |
| WO | 2005/112919 | 12/2005 |
| WO | WO 2006002895 A2 * | 1/2006 |
| WO | 2006/043839 | 4/2006 |

OTHER PUBLICATIONS

Tietze et al. Eur. J. Org. Chem. 2002, 1634-1645.*
Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Parrish et al. Bioorganic & Medicinal Chemistry 2003, 3815-3838.*
Tietze et al. ChemBioChem 2001, 2, 758-765.*
Milbank et al. J. Med. Chem. 1999, 42, 649-658.*
Tietze et al. Angew. Chem. Int. Ed. 2006, 45, 6570-6574.*
Tietze et al. Angew. Chem. Int. Ed. 2006, 45, 6574-6577.*
Tietze et al. Eur. J. Org. Chem. 2006, 2314-2321.*
Boger et al. J. Am. Chem. Soc. 1994, 116, 1635-1656.*
Tietze et al., "Highly Selective Glycosylated Prodrugs of Cytostatic cc-1065 Analogues for Antibody-Directed Enzyme Tumor Therapy," *Chembiochem.*, 2(10):758-765 (2001).
Tietze et al., "Synthesis and Biological Evaluation of Novel Analogues and Prodrugs of the Cytotoxic Antibiotic cc-1065 for Selective Cancer Therapy," *Eur. J. Org. Chem.*, pp. 1634-1645 (2002).
Tietze et al., "Antitumor Agents: Development of Highly Potent Glycosidic Duocarmycin Analogues for Selective Cancer Therapy," Angew. Chem. Int. Ed., 45:6574-6577, 2006.
Tietze et al., "Synthesis of New Water-Soluble DNA-Binding Subunits for Analogues of the Cytotoxic Antibiotic CC-1065 and Their Prodrugs," Eur. J. Org. Chem., 2006, pp. 2314-2321.

* cited by examiner

*Primary Examiner* — Joseph Kosack
*Assistant Examiner* — Matthew Coughlin
(74) *Attorney, Agent, or Firm* — Mark R. Buscher

(57) ABSTRACT

This invention relates to novel analogs of the DNA-binding alkylating agent CC-1065 and to their conjugates. Furthermore this invention concerns intermediates for the preparation of said agents and their conjugates. The conjugates are designed to release their (multiple) payload after one or more activation steps and/or at a rate and time span controlled by the conjugate in order to selectively deliver and/or controllably release one or more of said DNA alkylating agents. The agents, conjugates, and intermediates can be used to treat an illness that is characterized by undesired (cell) proliferation. As an example, the agents and the conjugates of this invention may be used to treat a tumor.

2 Claims, 11 Drawing Sheets a) HCl/EtOAc; b) 2, EDC·HCl; c) HCl/EtOAc; d) Pd/C, NH₄HCO₂

Fig 12

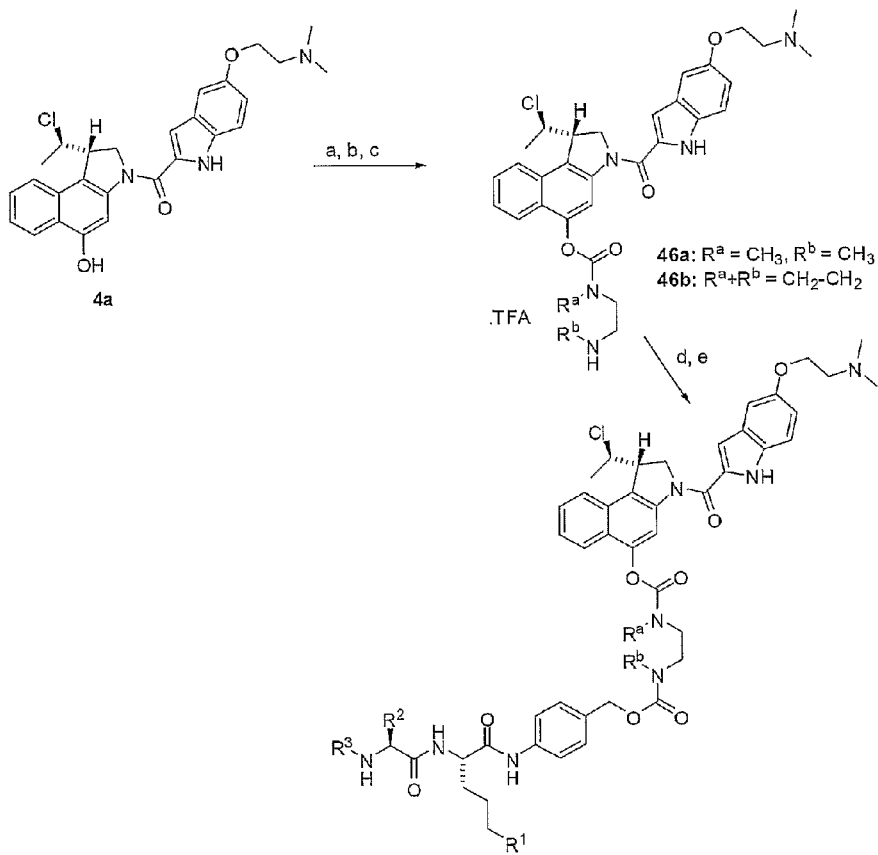

47a: $R^1$ = NHC(O)NH$_2$, $R^2$ = CH(CH$_3$)$_2$, $R^3$ = maleimidocaproyl, $R^a$ = CH$_3$, $R^b$ = CH$_3$
47b: $R^1$ = NHC(O)NH$_2$, $R^2$ = CH(CH$_3$)$_2$, $R^3$ = maleimidocaproyl, $R^a$+$R^b$ = CH$_2$-CH$_2$
47c: $R^1$ = NHC(O)NH$_2$, $R^2$ = CH(CH$_3$)$_2$, $R^3$ = C(O)-(OCH$_2$CH$_2$)$_2$-N$_3$, $R^a$ = CH$_3$, $R^b$ = CH$_3$
47d: $R^1$ = NHC(O)NH$_2$, $R^2$ = CH(CH$_3$)$_2$, $R^3$ = C(O)-(OCH$_2$CH$_2$)$_2$-N$_3$, $R^a$+$R^b$ = CH$_2$-CH$_2$
47e: $R^1$ = CH$_2$NH$_2$, $R^2$ = CH$_2$Ph, $R^3$ = C(O)-(OCH$_2$CH$_2$)$_2$-N$_3$, $R^a$ = CH$_3$, $R^b$ = CH$_3$
47f: $R^1$ = CH$_2$NH$_2$, $R^2$ = CH$_2$Ph, $R^3$ = C(O)-(OCH$_2$CH$_2$)$_2$-N$_3$, $R^a$+$R^b$ = CH$_2$-CH$_2$ a) *p*-nitrophenyl chloroformate, DIPEA, THF; b) *N*-Boc-piperazine or *N*-Boc-*N*,*N*'-dimethylethylenediamine, THF; c) TFA; d) activated linker 57a-b or 58, DIPEA, DMF; e) Pd(PPh$_3$)$_4$, morpholine, CH$_2$Cl$_2$ (only 47e-f)

50a: $R^1$ = NHC(O)NH$_2$, $R^2$ = CH(CH$_3$)$_2$, $R^3$ = maleimidocaproyl
50b: $R^1$ = NHC(O)NH$_2$, $R^2$ = CH(CH$_3$)$_2$, $R^3$ = C(O)-(OCH$_2$CH$_2$)$_2$-N$_3$
50c: $R^1$ = CH$_2$NH$_2$, $R^2$ = CH$_2$Ph, $R^3$ = C(O)-(OCH$_2$CH$_2$)$_2$-N$_3$ a) HCl/EtOAc; b) activated linker 59a-b or 60, NEt$_3$, DMF; c) Pd(PPh$_3$)$_4$, morpholine, CH$_2$Cl$_2$ (only 50c)

| | |
|---|---|
| ■ (1R,10S)-8a' without enzyme | IC$_{50}$ > 78110 nM |
| □ (1R,10S)-8a' with enzyme | IC$_{50}$ = 550 nM |
| ● (1S,10R)-8a without enzyme | IC$_{50}$ = 3600 nM |
| ○ (1S,10R)-8a with enzyme | IC$_{50}$ = 0.75 nM |
| ▲ (1R,10S)-8a'/(1S,10R)-8a without enzyme | IC$_{50}$ = 7900 nM |
| △ (1R,10S)-8a'/(1S,10R)-8a with enzyme | IC$_{50}$ = 1.2 nM |

WATER-SOLUBLE CC-1065 ANALOGS AND THEIR CONJUGATES

CROSS-REFERENCE TO RELATED APPLICATIONS

This application is the national phase of International (PCT) Patent Application Serial No. PCT/NL2007/050043, filed on Feb. 2, 2007, which claims priority to and the benefit of International (PCT) Patent Application Serial No. PCT/NL2006/050020, filed on Feb. 2, 2006.

FIELD OF THE INVENTION

This invention relates to novel analogs of the DNA-binding alkylating agent CC-1065 and to their conjugates. Furthermore this invention concerns intermediates for the preparation of said agents and their conjugates. The conjugates are designed to release their (multiple) payload after one or more activation steps and/or at a rate and time span controlled by the conjugate in order to selectively deliver and/or controllably release one or more of said DNA alkylating agents. The agents, conjugates, and intermediates can be used to treat an illness that is characterized by undesired (cell) proliferation. As an example, the agents and the conjugates of this invention may be used to treat a tumor.

BACKGROUND OF THE INVENTION

The duocarmycins, first isolated from a culture broth of *Streptomyces* species, are parent members of a family of antitumor antibiotics that also includes CC-1065. These extremely potent agents allegedly derive their biological activity from an ability to sequence-selectively alkylate DNA at the N3 of adenine in the minor groove, which initiates a cascade of events that terminates in an apoptotic cell death mechanism.[1]

Although CC-1065 has shown very potent cytotoxicity, it could not be used in the clinic because of serious delayed hepatotoxicity.[2] This observation led to the development of synthetic analogs of CC-1065 (see for CC-1065 derivatives for example Aristoff et al., *J. Org. Chem.* 1992, 57, 6234; Boger et al., *Bioorg. Med. Chem. Lett.* 1996, 6, 2207; Boger et al., *Chem. Rev.* 1997, 97, 787; Milbank et al., *J. Med. Chem.* 1999, 42, 649; Atwell et al., *J. Med. Chem.* 1999, 42, 3400; Wang et al., *J. Med. Chem.* 2000, 43, 1541; Boger et al., *Bioorg. Med. Chem. Lett* 2001, 11, 2021; Parrish et al., *Bioorg. Med. Chem.* 2003, 11, 3815; Daniell et al., *Bioorg. Med. Chem. Lett.* 2005, 15, 177; Tichenor et al., *J. Am. Chem. Soc.* 2006, 128, 15683; Purnell et al., *Bioorg. Med. Chem.* 2006, 16, 5677; EP0154445; WO 88/04659; WO 90/02746; WO 97/12862; WO 97/32850; WO 97/45411; WO 98/52925; WO 99/19298; WO 01/83482; WO 02/067937; WO 02/067930; WO 02/068412; WO 03/022806; WO 2004/101767; and WO 2006/043839), which generally showed to have similar cytotoxicity, but reduced hepatotoxicity. Still, however, these derivatives lack sufficient selectivity for tumor cells as the selectivity of these agents—and cytotoxic agents in general—is for a considerable part based on the difference in the rate of proliferation of tumor cells and normal cells, and therefore they also affect healthy cells that show a high proliferation rate. This typically leads to severe side effects. Drug concentrations that would completely eradicate the tumor cannot be reached because of dose-limiting side effects such as gastrointestinal tract and bone marrow toxicity. In addition, tumors can develop resistance against anticancer agents after prolonged treatment. In modern drug development, targeting of cytotoxic drugs to the tumor site can be considered one of the primary goals.

One promising approach to obtain selectivity for tumor cells or tumor tissue is to exploit the existence of tumor-associated antigens, receptors, and other receptive moieties, which can serve as a target. Such a target may be upregulated or to some degree be specifically present in tumor tissue or in closely associated tissue, such as neovascular tissue, with respect to other tissues in order to achieve efficient targeting. Many targets have been identified and validated and several methods to identify and validate targets have been developed.[3]

By coupling a ligand, e.g. an antibody or antibody fragment, for such a tumor-associated antigen, receptor, or other receptive moiety to a therapeutic agent, this agent can be selectively targeted to tumor tissue.

Another promising approach to obtain selectivity for tumor cells or tumor tissue is to exploit the existence of tumor-associated enzymes. A relatively high level of tumor-specific enzyme can convert a pharmacologically inactive prodrug, which consists of an enzyme substrate directly or indirectly linked to the toxic drug, to the corresponding drug in the vicinity of or inside the tumor. Via this concept a high concentration of toxic anticancer agent can be selectively generated at the tumor site. All tumor cells may be killed if the dose is sufficiently high, which may decrease development of drug-resistant tumor cells.

Enzymes have also been transported to the vicinity of or inside target cells or target tissue via for example antibody-directed enzyme prodrug therapy (ADEPT)[4], polymer-directed enzyme prodrug therapy (PDEPT) or macromolecular-directed enzyme prodrug therapy (MDEPT)[5], virus-directed enzyme prodrug therapy (VDEPT)[6], or gene-directed enzyme prodrug therapy (GDEPT)[7]. With ADEPT, for example, a non-toxic prodrug is selectively converted into a cytotoxic compound at the surface of target cells by an antibody-enzyme conjugate that has been pretargeted to the surface of those cells.

Yet another promising approach to obtain selectivity for tumor cells or tumor tissue is to exploit the enhanced permeability and retention (EPR) effect. Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.[8]

By coupling a therapeutic agent directly or indirectly to a macromolecule, said agent can be selectively targeted to tumor tissue.

Besides efficient targeting, another criterion for the successful application of targeted conjugates of cytotoxic agents in tumor therapy is that the one or more agents are released efficiently from the conjugate. A further important criterion is that the conjugate is non-cytotoxic or only very weakly cytotoxic, whereas the cytotoxic agent itself exhibits highly potent cytotoxicity. Again another important criterion is that the conjugate must have suitable pharmacological properties, such as sufficient stability hi the circulation, low aggregation tendency, and good water solubility.

Several conjugates of CC-1065 and derivatives have been described (see for conjugates of CC-1065 derivatives for example Suzawa et al., *Bioorg. Med. Chem.* 2000, 8, 2175; Jeffrey et al., *J. Med. Chem.* 2005, 48, 1344; Wang et al., *Bioorg. Med Chem.* 2006, 14, 7854; WO 91/16324; WO 94/04535; WO 95/31971; U.S. Pat. No. 5,475,092; U.S. Pat. No. 5,585,499; U.S. Pat. No. 5,646,298; WO 97/07097; WO 97/44000; U.S. Pat. No. 5,739,350; WO 98/11101; WO 98/25898; U.S. Pat. No. 5,843,937; U.S. Pat. No. 5,846,545; WO 02/059122; WO 02/30894; WO 03/086318; WO 2005/103040; WO 2005/112919; WO 2006/002895; and WO 2006/110476). These conjugates do not possess all of the favorable properties mentioned above. As an illustrative example, glycoside conjugates of seco CC-1065 analogs (analogs in which the cyclopropyl ring as present in CC-1065 is "opened") have been described that can be activated at the lesion site via an ADEPT approach.[9] The difference in cytotoxicity between the conjugates and the corresponding drugs (the cytotoxicity quotient, herein defined as $IC_{50, \ conjugate}/IC_{50, \ parent \ drug}$) was however relatively low, and the seco CC-1065 analogs themselves did not show extremely potent cytotoxicity. Improvements to the cytotoxicity quotient were made through the development of glycoside conjugates of seco CC-1065 derivatives with a secondary leaving group.[10] Although these conjugates demonstrated a high cytotoxicity quotient, their pharmacological properties were non-optimal. For instance, they showed poor water solubility, a consequence of the inherent lipophilic nature of the CC-1065 class of compounds.

Accordingly, there is a clear need in the art for conjugates of CC-1065 derivatives that show high cytotoxicity quotients, contain CC-1065 derivatives that have potent cytotoxicity and favorable pharmacological properties, and release the CC-1065 derivatives effectively.

SUMMARY OF THE INVENTION

The present invention fulfils the above-mentioned need with a compound of formula (I) or (II):

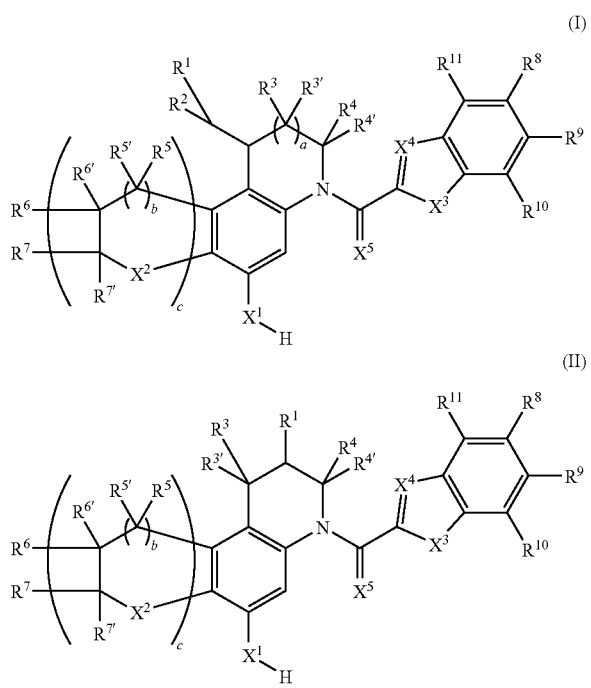

or a pharmaceutically acceptable salt or solvate thereof, wherein $R^1$ is selected from halogen and $OSO_2R^u$, wherein $R^u$ is selected from optionally substituted $C_{1-6}$ alkyl, $C_{1-6}$ perhaloalkyl, benzyl, and phenyl;

$R^2$ is selected from H and optionally substituted $C_{1-8}$ alkyl;

$R^3$, $R^{3'}$, $R^4$, and $R^{4'}$ are independently selected from H and optionally substituted $C_{1-8}$ alkyl, wherein two or more of $R^2$, $R^3$, $R^{3'}$, $R^4$, and $R^{4'}$ are optionally joined to form one or more optionally substituted carbocycles or heterocycles;

$X^2$ is selected from O, $C(R^{14})(R^{14'})$, and $NR^{14'}$, wherein $R^{14}$ is selected from H and optionally substituted $C_{1-8}$ alkyl or acyl and wherein $R^{14'}$ may be absent or be selected from H and optionally substituted $C_{1-8}$ alkyl or acyl;

Each $R^5$, $R^{5'}$, $R^6$, $R^{6'}$, $R^7$, and $R^{7'}$ is independently selected from H, OH, SH, $NH_2$, $N_3$, $NO_2$, NO, $CF_3$, CN, $C(O)NH_2$, C(O)H, C(O)OH, halogen, $R^k$, $SR^k$, $S(O)R^k$, $S(O)_2R^k$, $S(O)OR^k$, $S(O)_2OR^k$, $OS(O)R^k$, $OS(O)_2R^k$, $OS(O)OR^k$, $OS(O)_2OR^k$, $OR^k$, $NHR^k$, $N(R^k)R^L$, $^+N(R^k)(R^L)R^m$, $P(O)(OR^k)(OR^L)$, $OP(O)(OR^k)(OR^L)$, $SiR^kR^LR^m$, $C(O)R^k$, $C(O)OR^k$, $C(O)N(R^L)R^k$, $OC(O)R^k$, $OC(O)OR^k$, $OC(O)N(R^k)R^L$, $N(R^L)C(O)R^k$, $N(R^L)C(O)OR^k$, and $N(R^L)C(O)N(R^m)R^k$, wherein $R^k$, $R^L$, and $R^m$ are independently selected from H and optionally substituted $C_{1-4}$ alkyl, $C_{1-4}$ heteroalkyl, $C_{3-7}$ cycloalkyl, $C_{3-7}$ heterocycloalkyl, $C_{4-12}$ aryl, or $C_{4-12}$ heteroaryl, two or more of $R^k$, $R^L$, and $R^m$ optionally being joined to form one or more optionally substituted aliphatic or aromatic carbocycles or heterocycles, and/or $R^5+R^{5'}$, and/or $R^6+R^{6'}$, and/or $R^7+R^{7'}$ are independently =O, =S, or =NR$^{12}$, $R^{12}$ being selected from H and optionally substituted $C_{1-6}$ alkyl, and/or $R^{5'}$ and $R^6$, and/or $R^{6'}$ and $R^{7'}$, and/or $R^{7'}$ and $R^{14'}$ are absent, which means that a double bond is present between the atoms bearing $R^{5'}$ and $R^6$, and/or $R^{6'}$ and $R^{7'}$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined to form one or more optionally substituted aliphatic or aromatic carbocycles or heterocycles;

$X^1$ is selected from O, S, and $NR^{13}$, wherein $R^{13}$ is selected from H and optionally substituted $C_{1-8}$ alkyl;

$X^3$ is selected from O, S, and $NR^{15}$, wherein $R^{15}$ is selected from H and optionally substituted $C_{1-8}$ alkyl or acyl, or —$X^3$— represents —$X^{3a}$ and $X^{3b}$— wherein $X^{3a}$ is connected to the carbon to which $X^4$ is attached and $X^{3b}$ is connected to the phenyl ring ortho to $R^{10}$, wherein $X^{3a}$ is independently selected from H and optionally substituted $C_{1-8}$ alkyl or acyl and $X^{3b}$ is selected from the same group of substituents as $R^8$;

$X^4$ is selected from N and $CR^{16}$, wherein $R^{16}$ is selected from H and optionally substituted $C_{1-8}$ alkyl or acyl;

$X^5$ is selected from O, S, and $NR^{17}$, wherein $R^{17}$ is selected from H and optionally substituted $C_{1-8}$ alkyl or acyl;

$R^8$, $R^9$, $R^{10}$, and $R^{11}$ are each independently selected from H, OH, SH, $NH_2$, $N_3$, $NO_2$, NO, $CF_3$, CN, $C(O)NH_2$, C(O)H, C(O)OH, halogen, $R^x$, $SR^x$, $S(O)R^x$, $S(O)_2R^x$, $S(O)OR^x$, $S(O)_2OR^x$, $OS(O)R^x$, $OS(O)_2R^x$, $OS(O)OR^x$, $OS(O)_2OR^x$, $OR^x$, $NHR^x$, $N(R^x)R^y$, $^+N(R^x)(R^y)R^z$, $P(O)(OR^x)(OR^y)$, $OP(O)(OR^x)(OR^y)$, $SiR^xR^yR^z$, $C(O)R^x$, $C(O)OR^x$, $C(O)N(R^y)R^x$, $OC(O)R^x$, $OC(O)OR^x$, $OC(O)N(R^x)R^y$, $N(R^y)C(O)R^x$, $N(R^y)C(O)OR^x$, $N(R^y)C(O)N(R^z)R^x$, and a water-soluble group, wherein $R^x$, $R^y$, and $R^z$ are independently selected from H and optionally substituted $C_{1-15}$ alkyl, $C_{1-15}$ heteroalkyl, $C_{3-15}$ cycloalkyl, $C_{3-15}$ heterocycloalkyl, $C_{4-15}$ aryl, or $C_{4-15}$ heteroaryl, one or more of the optional substituents in $R^x$, $R^y$, and $R^z$ optionally being a water-soluble group, and two or more of $R^x$, $R^y$, and $R^z$ optionally being joined to form one or more optionally substituted aliphatic or aromatic carbocycles or heterocycles, and at least one of $R^8$, $R^9$, $R^{10}$, and $R^{11}$ comprises at least one water-soluble group, two or more of $R^8$, $R^9$, $R^{10}$, $R^{11}$, or $X^{3b}$ optionally being joined to form one or more optionally substituted aliphatic or aromatic carbocycles or heterocycles;

a and b are independently selected from 0 and 1;

c is selected from 0, 1, and 2;

provided that in the compound of formula (I) at least one of $R^2$, $R^3$, $R^{3'}$, $R^4$, $R^{4'}$, $R^5$, and $R^{5'}$ present is not hydrogen.

In another aspect, the invention relates to a compound of formula (III):

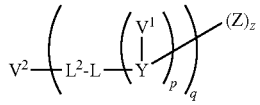

(III)

or a pharmaceutically acceptable salt or solvate thereof, wherein $V^2$ is either absent or a functional moiety;

Each $L^2$ is independently absent or a linking group linking $V^2$ to L or to $V^1$ or Y when L is absent;

Each L is independently absent or a linking group linking $L^2$ or $V^2$ when $L^2$ is absent to one or more $V^1$ and/or Y;

Each $V^1$ is independently H or a conditionally-cleavable or conditionally-transformable moiety, which can be cleaved or transformed by a chemical, photochemical, physical, biological, or enzymatic process;

Each Y is independently absent or a self-eliminating spacer system which is comprised of 1 or more self-elimination spacers and is linked to $V^1$, optionally L, and one or more Z;

Each p and q are numbers representing a degree of branching and are each independently a positive integer;

z is a positive integer equal to or smaller than the total number of attachment sites for Z in the one or more $V^1$—Y moieties;

Each Z is independently a compound of formula (I) or (II) as defined hereinabove wherein one or more of $X^1$, $R^6$, $R^7$, $R^8$, $R^9$, $R^{10}$, and $R^{11}$ may optionally in addition be substituted by a substituent of formula (V):

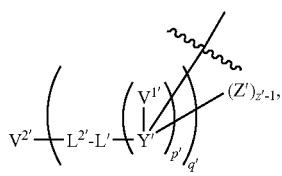

(V)

wherein each $V^{2'}$, $L^{2'}$, $L'$, $V^{1'}$, $Y'$, $Z'$, $p'$, $q'$, and $z'$ have the same meaning as defined for $V^2$, $L^2$, L, $V^1$, Y, Z, p, q, and z, the one or more substituents of formula (V) being independently connected to one or more of $X^1$, $R^6$, $R^7$, $R^8$, $R^9$, $R^{10}$, and $R^{11}$ via $Y'$ or $V^{1'}$ when $Y'$ is absent, each Z being connected to Y or $V^1$ when Y is absent through either $X^1$ or an atom in $R^6$, $R^7$, $R^8$, $R^9$, $R^{10}$, or $R^{11}$;

with the proviso that at least one of the one or more $V^1$ and the one or more $V^{1'}$ is not H.

It is noted that z does not represent a degree of polymerization; hence z does not indicate that a number of moieties Z are connected to one another.

The present invention also relates to a compound of formula (IV):

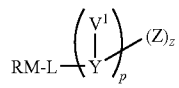

(IV)

or a pharmaceutically acceptable salt or solvate thereof, wherein

RM is a reactive moiety and L, $V^1$, Y, Z, p, and z are as defined above, except that L is now linking RM to one or more $V^1$ and/or Y, and $V^1$, Y, and Z may contain protecting groups and the one or more $V^{2'}$-$L^{2'}$ moieties optionally present in Z as defined hereinabove may optionally and independently be replaced by RM', which is a reactive moiety, and wherein, if there is more than 1 reactive moiety in (IV), the reactive moieties are the same or different. These linker-agent conjugates may or may not be considered intermediates for compounds of formula (III).

Furthermore, this invention relates to the cyclopropyl ring-containing analogs of compounds of formulae (I) and (II) which result from rearrangement of and concomitant elimination of H—$R^1$ from the corresponding seco compounds of formulae (I) and (II) (FIG. 1). Said cyclopropyl ring—containing analogs are believed to be the active species, allegedly being formed from compounds of formulae (I) and (II) in vivo via said rearrangement.

This invention relates to enantiomerically pure and/or diastereomerically pure compounds of formulae (I)-(IV) as well as to enantiomeric and/or diastereomeric mixtures of compounds of formulae (I)-(IV).

Compounds of formula (III) were unexpectedly found to exhibit a high cytotoxicity quotient, and in addition, parent compounds of formulae (I) and (II) were shown to be highly cytotoxic and more water-soluble than similar compounds from the prior art. These properties make the compounds of formula (III) very suited for drug delivery purposes, including drug targeting and controlled release applications.

BRIEF DESCRIPTION OF DRAWINGS

FIG. 12 describes the synthesis of linker-agent conjugates 47a-f.

DESCRIPTION OF THE INVENTION

Figure 1:
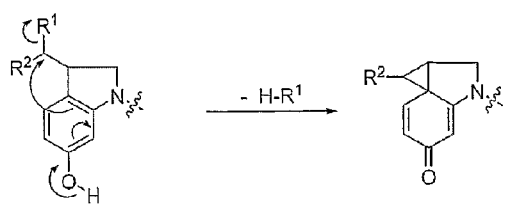
FIG. 1 illustrates the rearrangement of a seco compound to a cyclopropyl-containing compound.

The following detailed description is provided so that the invention may be more fully understood.

Definitions

Unless defined otherwise, all technical and scientific terms used herein generally have the same meaning as commonly understood by one of ordinary skill in the art.

The term "antibody", as used herein, refers to a full length immunoglobulin molecule, an immunologically active portion of a full-length immunoglobulin molecule, or a derivative of a fall length immunoglobulin molecule or an active portion thereof, i.e., a molecule that contains an antigen-binding site that immunospecifically binds an antigen of a target of interest or part thereof, such targets including, but not limited to, tumor cells. The immunoglobulin can be of any type (e.g., IgG, IgE, IgM, IgD, IgA, and IgY), class (e.g., IgG1, IgG2, IgG3, IgG4, IgA1, and IgA2), or subclass of immunoglobulin molecule. The immunoglobulin can be derived from any species, e.g., human, rodent (e.g., mouse, rat, or hamster), donkey, sheep, rabbit, goat, guinea pig, camelid, horse, cow, or chicken, but preferably, it is of human, murine, or rabbit origin. Antibodies useful in the invention include, but are not limited to, monoclonal, polyclonal, bispecific, human, humanized, or chimeric antibodies, single chain antibodies, Fv fragments, Fab fragments, F(ab') fragments, F(ab')$_2$ fragments, fragments produced by a Fab expression library, anti-idiotypic antibodies, CDRs, and epitope-binding fragments of any of the above which immunospecifically bind to an antigen-of-interest.

The term "leaving group" refers to a group that can be substituted by another group. Such leaving groups are well-known in the art, and examples include, but are not limited to, a halide (fluoride, chloride, bromide, iodide), a sulfonate (e.g., methanesulfonate, p-toluenesulfonate, and trifluoromethanesulfonate), succinimide-N-oxide, p-nitrophenoxide, pentafluorophenoxide, tetrafluorophenoxide, a carboxylate, and an alkoxycarboxylate.

The term "water-soluble group" refers to a functional group that is well solvated in aqueous environments and that imparts improved water solubility to the compound to which it is attached. Examples of water-soluble groups include, but are not limited to, alcohols and polyalcohols, straight chain or cyclic saccharides, primary, secondary, tertiary, or quaternary amines and polyamines, sulfate groups, carboxylate groups, phosphate groups, phosphonate groups, ascorbate groups, glycols, including polyethylene glycols, and polyethers.

The term "substituted", when used as adjective to "alkyl", "heteroalkyl", "cycloalkyl", "heterocycloalkyl", "aryl", "heteroaryl", and the like, indicates that said "alkyl", "heteroalkyl", "cycloalkyl", "heterocycloalkyl", "aryl", or "heteroaryl" group contains one or more substituents, which include, but are not limited to, OH, =O, =S, =NR$^h$, =N—OR$^h$, SH, NH$_2$, NO$_2$, NO, N$_3$, CF$_3$, CN, OCN, SCN, NCO, NCS, C(O)NH$_2$, C(O)H, C(O)OH, halogen, R$^h$, SR$^h$, S(O)R$^h$, S(O)OR$^h$, S(O)$_2$R$^h$, S(O)$_2$OR$^h$, OS(O)R$^h$, OS(O)OR$^h$, OS(O)$_2$R$^h$, OS(O)$_2$OR$^h$, OP(O)(OR$^h$)(OR$^i$), P(O)(OR$^h$)(OR$^i$), OR$^h$, NHR$^i$, N(R$^h$)R$^i$, $^+$N(R$^h$)(R$^i$)R$^j$, Si(R$^h$)(R$^i$)(R$^j$), C(O)R$^h$, C(O)OR$^h$, C(O)N(R$^i$)R$^h$, OC(O)R$^h$, OC(O)OR$^h$, OC(O)N(R$^h$)R$^i$, N(R$^i$)C(O)R$^h$, N(R$^i$)C(O)OR$^h$, N(R$^i$)C(O)N(R$^j$)R$^h$, and the thio derivatives of these substituents, or a protonated or deprotonated form of any of these substituents, wherein R$^h$, R$^i$, and R$^j$ are independently selected from H and optionally substituted C$_{1-15}$ alkyl, C$_{1-15}$ heteroalkyl, C$_{3-15}$ cycloalkyl, C$_{3-15}$ heterocycloalkyl, C$_{4-15}$ aryl, or C$_{4-15}$ heteroaryl or a combination thereof, two or more of R$^h$, R$^i$, and R$^j$ optionally being joined to form one or more carbocycles or heterocycles.

The term "aryl" as used herein refers to a carbocyclic aromatic substituent, which may consist of one ring or two or more rings fused together. Examples of aryl groups include, but are not limited to, phenyl, naphthyl, and anthracenyl.

The term "heteroaryl" as used herein refers to a carbocyclic aromatic substituent, which may consist of one ring or two or more rings fused together, wherein at least one carbon in one of the rings is replaced by a heteroatom. Examples of heteroaryl groups include, but are not limited to, pyridinyl, furanyl, pyrrolyl, triazolyl, pyrazolyl, imidazolyl, thiophenyl, indolyl, benzofuranyl, benzimidazolyl, indazolyl, benzotriazolyl, benzisoxazolyl, and quinolinyl.

The term "alkyl" as used herein refers to a straight chain or branched, saturated or unsaturated hydrocarbon substituent. Examples of alkyl groups include, but are not limited to, methyl, ethyl, propyl, butyl, pentyl, hexyl, octyl, decyl, isopropyl, sec-butyl, isobutyl, tert-butyl, isopentyl, 2-methylbutyl, vinyl, allyl, 1-butenyl, 2-butenyl, isobutylenyl, 1-pentenyl, and 2-pentenyl.

The term "heteroalkyl" as used herein refers to a straight chain or branched, saturated or unsaturated hydrocarbon substituent in which at least one carbon is replaced by a heteroatom. Examples include, but are not limited to, methyloxymethyl, ethyloxymethyl, methyloxyethyl, ethyloxyethyl, methylaminomethyl, dimethylaminomethyl, methylaminoethyl, dimethylaminoethyl, methylthiomethyl, ethylthiomethyl, ethylthioethyl, and methylthioethyl.

The term "cycloalkyl" as used herein refers to a saturated or unsaturated non-aromatic carbocycle substituent, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocycloalkyl" as used herein refers to a saturated or unsaturated non-aromatic cyclic hydrocarbon substituent, which may consist of one ring or two or more rings fused together, wherein at least one carbon in one of the rings is replaced by a heteroatom. Examples include, but are not limited to, tetrahydrofuranyl, pyrrolidinyl, piperidinyl, 1,4-dioxanyl, decahydroquinolinyl, piperazinyl, oxazolidinyl, and morpholinyl.

The extension "-ylene" as opposed to "-yl" in for example "alkylene" as opposed to "alkyl" indicates that said for example "alkylene" is a divalent moiety connected to one or two other moieties via two covalent single bonds or one double bond as opposed to being a monovalent group connected to one moiety via one covalent single bond in said for example "alkyl". The term "alkylene" therefore refers to a straight chain or branched, saturated or unsaturated hydrocarbon moiety; the term "heteroalkylene" as used herein refers to a straight chain or branched, saturated or unsaturated hydrocarbon moiety in which at least one carbon is replaced by a heteroatom; the term "arylene" as used herein refers to a carbocyclic aromatic moiety, which may consist of one ring or two or more rings fused together; the term "heteroarylene" as used herein refers to a carbocyclic aromatic moiety, which may consist of one ring or two or more rings fused together, wherein at least one carbon in one of the rings is replaced by a heteroatom; the term "cycloalkylene" as used herein refers to a saturated or unsaturated non-aromatic carbocycle moiety, which may consist of one ring or two or more rings fused together; the term "heterocycloalkylene" as used herein refers to a saturated or unsaturated non-aromatic cyclic hydrocarbon moiety, which may consist of one ring or two or more rings fused together, wherein at least one carbon in one of the rings is replaced by a heteroatom. Exemplary divalent moieties include those examples given for the monovalent groups hereinabove in which one hydrogen atom is removed.

The prefix "poly" in "polyalkylene", "polyheteroalkylene", "polyarylene", "polyheteroarylene", polycycloalkylene", "polyheterocycloalkylene", and the like, indicates that two or more of such "-ylene" moieties, e.g., alkylene moieties, are joined together to form a branched or unbranched multivalent moiety containing one or more attachment sites for adjacent moieties.

Certain compounds of the invention possess chiral centers or double bonds; the enantiomeric, diastereomeric, and geometric mixtures of two or more isomers, in any composition, as well as the individual isomers are encompassed within the scope of the present invention.

The compounds of the invention may also contain unnatural proportions of atomic isotopes at one or more atoms that constitute such compounds. All isotopic variations of the compounds of this invention, whether radioactive or not, are intended to be encompassed within the scope of this invention.

The phrase "pharmaceutically active salt" as used herein refers to a pharmaceutically acceptable organic or inorganic salt of a compound of the invention. For compounds containing one or more basic groups, e.g., an amine group, acid addition salts can be formed. For compounds containing one or more acidic groups, e.g., a carboxylic acid group, base addition salts can be formed. For compounds containing both acidic and basic groups, zwitterions may in addition be obtained as salts. Instances where multiple charged atoms are part of the pharmaceutically acceptable salt can have multiple counterions.

The phrase "pharmaceutically acceptable solvate" refers to an association of one or more solvent molecules and a compound of the invention. Examples of solvents that form pharmaceutically acceptable solvates include, but are not limited to, water, isopropyl alcohol, ethanol, methanol, DMSO, ethyl acetate, and acetic acid.

The term "conjugate" hereinbelow refers to a compound of formula (III).

The term "linker-agent conjugate" hereinbelow refers to a compound of formula (IV).

The term "agent" hereinbelow refers to a compound of formula (I), (II), (VII), (VIII), (I'), or (II').

The term "targeting moiety" refers to any molecule that specifically binds or reactively associates or complexes with a moiety specifically or in relative excess present at or near the target site, on, in, or near the target cell, or in (the proximity of) the target tissue or organ, e.g., a receptor, a receptor complex, substrate, antigenic determinant, or other receptive moiety, or that can target the conjugate to the target site via other mechanisms by virtue of its nature, e.g., through the EPR effect. Examples of a targeting moiety include, but are not limited to, an aptamer, an antibody or antibody fragment, a polymer, a dendrimer, a lectin, a biologic response modifier, an enzyme, a vitamin, a growth factor, a steroid, a sugar residue, an oligosaccharide residue, a carrier protein, and a hormone, or any combination thereof.

The phrase "moiety that improves the pharmacokinetic properties of the compound" refers to a moiety that changes the pharmacokinetic properties of a compound of this invention in such a way that a better therapeutic effect can be obtained. The moiety can for example increase the water solubility, increase the circulation time, or reduce immunogenicity.

The term "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are each directly attached to the moiety immediately to the left of the corresponding opening bracket. For example, A-(B)$_b$ with b being a number representing a degree of branching means that b units B are all directly attached to A. This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_b$ with b being a number representing a degree of polymerization means that when b is 2, the formula reduces to A-B-B.

The term "single-release spacer" refers to a self-elimination spacer that can release one moiety upon self-immolation.

The term "multiple-release spacer" refers to a self-elimination spacer that can release two or more moieties upon repetitive self-immolation.

The term "electronic cascade spacer" refers to a self-elimination spacer, either branched or unbranched, which may self-eliminate through one or more 1,2+2n electronic cascade eliminations (n≥1).

The term "ω-amino aminocarbonyl cyclization spacer" refers to a self-elimination spacer that may eliminate through a cyclization process under formation of a cyclic ureum derivative.

The term "spacer system" refers to a single spacer moiety or to two or more of the same or different spacer moieties coupled together. A spacer system may be branched or unbranched and contain one or more attachment sites for Z as well as V$^1$ and optionally L.

In this document and in its claims, the verbs "to comprise", "to have", "to contain" and their conjugations are used in their non-limiting sense to mean that items following or preceding the verb are included, but items non-specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

In the generic structures throughout this description and in the claims letters are used to define structural elements. Some of these letters can be mistaken to represent an atom, such as C, N, O, P, K, B, F, S, U, V, W, I, and Y. To avoid confusion whenever these letters do not represent an atom they are given in bold typeface.

When there are one or more adjectives and/or adjective phrases to a noun that is a) the first in a list of nouns or b) that is anywhere in the middle of a list of nouns and said noun and adjectives together are preceded by the word "and", the adjectives do not only bear on said noun, but on all following nouns separately, unless the context dictates otherwise. This for example means that the phrase "optionally substituted $C_{1-4}$ alkyl, $C_{1-4}$ heteroalkyl, $C_{3-7}$ cycloalkyl, or $C_{3-7}$ heterocycloalkyl" should be read as "optionally substituted $C_{1-4}$ alkyl, optionally substituted $C_{1-4}$ heteroalkyl, optionally substituted $C_{3-7}$ cycloalkyl, or optionally substituted $C_{3-7}$ heterocycloalkyl".

Throughout this description and in the claims molecular structures or parts thereof are drawn. As usual in such drawings bonds between atoms are represented by lines, in some cases, to indicate stereochemistry, by bold or broken or wedged lines. Usually a line ending in space (a "loose" end), i.e., at one end not having another line or specific atom connected to it, represents a $CH_3$ group. This is correct for the drawings representing the compounds according to the invention. For those structures representing a structural element of the compounds according to the invention a line ending in space may indicate the position of attachment of another structural element of the compound. This has been indicated with a wavy line perpendicular to and crossing the "loose" line in most drawings.

Furthermore, the structures or parts thereof have been drawn, under the assumption that the structures are read from left to right, meaning that for example in the drawings of compounds of formula (III) $V^2$ is always located on the left side (when present) and Z is always located on the right side of such structures.

The following abbreviations are used herein and have the indicated definitions: Aloc: allyloxycarbonyl; Asc: ascorbate; Boc=tert-butyloxycarbonyl; DCC=N,N'-dicyclohexylcarbodiimide; DIPEA: diisopropylethylamine; DME: 1,2-dimethoxyethane; DMF=N,N-dimethylformamide; Fmoc=9-fluorenylmethyloxycarbonyl; HOBt: 1-hydroxybenzotriazole; HOSu=N-hydroxysuccinimide; NMM: N-methylmorpholine; PABA=p-aminobenzyl alcohol; PBS: phosphate-buffered saline; PNP=p-nitrophenoxide; PNPCl=p-nitrophenyl chloroformate; PNP$_2$O=bis(p-nitrophenyl) carbonate; SCID: severe combined immunodeficiency; TFA: trifluoroacetic acid; THF: tetrahydrofuran.

Agents, Linker-Agent Conjugates, and Conjugates

The present invention provides novel agents that can be classified as belonging to the class of DNA-binding alkylating agents CC-1065 and the duocarmycins. Furthermore, the invention relates to novel conjugates of these agents and to linker-agent conjugates, which may or may not serve as intermediates for said conjugates.

The agents of the present invention are deemed to be used to treat an illness that is characterized by undesired (cell) proliferation. For example, an agent of this invention can be used to treat a tumor, cancer, an autoimmune disease, or an infectious disease.

The conjugates of the present invention are in one aspect deemed to be applicable to target agents of formulae (I) and (II) to a specific target site where the conjugate can be converted into one or more agents or be induced to be converted into one or more of said agents. This invention can furthermore find application in (non-specific) controlled release of one or more of said agents from a conjugate, with the aim of for example enhancing pharmacokinetic properties.

Compounds of formula (III) were unexpectedly found to exhibit a high cytotoxicity quotient, and in addition, parent compounds of formulae (I) and (II) were shown to be highly cytotoxic and more water-soluble than similar compounds from the prior art. Without being bound by any theory, an explanation for the high cytotoxicity quotient might be the presence of a water-soluble group on such an agent in combination with the somewhat shielded carbon to which the leaving group is attached. The increased water-solubility of the agent may cause the compound to better be able to reach its (intracellular) target and thus increase its cytotoxicity after release from the conjugate, while it may also reduce aggregation of the conjugate and reduce side effects of the conjugate due to premature release of the agent from the conjugate as the liberated agent may be less effective in entering (non-targeted) cells due to its increased polarity. Steric hindrance may reduce direct alkylation of biomolecules by the conjugate and non-DNA alkylation by the agent, thereby reducing aspecific (cyto)toxicity. Thus, the inventive concept of combining water solubility and steric shielding in compounds of formulae (I) and (II) may lead to agents that are more water-soluble and more selective and to an increased cytotoxicity quotient for conjugates of this invention.

Agents

In one aspect, the invention provides a compound of formula (I) or (II):

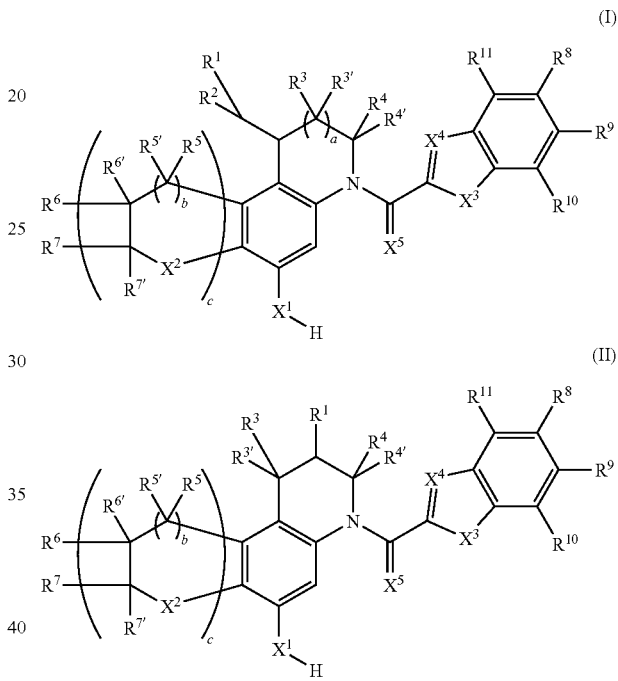

or a pharmaceutically acceptable salt or solvate thereof, wherein $R^1$ is selected from halogen and $OSO_2R^u$, wherein $R^u$ is selected from optionally substituted $C_{1-6}$ alkyl, $C_{1-6}$ perhaloalkyl, benzyl, and phenyl;

$R^2$ is selected from H and optionally substituted $C_{1-8}$ alkyl;

$R^3$, $R^{3'}$, $R^4$, and $R^{4'}$ are independently selected from H and optionally substituted $C_{1-8}$ alkyl, wherein two or more of $R^2$, $R^3$, $R^{3'}$, $R^4$, and $R^{4'}$ are optionally joined to form one or more optionally substituted carbocycles or heterocycles;

$X^2$ is selected from O, $C(R^{14})(R^{14'})$, and $NR^{14'}$, wherein $R^{14}$ is selected from H and optionally substituted $C_{1-8}$ alkyl or acyl and wherein $R^{14'}$ may be absent or be selected from H and optionally substituted $C_{1-8}$ alkyl or acyl;

Each $R^5$, $R^{5'}$, $R^6$, $R^{6'}$, $R^7$, and $R^{7'}$ is independently selected from H, OH, SH, $NH_2$, $N_3$, $NO_2$, NO, $CF_3$, CN, $C(O)NH_2$, C(O)H, C(O)OH, halogen, $R^k$, $SR^k$, $S(O)R^k$, $S(O)_2R^k$, $S(O)OR^k$, $S(O)_2OR^k$, $OS(O)R^k$, $OS(O)_2R^k$, $OS(O)OR^k$, $OS(O)_2OR^k$, $OR^k$, $NHR^k$, $N(R^k)R^L$, $^+N(R^k)(R^L)R^m$, $P(O)(OR^k)(OR^L)$, $OP(O)(OR^k)(OR^L)$, $SiR^kR^LR^m$, $C(O)R^k$, $C(O)OR^k$, $C(O)N(R^L)R^k$, $OC(O)R^k$, $OC(O)OR^k$, $OC(O)N(R^k)R^L$, $N(R^L)C(O)R^k$, $N(R^L)C(O)OR^k$, and $N(R^L)C(O)N(R^m)R^k$, wherein $R^k$, $R^L$, and $R^m$ are independently selected from H and optionally substituted $C_{1-4}$ alkyl, $C_{1-4}$ heteroalkyl, $C_{3-7}$ cycloalkyl, $C_{3-7}$ heterocycloalkyl, $C_{4-12}$ aryl, or $C_{4-12}$ heteroaryl, two or more of $R^k$, $R^L$, and $R^m$ optionally being joined to form one or more optionally substituted aliphatic or aromatic carbocycles or heterocycles, and/or $R^5+R^{5'}$, and/or $R^6+R^{6'}$, and/or $R^7+R^{7'}$ are independently =O, =S, or =$NR^{12}$, $R^{12}$ being selected from H and optionally substituted $C_{1-6}$ alkyl, and/or $R^{5'}$ and $R^{6'}$, and/or $R^{6'}$ and $R^{7'}$, and/or $R^{7'}$ and $R^{14'}$ are absent, which means that a double bond is present between the atoms bearing $R^{5'}$ and $R^{6'}$, and/or $R^{6'}$ and $R^{7'}$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined to form one or more optionally substituted aliphatic or aromatic carbocycles or heterocycles;

$X^1$ is selected from O, S, and $NR^{13}$, wherein $R^{13}$ is selected from H and optionally substituted $C_{1-8}$ alkyl;

$X^3$ is selected from O, S, and $NR^{15}$, wherein $R^{15}$ is selected from H and optionally substituted $C_{1-8}$ alkyl or acyl, or —$X^3$— represents —$X^{3a}$ and $X^{3b}$— wherein $X^{3a}$ is connected to the carbon to which $X^4$ is attached and $X^{3b}$ is connected to the phenyl ring ortho to $R^{10}$, wherein $X^{3a}$ is independently selected from H and optionally substituted $C_{1-8}$ alkyl or acyl and $X^{3b}$ is selected from the same group of substituents as $R^8$;

$X^4$ is selected from N and $CR^{16}$, wherein $R^{16}$ is selected from H and optionally substituted $C_{1-8}$ alkyl or acyl;

$X^5$ is selected from O, S, and $NR^{17}$, wherein $R^{17}$ is selected from H and optionally substituted $C_{1-8}$ alkyl or acyl;

$R^8$, $R^9$, $R^{10}$, and $R^{11}$ are each independently selected from H, OH, SH, $NH_2$, $N_3$, $NO_2$, NO, $CF_3$, CN, $C(O)NH_2$, $C(O)H$, $C(O)OH$, halogen, $R^x$, $SR^x$, $S(O)R^x$, $S(O)_2R^x$, $S(O)OR^x$, $S(O)_2OR^x$, $OS(O)R^x$, $OS(O)_2R^x$, $OS(O)OR^x$, $OS(O)_2OR^x$, $OR^x$, $NHR^x$, $N(R^x)R^y$, $^+N(R^x)(R^y)R^z$, $P(O)(OR^x)(OR^y)$, $OP(O)(OR^x)(OR^y)$, $SiR^xR^yR^z$, $C(O)R^x$, $C(O)OR^x$, $C(O)N(R^y)R^x$, $OC(O)R^x$, $OC(O)OR^x$, $OC(O)N(R^x)R^y$, $N(R^y)C(O)R^x$, $N(R^y)C(O)OR^x$, $N(R^y)C(O)N(R^z)R^x$, and a water-soluble group, wherein $R^x$, $R^y$, and $R^z$ are independently selected from H and optionally substituted $C_{1-15}$ alkyl, $C_{1-15}$ heteroalkyl, $C_{3-15}$ cycloalkyl, $C_{3-15}$ heterocycloalkyl, $C_{4-15}$ aryl, or $C_{4-15}$ heteroaryl, one or more of the optional substituents in $R^x$, $R^y$, and $R^z$ optionally being a water-soluble group, and two or more of $R^x$, $R^y$, and $R^z$ optionally being joined to form one or more optionally substituted aliphatic or aromatic carbocycles or heterocycles, and at least one of $R^8$, $R^9$, $R^{10}$, and $R^{11}$ comprises at least one water-soluble group, two or more of $R^8$, $R^9$, $R^{10}$, $R^{11}$, or $X^{3b}$ optionally being joined to form one or more optionally substituted aliphatic or aromatic carbocycles or heterocycles;

a and b are independently selected from 0 and 1;

c is selected from 0, 1, and 2;

provided that in the compound of formula (I) at least one of $R^2$, $R^3$, $R^{3'}$, $R^4$, $R^{4'}$, $R^5$, and $R^{5'}$ present is not hydrogen.

It should be understood that this invention relates to enantiomerically pure and/or diastereomerically pure compounds of formulae (I) and (II) as well as to enantiomeric and/or diastereomeric mixtures of compounds of formulae (I) and (II).

The considerations about substituent effects in compounds of formulae (I) and (II) and their cyclopropyl-containing analogs given in this document are presented without consenting to a specific mechanism of action for compounds of formulae (I) and (II) and their cyclopropyl-containing analogs.

$R^1$ in a compound of formula (I) or (II) is a leaving group. In one embodiment of this invention, the leaving group $R^1$ in a compound of formula (I) or (II) is a halide. In another embodiment, $R^1$ is selected from chloride (Cl), bromide (Br), and iodide (I). In yet another embodiment, $R^1$ is chloride (Cl).

In yet another embodiment, $R^1$ is bromide (Br). By varying the leaving group $R^1$, one may tune the alkylating activity of the seco agents and influence the transformation rate of a seco agent to a cyclopropyl-containing agent. If the leaving capability of $R^1$ is too good, this may cause the seco agent to become an alkylating agent as well, which may decrease the cytotoxicity quotient of conjugates of compounds of formulae (I) and (II) as the agent may be able to alkylate while still being bound in the conjugate. On the other hand, if $R^1$ is too bad a leaving group, the seco agent may not close to form a cyclopropyl-containing agent, believed to be the active species, which may reduce its cytotoxicity and, most likely, reduce the cytotoxicity quotient.

Another means to tune the alkylating activity of the seco agents and their cyclopropyl-containing derivatives may be to somewhat shield the carbon to which the leaving group is attached or on which nucleophilic attack can occur by choosing at least one of $R^2$, $R^3$, $R^{3'}$, $R^4$, $R^{4'}$, $R^5$, and $R^{5'}$ present to be other than hydrogen. Shielding of said carbon may reduce aspecific alkylation by compounds of formulae (I) and (II) and their cyclopropyl-containing analogs and by their conjugates as well. Although introduction of steric hindrance may also affect the DNA alkylation rate, it may be reasonable to assume that aspecific alkylation may be affected relatively more than DNA alkylation as the latter occurs presumably after the agent is ideally positioned for nucleophilic attack being bound to the DNA minor groove. The carbon bearing $R^1$ in a compound of formula (II), being a secondary carbon atom, is already somewhat shielded in comparison to the carbon bearing $R^1$ in a compound of formula (I) when $R^2$ is H. In this respect, a compound of formula (II) may be compared to a compound of formula (I) in which $R^2$ is other than hydrogen. Further shielding may however be accomplished by choosing one or more of $R^3$, $R^{3'}$, $R^4$, $R^{4'}$, $R^5$, and $R^{5'}$ present to be other than hydrogen.

In one embodiment, $R^2$ in a compound of formula (I) is optionally substituted $C_{1-8}$ alkyl. In another embodiment, $R^2$ is optionally substituted linear $C_{1-8}$ alkyl. In another embodiment, $R^2$ is unsubstituted linear $C_{1-8}$ alkyl. In another embodiment, $R^2$ is methyl.

Alternatively or simultaneously, steric shielding of the carbon bearing $R^1$ may be introduced by choosing one or more of $R^3$, $R^{3'}$, $R^4$, and $R^{4'}$ to be other than hydrogen. In one embodiment, $R^3$, $R^{3'}$, $R^4$, and $R^{4'}$ are each H. In another embodiment, $R^3$ and $R^{3'}$ are both H. In another embodiment, $R^4$ and $R^{4'}$ are both H. In another embodiment, one of $R^3$ and $R^{3'}$ is $C_{1-8}$ alkyl while the other is H. In another embodiment, one of $R^4$ and $R^{4'}$ is $C_{1-8}$ alkyl while the other is H. In another embodiment, one of $R^3$ and $R^{3'}$ is $C_{1-8}$ alkyl and one of $R^4$ and $R^{4'}$ is $C_{1-8}$ alkyl while the others are H. In another embodiment, both $R^3$ and $R^{3'}$ are independently selected from $C_{1-8}$ alkyl. In another embodiment, both $R^4$ and $R^{4'}$ are independently selected from $C_{1-8}$ alkyl. In another embodiment, $R^2$ is H and one of $R^3$, $R^{3'}$, $R^4$, and $R^{4'}$ is selected from $C_{1-8}$ alkyl. In another embodiment, $R^2$ is H and one of $R^3$, $R^{3'}$, $R^4$, and $R^{4'}$ is selected from methyl. In another embodiment, $R^2$ is H and two of $R^3$, $R^{3'}$, $R^4$, and $R^{4'}$ are independently selected from $C_{1-8}$ alkyl. In yet another embodiment, $R^2$ is H and two of $R^3$, $R^{3'}$, $R^4$, and $R^{4'}$ are methyl.

The alkylating activity of a compound of formula (I) or (II) or its cyclopropyl-containing analog may also be affected by the nature of $X^1$. The nature of $X^1$ may affect the rate at which and the conditions under which the seco agents ring close to the cyclopropyl analogs and/or the rate at which the cyclopropyl ring is opened by nucleophilic attack by DNA, and thus affect the alkylation behavior. In one embodiment, $X^1$ is O.

The substituents $R^5$, $R^{5'}$, $R^6$, $R^{6'}$, $R^7$, $R^{7'}$, and $X^2$ as well as the size of the ring(s) connected to the left-hand side of the ring bearing $X^1$ may for example, each independently or two or more taken together, affect the pharmacokinetic properties of the agent, affect the water solubility, affect the aggregation behavior, affect the DNA alkylation process, or affect the DNA binding strength. Furthermore, especially $R^5$ and $R^{5'}$ may also affect the degree of shielding of the carbon on which nucleophilic attack can occur. In one embodiment, $R^5$ and $R^{5'}$ are both H. In another embodiment, at least one of $R^5$ and $R^{5'}$ is not hydrogen. In another embodiment, $R^5$ is not hydrogen. In another embodiment, $R^2$ is hydrogen and at least one of $R^5$ or $R^{5'}$ is not hydrogen. In yet another embodiment, $R^5$ is selected from nitro, halogen, amino, hydroxy, and optionally substituted alkylamino, alkylcarbonylamino, alkoxycarbonylamino, alkyloxy, alkylcarbonyloxy, alkylaminocarbonyloxy, or $C_{1-4}$ alkyl. In yet another embodiment, $R^5$ is optionally substituted linear $C_{1-4}$ alkyl. In another embodiment, $R^5$ is unsubstituted linear $C_{1-4}$ alkyl. In another embodiment, $R^5$ is methyl.

Although the alkylation rate and efficiency of compounds like the ones of formulae (I) and (II) may be tuned in several ways, in one aspect of this invention, this is achieved by introducing steric shielding choosing for a compound of formula (I) at least one of $R^2$, $R^3$, $R^{3'}$, $R^4$, $R^{4'}$, $R^5$, and $R^{5'}$ present to be other than hydrogen and for a compound of formula (II) optionally one or more of $R^2$, $R^3$, $R^{3'}$, $R^4$, $R^{4'}$, $R^5$, and $R^{5'}$ present to be other than hydrogen.

In one aspect of the invention compounds of formulae (I) and (II) may be represented by compounds of formulae (Ia) and (IIa), respectively:

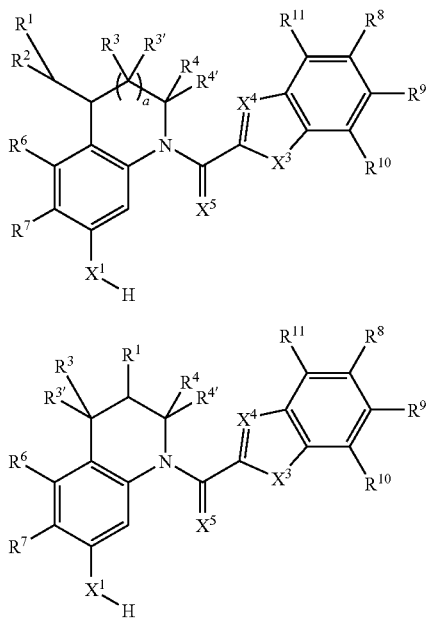

In one embodiment, $R^6$ and $R^7$ in (Ia) or (IIa) are both H.

In another aspect compounds of formulae (I) and (II) may be represented by compounds of formulae (Ib) and (IIb), respectively:

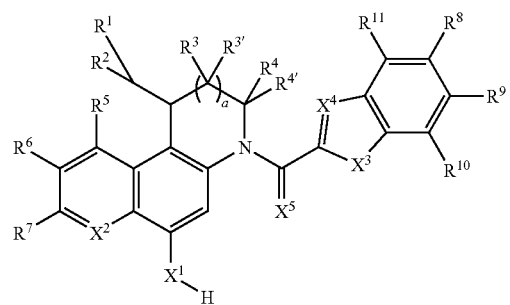

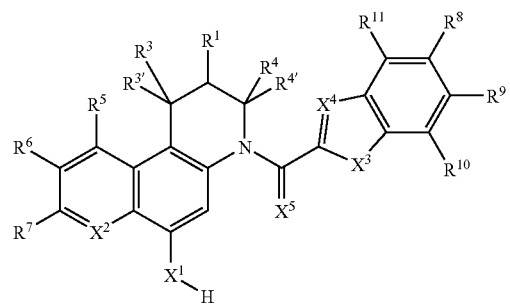

In one embodiment, $X^2$ in (Ib) or (IIb) is N.
In one embodiment, $X^2$ in (Ib) or (IIb) is CH.
In one embodiment, $R^5$, $R^6$, and $R^7$ in (Ib) or (IIb) are each H.
In one embodiment, $R^5$, $R^6$, and $R^7$ in (Ib) or (IIb) are each H and $X^2$ is CH.
In another embodiment, $R^5$ and $R^7$ in (Ib) or (IIb) are each H and $R^6$ is $CO_2Me$.
In another embodiment, $R^5$ and $R^7$ in (Ib) or (IIb) are each H and $R^6$ is OMe.
In another embodiment, $R^5$ and $R^7$ in (Ib) or (IIb) are each H and $R^6$ is CN.
In yet another embodiment, $R^5$ in (Ib) or (IIb) is selected from nitro, halogen, amino, hydroxy, and optionally substituted alkylamino, alkylcarbonylamino, alkoxycarbonylamino, alkyloxy, alkylcarbonyloxy, alkylaminocarbonyloxy, or $C_{1-4}$ alkyl. In yet another embodiment, $R^5$ in (Ib) or (IIb) is optionally substituted linear $C_{1-4}$ alkyl. In another embodiment, $R^5$ in (Ib) or (IIb) is unsubstituted linear $C_{1-4}$ alkyl. In another embodiment, $R^5$ in (Ib) or (IIb) is methyl.

In yet another aspect, compounds of formulae (J) and (II) may be represented by compounds of formulae (Ic) and (IIc), respectively:

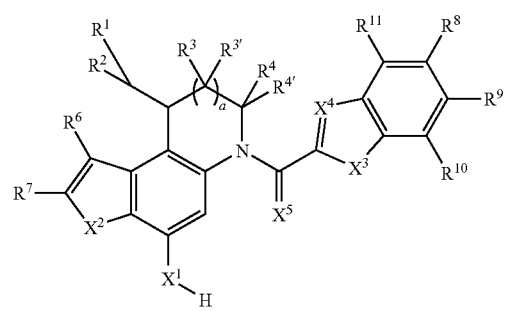

-continued (IIc)

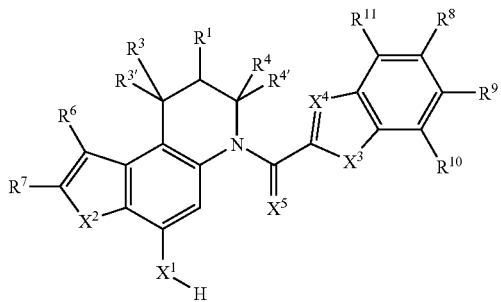

In one embodiment, $X^2$ in (Ic) or (IIc) is NH.

In another embodiment, $R^6$ and $R^7$ in (Ic) or (IIc) are H and $CO_2CH_3$, respectively, and $X^2$ is NH.

In another embodiment, $R^7$ and $R^6$ in (Ic) or (IIc) are H and $CO_2CH_3$, respectively, and $X^2$ is NH.

In another embodiment, $R^6$ in (Ic) or (IIc) is $CH_3$ and $X^2$ is NH.

In yet another aspect, compounds of formulae (I) and (II) may be represented by compounds of formulae (Id) and (IId), respectively:

(Id)

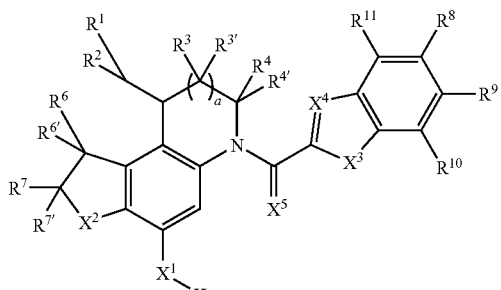

(IId)

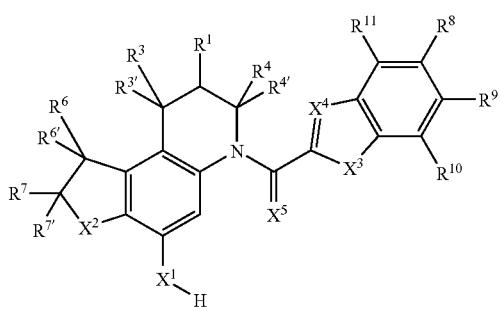

In one embodiment, $X^2$ in (Id) or (IId) is NH.

In one embodiment, $R^6$ and $R^{6'}$ in (Id) or (IId) together are =O.

In another embodiment, $R^7$ and $R^{7'}$ in (Id) or (IId) are $CO_2CH_3$ and $CH_3$, respectively.

In another embodiment, in a compound of formula (Id) or (IId), $X^2$ is NH, $R^6$ and $R^{6'}$ together are =O, and $R^7$ and $R^{7'}$ are $CO_2CH_3$ and $CH_3$, respectively.

In another embodiment, $X^3$ is NH.
In another embodiment, $X^3$ is O.
In one embodiment, $X^4$ is CH.
In one embodiment, $X^5$ is O.

The water-soluble group is a group that imparts an increased solubility on the compounds of formulae (I) and (II) with respect to similar compounds from the prior art. It may also contribute to prevent or reduce aggregation of compounds of this invention or to reduce side effects. Examples of water-soluble groups include, but are not limited to, $-NH_2$, $-NH-$, $-NHR^a$, $-NR^a$, $-N(R^a)(R^b)$, $-^+N(R^a)(R^b)-$, $-^+N(R^a)(R^b)(R^c)$, $-COOH$, $-COOR^a$, $-OP(O)(OH)_2$, $-OP(O)(OH)O-$, $-OP(O)(OR^a)O-$, $OP(O)(OH)OR^a$, $-OP(O)(OR^b)OR^a$, $-P(O)(OH)_2$, $-P(O)(OH)O-$, $P(O)(OR^a)OH$, $-P(O)(OR^a)O-$, $-P(O)(OR^a)(OR^b)$, $-OS(O)_2OH$, $-OS(O)_2O-$, $-OS(O)_2OR^a$, $-S(O)_2OH$, $-S(O)_2O-$, $-S(O)_2OR^a$, $-OS(O)OH$, $-OS(O)O-$, $-OS(O)OR^a$, $-S(O)OH$, $-S(O)O-$, $-OS(O)-$, $-S(O)OR^a$, $-OS(O)_2-$, $-OS(O)_2R^a$, $-S(O)_2-$, $-S(O)_2R^a$, $-OS(O)R^a$, $-S(O)-$, $-S(O)R^a$, $-OH$, $-SH$, $-(OCH_2CH_2)_{v'}OH$, $-(OCH_2CH_2)_{v'}O-$, $-(OCH_2CH_2)_{v'}OR^a$, a sugar moiety, an oligosaccharide moiety, and an oligopeptide moiety, or a protonated or deprotonated form thereof and further any combination thereof, wherein $R^a$, $R^b$, and $R^c$ are independently selected from H and optionally substituted $C_{1-3}$ alkyl, two or more of $R^a$, $R^b$, and $R^c$ optionally being joined to form one or more carbocycles or heterocycles, and v' is an integer selected from 1 to 100. The water-soluble group may be at any position within $R^8$, $R^9$, $R^{10}$, and/or $R^{11}$ or may constitute the whole $R^8$, $R^9$, $R^{10}$, or $R^{11}$ moiety. The water-soluble group may for example be located at any interior position, be part of the main chain, be part of a ring structure, be a functional group pending to the main chain or a ring, or be placed at the position at which the $R^8$, $R^9$, $R^{10}$, or $R^{11}$ substituent is attached to the remainder of the molecule.

In one embodiment, one of $R^8$, $R^9$, $R^{10}$, and $R^{11}$ contains a water-soluble group.

In another embodiment, one of $R^8$, $R^9$, and $R^{10}$ contains a water-soluble group.

In yet another embodiment, $R^8$ contains a water-soluble group.

In yet another embodiment, $R^9$ contains a water-soluble group.

In yet another embodiment, $R^{10}$ contains a water-soluble group.

In one embodiment, the water-soluble group is a carboxylic acid group.

In another embodiment, the water-soluble group is an amino group.

In a further embodiment, the water-soluble group is a primary amino group.

In another embodiment, the water-soluble group is a secondary amino group.

In another embodiment, the water-soluble group is a tertiary amino group.

In another embodiment, the water-soluble group is a quaternary amino group.

In one embodiment, the water-soluble group is a dimethylamino group.

In another embodiment, the water-soluble group is a morpholino group.

In yet another embodiment, the water-soluble group is a 1-methylpiperidin-4-yl group.

In another embodiment, the water-soluble group is a methylamino group.

In another embodiment, the water-soluble group is a piperidin-4-yl group.

In yet another embodiment, the water-soluble group is an amino ($NH_2$) group.

In yet another embodiment, the water-soluble group is an N-methyl-N-(carboxymethyl)amino group.

In yet another embodiment, the water-soluble group is an N-methyl-N-(2-methoxy-2-oxoethyl)amino group.

In yet another embodiment, the water-soluble group is not an ether group (—O—, —OR$^a$), not being an oligoether or polyether group.

In yet another embodiment, the water-soluble group is not an amide group, not being an oligopeptide or polypeptide group.

In yet another embodiment, the water-soluble group is not a primary, secondary, or tertiary amino group of which the nitrogen is directly connected (and thus conjugated) to an aromatic moiety or a secondary or tertiary amino group being part of an aromatic moiety, the nitrogen atom being an atom in the aromatic ring system.

In yet another embodiment, the water-soluble group is not a hydroxyl group connected to an aromatic ring system.

In one embodiment, $R^8$, $R^9$, $R^{10}$, or $R^{11}$ is selected from —O—$C_{1-6}$ alkylene-N($R^{100}$)$_2$, —NC(O)—$C_{1-5}$ alkylene-N($R^{100}$)$_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or COOR$^{300}$, $R^{300}$ being $C_{1-4}$ alkyl.

In another embodiment, $R^8$, $R^9$, or $R^{10}$ is selected from —O—$C_{1-6}$ alkylene-N($R^{100}$)$_2$, —NC(O)—$C_{1-5}$ alkylene-N($R^{100}$)$_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or COOR$^{300}$, $R^{300}$ being $C_{1-4}$ alkyl.

In another embodiment, $R^8$ is selected from —O—$C_{1-6}$ alkylene-N($R^{100}$)$_2$, —NC(O)—$C_{1-5}$ alkylene-N($R^{100}$)$_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or COOR$^{300}$, $R^{300}$ being $C_{1-4}$ alkyl.

In another embodiment, $R^9$ is selected from —O—$C_{1-6}$ alkylene-N($R^{100}$)$_2$, —NC(O)—$C_{1-5}$ alkylene-N($R^{100}$)$_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or COOR$^{300}$, $R^{300}$ being $C_{1-4}$ alkyl.

In another embodiment, $R^{10}$ is selected from —O—$C_{1-6}$ alkylene-N($R^{100}$)$_2$, —NC(O)—$C_{1-5}$ alkylene-N($R^{100}$)$_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or COOR$^{300}$, $R^{300}$ being $Cl_4$ alkyl.

In one embodiment, $R^8$, $R^9$, $R^{10}$, or $R^{11}$ is selected from 2-(morpholin-4-yl)ethoxy, (1-methylpiperidin-4-yl)methoxy, 2-(N,N-dimethylamino)ethoxy, and 2-(N,N-dimethylamino)-acetylamino.

In another embodiment, $R^8$, $R^9$, or $R^{10}$ is selected from 2-(morpholin-4-yl)ethoxy, (1-methylpiperidin-4-yl)methoxy, 2-(N,N-dimethylamino)ethoxy, and 2-(N,N-dimethylamino)-acetylamino.

In another embodiment, $R^8$ is selected from 2-(morpholin-4-yl)ethoxy, (1-methylpiperidin-4-yl)methoxy, 2-(N,N-dimethylamino)ethoxy, and 2-(N,N-dimethylamino)acetylamino.

In one embodiment, $R^8$ is 2-(morpholin-4-yl)ethoxy.

In another embodiment, $R^8$ is (1-methylpiperidin-4-yl)methoxy.

In yet another embodiment, $R^8$ is 2-(N,N-dimethylamino)ethoxy.

In yet another embodiment, $R^8$ is 2-(N,N-dimethylamino)acetylamino.

In yet another embodiment, $R^9$ is 2-(N,N-dimethylamino)ethoxy.

In yet another embodiment, $R^{10}$ is 2-(N,N-dimethylamino)ethoxy.

In another embodiment, $R^8$, $R^9$, $R^{10}$, or $R^{11}$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)-ethoxy.

In another embodiment, $R^8$, $R^9$, $R^{10}$, or $R^{11}$ is selected from 2-(morpholin-4-yl)ethoxy, (1-methylpiperidin-4-yl)methoxy, 2-(N,N-dimethylamino)ethoxy, 2-(N,N-dimethylamino)-acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, $R^8$, $R^9$, or $R^{10}$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)-ethoxy.

In another embodiment, $R^8$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, $R^8$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, $R^9$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, $R^{10}$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, $R^8$ is 2-(methylamino)ethoxy.

In yet another embodiment, $R^8$ is 2-aminoethoxy.

In yet another embodiment, $R^8$ is 2-(N-methyl-N-(carboxymethyl)amino)ethoxy.

In yet another embodiment, $R^8$ is 2-(N-methyl-N-(2-methoxy-2-oxoethyl)amino)ethoxy.

When one of $R^8$, $R^9$, $R^{10}$, or $R^{11}$ contains a water-soluble group, the other substituents may each independently either be hydrogen, a substituent containing another water-soluble group or a substituent containing no water-soluble group.

In one embodiment, $R^9$, $R^{10}$, and $R^{11}$ are each hydrogen.

In one embodiment, $R^8$ contains a water-soluble group and $R^9$, $R^{10}$, and $R^{11}$ are each hydrogen.

In another embodiment, $R^8$ contains a water-soluble group and $R^9$ is methoxy.

In another embodiment, $R^9$ is methoxy and $R^{10}$ and $R^{11}$ are each hydrogen.

In another embodiment, $R^8$ contains a water-soluble group and $R^9$ is methoxy and $R^{10}$ and $R^{11}$ are each hydrogen.

In a further embodiment, $R^8$ is 2-(N,N-dimethylamino)ethoxy, $R^9$ is methoxy, and $R^{10}$ and $R^{11}$ are each hydrogen.

In another embodiment, $R^9$ or $R^{10}$ is a substituent containing a water-soluble group and $R^8$ is not hydrogen.

In another embodiment, $R^9$ is a substituent containing a water-soluble group and $R^8$ is not hydrogen.

In another embodiment, $R^{10}$ is a substituent containing a water-soluble group and $R^8$ is not hydrogen.

In another embodiment, $R^8$ is selected from

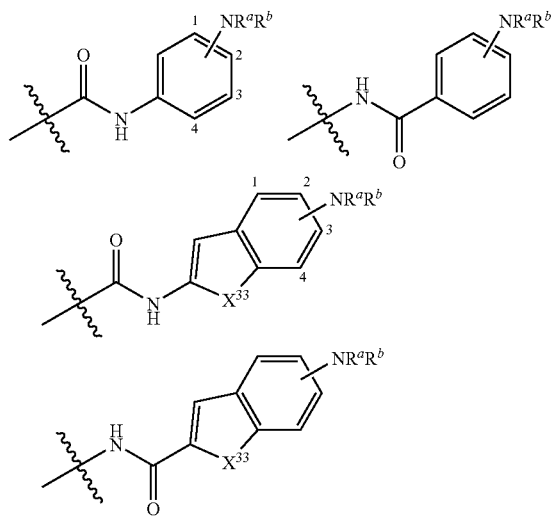

wherein $X^{33}$ is selected from O, S, and $NR^{15}$, wherein $R^{15}$ is as defined hereinabove, $R^a$ and $R^b$ are as defined hereinabove, and $NR^aR^b$ is connected to the phenyl ring through any one of the carbon atoms 1-4. In another embodiment, $NR^aR^b$ is connected to the phenyl ring through carbon atom 2 or 4.

$R^8$ may also be a substituent of the formula:

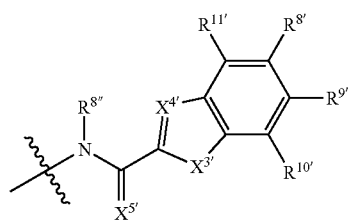

wherein $X^{3'}$, $X^{4'}$, $X^{5'}$, $R^{8'}$, $R^{9'}$, $R^{10'}$, and $R^{11'}$ have the same meaning as defined above for $X^3$, $X^4$, $X^5$, $R^8$, $R^9$, $R^{10}$, and $R^{11}$, respectively, except that $R^{8'}$, $R^{9'}$, $R^{10'}$, and $R^{11'}$ do not have to contain a water-soluble group when there is already another water-soluble group present in $R^8$, $R^9$, $R^{10}$, or $R^{11}$, and wherein $R^{8''}$ may be selected from H and optionally substituted $C_{1-5}$ alkyl or $C_{1-5}$ heteroalkyl and optionally be joined with $R^9$ or $R^{11}$ to form an optionally substituted aliphatic or aromatic heterocycle.

In one embodiment, $R^8$ or $R^{8''}$ and $R^{11}$, and/or $R^{8'}$ and $R^{11'}$ may be joined to form together with the linking atoms an optionally substituted dihydropyrrole.

Compounds of formulae (I) and (II) have as one advantage that they have an increased water solubility with respect to similar compounds from the prior art. The presence of for example a carboxylic acid group or a secondary aliphatic amino group may significantly contribute to water solubility. At the same time, such a group may prevent a compound of formula (I) or (II) from crossing a biological barrier, especially when it is an apolar barrier such as a cell membrane. This may be advantageous, especially when a compound of formula (I) or (II) is delivered into a targeted cell through conjugation to a targeting moiety before it is released from the conjugate. When a compound of formula (I) or (II) is prematurely released from the conjugate, e.g., in the circulation, it may be unable or only moderately able to enter (non-targeted) cells aspecifically as its membrane translocation capabilities may be impaired. This may lead to increased selectivity and therefore to fewer side effects.

In one embodiment, $R^2$ is not hydrogen.

In another embodiment, $R^2$ is H and at least one of $R^3$, $R^{3'}$, $R^4$, $R^{4'}$, $R^5$, and $R^{5'}$ present is not H.

In another embodiment, $R^2$ is H, $X^1$ is O, and at least one of $R^3$, $R^{3'}$, $R^4$, $R^{4'}$, $R^5$, and $R^{5'}$ present is not H.

In another embodiment, in a compound of formula (Ib) or (IIb), $R^2$ is H, $X^1$ is O, $X^2$ is $CR^{14}$, and at least one of $R^3$, $R^{3'}$, $R^4$, $R^{4'}$, $R^5$, and $R^{5'}$ present is not H.

In another embodiment, in a compound of formula (Ib) or (IIb), $R^2$ is H, $X^1$ is O, $X^2$ is $CR^{14}$, $X^5$ is O, and at least one of $R^3$, $R^{3'}$, $R^4$, $R^{4'}$, $R^5$, and $R^{5'}$ present is not H.

In another embodiment, in a compound of formula (Ib) or (IIb), $R^2$ is H, $X^1$ is O, $X^2$ is $CR^{14}$, $X^5$ is O, $X^3$ is $NR^{15}$, and at least one of $R^3$, $R^{3'}$, $R^4$, $R^{4'}$, $R^5$, and $R^{5'}$ present is not H.

In another embodiment, in a compound of formula (Ib) or (IIb), $R^2$ is H, $X^1$ is O, $X^2$ is CH, $X^5$ is O, $X^3$ is NH, and at least one of $R^3$, $R^{3'}$, $R^4$, $R^{4'}$, $R^5$, and $R^{5'}$ present is not H.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^8$, $R^9$, $R^{10}$, or $R^{11}$ is selected from —O—$C_{1-6}$ alkylene-$N(R^{100})_2$, —NC(O)—$C_{1-5}$ alkylene-$N(R^{100})_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^8$, $R^9$, or $R^{10}$ is selected from —O—$C_{1-6}$ alkylene-$N(R^{100})_2$, —NC(O)—$C_{1-5}$ alkylene-$N(R^{100})_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^8$ is selected from —O—$C_{1-6}$ alkylene-$N(R^{100})_2$, —NC(O)—$C_{1-5}$ alkylene-$N(R^{100})_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^9$ is selected from —O—$C_{1-6}$ alkylene-$N(R^{100})_2$, —NC(O)—$C_{1-5}$ alkylene-$N(R^{100})_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^{10}$ is selected from —O—$C_{1-6}$ alkylene-$N(R^{100})_2$, —NC(O)—

$C_{1-5}$ alkylene-$N(R^{100})_2$, $(1\text{-}(R^{100})\text{piperidin-4-yl})\text{-}C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^8$, $R^9$, $R^{10}$, or $R^{11}$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^8$, $R^9$, or $R^{10}$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, in a compound of formula (Ib) or (IIb), $R^2$ is H, $X^1$ is O, $X^2$ is $CR^{14}$, $X^5$ is O, $X^3$ is $NR^{15}$, at least one of $R^3$, $R^{3'}$, $R^4$, $R^{4'}$, $R^5$, and $R^{5'}$ present is not H, and $R^8$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, in a compound of formula (Ib) or (IIb), $R^2$ is H, $X^1$ is O, $X^2$ is $CR^{14}$, $X^4$ is $CR^{16}$, $X^5$ is O, $X^3$ is $NR^{15}$, at least one of $R^3$, $R^{3'}$, $R^4$, $R^{4'}$, $R^5$, and $R^{5'}$ present is not H, and $R^8$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, in a compound of formula (Ib) or (IIb), $R^2$ is H, $X^1$ is O, $X^2$ is $CR^{14}$, $X^4$ is $CR^{16}$, $X^5$ is O, $X^3$ is $NR^{15}$, at least one of $R^3$, $R^{3'}$, $R^4$, $R^{4'}$, $R^5$, and $R^{5'}$ present is not H, $R^{10}$ and $R^{11}$ are both H, and $R^8$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, in a compound of formula (Ib) or (IIb), $R^2$ is H, $X^1$ is O, $X^2$ is $CR^{14}$, $X^4$ is $CR^{16}$, $X^5$ is O, $X^3$ is $NR^{15}$, at least one of $R^3$, $R^{3'}$, $R^4$, $R^{4'}$, $R^5$, and $R^{5'}$ present is not H, $R^{10}$ and $R^{11}$ are both H, $R^9$ is selected from H and OMe, and $R^8$ is selected from 2-(morpholin-4-yl)ethoxy, (1-methylpiperidin-4-yl)methoxy, 2-(N,N-dimethylamino)ethoxy, 2-(N,N-dimethylamino)-acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, $R^2$ is H, at least one of $R^3$, $R^{3'}$, $R^4$, $R^{4'}$, $R^5$, and $R^{5'}$ present is not H, and $R^8$ is selected from —O—$C_{1-6}$ alkylene-$N(R^{100})_2$, —NC(O)—$C_{1-5}$ alkylene-$N(R^{100})_2$, $(1\text{-}(R^{100})\text{piperidin-4-yl})\text{-}C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, $R^2$ is H, at least one of $R^3$, $R^{3'}$, $R^4$, $R^{4'}$, $R^5$, and $R^{5'}$ present is not H, and $R^9$ is selected from —O—$C_{1-6}$ alkylene-$N(R^{100})_2$, —NC(O)—$C_{1-5}$ alkylene-$N(R^{100})_2$, $(1\text{-}(R^{100})\text{piperidin-4-yl})\text{-}C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, $R^2$ is H, at least one of $R^3$, $R^{3'}$, $R^4$, $R^{4'}$, $R^5$, and $R^{5'}$ present is not H, and $R^{10}$ is selected from —O—$C_{1-6}$ alkylene-$N(R^{100})_2$, —NC(O)—$C_{1-5}$ alkylene-$N(R^{100})_2$, $(1\text{-}(R^{100})\text{piperidin-4-yl})\text{-}C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or $COOR^{300}$, $R^{300}$ being $C_{1-4}$ alkyl.

In another embodiment, $R^2$ is H, at least one of $R^3$, $R^{3'}$, $R^4$, $R^{4'}$, $R^5$, and $R^{5'}$ present is not H, and $R^8$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In one embodiment, $R^5$ is not $NO_2$.

In another embodiment, at least one of the substituents $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^9$, $R^{10}$, $R^{11}$, $R^{12}$, $R^{13}$, $R^{14}$, $R^{15}$, $R^{16}$, and $R^{17}$ contains or is the moiety COOH.

In another embodiment, at least one of the substituents $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^9$, $R^{10}$, $R^{11}$, $R^{12}$, $R^{13}$, $R^{14}$, $R^{15}$, $R^{16}$, and $R^{17}$ contains or is the moiety COOH, and if there is only one COOH moiety and said COOH moiety is contained within $R^8$, $R^9$, $R^{10}$, or $R^{11}$, there is at least another water-soluble group present in $R^8$, $R^9$, $R^{10}$, or $R^{11}$.

In another embodiment, at least one of the substituents $R^8$, $R^9$, $R^{10}$, and $R^{11}$ contains or is the moiety COOH.

In another embodiment, at least one of the substituents $R^8$, $R^9$, $R^{10}$, and $R^{11}$ contains or is the moiety COOH and there is at least another water-soluble group present in $R^8$, $R^9$, $R^{10}$, or $R^{11}$.

In another embodiment, at least one of the water-soluble groups in $R^8$, $R^9$, $R^{10}$, and $R^{11}$ is an aliphatic secondary amine moiety not being conjugated to an aromatic moiety or a carbonyl group.

In yet another embodiment, $R^8$ is selected from

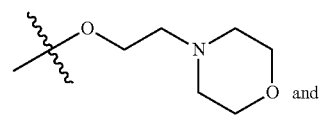 and

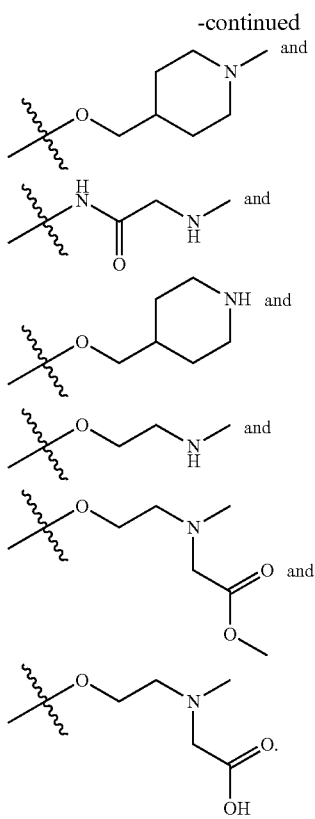

In yet another embodiment, at least one of the water-soluble groups in $R^8$, $R^9$, $R^{10}$, and $R^{11}$ is an aliphatic secondary amine moiety not being conjugated to an aromatic moiety or a carbonyl group and at least one of the substituents $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^9$, $R^{10}$, $R^{11}$, $R^{12}$, $R^{13}$, $R^{14}$, $R^{15}$, $R^{16}$, and $R^{17}$ contains or is the moiety COOH.

In yet another embodiment, at least one of the water-soluble groups in $R^8$, $R^9$, $R^{10}$, and $R^{11}$ is an aliphatic secondary amine moiety not being conjugated to an aromatic moiety or a carbonyl group and at least one of the substituents $R^8$, $R^9$, $R^{10}$, and $R^{11}$ contains or is the moiety COOH.

In yet another embodiment at least one of the substituents $R^8$, $R^9$, $R^{10}$, and $R^{11}$ contains a COOH moiety and an aliphatic secondary amine moiety not being conjugated to an aromatic moiety or a carbonyl group.

In one embodiment, a compound of this invention is represented by formula (Ib1):

(Ib1)

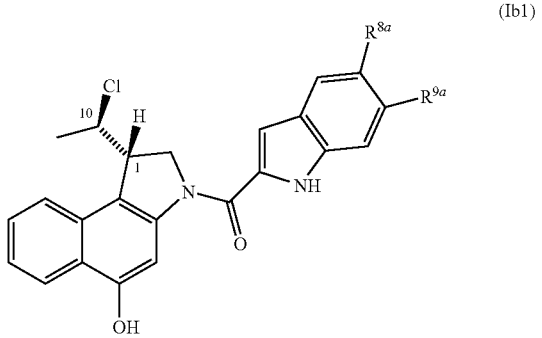

or by its (1R,10S) isomer, its (1R,10R) isomer, its (1S,10S) isomer, or by a mixture of two or more of said isomers, wherein $R^{8a}$ is a substituent containing a water-soluble group and $R^{9a}$ is H or optionally substituted $C_{1-15}$ alkoxy.

In another embodiment, a compound of this invention is represented by formula (Ib2):

(Ib2)

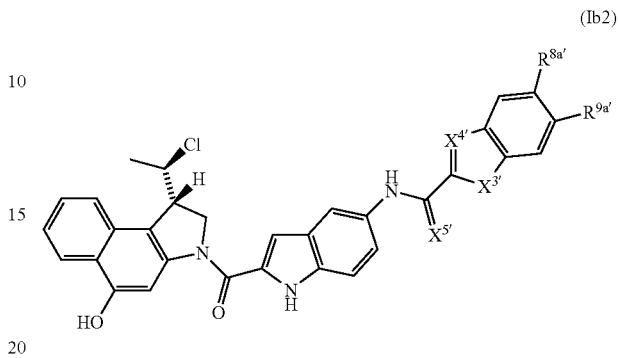

or by its (1R,10S) isomer, its (1R,10R) isomer, its (1S,10S) isomer, or by a mixture of two or more of said isomers, wherein $R^{8a'}$ is a substituent containing a water-soluble group and $R^{9a'}$ is H or optionally substituted $C_{1-15}$ alkoxy.

In one embodiment, this invention relates to a compound of formula (Ib1) or (Ib2) wherein $R^{8a}$ or $R^{8a'}$, respectively, is selected from —O—$C_{1-6}$ alkylene-N($R^{100}$)$_2$, —NC(O)—$C_{1-5}$ alkylene-N($R^{100}$)$_2$, (1-($R^{100}$)piperidin-4-yl)-$C_{1-5}$ alkylene-O—, and (morpholin-4-yl)-$C_{1-8}$ alkylene-O—, wherein each $R^{100}$ is independently selected from H and $C_{1-3}$ alkyl, the latter being optionally substituted with COOH or COOR$^{300}$, $R^{300}$ being $C_{1-4}$ alkyl.

In one embodiment, this invention relates to a compound of formula (Ib1) or (Ib2) wherein $R^{8a}$ or $R^{8a'}$, respectively, is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, this invention relates to a compound of formula (Ib1) wherein $R^{8a}$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy.

In another embodiment, this invention relates to a compound of formula (Ib1) wherein $R^{8a}$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy and $R^{9a}$ is H.

In another embodiment, this invention relates to a compound of formula (Ib1) wherein $R^{8a}$ is selected from 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy and $R^{9a}$ is methoxy.

In one embodiment, a compound of this invention is represented by the formula:

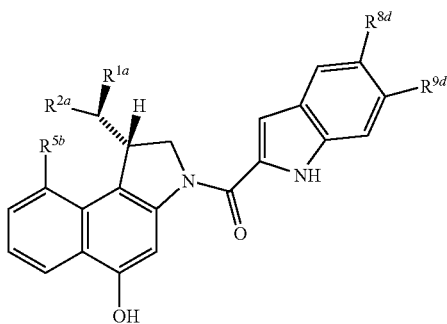

or by its (1R,10S) isomer, its (1R,10R) isomer, its (1S,10S) isomer, or by a mixture of two or more of said isomers, wherein $R^{1a}$ is chloro (Cl) or bromo (Br), $R^{2a}$ and $R^{5b}$ are methyl and H, respectively, or H and methyl, respectively, $R^{8d}$ is selected from 2-(morpholin-4-yl)ethoxy, (1-methylpiperidin-4-yl)methoxy, 2-(N,N-dimethylamino)ethoxy, 2-(N,N-dimethylamino)-acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy, and $R^{9d}$ is selected from H and methoxy.

In another embodiment, a compound of this invention is represented by the formula:

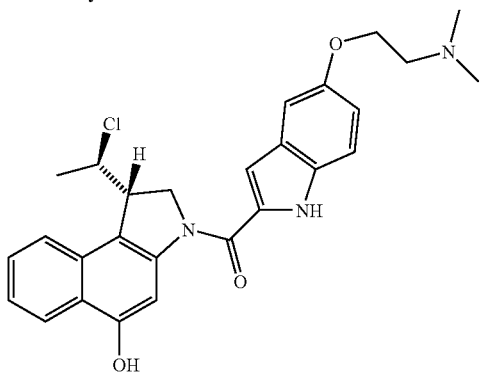

or by its (1R,10S) isomer, its (1R,10R) isomer, its (1S,10S) isomer, or by a mixture of two or more of said isomers.

In another embodiment, a compound of this invention is represented by the formula:

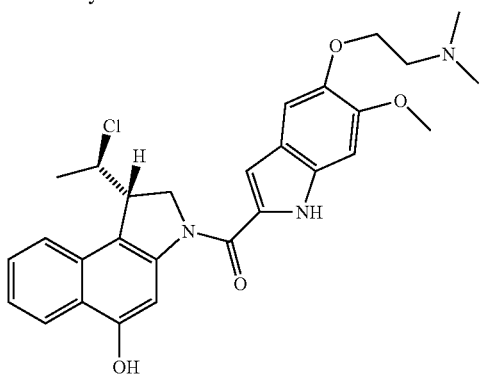

or by its (1R,10S) isomer, its (1R,10R) isomer, its (1S,10S) isomer, or by a mixture of two or more of said isomers.

In another embodiment, a compound of this invention is represented by the formula:

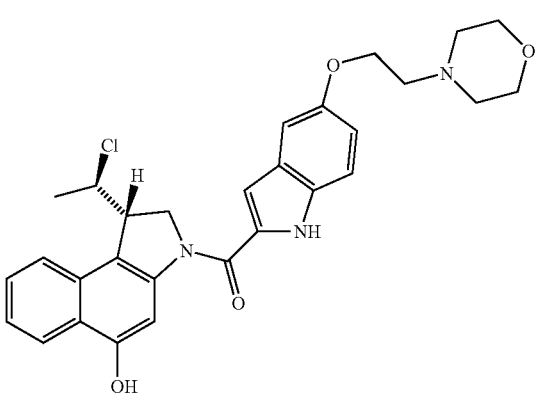 [SMILES: C[C@@H](Cl)[C@@H]1CN(C(=O)c2cc3cc(OCCN4CCOCC4)ccc3[nH]2)c2cc(O)c3ccccc3c21]

or by its (1R,10S) isomer, its (1R,10R) isomer, its (1S,10S) isomer, or by a mixture of two or more of said isomers.

In another embodiment, a compound of this invention is represented by the formula:

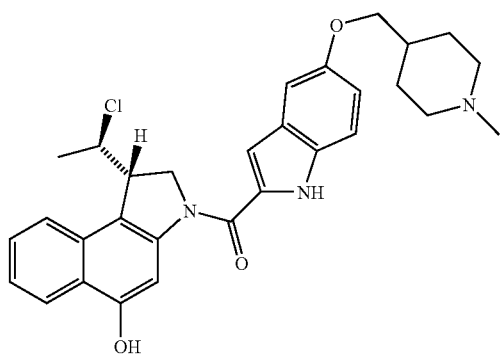 [SMILES: C[C@@H](Cl)[C@@H]1CN(C(=O)c2cc3cc(OCC4CCN(C)CC4)ccc3[nH]2)c2cc(O)c3ccccc3c21]

or by its (1R,10S) isomer, its (1R,10R) isomer, its (1S,10S) isomer, or by a mixture of two or more of said isomers.

In yet another embodiment, a compound of this invention is represented by the formula:

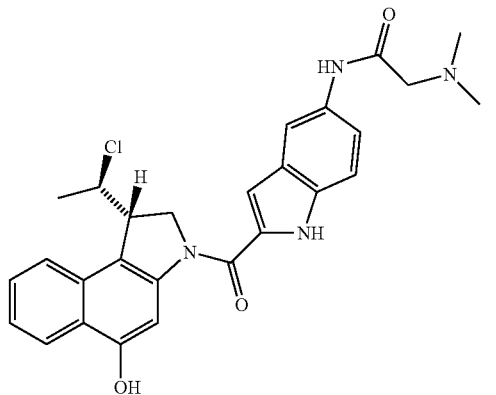 [SMILES: C[C@@H](Cl)[C@@H]1CN(C(=O)c2cc3cc(NC(=O)CN(C)C)ccc3[nH]2)c2cc(O)c3ccccc3c21]

or by its (1R,10S) isomer, its (1R,10R) isomer, its (1S,10S) isomer, or by a mixture of two or more of said isomers.

In yet another embodiment, a compound of this invention is represented by the formula:

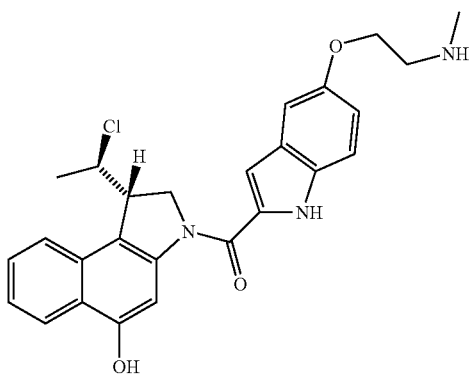 [SMILES: CNCCOc1ccc2[nH]c(C(=O)N3C[C@@H]([C@@H](C)Cl)c4c3cc(O)c3ccccc43)cc2c1]

or by its (1R,10S) isomer, its (1R,10R) isomer, its (1S,10S) isomer, or by a mixture of two or more of said isomers.

In yet another embodiment, a compound of this invention is represented by the formula:

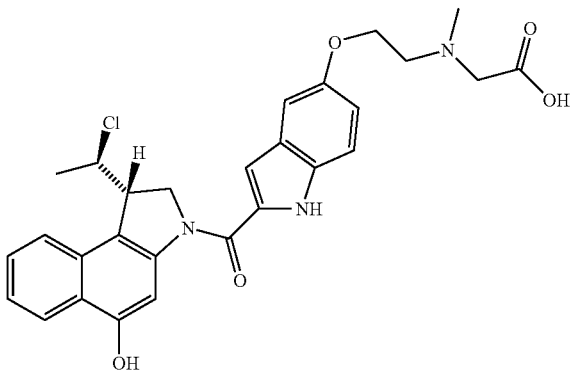 [SMILES: C[C@@H](Cl)[C@@H]1CN(C(=O)c2cc3cc(OCCN(C)CC(=O)O)ccc3[nH]2)c2cc(O)c3ccccc3c21]

or by its (1R,10S) isomer, its (1R,10R) isomer, its (1S,10S) isomer, or by a mixture of two or more of said isomers.

In yet another embodiment, a compound of this invention is represented by the formula:

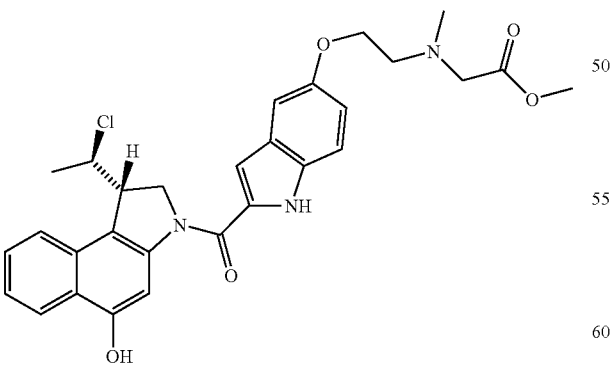

or by its (1R,10S) isomer, its (1R,10R) isomer, its (1S,10S) isomer, or by a mixture of two or more of said isomers.

In another embodiment, a compound of this invention is represented by formula (Ib3):

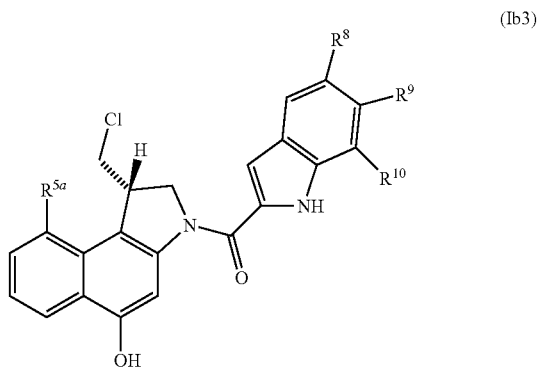

or by its (1R) isomer or by a mixture of the two isomers, wherein $R^{5a}$ has the same meaning as $R^5$ defined above except that it cannot be hydrogen.

In one embodiment, $R^{5a}$ in a compound of formula (Ib3) is selected from nitro, halogen, amino, hydroxy, optionally substituted alkylamino, optionally substituted alkylcarbonylamino, optionally substituted alkoxycarbonylamino, optionally substituted alkyloxy, optionally substituted alkylcarbonyloxy, optionally substituted alkylaminocarbonyloxy, and optionally substituted $C_{1-4}$ alkyl. In yet another embodiment, $R^{5a}$ in a compound of formula (Ib3) is optionally substituted linear $C_{1-4}$ alkyl. In another embodiment, $R^{5a}$ in a compound of formula (Ib3) is unsubstituted linear $C_{1-4}$ alkyl. In another embodiment, $R^{5a}$ in a compound of formula (Ib3) is methyl.

In another embodiment, a compound of this invention is represented by formula (Ib3-1):

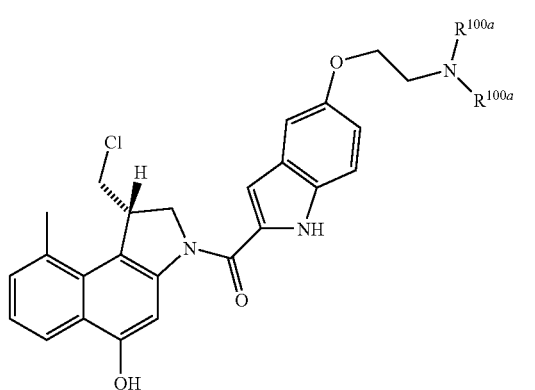

or by its (1R) isomer or by a mixture of the two isomers, wherein each $R^{100a}$ is independently methyl, carboxymethyl, 2-methoxy-2-oxoethyl, or hydrogen.

In another embodiment, a compound of this invention is represented by the formula:

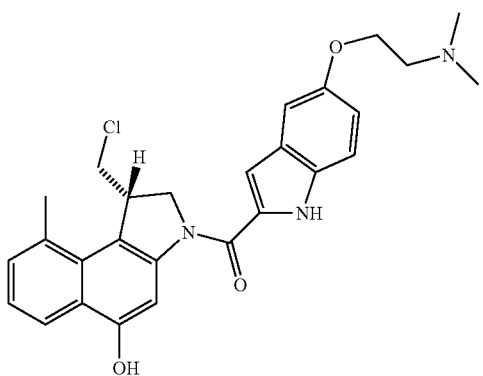 [SMILES: Cc1cccc2c(O)cc3c(c12)[C@H](CCl)CN3C(=O)c1cc2cc(OCCN(C)C)ccc2[nH]1]

or by its (1R) isomer or by a mixture of the two isomers.

In a further aspect, this invention relates to a compound of formula (I') or (II'):

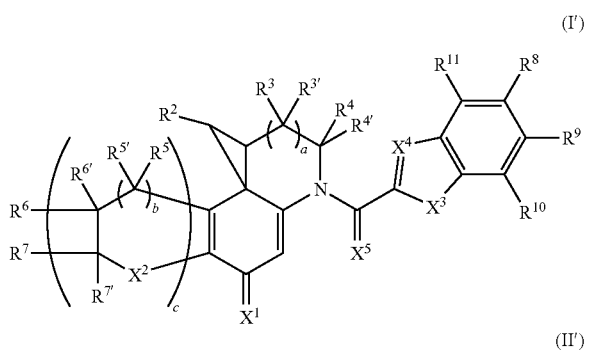

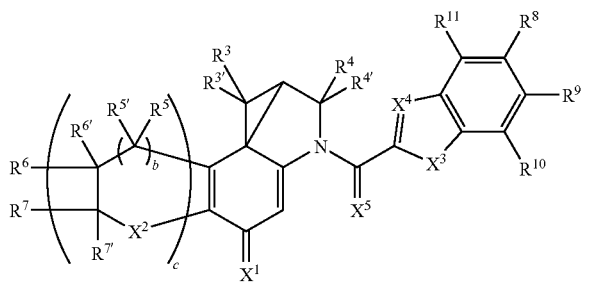

wherein all substituents have the same meaning as described for compounds of formulae (I) and (II) above. Compounds of formulae (I) and (II) are alleged to be converted in vivo to (I') and (II'), respectively, with concomitant elimination of H—$R^1$, as schematically illustrated in FIG. 1 for a compound of formula (I).

Therefore, this invention relates to a compound of formula (I') or (II'), said compound containing a cyclopropyl group, which results from rearrangement of and concomitant elimination of H—$R^1$ from a compound of formula (I) or (II).

It should be understood that in this entire document, when referring to a compound of formula (I) or (II), this includes reference to a compound of formula (I') or (II'), respectively, unless structural parts of (I) and (II) not present in (I') and (II') are concerned or the context dictates otherwise. Similarly, when referring to a structural part (fragment), linker-agent conjugate, or conjugate of formula (I) or (II), this includes reference to a similar structural part (fragment), linker-agent conjugate, or conjugate of formula (I') or (II'), respectively, unless structural parts of (I) and (II) not present in (I') and (II') are concerned or the context dictates otherwise.

In a different aspect, this invention relates to a compound of formula (VII) or (VIII):

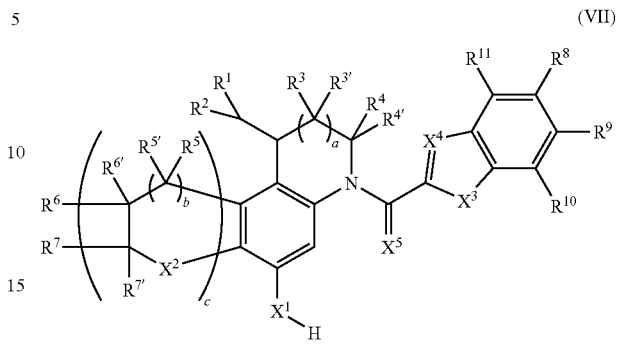

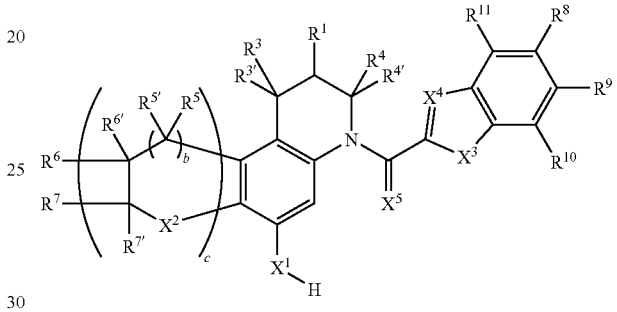

or a pharmaceutically acceptable salt or solvate thereof, wherein $R^1$ is selected from halogen and $OSO_2R^u$, wherein $R^u$ is selected from optionally substituted $C_{1-6}$ alkyl, $C_{1-6}$ perhaloalkyl, benzyl, and phenyl;

$R^2$ is selected from H and optionally substituted $C_{1-8}$ alkyl;

$R^3$, $R^{3'}$, $R^4$, and $R^{4'}$ are independently selected from H and optionally substituted $C_{1-8}$ alkyl, wherein two or more of $R^2$, $R^3$, $R^{3'}$, $R^4$, and $R^{4'}$ are optionally joined to form one or more optionally substituted carbocycles or heterocycles;

$X^2$ is selected from O, $C(R^{14})(R^{14'})$, and $NR^{14'}$, wherein $R^{14}$ is selected from H and optionally substituted $C_{1-8}$ alkyl or acyl and wherein $R^{14'}$ may be absent or be selected from H and optionally substituted $C_{1-8}$ alkyl or acyl;

Each $R^5$, $R^{5'}$, $R^6$, $R^{6'}$, $R^7$, and $R^{7'}$ is independently selected from H, OH, SH, $NH_2$, $N_3$, $NO_2$, NO, $CF_3$, CN, $C(O)NH_2$, C(O)H, C(O)OH, halogen, $R^k$, $SR^k$, $S(O)R^k$, $S(O)_2R^k$, $S(O)OR^k$, $S(O)_2OR^k$, $OS(O)R^k$, $OS(O)_2R^k$, $OS(O)OR^k$, $OS(O)_2OR^k$, $OR^k$, $NHR^k$, $N(R^k)R^L$, $^+N(R^k)(R^L)R^m$, $P(O)(OR^k)(OR^L)$, $OP(O)(OR^k)(OR^L)$, $SiR^kR^LR^m$, $C(O)R^k$, $C(O)OR^k$, $C(O)N(R^L)R^k$, $OC(O)R^k$, $OC(O)OR^k$, $OC(O)N(R^k)R^L$, $N(R^L)C(O)R^k$, $N(R^L)C(O)OR^k$, and $N(R^L)C(O)N(R^m)R^k$, wherein $R^k$, $R^L$, and $R^m$ are independently selected from H and optionally substituted $C_{1-4}$ alkyl, $C_{1-4}$ heteroalkyl, $C_{3-7}$ cycloalkyl, $C_{3-7}$ heterocycloalkyl, $C_{4-12}$ aryl, or $C_{4-12}$ heteroaryl, two or more of $R^k$, $R^L$, and $R^m$ optionally being joined to form one or more optionally substituted aliphatic or aromatic carbocycles or heterocycles, and/or $R^5+R^{5'}$, and/or $R^6+R^{6'}$, and/or $R^7+R^{7'}$ are independently =O, =S, or =$NR^{12}$, $R^{12}$ being selected from H and optionally substituted $C_{1-6}$ alkyl, and/or $R^{5'}$ and $R^6$, and/or $R^{6'}$ and $R^7$, and/or $R^{7'}$ and $R^{14'}$ are absent, which means that a double bond is present between the atoms bearing $R^{5'}$ and $R^6$, and/or $R^{6'}$ and $R^7$, and/or $R^{7'}$ and $R^{14'}$, respectively, two or more of $R^5$, $R^{5'}$, $R^6$, $R^{6'}$, $R^7$, $R^{7'}$, $R^{14}$, and $R^{14'}$ optionally being joined to form one or more optionally substituted aliphatic or aromatic carbocycles or heterocycles;

$X^1$ is selected from O, S, and $NR^{13}$, wherein $R^{13}$ is selected from H and optionally substituted $C_{1-8}$ alkyl;

$X^3$ is selected from O, S, and $NR^{15}$, wherein $R^{15}$ is selected from H and optionally substituted $C_{1-8}$ alkyl or acyl, or —$X^3$— represents —$X^{3a}$ and $X^{3b}$— wherein $X^{3a}$ is connected to the carbon to which $X^4$ is attached and $X^{3b}$ is connected to the phenyl ring ortho to $R^{10}$, wherein $X^{3a}$ is independently selected from H and optionally substituted $C_{1-8}$ alkyl or acyl and $X^{3b}$ is selected from the same group of substituents as $R^8$;

$X^4$ is selected from N and $CR^{16}$, wherein $R^{16}$ is selected from H and optionally substituted $C_{1-8}$ alkyl or acyl;

$X^5$ is selected from O, S, and $NR^{17}$, wherein $R^{17}$ is selected from H and optionally substituted $C_{1-8}$ alkyl or acyl;

$R^8$, $R^9$, $R^{10}$, and $R^{11}$ are each independently selected from H, OH, SH, $NH_2$, $N_3$, $NO_2$, NO, $CF_3$, CN, $C(O)NH_2$, $C(O)H$, $C(O)OH$, halogen, $R^x$, $SR^x$, $S(O)R^x$, $S(O)_2R^x$, $S(O)OR^x$, $S(O)_2OR^x$, $OS(O)R^x$, $OS(O)_2R^x$, $OS(O)OR^x$, $OS(O)_2OR^x$, $OR^x$, $NHR^x$, $N(R^x)R^y$, $^+N(R^x)(R^y)R^z$, $P(O)(OR^x)(OR^y)$, $OP(O)(OR^x)(OR^y)$, $SiR^xR^yR^z$, $C(O)R^x$, $C(O)OR^x$, $C(O)N(R^x)R^x$, $OC(O)R^x$, $OC(O)OR^x$, $OC(O)N(R^x)R^y$, $N(R^y)C(O)R^x$, $N(R^y)C(O)OR^x$, $N(R^y)C(O)N(R^z)R^x$, and a water-soluble group, wherein $R^x$, $R^y$, and $R^z$ are independently selected from H and optionally substituted $C_{1-15}$ alkyl, $C_{1-15}$ heteroalkyl, $C_{3-15}$ cycloalkyl, $C_{3-15}$ heterocycloalkyl, $C_{4-15}$ aryl, or $C_{4-15}$ heteroaryl, one or more of the optional substituents in $R^x$, $R^y$, and $R^z$ optionally being a water-soluble group, and two or more of $R^x$, $R^y$, and $R^z$ optionally being joined to form one or more optionally substituted aliphatic or aromatic carbocycles or heterocycles, and at least one of $R^8$, $R^9$, $R^{10}$, and $R^{11}$ comprises at least one water-soluble group, two or more of $R^8$, $R^9$, $R^{10}$, $R^{11}$, or $X^{3b}$ optionally being joined to form one or more optionally substituted aliphatic or aromatic carbocycles or heterocycles;

a and b are independently selected from 0 and 1;
c is selected from 0, 1, and 2;
provided that
a) at least one of the substituents $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^9$, $R^{10}$, $R^{11}$, $R^{12}$, $R^{13}$, $R^{14}$, $R^{15}$, $R^{16}$, and $R^{17}$ contains or is the moiety COOH, and if there is only one COOH moiety and said COOH moiety is contained within $R^8$, $R^9$, $R^{10}$, or $R^{11}$, there is at least another water-soluble group present in $R^8$, $R^9$, $R^{10}$, or $R^{11}$, and/or
b) at least one of the water-soluble groups in $R^8$, $R^9$, $R^{10}$, and $R^{11}$ is an aliphatic secondary amine moiety not being conjugated to an aromatic moiety or a carbonyl group, and/or
c) $R^8$ is selected from

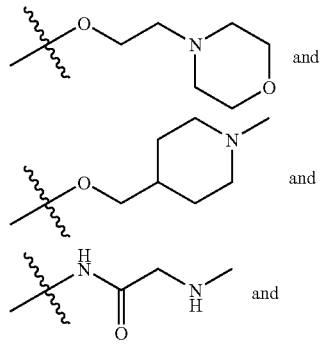

and

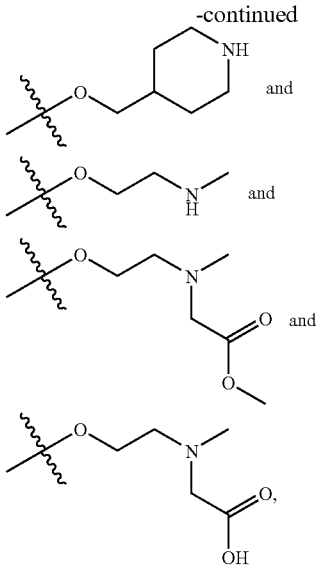

and/or
d) $R^9$ is OMe and $R^8$ is $OCH_2CH_2N(CH_3)_2$.

Compounds of formulae (VII) and (VIII) have a water solubility that is increased with respect to similar compounds from the prior art. Conjugates of compounds of formulae (VII) and (VIII) may therefore have improved properties with respect to conjugates of similar compounds from the prior art. Conjugates of formulae (VII) and (VIII) may for example have improved water solubility, show less aggregation, and show less side effects as premature liberation of a compound of formula (VII) or (VIII) from such a conjugate before such a conjugate has entered a target cell liberates a compound that is less effective of entering cells, including non-targeted cells, due to its increased polarity with respect to a compound lacking a water-soluble group. The optional presence of a carboxylic acid group or secondary aliphatic amino group in a compound of formula (VII) or (VIII) furthermore provides for a useful (additional) handle for the preparation of conjugates.

It should be noted that the alleged properties and embodiments provided for compounds of formulae (I) and (II) hereinabove are also applicable to compounds of formulae (VII) and (VIII), unless they concern structural parts of (I) and (II) not present in (VII) and (VIII) or the context dictates otherwise. It should therefore be understood that in this entire document, when referring to a compound of formula (I) or (II), this includes reference to a compound of formula (VII) or (VIII), respectively, unless structural parts of (I) and (II) not present in (VII) and (VIII) are concerned or the context dictates otherwise. Similarly, when referring to a structural part (fragment), linker-agent conjugate, or conjugate of formula (I) or (II), this includes reference to a similar structural part (fragment), linker-agent conjugate, or conjugate of formula (VII) or (VII), respectively, unless structural parts of (I) and (II) not present in (VII) and (VIII) are concerned or the context dictates otherwise. Similarly, when referring to a compound of formula (I') or (II'), it should be understood that this includes reference to the cyclopropyl-containing analog of compound (VII) or (VIII), unless structural parts of (I') and (II') not present in the cyclopropyl-containing analogs of (VII) and (VIII) are concerned or the context dictates otherwise.

Conjugates and Linker-Agent Conjugates

In another aspect, this invention relates to conjugates of a compound of formula (I) or (II) that can be converted in vivo and in one or more steps to a compound of formula (I) or (II), respectively. These conjugates may favorably affect the pharmacokinetic properties and other characteristics of a compound of formula (I) or (II). In one embodiment, this invention relates to a conjugate comprising a compound of formula (I) or (II) conjugated to at least one promoiety, i.e., a moiety that can be removed in vivo to release a compound of formula (I) or (II). In another embodiment, this invention relates to a conjugate comprising a compound of formula (I) or (II) conjugated to one promoiety.

In a further aspect, this invention relates to a compound of formula (III):

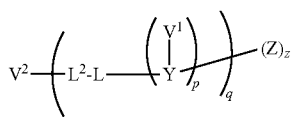

or a pharmaceutically acceptable salt or solvate thereof, wherein $V^2$ is either absent or a functional moiety;

Each $L^2$ is independently absent or a linking group linking $V^2$ to L or to $V^1$ or Y when L is absent;

Each L is independently absent or a linking group linking $L^2$ or $V^2$ when $L^2$ is absent to one or more $V^1$ and/or Y;

Each $V^1$ is independently H or a conditionally-cleavable or conditionally-transformable moiety, which can be cleaved or transformed by a chemical, photochemical, physical, biological, or enzymatic process;

Each Y is independently absent or a self-eliminating spacer system which is comprised of 1 or more self-elimination spacers and is linked to $V^1$, optionally L, and one or more Z;

Each p and q are numbers representing a degree of branching and are each independently a positive integer;

z is a positive integer equal to or smaller than the total number of attachment sites for Z in the one or more $V^1$—Y moieties;

Each Z is independently a compound of formula (I) or (II) as defined hereinabove wherein one or more of $X^1$, $R^6$, $R^7$, $R^8$, $R^9$, $R^{10}$, and $R^{11}$ may optionally in addition be substituted by a substituent of formula (V):

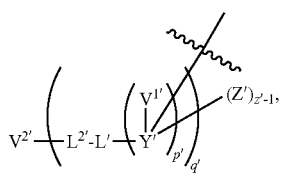

wherein each $V^{2'}$, $L^{2'}$, $L'$, $V^{1'}$, $Y'$, $Z'$, $p'$, $q'$, and $z'$ have the same meaning as defined for $V^2$, $L^2$, $L$, $V^1$, $Y$, $Z$, $p$, $q$, and $z$, the one or more substituents of formula (V) being independently connected to one or more of $X^1$, $R^6$, $R^7$, $R^8$, $R^9$, $R^{10}$, and $R^{11}$ via $Y'$ or $V^{1'}$ when $Y'$ is absent, each Z being connected to Y or $V^1$ when Y is absent through either $X^1$ or an atom in $R^6$, $R^7$, $R^8$, $R^9$, $R^{10}$, or $R^{11}$;

with the proviso that at least one of the one or more $V^1$ and the one or more $V^{1'}$ is not H.

It should be understood from formula (III) that L can either be connected to $V^1$ and/or to Y. If L is connected to Y, this means that both $V^1$ and L, as well as one or more Z, are connected to Y. If Y is absent, L must be connected to $V^1$; L cannot be directly connected to Z.

The $V^2(-L^2-L(-V^1—Y)_p)_q(Z)_{z-1}$ and one or more $V^{2'}(-L^{2'}-L'(-V^{1'}—Y')_{p'})_{q'}(Z')_{z'-1}$ moieties connected to a compound of formula (I) or (II) are herein referred to as promoieties.

The present invention also relates to a compound of formula (IV):

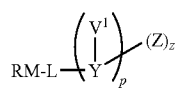

or a pharmaceutically acceptable salt or solvate thereof, wherein

RM is a reactive moiety and L, $V^1$, Y, Z, p, and z are as defined above, except that L is now linking RM to one or more $V^1$ and/or Y, and $V^1$, Y, and Z may contain protecting groups and the one or more $V^{2'}$-$L^{2'}$ moieties optionally present in Z as defined hereinabove may optionally and independently be replaced by RM', which is a reactive moiety, and wherein, if there is more than 1 reactive moiety in (IV), the reactive moieties are the same or different. These linker-agent conjugates may or may not be considered intermediates for compounds of formula (III).

The RM-L(-$V^1$—Y)$_p$(Z)$_{z-1}$ and one or more RM'-L'(-$V^{1'}$—Y')$_{p'}$(Z')$_{z'-1}$ moieties connected to a compound of formula (I) or (II) are herein referred to as promoieties.

It should be understood that this invention relates to enantiomerically pure and/or diastereomerically pure compounds of formulae (III) and (IV) as well as to enantiomeric and/or diastereomeric mixtures of compounds of formulae (III) and (IV).

When the one or more Y and/or $V^1$ moieties in a compound of formula (III) or (IV) contain attachment sites for Z that are not coupled to Z, for instance as a consequence of an incomplete coupling reaction during synthesis, these attachment sites are considered to be attached to H, OH, or a leaving group instead. If all of said attachment sites are connected to Z, then z equals the number of said attachment sites; otherwise, z is lower. Compounds of this invention may exist as a mixture, wherein each component of the mixture has a different z value. For example, the compound may exist as a mixture of two separate compounds, one compound wherein z is 4 and another compound wherein z is 3. Furthermore, for a given z, the compound may exist as a mixture of isomers as Z may be connected to distinct sets of attachment sites in the one or more Y and/or $V^1$ moieties.

For reasons of clarity, when referring to the connections of one first moiety to other moieties within formula (III) or (IV), in general only those said other moieties are mentioned that are directly next to said first moiety in formula (III) or (IV). It should be understood that if one of said other moieties is not present, said first moiety is actually connected to the moiety first in line that is present, unless explicitly stated otherwise. For example, if it is stated that "$V^1$ is cleaved from Y", this phrase actually means "$V^1$ is cleaved from Y, or from Z if Y is absent" and should be read as "$V^1$ is cleaved from Z" when reference is made to a compound ladling Y.

In a compound of formula (III) or (IV), a compound of formula (I) or (II) may be conjugated to a promoiety through its water-soluble group. In this way, the water-soluble group may contribute less to the water solubility of the compound of formula (III) or (IV), but may contribute again to the water solubility of Z upon removal of said promoiety.

In this document, whenever $V^2$, $L^2$, L, $V^1$, Y, Z, RM, p, q, or z is mentioned, it should be understood that the same can apply for each $V^{2'}$, $L^{2'}$, L', $V^{1'}$, Y', Z', RM', p', q', or z', respectively.

The $V^1$ Moiety

In a compound of formula (III) or (IV), the $V^1$ moiety can be a group that is conditionally cleavable or transformable. In other words, it is designed to be transformed and/or cleaved from Y by a chemical, photochemical, physical, biological, or enzymatic process upon being brought in or under a certain condition. This condition may for example be bringing a compound of the invention in an aqueous environment, which leads to hydrolysis of $V^1$, or bringing a compound of the invention in an environment that contains an enzyme that recognizes and cleaves $V^1$, or bringing a compound of the invention under reducing conditions, which leads to reduction and/or removal of $V^1$, or bringing a compound of the invention in contact with radiation, e.g., UV light, which leads to transformation and/or cleavage, or bringing a compound of the invention in contact with heat, which leads to transformation and/or cleavage, or bringing a compound of the invention under reduced pressure, which leads to transformation, e.g., a retrocycloaddition, and/or cleavage, or bringing a compound of the invention under elevated or high pressure, which leads to transformation and/or cleavage. This condition may be met after administrating a compound of this invention to an animal, e.g., a mammal, for example a human: the condition may be met when the compound localizes to for example a specific organ, tissue, cell, subcellular target, or microbial target, for example by the presence of internal factors (e.g., target-specific enzymes or hypoxia) or application of external factors (e.g., radiation, magnetic fields) or the condition may already be met directly upon administration (e.g., ubiquitous enzymes).

In general, transformation of $V^1$ will directly or indirectly lead to cleavage of $V^1$ from Y. A compound of this invention may contain more than one $V^1$ moiety per promoiety (p and/or q>1). These $V^1$ moieties may or may not be the same and may or may not require the same conditions for transformation and/or cleavage.

In one aspect of this invention, a conjugate is used to target one or more moieties Z to target cells. In this instance, a $V^1$ moiety may for example contain a substrate molecule that is cleaved by an enzyme present in the vicinity of the target cells or inside the target cells, for example tumor cells. $V^1$ can for example contain a substrate that is cleaved by an enzyme present at elevated levels in the vicinity of or inside the target cells as compared to other parts of the body, or by an enzyme that is present only in the vicinity of or inside the target cells.

It is important to recognize that if target cell specificity is achieved solely based upon the selective transformation and/or cleavage of said $V^1$ at the target site, the condition causing the cleavage should preferably, at least to a certain degree, be target cell-specific, whereas the presence of another target-specific moiety in the compound of the invention, for instance in a $V^2$ moiety, reduces or takes away this requirement. For example, when $V^2$ causes selective internalization into a target cell, an enzyme also present in other cells may transform and/or cleave $V^1$. In one embodiment, transformation and/or cleavage of $V^1$ occur intracellularly. In another embodiment, transformation and/or cleavage of $V^1$ occur extracellularly.

In one embodiment, $V^1$ contains a di-, tri-, tetra-, or oligopeptide which consists of an amino acid sequence recognized by a proteolytic enzyme, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment, $V^1$ is a peptide. In another embodiment, $V^1$ is a dipeptide. In another embodiment, $V^1$ is a tripeptide. In another embodiment, $V^1$ is a tetrapeptide. In yet another embodiment, $V^1$ is a peptidomimetic.

In another embodiment, $V^1$ contains a β-glucuronide that is recognized by β-glucuronidase present in the vicinity of or inside tumor cells.

In one embodiment, $V^1$ contains a substrate for an enzyme.

In one embodiment, $V^1$ contains a substrate for an extracellular enzyme.

In another embodiment, $V^1$ contains a substrate for an intracellular enzyme.

In yet another embodiment, $V^1$ contains a substrate for a lysosomal enzyme.

In yet another embodiment, $V^1$ contains a substrate for the serine protease plasmin.

In yet another embodiment, $V^1$ contains a substrate for one or more of the cathepsins, for example cathepsin B.

In yet another embodiment, $V^1$ contains a substrate for a galactosidase.

When $V^1$ is cleaved extracellularly, the one or more Z moieties may be released extracellularly. This may provide the advantage that these Z moieties are not only able to affect the cell(s) directly surrounding the site of activation (e.g., target-positive cells), but also cells somewhat further away from the site of activation (e.g., target-negative cells) due to diffusion (bystander effect).

An enzyme to cleave $V^1$ can also be transported to the vicinity of or inside target cells or target tissue via for example antibody-directed enzyme prodrug therapy (ADEPT), polymer-directed enzyme prodrug therapy (PDEPT) or macromolecular-directed enzyme prodrug therapy (MDEPT), virus-directed enzyme prodrug therapy (VDEPT), or gene-directed enzyme prodrug therapy (GDEPT).

In one embodiment, transformation and/or cleavage of $V^1$ occur through an enzyme linked to an antibody.

In again another embodiment $V^1$ contains a moiety, for example a nitro(hetero)aromatic moiety, that can be transformed and/or cleaved by reduction under hypoxic conditions or by reduction by a nitroreductase. After reduction of the nitro group and cleavage of the resulting moiety, elimination of the spacer system Y, if present, leads to release of one or more moieties Z.

In one embodiment, the invention relates to a compound wherein $V^1$ is a monosaccharide, disaccharide, or oligosaccharide of hexoses or pentoses or heptoses that may also be included among the group of desoxy sugars or amino sugars and belong to the D-series or L-series and in the disaccharides or oligosaccharides are either identical or different. Such a $V^1$ is typically cleaved by a glycosidase.

In another embodiment, $V^1$ has the formula $C(OR^{a'})R^{b'}CHR^{c'}R^{d'}$, wherein $R^{a'}$ is a hydroxy protecting group, an optionally substituted $C_{1-8}$ alkyl group that optionally forms a ring with $R^5$, $R^{5'}$, $R^6$, $R^{6'}$, $R^7$, $R^{7'}$, $R^{14}$, or $R^{14'}$, or a monosaccharide, a disaccharide, or an oligosaccharide residue optionally substituted with a methyl group, hydroxymethyl group, and/or a radical of the formula —$NR^{e'}R^{f'}$, wherein $R^{e'}$ and $R^{f'}$ are identical or different and are selected from hydrogen, $C_{1-6}$ alkyl, or an amino protecting group, and wherein the hydroxy groups of the saccharide residues are optionally protected; $R^{b'}$, $R^{c'}$, and $R^{d'}$ are independently selected from hydrogen, optionally substituted $C_{1-8}$ alkyl or $C_{1-8}$ cycloalkyl, or a group of the formula —$NR^{e'}R^{f'}$, where $R^{e'}$ and $R^{f'}$ have the same meaning as hereinabove.

In one embodiment the invention relates to a conjugate wherein $V^1$ is a dipeptide, tripeptide, tetrapeptide, or oligopeptide moiety comprised of natural L amino acids, unnatural D amino acids, or synthetic amino acids, or a peptidomimetic, or any combination thereof.

In another embodiment the invention relates to a compound wherein $V^1$ comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from any natural or unnatural amino acid.

In another embodiment the invention relates to a compound wherein $V^1$ comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid.

In one embodiment, when the α-amino group of the N-terminal amino acid of $V^1$ is not coupled to L, this amino acid may be functionalized with a suitable blocking group coupled to the α-amino group or may be an unnatural amino acid such that undesired premature degradation of $V^1$ by for example ubiquitous enzymes or exopeptidases is prevented.

In a further embodiment $V^1$ is selected from D-alanylphenylalanyllysine, D-valylleucyllysine, D-alanylleucyllysine, D-valylphenylalanyllysine, D-valyltryptophanyllysine, D-alanyltryptophanyllysine, alanylphenylalanyllysine, valylleucyllysine, alanylleucyllysine, valylphenylalanyllysine, valyltlyptophanyllysine, alanyltryptophanyllysine, D-alanylphenylalanylcitrulline, D-valylleucylcitrulline, D-alanylleucylcitrulline, D-valylphenylalanylcitrulline, D-valyltryptophanylcitrulline, D-alanyltryptophanylcitrulline, alanylphenylalanylcituulline, valylleucylcitlulline, alanylleucylcitrulline, valylphenylalanylcitrulline, valyltryptophanylcitrulline, and alanyltryptophanylcitrulline.

In yet another embodiment, $V^1$ is selected from phenylalanyllysine, valyllysine, valylalanine, D-phenylalanylphenylalanyllysine, phenylalanylphenylalanyllysine, glycylphenylalanyllysine, alanyllysine, valylcitrulline, N-methylvalylcitrulline, phenylalanylcitrulline, isoleucylcitrulline, tryptophanyllysine, tryptophanylcitrulline, phenylalanylarginine, phenylalanylalanine, glycylphenylalanylleucylglycine, alanylleucylalanylleucine, alanylarginylarginine, phenylalanyl-$N^9$-tosylarginine, phenylalanyl-$N^9$-nitroarginine, leucyllysine, leucylcitrulline, and phenylalanyl-O-benzoylthreonine.

In a further embodiment, $V^1$ is selected from phenylalanyllysine, valyllysine, and valylcitrulline. Therefore, in one embodiment this invention relates to a compound wherein $V^1$ contains a substrate that can be cleaved by a proteolytic enzyme, plasmin, a cathepsin, cathepsin B, β-glucuronidase, a galactosidase, prostate-specific antigen (PSA), urokinase-type plasminogen activator (u-PA), a member of the family of matrix metalloproteinases, or an enzyme localized by means of directed enzyme prodrug therapy, such as ADEPT, VDEPT, MDEPT, GDEPT, or PDEPT, or wherein $V^1$ contains a moiety that can be cleaved or transformed through reduction under hypoxic conditions or through reduction by a nitroreductase.

In another aspect of this invention, a conjugate of this invention is used to (also) improve the (pharmacokinetic) properties of Z. When a promoiety does not need to be selectively removed at a target site, $V^1$ of said promoiety may for example be or contain a group that is cleaved by ubiquitous enzymes, e.g., esterases that are present in the circulation or intracellular enzymes, such as for example proteases and phosphatases, by pH-controlled intramolecular cyclization, or by acid-catalyzed, base-catalyzed, or non-catalyzed hydrolysis, or $V^1$ may for example be or contain a disulfide or form a disulfide with a neighboring moiety. $V^1$ may therefore, optionally together with the connecting atom(s) of L and/or Y, for example form a carbonate, carbamate, ureum, ester, amide, imine, hydrazone, oxime, disulfide, acetal, or ketal group. This means that $V^1$, optionally together with the connecting atom(s) of L and/or Y, can for example also represent —OC(O)—, —C(O)O—, —OC(O)O—, —OC(O)N($R^d$)—, —N($R^d$)C(O)—, —C(O)N($R^d$)—, —N($R^d$)C(O)O—, —N($R^d$)C(O)N($R^e$)—, —C(O)—, —OC($R^d$)($R^e$)—, —C($R^d$)($R^e$)O—, —OC($R^d$)($R^e$)O—, —C($R^d$)($R^e$)—, —S—, —S—S—, —C=, =C—, —N=, =N—, —C=N—, —N=C—, —O—N=, =N—O—, —C=N—O—, —O—N=C—, —N($R^f$)—N=, =N—N($R^f$)—, —N($R^f$)—N=C—, or —C=N—N($R^f$)—, wherein $R^d$, $R^e$, and $R^f$ are independently selected from H and optionally substituted $C_{1-10}$ alkyl or aryl, two or more of $R^d$, $R^e$, and $R^f$ being joined to form one or more optionally substituted aliphatic or aromatic carbocycles or heterocycles.

If $V^1$ or $V^1$—Y represents a whole promoiety or L is connected to Y and not to $V^1$, $V^1$ may in this case for example be selected from $R^g$—[O($R''$O)P(O)]$_{pp}$—, $R^g$—C(O)—, $R^g$—OC(O)—, and $R^g$—N($R''$)C(O)—, wherein pp is selected from 1 to 3 and each $R^g$ and $R''$ are independently selected from H and optionally substituted $C_{1-15}$ alkyl, $C_{1-15}$ heteroalkyl, $C_{1-15}$ cycloalkyl, $C_{1-15}$ heterocycloalkyl, $C_{4-15}$ aryl, or $C_{4-15}$ heteroaryl, $R^g$ and $R''$ optionally being joined to form an optionally substituted carbocycle or heterocycle.

In one embodiment, $V^1$ is selected from phosphono, phenylaminocarbonyl, 4-(piperidino)piperidinocarbonyl, piperazinocarbonyl, and 4-methylpiperazinocarbonyl.

It should be noted that $V^1$, either in the form of a mono-, di-, or oligosaccharide moiety or a di-, tri-, tetra-, or oligopeptide, or in any other form, may contain protecting groups. Compounds of the invention comprising such a protected $V^1$ may not release any Z moiety when put under conditions that will transform and/or cleave the corresponding unprotected $V^1$. However, when said compounds are deprotected, such compounds will release one or more Z moieties when put under the appropriate conditions. Compounds comprising such a protected $V^1$ also fall under the scope of this invention. In particular the above can be envisioned for compounds of formula (IV). Suitable protecting groups for functional groups, in particular for amino acids, are well-known to the organic chemist and may for example be found in T. W. Greene, *Protective Groups in Organic Synthesis*, John Wiley & Sons, New York, 1981.

The compounds of formulae (III) and (IV) are designed to eventually release a compound of formula (I) or (II), or a compound of formula (I') or (II'), after transformation and/or cleavage of the one or more $V^1$ and $V^{1'}$ moieties. Release of a compound of formula (I) or (II), a compound of formula (I') or (II'), or a derivative thereof, from a conjugate of this invention via another mechanism is however not excluded from this invention.

In another aspect of this invention, a compound of formula (III) represents an intermediate for the preparation of a compound of formula (I) or (II) or another compound of formula (III). In this instance, for example, $V^2$, $L^2$, L, and Y are absent, p, q, and z all are 1, and the $V^1$ moiety may be a protecting group. There may or may not be one or more $V^{2'}$(-$L^{2'}$-L'(-

$V^{1'}$—$Y')_{p'})_{q'}(Z')_{z'-1}$ moieties, in which $V^{2'}$, $L^{2'}$, $L'$, and $Y'$ may or may not be absent, and $p'$, $q'$, and $z'$ all may or may not be 1. In one embodiment, a compound of formula (III) is a compound of formula (I) or (II) to which a $V^1$ moiety is attached. In another embodiment, a compound of formula (III) is a compound of formula (I) or (II) to which a $V^1$ moiety and a $V^{2'}(-L^{2'}-L'(-V^{1'}-Y')_{p'})_{q'}(Z')_{z'-1}$ moiety are attached. In yet another embodiment, a compound of formula (III) is a compound of formula (I) or (II) to which a $V^1$ moiety and a $V^{1'}$ moiety are attached.

In one embodiment, $V^1$ is not a protecting group.

In another embodiment, $V^2$, $L^2$, $L$, and $Y$ are absent, and p, q, and z all are 1.

In a further embodiment, $V^1$ is a chemically removable group.

In yet a further embodiment, $V^1$ is a chemically removable group connected to Z via $X^1$.

In yet another further embodiment, $V^1$ is a benzyl group connected to Z via $X^1$.

In one embodiment, $V^1$ is connected to L via more than one functional group on $V^1$.

In one embodiment, $V^1$ is connected to L via one functional group on $V^1$.

In one embodiment $V^1$ is connected to L via a functional group in the side chain of one of the natural or unnatural amino acids of $V^1$.

In another embodiment, the N-terminal amino acid of $V^1$ is connected via its α amino group to L.

The Self-Eliminating Spacer System Y

The self-elimination spacer system Y, when present, links $V^1$ and optionally L to one or more moieties Z.

A self-elimination spacer system Y may be incorporated in a conjugate of this invention to for example improve the properties of Z or the conjugate in general, to provide for suitable coupling chemistries, and/or to create space between $V^1$ and Z.

A compound of this invention may contain more than one spacer system Y per promoiety. These moieties Y may or may not be the same.

After cleavage or transformation of $V^1$, the left-hand side of Y may become unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art.

In one aspect the invention is related to compounds wherein Y is selected from (W—)$_w$(X—)$_x$(A-)$_s$ (W—)$_w$(X—)$_x$C((A)$_s$-)$_r$ or (W—)$_w$(X—)$_x$C(D((A)$_s$-)$_d$)$_r$ or (W—)$_w$(X—)$_x$C(D(E((A)$_s$-)$_e$)$_d$)$_r$, or (W—)$_w$(X—)$_x$C(D(E(F((A)$_s$-)$_f$)$_e$)$_d$)$_r$ wherein W and X are each a single-release 1,2+2n electronic cascade spacer (n≥1), being the same or different;

A is an ω-amino aminocarbonyl cyclization spacer that forms a cyclic ureum derivative upon cyclization;

C, D, E, and F are each a self-eliminating multiple-release spacer or spacer system that upon activation can maximally release r, d, e, and f groups, respectively;

s is 0 or 1;

r, d, e, and f are numbers representing degree of branching;

w and x are numbers representing degree of polymerization;

r, d, e, and f are independently an integer from 2 (included) to 24 (included);

w and x are independently an integer from 0 (included) to 5 (included).

In a further aspect of the invention, the self-elimination multiple-release spacer systems C, D, E, and F are independently selected from a moiety having the formula:

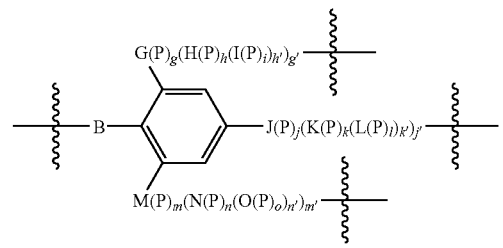

wherein

B is selected from $NR^{21}$, O, and S;

P is $C(R^{22})(R^{23})Q$—(W—)$_w$(X—)$_x$;

Q is absent or is —O—CO—;

W and X are each a single-release 1,2+2n electronic cascade spacer (n≥1), being the same or different;

G, H, I, J, K, L, M, N, and O are independently selected from moieties having the formula:

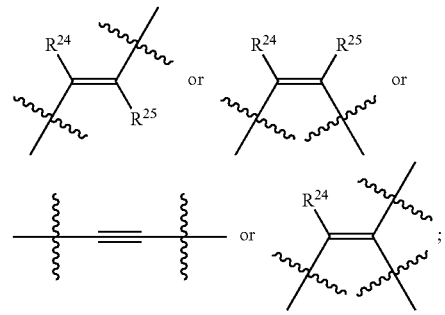

G, J, and M may in addition be selected from the group of P and hydrogen with the proviso that if two of G, J, and M are hydrogen, the remaining group must be

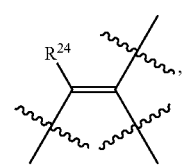

or be

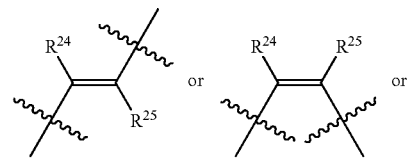

-continued and at the same time be conjugated to $R^{21}$ is selected from H and optionally substituted $C_{1-6}$ alkyl;

$R^{22}$, $R^{23}$, $R^{24}$, and $R^{25}$ are independently selected from H, OH, SH, $NH_2$, $N_3$, $NO_2$, NO, $CF_3$, CN, $C(O)NH_2$, $C(O)H$, $C(O)OH$, halogen, $R_x$, $SR_x$, $S(O)R_x$, $S(O)_2R_x$, $S(O)OR_x$, $S(O)_2OR_x$, $OS(O)R_x$, $OS(O)_2R_x$, $OS(O)OR_x$, $OS(O)_2OR_x$, $OR_x$, $NHR_x$, $N(R_x)R_x^1$, $^+N(R_x)(R_x^1)R_x^2$, $P(O)(OR_x)(OR_x^1)$, $OP(O)(OR_x)(OR_x^1)$, $C(O)R_x$, $C(O)OR_x$, $C(O)N(R_x^1)R_x$, $OC(O)R_x$, $OC(O)OR_x$, $OC(O)N(R_x)R_x^1$, $N(R_x^1)C(O)R_x$, $N(R_x^1)C(O)OR_x$, and $N(R_x^1)C(O)N(R_x^2)R_x$, wherein $R_x$, $R_x^1$ and $R_x^2$ are independently selected from H and optionally substituted $C_{1-6}$ alkyl, $C_{1-6}$ heteroalkyl, $C_{3-20}$ cycloalkyl, $C_{3-20}$ heterocycloalkyl, $C_{4-20}$ aryl, or $C_{4-20}$ heteroaryl, $R_x$, $R_x^1$, and $R_x^2$ optionally being joined to form one or more optionally substituted aliphatic or aromatic carbocycles or heterocycles, two or more of the substituents $R^{21}$, $R^{22}$, $R^{23}$, $R^{24}$, and $R^{25}$ optionally being connected to one another to form one or more aliphatic or aromatic cyclic structures;

g, h, i, j, k, l, m, n, o, h', g', k', j', n', m' are numbers representing degree of branching and are independently 0, 1, or 2 with the provisos that if G=hydrogen or P, g, h, i, h', and g' all equal 0;
if J=hydrogen or P, j, k, l, k', and j' all equal 0;
if M=hydrogen or P, m, n, o, n', and m' all equal 0;
if G, H, I, J, K, L, M, N, or O is then g+g'=1, h+h'=1, i=1, j+j'=1, k+k'=1, l=1, m+m'=1, n+n'=1, or o=1, respectively;
if G, H, I, J, K, L, M, N, or O is then g+g'=2, h+h'=2, i=2, j+j'=2, k+k'=2, l=2, m+m'=2, n+n'=2, or o=1, respectively;

if g'=0 and G is not hydrogen or P, then h, h', and i equal 0 and g>0;
if g=0 and G is not hydrogen or P, then g'>0;
if g'>0 and h'=0, then i=0 and h>0;
if g'>0 and h=0, then h'>0 and i>0;
if j'=0 and J is not hydrogen or P, then k, k', and l equal 0 and j>0;
if j=0 and J is not hydrogen or P, then j'>0;
if j'>0 and k'=0, then l=0 and k>0;
if j'>0 and k=0, then k'>0 and l>0;
if m'=0 and M is not hydrogen or P, then n, n', and o equal 0 and m>0;
if m=0 and M is not hydrogen or P, then m'>0;
if m'>0 and n'=0, then o=0 and n>0;
if m'>0 and n=0, then n'>0 and o>0;

w and x are numbers of polymerization and are independently an integer from 0 (included) to 5 (included).

According to a further embodiment of the invention, the 1,2+2n electronic cascade spacers W and X are independently selected from a moiety having the formula:

wherein
$Q'=$—$R^{30}C$=$CR^{31}$—, S, O, $NR^{31}$, —$R^{31}C$=N—, or —N=$CR^{31}$—;
B=$NR^{32}$, O, S;
P=$C(R^{28})(R^{29})Q$;
$R^{26}$, $R^{27}$, B, and $(T-)_t(T'-)_{t'}(T''-)_{t''}P$ are connected to $C^a$, $C^b$, $C^c$, and $C^d$ in such a way that B and $(T-)_t(T'-)_{t'}(T''-)_{t''}P$ are connected to two adjacent carbon atoms or to $C^a$ and $C^d$;
Q is absent or is —O—CO—;
t, t', and t'' are numbers representing degree of polymerization and are independently an integer from 0 (included) to 5 (included);
T, T', and T'' are independently selected from moieties having the formula:

$R^{26}$, $R^{27}$, $R^{28}$, $R^{29}$, $R^{30}$, $R^{31}$, $R^{32}$, $R^{33}$, and $R^{34}$ are independently selected from H, OH, SH, $NH_2$, $N_3$, $NO_2$, NO, $CF_3$, CN, $C(O)NH_2$, $C(O)H$, $C(O)OH$, halogen, $R_x$, $SR_x$, $S(O)R_x$, $S(O)_2R_x$, $S(O)OR_x$, $S(O)_2OR_x$, $OS(O)R_x$, $OS(O)_2R_x$, $OS(O)OR_x$, $OS(O)_2OR_x$, $OR_x$, $NHR_x$, $N(R_x)R_x^1$, $^+N(R_x)(R_x^1)R_x^2$, $P(O)(OR_x)(OR_x^1)$, $OP(O)(OR_x)(OR_x^1)$, $C(O)R_x$, $C(O)OR_x$, $C(O)N(R_x^1)R_x$, $OC(O)R_x$, $OC(O)OR_x$, $OC(O)N(R_x)R_x^1$, $N(R_x^1)C(O)R_x$, $N(R_x^1)C(O)OR_x$, and $N(R_x^1)C(O)N(R_x^2)R_x$, wherein $R_x$, $R_x^1$ and $R_x^2$ are independently selected from H and optionally substituted $C_{1-6}$ alkyl, $C_{1-6}$ heteroalkyl, $C_{3-20}$ cycloalkyl, $C_{3-20}$ heterocycloalkyl, $C_{4-20}$ aryl, or $C_{4-20}$ heteroaryl, $R_x$, $R_x^1$, and $R_x^2$ optionally being joined to form one or more optionally substituted aliphatic or aromatic carbocycles or heterocycles, two or more of the substituents $R^{26}$, $R^{27}$, $R^{28}$, $R^{29}$, $R^{30}$, $R^{31}$, $R^{32}$, $R^{33}$, or $R^{34}$ optionally being connected to one another to form one or more aliphatic or aromatic cyclic structures.

In the formulae above, Q may be O—CO, but it may also be absent. For example, a compound with a benzyl ether linkage between self-elimination spacer and the group that leaves, the oxycarbonyl function being absent (Q is absent), has been reported to undergo self-elimination[11].

According to a further embodiment of the invention, the ω-amino aminocarbonyl cyclization elimination spacer A is a moiety having the formula:

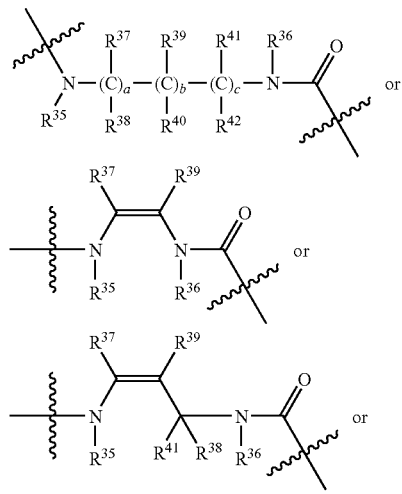

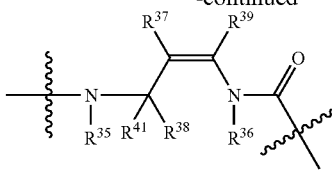

wherein
  a is an integer of 0 or 1;
  b is an integer of 0 or 1;
  c is an integer of 0 or 1, provided that a+b+c=2 or 3;
  $R^{35}$ and $R^{36}$ are independently selected from H and optionally substituted $C_{1-6}$ alkyl;
  $R^{37}$, $R^{38}$, $R^{39}$, $R^{40}$, $R^{41}$, and $R^{42}$ are independently selected from H, OH, SH, $NH_2$, $N_3$, $NO_2$, NO, $CF_3$, CN, $C(O)NH_2$, C(O)H, C(O)OH, halogen, $R_x$, $SR_x$, $S(O)R_x$, $S(O)_2R_x$, $S(O)OR_x$, $S(O)_2OR_x$, $OS(O)R_x$, $OS(O)_2R_x$, $OS(O)OR_x$, $OS(O)_2OR_x$, $OR_x$, $NHR_x$, $N(R_x)R_x^1$, $^+N(R_x)(R_x^1)R_x^2$, $P(O)(OR_x)(OR_x^1)$, $OP(O)(OR_x)(OR_x^1)$, $C(O)R_x$, $C(O)OR_x$, $C(O)N(R_x^1)R_x$, $OC(O)R_x$, $OC(O)OR_x$, $OC(O)N(R_x)R_x^1$, $N(R_x^1)C(O)R_x$, $N(R_x^1)C(O)OR_x$, and $N(R_x^1)C(O)N(R_x^2)R_x$, wherein $R_x$, $R_x^1$ and $R_x^2$ are independently selected from H and optionally substituted $C_{1-6}$ alkyl, $C_{1-6}$ heteroalkyl, $C_{3-20}$ cycloalkyl, $C_{3-20}$ heterocycloalkyl, $C_{4-20}$ aryl, or $C_{4-20}$ heteroaryl, $R_x$, $R_x^1$, and $R_x^2$ optionally being joined to form one or more optionally substituted aliphatic or aromatic carbocycles or heterocycles, and $R^{35}$, $R^{36}$, $R^{37}$, $R^{38}$, $R^{39}$, $R^{40}$, $R^{41}$, and $R^{42}$ are optionally part of one or more optionally substituted aliphatic or aromatic cyclic structures, two or more of the substituents $R^{35}$, $R^{36}$, $R^{37}$, $R^{38}$, $R^{39}$, $R^{40}$, $R^{41}$, or $R^{42}$ optionally being connected to one another to form one or more aliphatic or aromatic carbocycles or heterocycles.

In one embodiment, this invention relates to a compound wherein $X^1$ is O and Y is connected to $X^1$ via an ω-amino aminocarbonyl cyclization spacer being part of Y.

In one embodiment, the spacer system Y is selected from

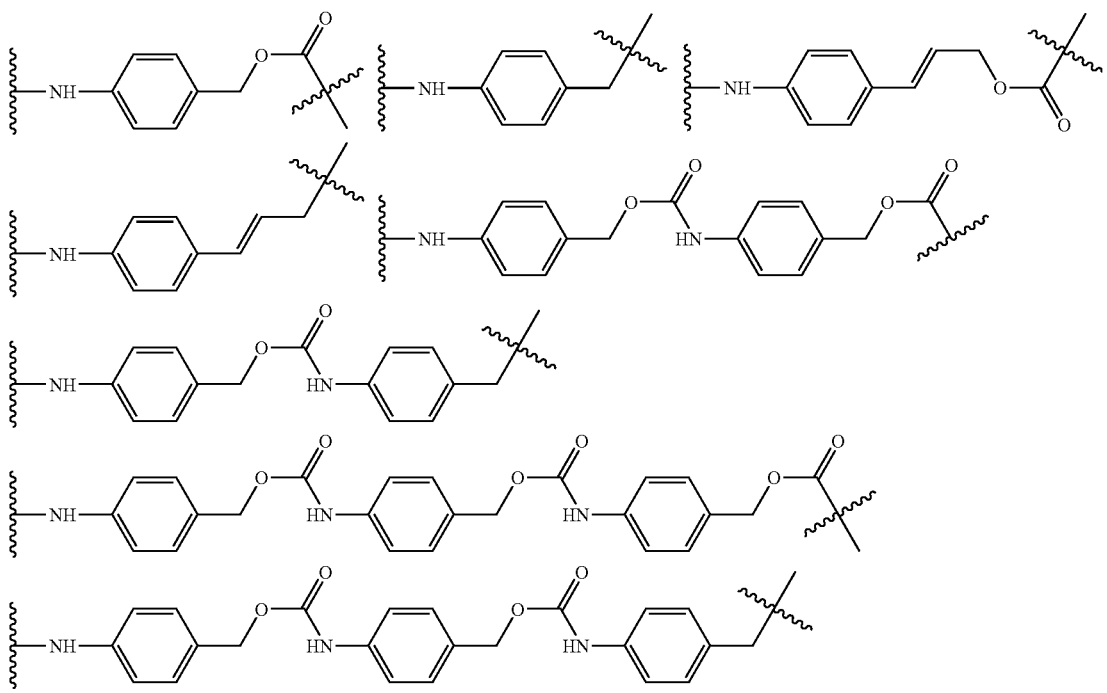

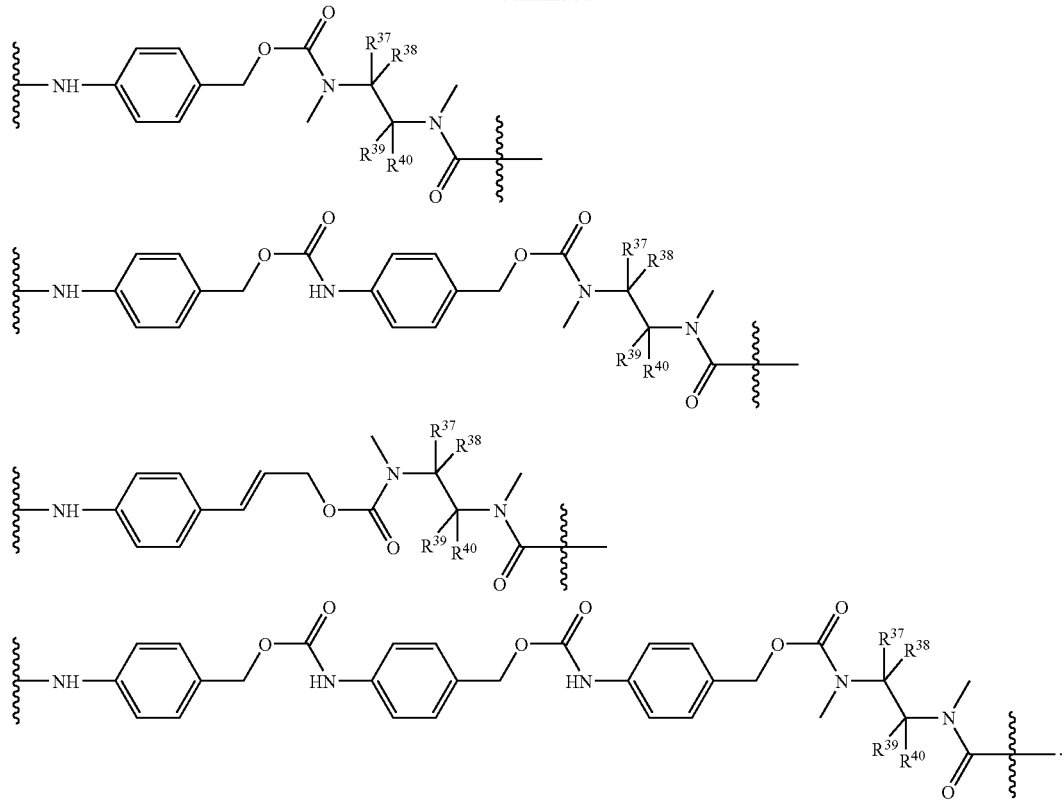

In another embodiment, the spacer system Y is

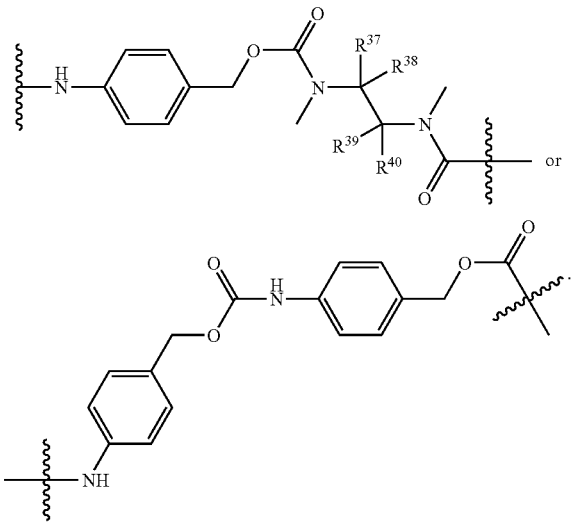

In another embodiment, the spacer system Y is

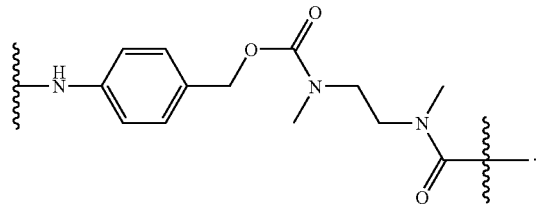 [SMILES: *Nc1ccc(COC(=O)N(C)CCN(C)C(*)=O)cc1]

Other examples of self-eliminating spacers include, but are not limited to, spacers that can undergo cyclization[12], such as optionally substituted 4-aminobutyric acid amides, appropriately substituted bicyclo[2.2.1] and bicyclo[2.2.2] ring systems, and 2-aminophenylpropionic acid amides and "trimethyl-lock" cyclization spacers[13]. A glycine spacer in which an amine-containing leaving group is connected at the α-position is another useful spacer for the compounds of the invention.[14]

In a conjugate of this invention, a spacer system Y may be connected to more than one $V^1$ moiety. In this case, transformation and/or cleavage of one of these $V^1$ moieties may trigger the release of one or more Z moieties. When $V^1$ moieties that are transformed or cleaved under different conditions are connected to the same Y, release of one or more Z moieties may occur when a conjugate of this invention is brought under one of several different conditions. Alternatively, a spacer system Y may be used that requires to be triggered twice or even more times in order to self-eliminate. An example of such a self-elimination spacer is a bicine spacer.[15] When such a spacer is used in combination with different, selectively cleavable $V^1$ moieties connected to said spacer, selectivity of release of Z may be increased as two different conditions must be met before Z is released.

The Linking Group L

The linking group L links one or more $V^1$ and/or Y moieties to $L^2$ or RM. Synthesis may be more straightforward when L is connected to $V^1$ and the compound may be less prone to premature degradation. Connection of L to Y may have the advantage that $V^1$ may be transformed and/or cleaved with more ease. Other reasons to connect L to Y may for example be that (part of) Y remains bound to L upon cleavage of $V^1$, which prevents the release of reactive small molecules, or that the compound displays improved (pharmacokinetic) properties, solubility, or aggregation behavior. L may be a bond connecting $V^1$ or Y directly to either $L^2$ or RM. In another aspect, however, L is a linking group that functionally links or spaces the one or more moieties $V^1$/Y and the $L^2$ or RM moiety. In a compound of formula (IV), spacing may make the reactive moiety RM more accessible to the reaction partner, for example when the functional moiety is being coupled. In a compound of formula (III), spacing may provide for a better accessibility of $V^1$, because $V^2$ is further removed, which, especially in the case of enzymatic cleavage or transformation of $V^1$, may improve the rate at which $V^1$ is transformed and/or cleaved. The linking group L may be a water-soluble moiety or contain one or more water-soluble moieties, such that L contributes to the water solubility of a compound of formula (III) or (IV). L may also be a moiety or contain one or more moieties that reduce(s) aggregation of a compound of formula (III) or (IV), which may or may not be a moiety/moieties that also increase(s) the water solubility of a compound of formula (III) or (IV). The linking group L must contain suitable functional groups at both of its ends to provide for selective coupling with the one or more $V^1$ and/or Y moieties and $L^2$ or RM.

In one aspect, the L moiety is a linear, branched, or dendritic moiety, so that it can optionally be connected to more than one $V^1$ and/or Y moiety. Branching can occur via one or more cyclic structures or at one or more branching atoms that may for example be carbon, nitrogen, silicon, or phosphorus.

The number of branches in L that are connected to $V^1$ and/or Y does not necessarily equal the total number of branches as in the coupling reaction with $V^1$/Y not all branches may be coupled to $V^1$ and/or Y moieties due to incomplete chemical conversion. This means that L may contain branches that are not coupled to $V^1$ or Y, but instead end in for example a functional group, H, OH, or a leaving group.

Therefore, when L is branched, compounds of this invention may exist as a mixture, wherein each component of the mixture has a different p value. For example, the compound may exist as a mixture of two separate compounds, one compound wherein p is 2 and another compound wherein p is 3. Furthermore, for a given p, the compound may exist as a mixture of isomers as $V^1$/Y may be connected to distinct sets of branches on L.

In one embodiment, L is a bond.

In another embodiment, L is a linear linker.

In another embodiment, L is a linear linker built up through a cycloaddition reaction between a molecule containing an azide group and one containing an acetylene group.

In another embodiment, L is a branched linker.

In another embodiment, L is a dendritic linker. The dendritic structure may for example be built up through cycloaddition reactions between molecules containing an azide group and ones containing an acetylene group.

In one embodiment, p is 1.

In other embodiments, p is 2 or 3 or 4 or 6 or 8 or 9.

In another embodiment, L is represented by the formula:

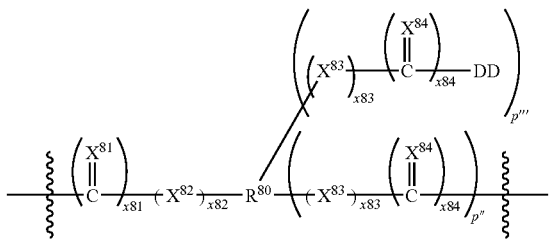

wherein $X^{81}$ and $X^{82}$ are each independently O, $NR^{85}$, or S;

Each $X^{83}$ and $X^{84}$ are each independently O, $NR^{86}$, or S;

Each x81, x82, x83, and x84 are independently 0 or 1;

p" is a number representing a degree of branching and is an integer selected from 1 (included) to 128 (included);

p''' is a number representing a degree of branching and is an integer selected from 0 (included) to 127 (included);

p"+p'''≤128;

Each DD is independently H, OH, or a leaving group;

$R^{80}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —$(CH_2CH_2O)_v$—, -alkylene-$(CH_2CH_2O)_v$—, —$(CH_2CH_2O)_v$-alkylene-, -alkylene-$(CH_2CH_2O)_v$-alkylene-, -heteroalkylene-$(CH_2CH_2O)_v$—, —$(CH_2CH_2O)_v$-heteroalkylene-, -heteroalkylene-$(CH_2CH_2O)_v$-alkylene-, -heteroalkylene-$(CH_2CH_2O)_v$-heteroalkylene-, -alkylene-$(CH_2CH_2O)_v$-heteroalkylene-, a dendritic structure, and an oligopeptide, or any combination of two or more of the above;

$R^{85}$ and $R^{56}$ are independently selected from H and $C_{1-8}$ alkyl;

v is selected from 1 (included) to 500 (included).

For example, L may be selected from optionally substituted $C_{1-10}$ alkylene, $C_{1-10}$ alkylenecarbonyl, $C_{1-12}$ alkyleneoxycarbonyl, $C_{1-12}$ carbonylalkylene, $C_{1-12}$ carbonylalkyleneoxycarbonyl, and $(CH_2CH_2O)_v$-carbonyl.

In one embodiment, L is selected from

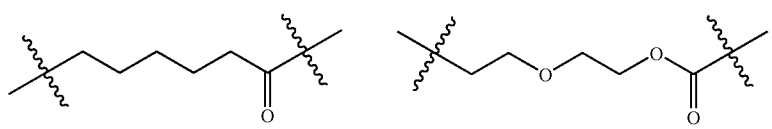

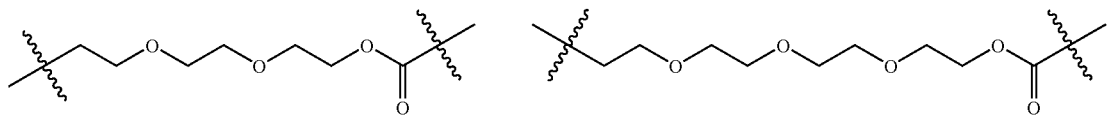

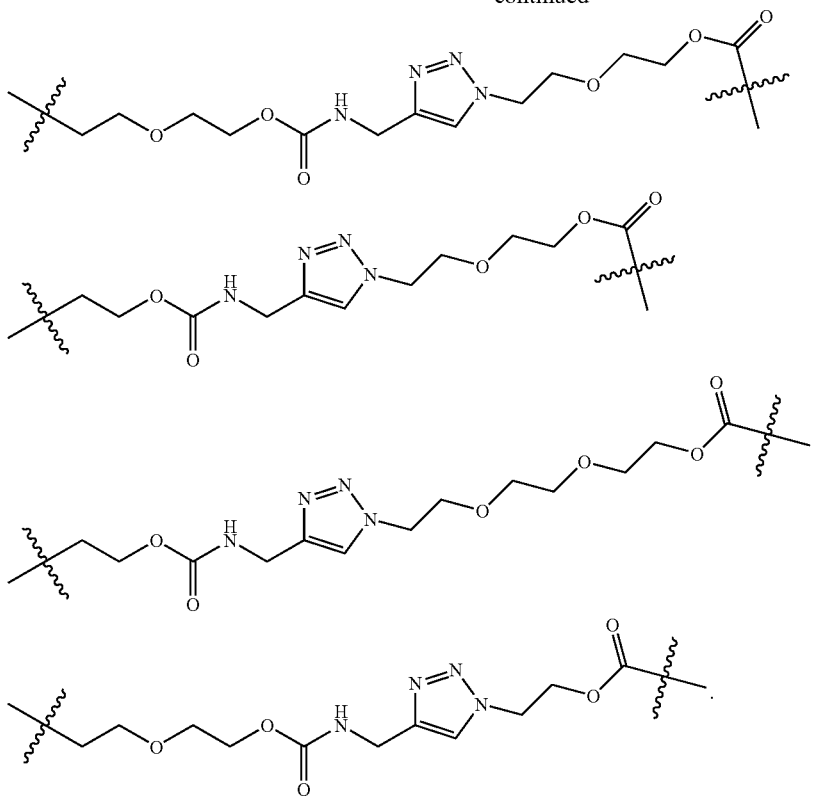

The Reactive Moiety RM and the Linking Group $L^2$

The reactive moiety RM in a compound of formula (IV) is connected to the linking group L and is able to react with a suitable functional group on a reaction partner.

In one embodiment of this invention, the reactive moiety RM is designed to react with a functional group on the moiety $V^2$, which results in formation of a compound of formula (III). In this reaction, the moiety RM is transformed into the moiety $L^2$. In another embodiment, the reactive moiety RM is designed to react with a complementary moiety in situ, e.g., in vivo, to give a compound that may or may not be a compound of formula (III).

In one aspect of the invention, the reactive moiety RM contains an electrophilic group that reacts with a nucleophilic group on the reaction partner, for example $V^2$, e.g., a thiol group, an amino group, or a hydroxy group.

In another aspect of the invention, the reactive moiety RM contains a nucleophilic group that reacts with an electrophilic group on the reaction partner, for example $V^2$, e.g., an aldehyde group.

In another aspect of the invention, the reactive moiety RM contains a cycloaddition partner moiety, e.g., an alkene, a diene, a 1,3-dipole, or a 1,3-dipolarophile, that reacts with a suitable complementary cycloaddition partner moiety on the reaction partner, for example $V^2$, e.g., a diene, an alkene, a 1,3-dipolarophile, or a 1,3-dipole.

In another aspect of the invention, the reactive moiety RM contains a group that can be coupled with a suitable complementary group on the reaction partner, for example $V^2$, under metal-catalyzed, biocatalyzed, or enzyme-catalyzed conditions, e.g., palladium-catalyzed conditions.

In one aspect of the invention, the reactive moiety RM is, without limitation,

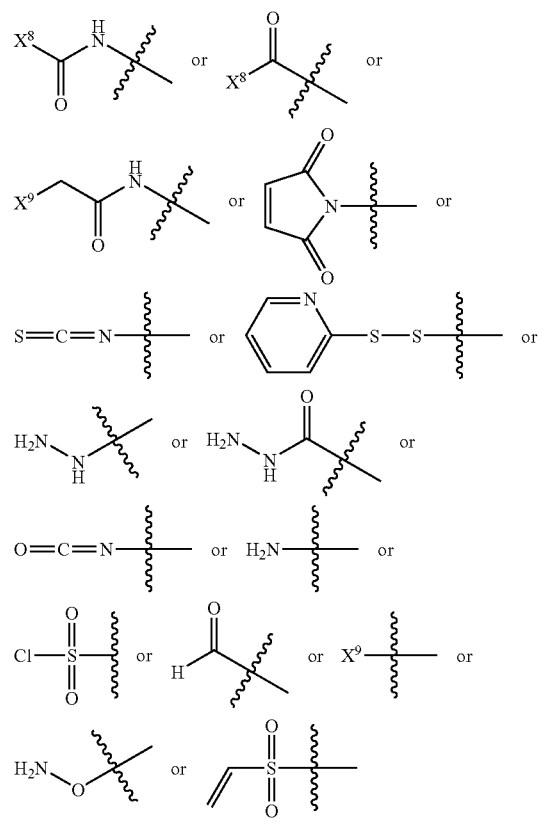

wherein $X^8$ is selected from —Cl, —Br, —I, —F, —OH, —O—N-succinimide, —O-(4-nitrophenyl), —O-pentafluorophenyl, —O-tetrafluorophenyl, —O—C(O)—$R^{50}$, and —O—C(O)—$OR_{50}$;

$X^9$ is selected from —Cl, —Br, —I, —O-mesyl, —O-triflyl, and —O-tosyl;

$R^{50}$ is $C_1$-$C_{10}$ alkyl or aryl.

In one embodiment, the moiety RM is chosen from

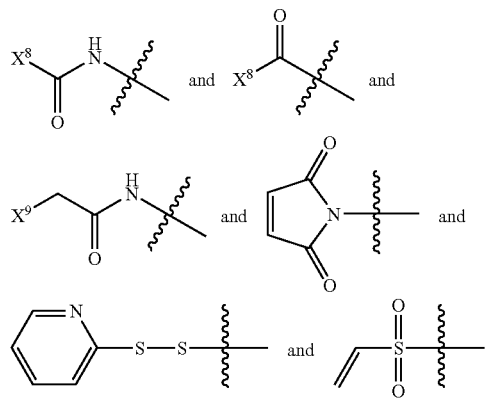

which makes it able to react with a thiol group on the reaction partner, for example moiety $V^2$.

In one embodiment, the moiety RM is

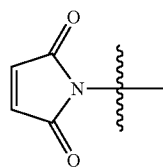 [SMILES: *N1C(=O)C=CC1=O]

which makes it able to react with a thiol group on the reaction partner, for example moiety $V^2$.

In another embodiment, the moiety RM is chosen from

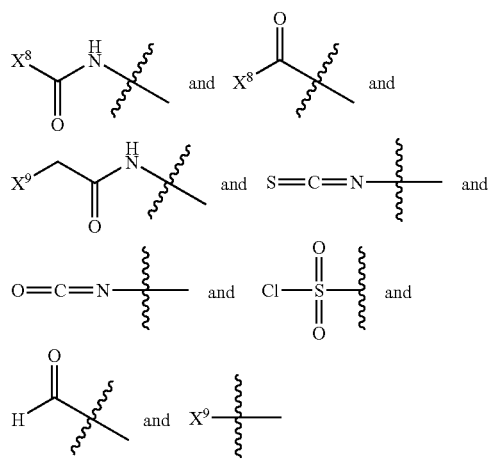

which makes it able to react with an amino group, e.g., a primary or secondary amino group, on the reaction partner, for example moiety $V^2$.

In another embodiment, the moiety RM is chosen from

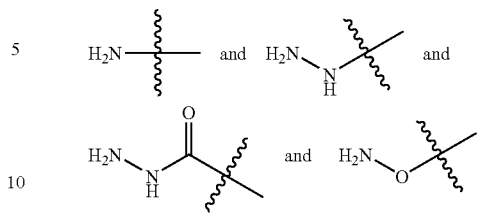

which makes it able to react with an aldehyde group on the reaction partner, for example moiety $V^2$.

The linking group $L^2$ in compounds of formula (III) represents the remainder of RM when the reactive moiety RM has reacted with $V^2$. This group then links the moiety $V^2$ with L. The group that remains may be a bond. Typically, however, $L^2$ is a linking group. When a compound of formula (III) is formed other than via a compound of formula (IV), $L^2$ does not represent the remainder of RM, but may represent a similar or the same moiety and in addition be selected from for example optionally substituted $C_{1-6}$ alkylene, $C_{1-6}$ heteroalkylene, $C_{3-7}$ cycloalkylene, $C_{3-7}$ heterocycloalkylene, $C_{5-10}$ arylene, and $C_{5-10}$ heteroarylene.

In one embodiment, the moiety $L^2$ is a bond.

In another embodiment, the moiety $L^2$ is, without limitation,

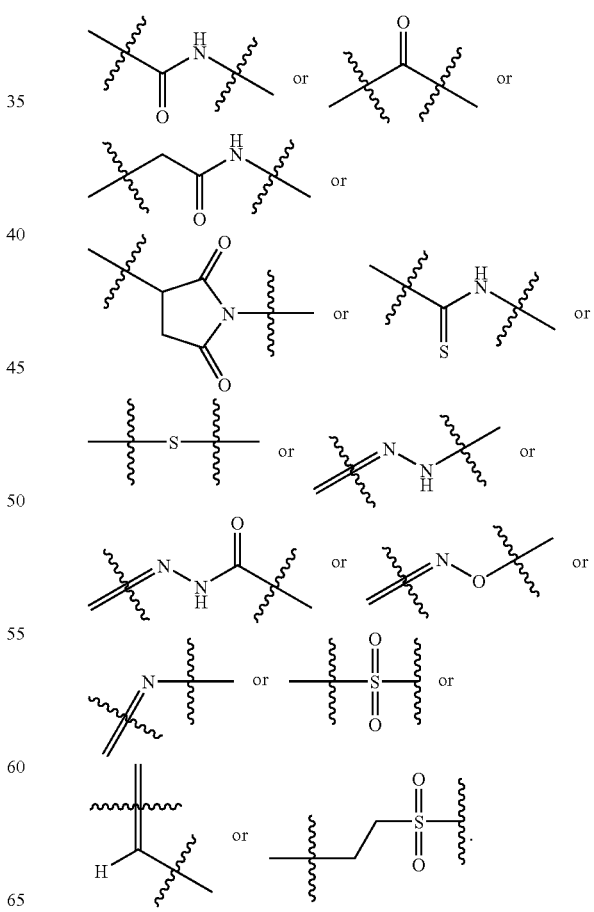

In a further embodiment, the moiety $L^2$ is

[Structure: succinimide linker]

The Moiety $V^2$

The moiety $V^2$ is a functional moiety, which means that it adds additional functionality to a compound of the invention.

In one embodiment, $V^2$ is a targeting moiety. In another embodiment, the $V^2$ moiety is a moiety that improves the pharmacokinetic properties of a compound of the invention. In yet another embodiment, the $V^2$ moiety is a moiety that causes accumulation of compounds of the invention at a target site. In yet another embodiment, the $V^2$ moiety is a moiety that improves the aqueous solubility of a compound of the invention. In yet another embodiment, the $V^2$ moiety is a moiety that increases the hydrophobicity of a compound of the invention. In yet another embodiment, the $V^2$ moiety is a moiety that reduces extravasation of a compound of the invention. In yet another embodiment, the $V^2$ moiety is a moiety that reduces excretion of a compound of the invention. In yet another embodiment, the $V^2$ moiety is a moiety that reduces the immunogenicity of a compound of the invention. In yet another embodiment, the $V^2$ moiety is a moiety that enhances the circulation time of a compound of the invention. In yet another embodiment, the $V^2$ moiety is a moiety that enhances the ability of a compound of the invention to cross a biological barrier, e.g., a membrane, cell wall, or the blood-brain barrier. In yet another embodiment, the $V^2$ moiety is a moiety that enhances the ability of a compound of the invention to internalize. In yet another embodiment, the $V^2$ moiety is a moiety that causes the compounds of the invention to aggregate. In yet another embodiment, the $V^2$ moiety is a moiety that reduces aggregation of compounds of the invention. In yet another embodiment, the $V^2$ moiety is a moiety that causes the compounds of the invention to form micelles or liposomes. In yet another embodiment, the $V^2$ moiety is a moiety that causes complexation of a compound of the invention to another molecule, e.g., a biomolecule. In yet another embodiment, the $V^2$ moiety is a polynucleotide moiety that complexes with a complementary nucleotide sequence, for example RNA or DNA. In yet another embodiment, the $V^2$ moiety is a moiety that causes a compound of the invention to bind, associate, interact, or complex to another moiety, for example a (functionalized) surface or solid support.

In another embodiment, $V^2$ exhibits two or more different functions.

In one aspect of the invention, the moiety $V^2$ includes within its scope any unit that binds or reactively associates or complexes with a receptor, a receptor complex, antigen, or other receptive moiety associated with a given target cell population. $V^2$ can be any molecule that binds to, complexes with, or reacts with a moiety of a cell population sought to be therapeutically or otherwise biologically modified. The $V^2$ moiety acts to deliver the one or more moieties Z to the particular target cell population with which $V^2$ reacts or to which $V^2$ binds. Such $V^2$ moieties include, but are not limited to, aptamers, full-length antibodies and antibody fragments, lectins, biologic response modifiers, enzymes, vitamins, growth factors, steroids, nutrients, sugar residues, oligosaccharide residues, hormones, and any derivatives thereof, or any combination of any of these. Upon binding, reactively associating, or complexing, the compounds of the invention may or may not be internalized. If internalization occurs, transformation and/or cleavage of $V^1$ preferably occur inside the target cell.

Useful non-immunoreactive protein, polypeptide, or peptide $V^2$ moieties include, but are not limited to, transferrin, epidermal growth factors ("EGF"), bombesin, gastrin and its derivatives, particularly those containing the tetrapeptide sequence Trp-Met-Asp-Phe-NH$_2$, gastrin-releasing peptide, platelet-derived growth factor, IL-2, IL-6, transforming growth factors ("TGF"), such as TGF-a and TGF-P, tumor growth factors, vaccinia growth factor ("VGF"), insulin and insulin-like growth factors I and II, lectins, and apoprotein from low density lipoprotein.

Useful polyclonal antibody $V^2$ moieties are heterogeneous populations of antibody molecules. Various procedures well-known in the art may be used for the production of polyclonal antibodies to an antigen-of-interest.

Useful monoclonal antibody $V^2$ moieties are homogeneous populations of antibodies to a particular antigen (e.g., a cancer cell antigen). A monoclonal antibody (mAb) to an antigen-of-interest can be prepared by using any technique known in the art which provides for the production of monoclonal antibody molecules.

Useful monoclonal antibody $V^2$ moieties include, but are not limited to, human monoclonal antibodies, humanized monoclonal antibodies, or chimeric human-mouse (or other species) monoclonal antibodies. Hunan monoclonal antibodies may be made by any of numerous techniques known in the art.

The $V^2$ moiety can also be a bispecific antibody. Methods for making bispecific antibodies are known in the art.

The $V^2$ moiety can be a functionally active fragment, derivative, or analog of an antibody that immunospecifically binds to antigens on the target cells, e.g., cancer cell antigens. In this regard, "functionally active" means that the fragment, derivative, or analog is able to elicit anti-anti-idiotype antibodies that recognize the same antigen that the antibody from which the fragment, derivative, or analog is derived, recognizes.

Other useful $V^2$ moieties comprise fragments of antibodies including, but not limited to, F(ab')$_2$ fragments, which contain the variable region, the light chain constant region and the CH1 domain of the heavy chain, which can be produced by pepsin digestion of the antibody molecule, and Fab fragments, which can be generated by reducing the disulfide bridges of the F(ab')$_2$ fragments. Other useful $V^2$ moieties are heavy chain and light chain dimers of antibodies, or any minimal fragment thereof such as Fvs or single chain antibodies (SCAs), domain antibodies, anticalins, affibodies, nanobodies, or any other molecule with the same, similar, or comparable specificity as the antibody. Additionally, recombinant antibodies, such as chimeric and humanized monoclonal antibodies, comprising both human and non-human portions, which can be made using standard recombinant DNA techniques, are useful $V^2$ moieties. A chimeric antibody is a molecule in which different portions are derived from different animal species, such as those having a variable region derived from a murine monoclonal and a human immunoglobulin constant region. Humanized antibodies are antibody molecules from non-human species having one or more complementarity determining regions (CDRs) from the non-human species and a framework region from a human immunoglobulin molecule.

Completely human antibodies are particularly desirable as $V^2$ moieties. Such antibodies can for example be produced using transgenic mice that are incapable of expressing endogenous immunoglobulin heavy and light chains genes, but which can express human heavy and light chain genes. In other embodiments, the $V^2$ moiety is a fusion protein of an antibody, or a functionally active fragment or derivative thereof, for example in which the antibody is fused via a covalent bond (e.g., a peptide bond), at either the N-terminus or the C-terminus to an amino acid sequence of another protein (or portion thereof, preferably at least a 10, 20, or 50 amino acid portion of the protein) that is not the antibody. Preferably, the antibody or fragment thereof is covalently linked to the other protein at the N-terminus of the constant domain.

The $V^2$ moiety antibodies include analogs and derivatives that are modified, i.e., by the covalent attachment of any type of molecule as long as such covalent attachment permits the antibody to retain its antigen binding immunospecificity. For example, but not by way of limitation, derivatives and analogs of antibodies include those that have been further modified, e.g., by glycosylation, acetylation, pegylation, disulfide reduction, phosphylation, amidation, derivatization by known protecting or blocking groups, proteolytic cleavage, linkage to an other protein, etc. Additionally, the analog or derivative can contain one or more unnatural amino acids.

The $V^2$ moiety antibodies include antibodies having modifications (e.g., substitutions (for example cysteine to serine), deletions, or additions) in amino acid residues that interact with Fc receptors. In particular, they include antibodies having modifications in amino acid residues identified as involved in the interaction between the Fc domain and the FcRn receptor. Modifications may also be introduced to be able to couple the antibody to linker-agent conjugates at specific positions on the antibody.

In a specific embodiment, an antibody immunospecific for a cancer or tumor antigen is used as a $V^2$ moiety in accordance with the compounds, compositions, and methods of the invention.

Antibodies immunospecific for a cancer cell antigen can be obtained commercially or produced by any method known to one of skill in the art such as, e.g., chemical synthesis or recombinant expression techniques. The nucleotide sequences encoding antibodies immunospecific for a cancer cell antigen can be obtained, e.g., from the GenBank database or a database like it, a commercial or other source, the literature publications, or by routine cloning and sequencing.

Examples of antibodies available for the treatment of cancer include, but are not limited to, HERCEPTIN (trastuzumab; Genentech, CA) which is a humanized anti-HER2 monoclonal antibody for the treatment of patients with metastatic breast cancer; RITUXAN (rituximab; Genentech, CA), which is a chimeric anti-CD20 monoclonal antibody for the treatment of patients with non-Hodgkin's lymphoma; OvaRex (oregovomab; AltaRex Corporation, MA) which is a murine antibody for the treatment of ovarian cancer; Panorex (edrecolomab; Glaxo Wellcome, NC) which is a murine $IgG_{2a}$ antibody for the treatment of colorectal cancer; IMC-BEC2 (mitumomab; ImClone Systems, NY) which is a murine IgG antibody for the treatment of lung cancer; IMC-C225 (erbitux; Imclone Systems, NY) which is a chimeric IgG antibody for the treatment of head and neck cancer; Vitaxin (MedImmune, MD) which is a humanized antibody for the treatment of sarcoma; Campath I/H (alemtuzumab, Leukosite, MA) which is a humanized $IgG_1$ antibody for the treatment of chronic lymphocytic leukemia (CLL); SGN-70 (Seattle Genetics, WA) which is a humanized anti-CD70 antibody for the treatment of hematologic malignancies; Smart MI95 (Protein Design Labs, CA) which is a humanized IgG antibody for the treatment of acute myeloid leukemia (AML); LymphoCide (epratuzumab, Immunomedics, NJ) which is a humanized IgG antibody for the treatment of non-Hodgkin's lymphoma; SGN-33 (Seattle Genetics, WA) which is a humanized anti-CD33 antibody for the treatment of acute myeloid leukemia; Smart ID 10 (Protein Design Labs, CA) which is a humanized antibody for the treatment of non-Hodgkin's lymphoma; Oncolym (Techniclone, CA) which is a murine antibody for the treatment of non-Hodgkin's lymphoma; Allomune (BioTransplant, CA) which is a humanized anti-CD2 mAb for the treatment of Hodgkin's disease or non-Hodgkin's lymphoma; anti-VEGF (Genentech, CA) which is a humanized antibody for the treatment of lung and colorectal cancers; SGN-40 (Seattle Genetics, WA) which is a humanized anti-CD40 antibody for the treatment of multiple myeloma; SGN-30 (Seattle Genetics, WA) which is a chimeric anti-CD30 antibody for the treatment of Hodgkin's disease; CEAcide (Immunomedics, NJ) which is a humanized anti-CEA antibody for the treatment of colorectal cancer; IMC-1C11 (ImClone Systems, NJ) which is an anti-KDR chimeric antibody for the treatment of colorectal cancer, lung cancers, and melanoma; and Cetuximab (ImClone Systems, NJ) which is an anti-EGFR chimeric antibody for the treatment of epidermal growth factor positive cancers.

Other antibodies useful in the treatment of cancer include, but are not limited to, antibodies against the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor receptors, HER2, EGFR, VEGF, MAGE-1, MAGE-2, MAGE-3, MAGE-4, anti-transferrin receptor, p97, MUC1-KLH, MUC18, PSMA, CTLA4, CEA, gp100, MART1, PSA, IL-2 receptor, CD2, CD4, CD20, CD30, CD52, CD56, CD74, CD33, CD22, HLA-DR, HLA-DR10, human chorionic gonadotropin, CD38, CD40, CD70, mucin, P21, MPG, and Neu oncogene product. Many other internalizing or non-internalizing antibodies that bind to tumor-associated antigens can be used in this invention, some of which have been reviewed[16].

In some embodiments, the antibody is an anti-nuclear antibody or an antibody that can bind to a receptor or receptor complex expressed on a target cell. The receptor or receptor complex can comprise an immunoglobulin gene superfamily member, an integrin, a chemokine receptor, a TNF receptor superfamily member, a cytokine receptor, a major histocompatibility protein, a complement control protein, or a lectin.

In another specific embodiment, an antibody immunospecific for an antigen associated with an autoimmune disease is used as a $V^2$ moiety in accordance with the compounds, compositions, and methods of the invention.

In another specific embodiment, an antibody immunospecific for a viral or microbial antigen is used as a $V^2$ moiety in accordance with the compounds, compositions, and methods of the invention. As used herein, the term "viral antigen"

includes, but is not limited to, any viral peptide or polypeptide protein that is capable of eliciting an immune response. As used herein, the term "microbial antigen" includes, but is not limited to, any microbial peptide, polypeptide, protein, saccharide, polysaccharide, or lipid that is capable of eliciting an immune response.

New antibodies are continually being discovered and developed, and the present invention provides that these new antibodies may also be incorporated into a compound of this invention.

$V^2$ can react with the reactive moiety RM via for example a heteroatom on $V^2$. Heteroatoms that may be present on $V^2$ include, without limitation, sulfur (in one embodiment, from a sulfhydryl group), oxygen (in one embodiment, from a carboxyl or hydroxyl group), and nitrogen (in one embodiment, from a primary or secondary amino group). $V^2$ may also react via for example a carbon atom (in one embodiment, from a carbonyl group). These atoms can be present on $V^2$ in $V^2$'s natural state, for example a naturally occurring antibody, or can be introduced into $V^2$ via chemical modification.

Free sulfhydryl groups can be generated in an antibody or antibody fragment by reduction of the antibody (fragment) with a reducing agent such as dithiothreitol (DTT) or tris(2-carboxyethyl)phosphine (TCEP). In this way, modified antibodies can be obtained that can have from 1 to about 20 sulfhydryl groups, but typically between about 1 and about 9 sulfhydryl groups.

Alternatively, $V^2$ can have one or more carbohydrate groups that can be chemically modified to have one or more sulfhydryl groups. As another alternative, sulfhydryl groups can be generated by reaction of amino groups, for example from lysine moieties, on $V^2$ with 2-iminothiolane (Traut's reagent) or another sulfhydryl-generating reagent.

In one embodiment, the $V^2$ moiety is a receptor-binding moiety.

In another embodiment, the $V^2$ moiety is an antibody or an antibody fragment.

In another embodiment, the $V^2$ moiety is a monoclonal antibody or a fragment thereof.

In one embodiment, $V^2$ has one or more sulfhydryl groups and $V^2$ reacts with one or more RM moieties of compounds of formula (IV) via one or more of these sulfhydryl groups' sulfur atoms to form a compound of formula (III).

In yet another embodiment, $V^2$ contains disulfide bonds that can be chemically reduced to sulfhydryl groups (two for each disulfide bond), which can then be reacted with one or more reactive moieties RM.

In another embodiment, $V^2$ contains about 1 to about 3 sulfhydryl groups, which can be reacted with one or more reactive moieties RM.

In another embodiment, $V^2$ contains about 3 to about 5 sulfhydryl groups, which can be reacted with one or more reactive moieties RM.

In another embodiment, $V^2$ contains about 7 to about 9 sulfhydryl groups, which can be reacted with one or more reactive moieties RM.

In another embodiment, $V^2$ can have one or more carbohydrate groups that can be chemically modified to have one or more sulfhydryl groups. $V^2$ reacts with RM moieties via these one or more sulfhydryl groups' sulfur atoms.

In another embodiment, $V^2$ can have one or more lysine groups that can be chemically modified to have one or more sulfhydryl groups, which can be reacted with one or more reactive moieties RM. Reactive moieties that can react with a sulfhydryl group include, but are not limited to, carbamoyl halide, acyl halide, α-haloacetamide, halomethyl ketone, vinyl sulfone, maleimide, and 2-disulfanylpyridine.

In yet another embodiment, $V^2$ can have one or more carbohydrate groups that can be oxidized to provide one or more aldehyde groups. The corresponding aldehyde(s) can then react with one or more reactive moieties RM. Reactive moieties that can react with a carbonyl group on $V^2$ include, but are not limited to, hydrazine, hydrazide, amine, and hydroxylamine.

In yet another embodiment, $V^2$ can have one or more amino groups, e.g., from lysine residues, which can be reacted with one or more reactive moieties RM. Reactive moieties that can react with an amino group include, but are not limited to, carbamoyl halide, α-haloacetamide, acyl halide, aldehyde, isocyanate, and isothiocyanate.

A conjugate of formula (III) may exist as a mixture, wherein each component of the mixture has a different q value. For example, the compound may exist as a mixture of two separate compounds, one compound wherein q is 3 and another compound wherein q is 4. When analyzing the compound of formula (III) it is understood that q may be the (rounded) average number of $L^2$-L(-$V^1$—Y—)$_p$(Z)$_{z/q}$ units per $V^2$ moiety. Furthermore, for a given q, the compound may exist as a mixture of isomers as the q $L^2$-L(-$V^1$—Y—)$_p$(Z)$_{z/q}$ moieties may be connected to distinct sets of functional groups on $V^2$. It should be noted that the number of Z moieties in each unit only equals z/q if all units are the same and/or contain the same number of Z moieties.

In one embodiment, the $V^2$ moiety is connected to $L^2$ via a sulfur atom.

In another embodiment, the $V^2$ moiety is connected to $L^2$ via a sulfur atom and q ranges from about 1 to about 20.

In another embodiment, the $V^2$ moiety is connected to $L^2$ via a sulfur atom and q ranges from about 1 to about 9.

In another embodiment, the $V^2$ moiety is connected to $L^2$ via a sulfur atom and q ranges from about 1 to about 3.

In another embodiment, the $V^2$ moiety is connected to $L^2$ via a sulfur atom and q is about 2.

In another embodiment, the $V^2$ moiety is connected to $L^2$ via a sulfur atom and q ranges from about 3 to about 5.

In another embodiment, the $V^2$ moiety is connected to $L^2$ via a sulfur atom and q is about 4.

In another embodiment, the $V^2$ moiety is connected to $L^2$ via a sulfur atom and q ranges from about 7 to about 9.

In another embodiment, the $V^2$ moiety is connected to $L^2$ via a sulfur atom and q is about 8.

In one embodiment, a compound of formula (III) exists as a mixture of separate compounds.

In one embodiment, a compound of formula (III) exists as a mixture of separate compounds wherein q for three compounds is 1, 2, and 3, respectively.

In one embodiment, a compound of formula (III) exists as a mixture of separate compounds wherein q for three compounds is 3, 4, and 5, respectively.

In one embodiment, a compound of formula (III) exists as a mixture of separate compounds wherein q for three compounds is 5, 6, and 7, respectively.

In one embodiment, a compound of formula (III) exists as a mixture of separate compounds wherein q for three compounds is 7, 8, and 9, respectively.

In another embodiment, the $V^2$ moiety is connected to $L^2$ via a nitrogen atom.

In yet another embodiment, the $V^2$ moiety is connected to $L^2$ via a carbon atom.

In another aspect of this invention, the $V^2$ moiety includes any unit that causes accumulation of compounds of the invention at the target site or in the vicinity thereof by a mechanism other than binding or reactively associating or complexing with a receptor, antigen, or other receptive moiety associated with a given target site, e.g., a target cell population. One way to achieve this is for example to use a large macromolecule as a $V^2$ moiety, which targets to solid tumor tissue through the enhanced permeability and retention (EPR) effect. Ringsdorf reported use of polymers to target antitumor agents to tumors.[17] Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.

The $V^2$ moiety may for example be a branched or unbranched polymer, such as for example poly[N-(2-hydroxypropyl)methacrylamide] (HPMA), poly(2-hydroxyethyl methacrylate) (HEMA), polyglutamic acid or poly-L-glutamic acid (PG), carboxymethyldextran (CMDex), a polyacetal, chitosan, a polypeptide, an oligoethylene glycol or polyethylene glycol (PEG), or a copolymer, such as an HPMA copolymer, an HPMA-methacrylic acid copolymer, a HEMA-methacrylic acid copolymer, a CMDex copolymer, a β-cyclodextrin copolymer, a PEG copolymer, or a poly(lactic-co-glycolic) acid copolymer.[18] In this document both polymer and copolymer are referred to as polymer.

The polymer may be connected to $L^2$ via any suitable functional group, which can be located at one or both ends of the polymer, meaning that in the conjugate q ranges from 1 to 2, or alternatively, the functional groups may (also) be located on groups pendant on the polymer such that $L^2$ is (also) connected to the polymer via these pendant groups with q typically ranging from 1 to about 1000. Optionally, the polymer may also contain an additional targeting group that can bind or reactively associate or complex with a receptive moiety, e.g., an antibody or antibody derivative, bonded to the polymer either via a pendant group or end group, such that improved targeting to the target site is achieved.

Alternatively, the $V^2$ moiety may be a dendrimer or a protein or protein fragment, e.g., albumin, which has no targeting properties except for its ability to accumulate at the target site because of its size or molecular weight.

In one embodiment, the $V^2$ moiety is a polymer.

In another embodiment, the $V^2$ moiety is a polymer and q ranges from 1 to about 1000.

In other embodiments, the $V^2$ moiety is a polymer and q ranges from 1 to about 500 or 400 or 300 or 200 or 100 or less than 100.

In another embodiment, the $V^2$ moiety is a polymer and q ranges from 1 to 2.

In a specific embodiment, the $V^2$ moiety is an oligoethylene glycol or a polyethylene glycol or a derivative thereof.

In another embodiment, the $V^2$ moiety is a dendrimer, a protein, or a protein fragment.

In another embodiment, the $V^2$ moiety is a moiety that is able to transport the conjugate across a biological barrier, e.g., a cell membrane, either with or without prior binding, associating, or complexing with a receptor or receptor complex. In one embodiment, the $V^2$ moiety is a Tat peptide or a derivative, fragment, or analog thereof, or a moiety that has similar transmembrane delivery properties. In another embodiment, the $V^2$ moiety is protein or protein fragment, an antibody or an antibody fragment, a receptor-binding or peptide vector moiety, or a polymeric or dendritic moiety, or any combination thereof, to which is attached a Tat peptide or a derivative, fragment, or analog thereof, or a moiety that has similar transmembrane delivery properties.

Thus, in one aspect of the invention, the moiety $V^2$ is a targeting moiety and is for example selected from the group consisting of a protein or protein fragment, an antibody or an antibody fragment, a receptor-binding or peptide vector moiety, and a polymeric or dendritic moiety, or any combination thereof.

In another aspect of the invention, the $V^2$ moiety is a moiety that improves the pharmacokinetic properties of a conjugate of the invention. For example, the moiety $V^2$ can be chosen such that the water solubility of the conjugate is (further) improved. This can be achieved by choosing $V^2$ to be a hydrophilic moiety. Alternatively, the $V^2$ moiety can be used to for example increase the residence time of the compound in the circulation, to reduce extravasation and excretion, to reduce aggregation, and/or to reduce the immunogenicity of the compound. This can for example be achieved by choosing $V^2$ to be a polyethylene glycol or oligoethylene glycol or derivative thereof. When the moiety $V^2$ is a moiety that improves the pharmacokinetic properties of the compound of the invention, $V^1$ is a moiety that can be cleaved or transformed aspecifically, and there are no $V^{1'}$ and $V^{2'}$ moieties, the compound solely serves to improve the (pharmacokinetic) properties of the one or more Z moieties.

In one embodiment, $V^2$ is a moiety that improves the pharmacokinetic properties and $V^1$ is a moiety that can be cleaved or transformed specifically.

In another embodiment, $V^2$ is an oligoethylene glycol or a polyethylene glycol or a derivative thereof and $V^1$ is a moiety that can be cleaved or transformed specifically.

In one embodiment, $V^2$ is a moiety that improves the pharmacokinetic properties and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved or transformed aspecifically.

In another embodiment, $V^2$ is an oligoethylene glycol or a polyethylene glycol or a derivative thereof and $V^1$ is a moiety that can be cleaved by ubiquitous enzymes.

In another embodiment, $V^2$ is an oligoethylene glycol or a polyethylene glycol or a derivative thereof and $V^1$ is a hydrolysable moiety.

In one aspect of this invention, the $V^2$ moiety is represented by formula (VI):

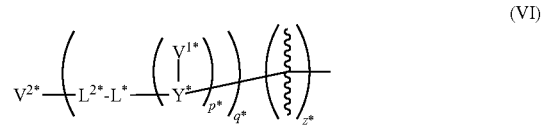

wherein $V^{2*}$, $L^{2*}$, $L^*$, $V^{1*}$, $Y^*$, $p^*$, $q^*$, and $z^*$ have the same meaning as $V^2$, $L^2$, $L$, $V^1$, Y, p, q, and z as defined in this document, except that $Y^*$ is connected to $L^2$. It should be noted that $z^*$ actually equals q. When a compound of formula (III) contains a $V^2$ moiety represented by formula (VI), the one or more $L^2$ moieties are thus connected to $Y^*$. It should be understood that in this document, whenever $V^2$, $L^2$, L, $V^1$, Y, p, q, or z is mentioned, the same can apply for each $V^{2*}$, $L^{2*}$, L*, $V^{1*}$, Y*, p*, q*, or z*, respectively.

Use of a $V^2$ moiety of formula (VI) in a conjugate of formula (III) implicates that two conditionally-cleavable or conditionally-transformable moieties may be present in the same promoiety, and therefore two separate cleavages/transformations may be required to completely remove the promoiety. The requirement that two different conditions need to have been met before one or more Z are released might favorably affect the properties of the conjugate. For instance, it may increase the targeting efficiency of the conjugate. The two transformations/cleavages may occur at different extracellular/intracellular locations. The moiety to be removed by the second cleavage or as a consequence of the second transformation may be used in this instance to help transport Z from a first extracellular or intracellular location to a second extracellular or intracellular location.

It will be apparent that a $V^2$ moiety of formula (VI) cannot only be useful in conjugates of a compound of formula (I) or (II), but may be used in similar conjugates of other therapeutic agents, diagnostic moieties, and the like.

It can be understood that the functional moiety $V^2$ can have several functional properties combined. For example, $V^2$ can be a moiety that improves the pharmacokinetic properties of a compound of this invention and at the same time be or contain a targeting moiety.

Conjugates of the invention may contain one or more promoieties. These promoieties may be the same or different. The presence of two or more promoieties may favorably affect the properties of the conjugate. For instance, it may improve the water solubility and/or increase the targeting efficiency of the conjugate. In one embodiment, when there are two or more promoieties, said promoieties are different from each other. The two or more different promoieties may have different functions and may be removed under different conditions and at different extracellular/intracellular locations.

In one embodiment, there is one promoiety linked to Z.

In another embodiment, there is one promoiety linked to Z via $X^1$.

In another embodiment, there are two promoieties linked to Z.

In another embodiment, there are two promoieties linked to Z, of which one is connected via $X^1$.

In yet another embodiment, there are three promoieties linked to Z.

In yet another embodiment, there are three promoieties linked to Z, of which one is connected via X.

In one embodiment, a compound of formula (III) is represented by a compound of formula (III-1) or (III-2):

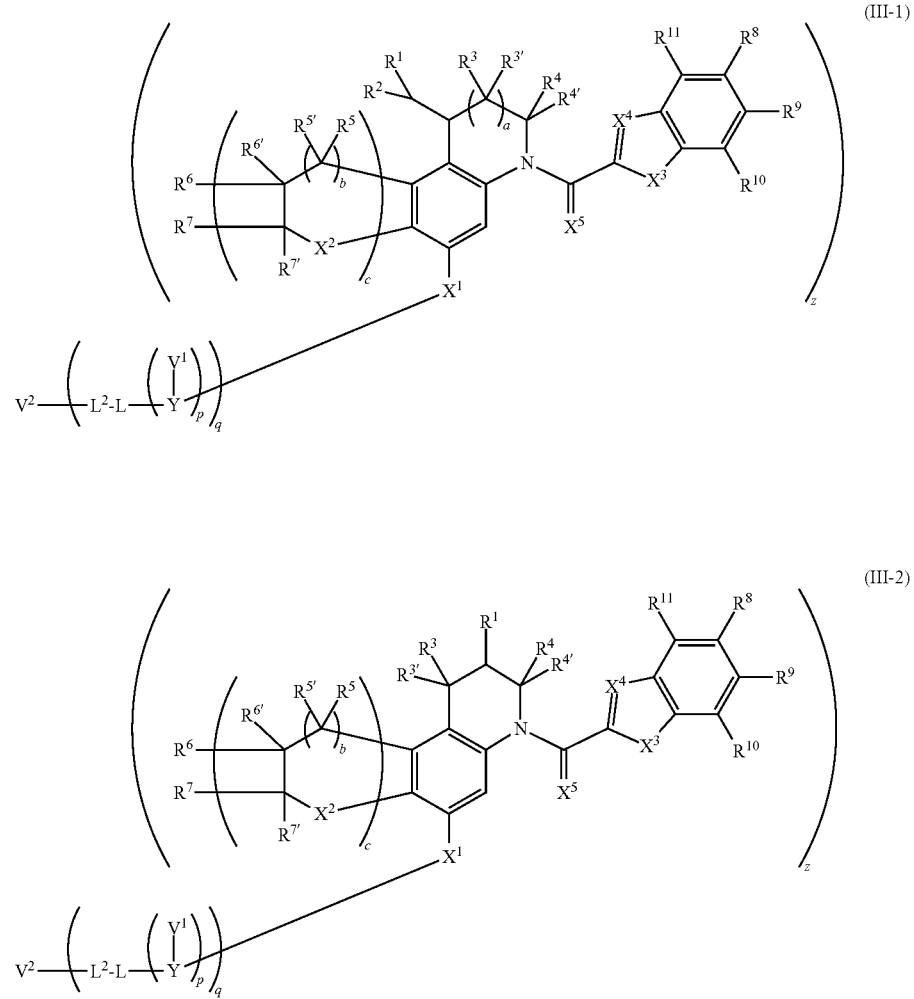

In another embodiment, a compound of formula (III) is represented by a compound of formula (III-3) or (III-4):

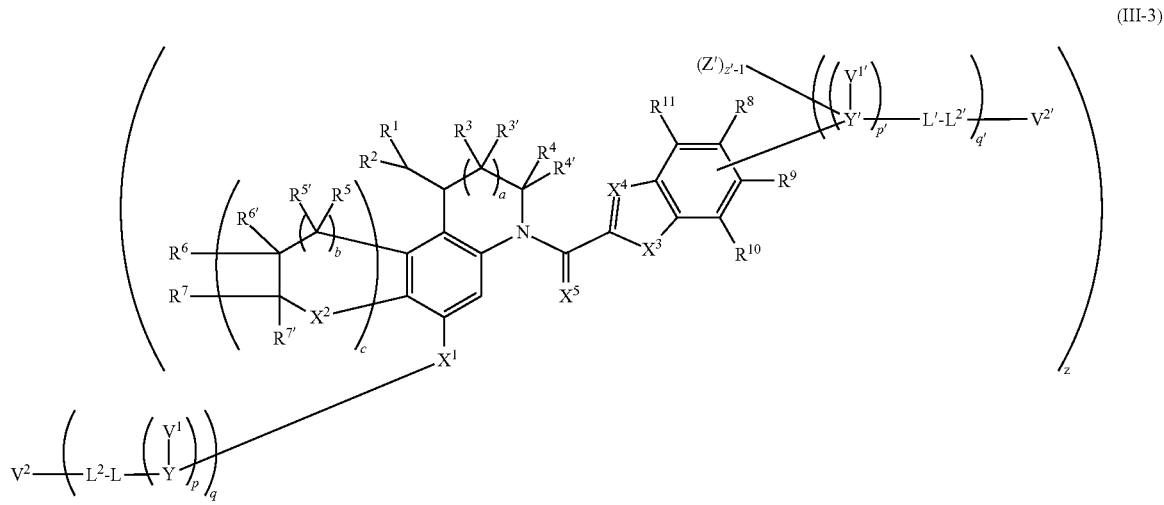

(III-3)

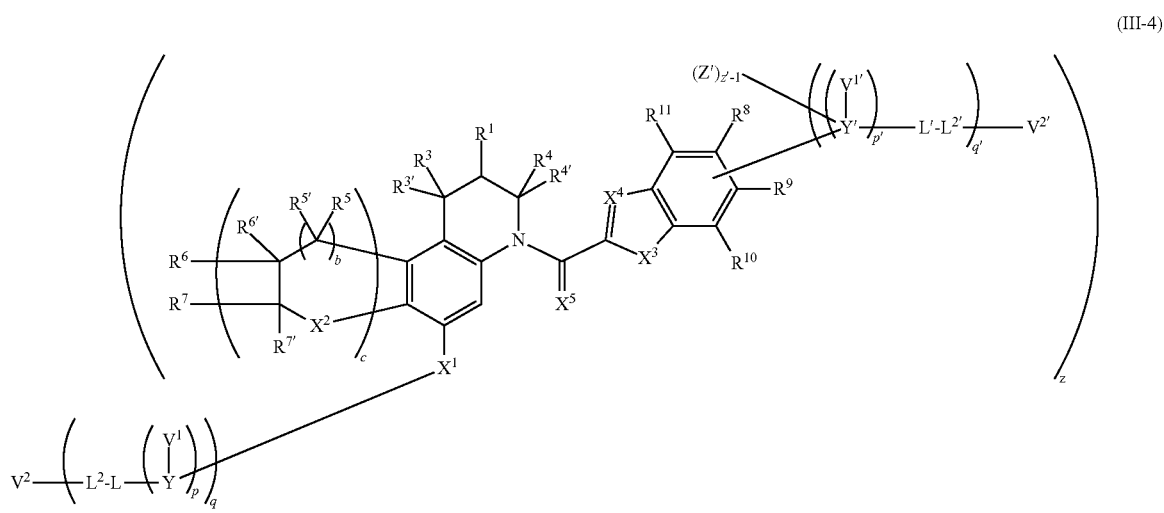

(III-4)

wherein Y' is connected to an atom being part of $R^8$, $R^9$, $R^{10}$, or $R^{11}$.

In one embodiment, p is an integer from 1 (included) to 128 (included). In another embodiment, q is an integer from 1 (included) to 1000 (included). In other embodiments, p is an integer from 1 (included) to 64 (included) or 32 (included) or 16 (included) or 8 (included) or 4 (included) or 2 (included). In again other embodiments, q is an integer from 1 (included) to 500 (included) or 400 (included) or 300 (included) or 200 (included) or 100 (included) or 16 (included) or 8 (included) or 6 (included) or 4 (included) or 2 (included).

In one embodiment, if more than 1 promoiety is connected to a first Z and in one of the promoieties there is more than one attachment site for Z moieties, then the other of said promoieties connected to said first Z contain a single attachment site for a Z moiety.

In one embodiment, a compound of formula (III) is represented by

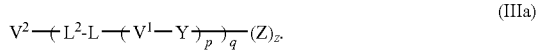

(IIIa)

In one embodiment, p in a compound of formula (IIIa) is 1.

In another embodiment, in a compound of formula (IIIa) p is 1 and z equals q.

In another embodiment, a compound of formula (IIIa) is represented by

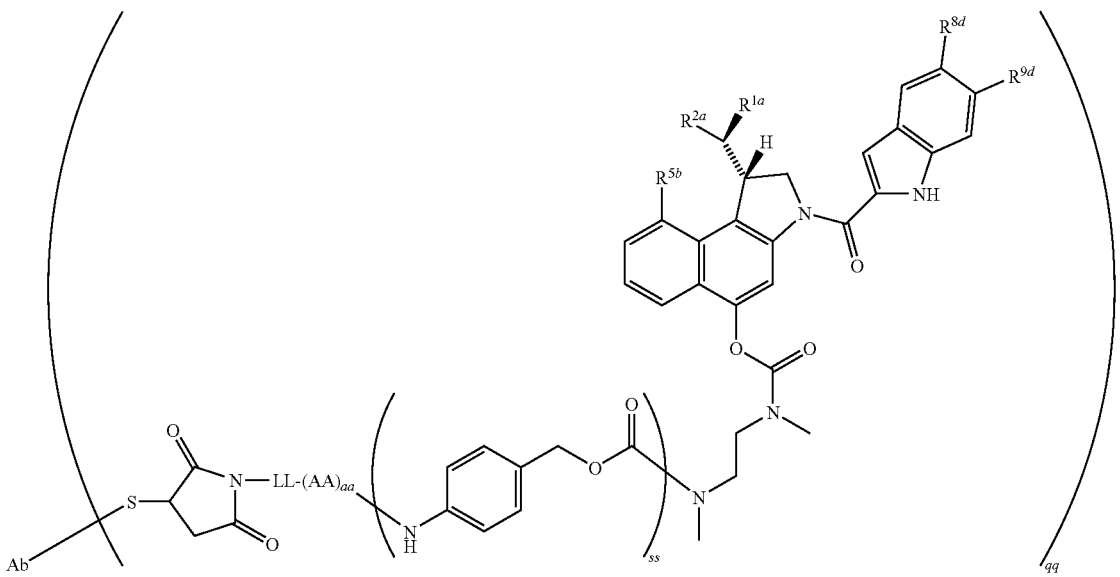

or by its (1R,10S) isomer, its (1R,10R) isomer, its (1S,10S) isomer, or by a mixture of two or more of said isomers, wherein $R^{1a}$ is chloro (Cl) or bromo (Br), $(AA)_{aa}$ is selected from valylcitrulline, valyllysine, phenylalanyllysine, alanylphenylalanyllysine, and D-alanylphenylalanyllysine, ss is 1 or 2, $R^{2a}$ and $R^{5b}$ are methyl and H, respectively, or H and methyl, respectively, $R^{8d}$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy, $R^{9d}$ is selected from H and methoxy, LL is selected from

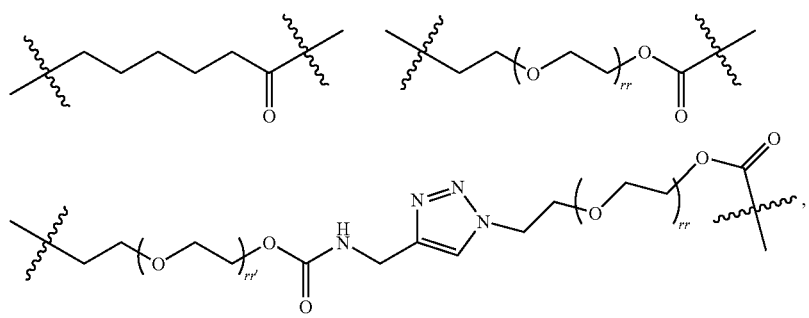

qq ranges from 1 to about 20, rr and rr' each independently range from 1 to about 4, and Ab is an antibody or a fragment or derivative thereof.

In one embodiment, a compound of formula (III) is represented by

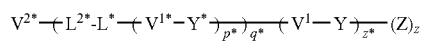
(IIIa*)

In one embodiment, p* in a compound of formula (IIIa*) is 1.

In another embodiment, in a compound of formula (IIIa*) p* is 1 and z* equals q*.

In another embodiment, a compound of formula (III) is represented by

(IIIb)

In one embodiment, p in a compound of formula (IIb) is 1.

In one embodiment, a compound of formula (III) is represented by

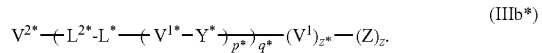
(IIIb*)

In one embodiment, p* in a compound of formula (IIIb*) is 1.

In another embodiment, in a compound of formula (IIIb*) p* is 1 and z* equals q*.

In another embodiment, $V^1$ in a compound of formula (IIIb*) is an enzyme-cleavable substrate. In a further embodiment, $V^1$ can be cleaved by an intracellular enzyme. In another embodiment, $V^1$ is an optionally substituted dialkylaminocarbonyl group wherein the two alkyl groups may be the same or different and optionally be connected to each other to form an optionally substituted carbocycle or heterocycle. In yet another embodiment, $V^1$ is piperazinocarbonyl.

In another embodiment, a compound of formula (IIIb*) is represented by

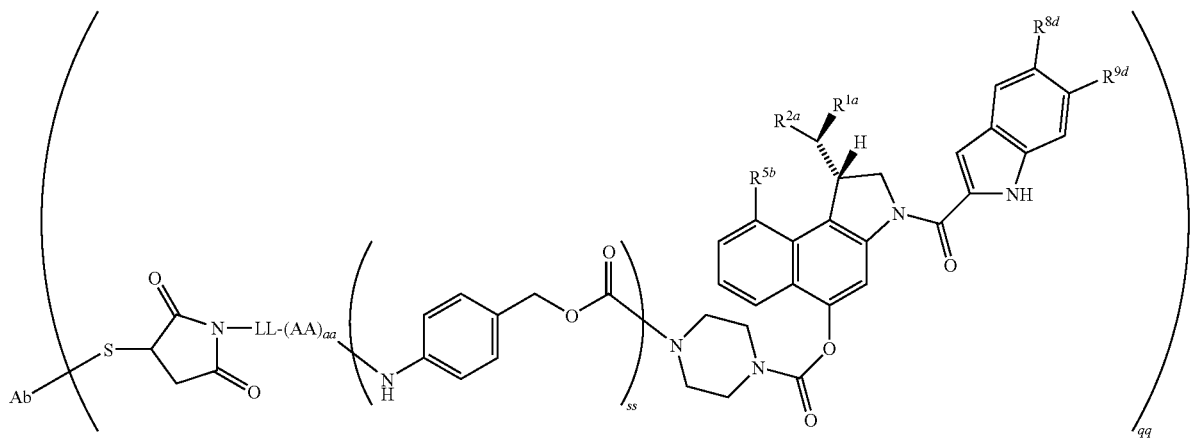

or by its (1R,10S) isomer, its (1R,10R) isomer, its (1S,10S) isomer, or by a mixture of two or more of said isomers, wherein $R^{1a}$ is chloro (Cl) or bromo (Br), $(AA)_{aa}$ is selected from valylcitrulline, valyllysine, phenylalanyllysine, alanylphenylalanyllysine, and D-alanylphenylalanyllysine, ss is 1 or 2, $R^{2a}$ and $R^{5b}$ are methyl and H, respectively, or H and methyl, respectively, $R^{8d}$ is selected from 2-(morpholin-4-yl)ethoxy, (1-methylpiperidin-4-yl)methoxy, 2-(N,N-dimethylamino)ethoxy, 2-(N,N-dimethylamino)acetylamino, 2-(methylamino)ethoxy, 2-(methylamino)acetylamino, 2-aminoethoxy, 2-aminoacetylamino, (piperidin-4-yl)methoxy, 2-(N-methyl-N-(carboxymethyl)amino)ethoxy, and 2-(N-methyl-N-(2-methoxy-2-oxoethyl)amino)ethoxy, $R^{9d}$ is selected from H and methoxy, LL is selected from qq ranges from 1 to about 20, rr and rr' each independently range from 1 to about 4, and Ab is an antibody or a fragment or derivative thereof.

In another embodiment, a compound of formula (III) is represented by $$V^2\!-\!\!\left(\!L^2\text{-}L\text{-}V^1\!-\!Z\right)_q. \tag{IIIc}$$

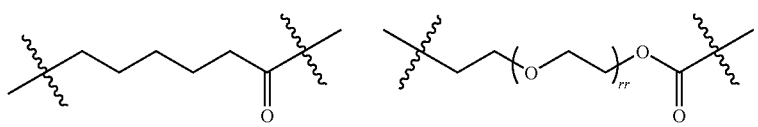

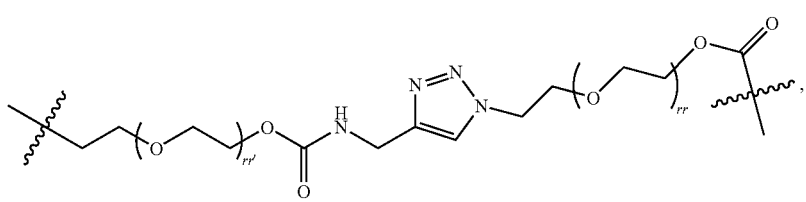

In yet another embodiment, a compound of formula (III) is represented by $$V^1\text{-}Z \quad \quad \text{(IIId).}$$

In one embodiment, a compound of formula (IIId) is represented by

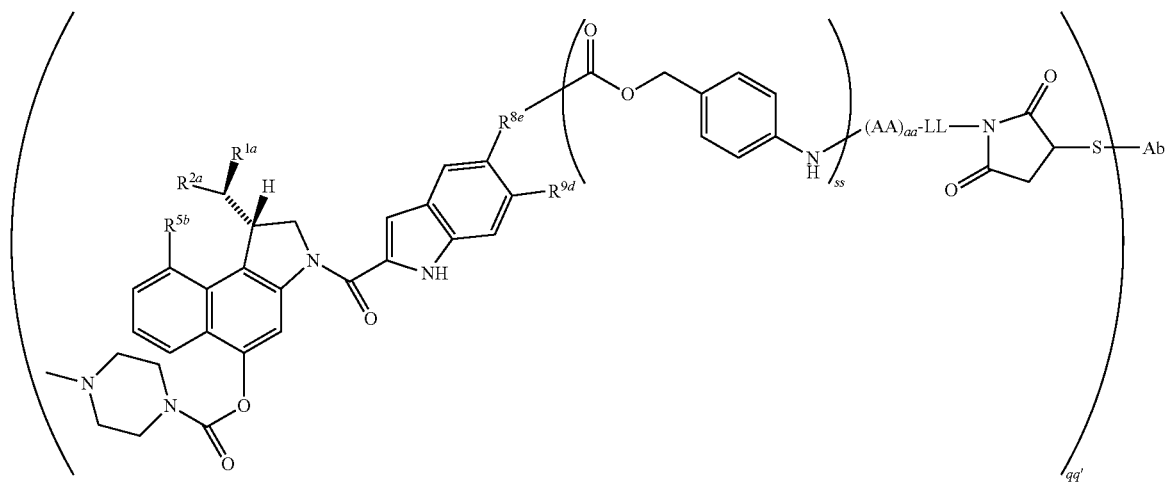

or by its (1R,10S) isomer, its (1R,10R) isomer, its (1S,10S) isomer, or by a mixture of two or more of said isomers, wherein $R^{1a}$ is chloro (Cl) or bromo (Br), $(AA)_{aa}$ is selected from valylcitrulline, valyllysine, phenylalanyllysine, alanylphenylalanyllysine, and D-alanylphenylalanyllysine, ss is 1 or 2, $R^{2a}$ and $R^{5b}$ are methyl and H, respectively, or H and methyl, respectively, $R^{8e}$ is selected from 2-(methylamino)ethoxy, 2-(methylamino)acetylamino, 2-aminoethoxy, 2-aminoacetylamino, and (piperidin-4-yl)methoxy, in which the carbonyl connected to $R^{8e}$ is attached to the nitrogen atom of $R^{8e}$, $R^{9d}$ is selected from H and methoxy, LL is selected from

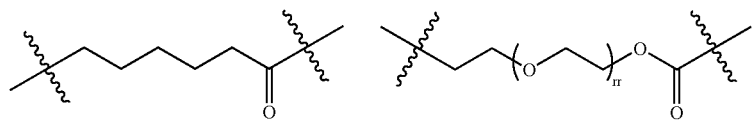

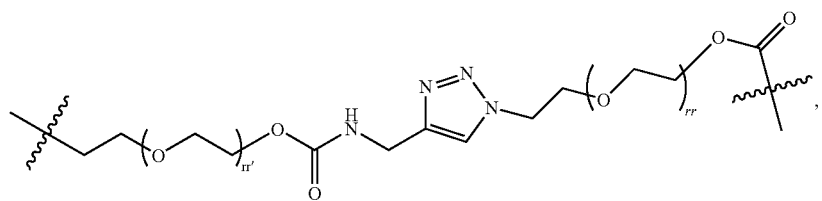

qq' ranges from 1 to about 20, rr and rr' each independently range from 1 to about 4, and Ab is an antibody or a fragment or derivative thereof.

In one embodiment, the invention relates to a compound of formula (IIId1) or (IIId2):

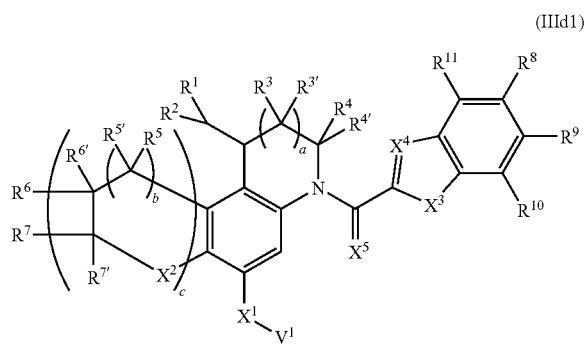

(IIId1)

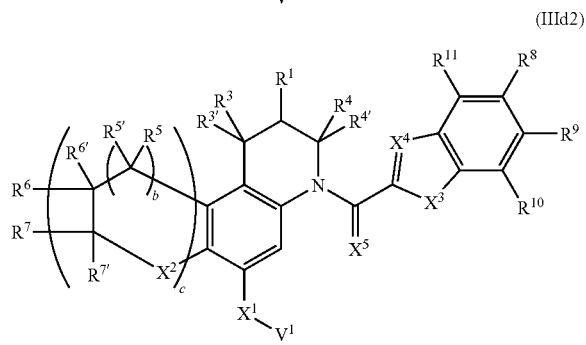

(IIId2)

wherein $V^1$ is a monosaccharide, disaccharide or oligosaccharide of hexoses or pentoses or heptoses that may also be included among the group of desoxy sugars or amino sugars and belong to the D-series or L-series and in the disaccharides or oligosaccharides are either identical or different, or wherein $V^1$ has the formula —$C(OR^{a'})R^{b'}CHR^{c'}R^{d'}$, wherein $R^{a'}$, $R^{b'}$, $R^{c'}$, and $R^{d'}$ have the same meaning as defined hereinabove.

In one embodiment, a compound of this invention is represented by

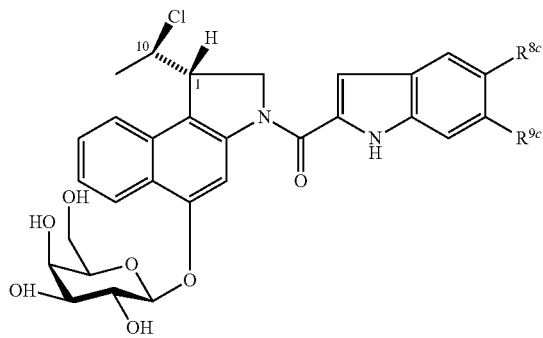

or by its (1R,10S) isomer, its (1R,10R) isomer, its (1S,10S) isomer, or by a mixture of two or more of said isomers, wherein $R^{8c}$ is selected from 2-(morpholin-4-yl)ethoxy, (1-methylpiperidin-4-yl)methoxy, 2-(N,N-dimethylamino)ethoxy, and 2-(N,N-dimethylamino)acetylamino, and $R^{9c}$ is selected from H and $OCH_3$.

In a more specific embodiment, a compound of this invention is represented by

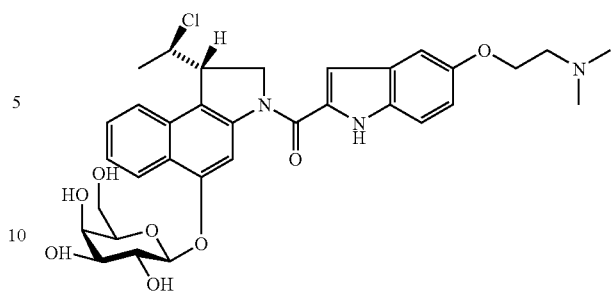

or by its (1R,10S) isomer, its (1R,10R) isomer, its (1S,10S) isomer, or by a mixture of two or more of said isomers.

In another more specific embodiment, a compound of this invention is represented by

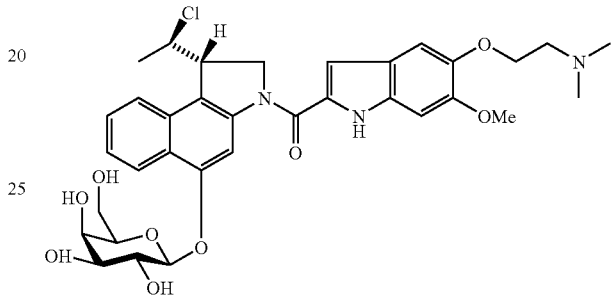

or by its (1R,10S) isomer, its (1R,10R) isomer, its (1S,10S) isomer, or by a mixture of two or more of said isomers.

In another more specific embodiment, a compound of this invention is represented by

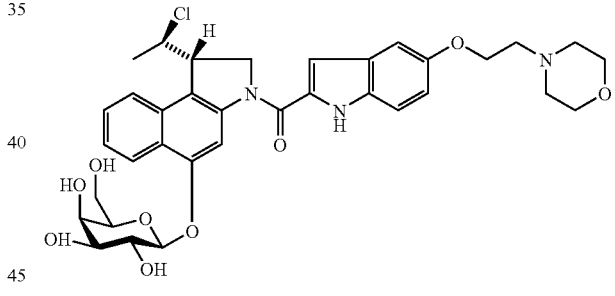

or by its (1R,10S) isomer, its (1R,10R) isomer, its (1S,10S) isomer, or by a mixture of two or more of said isomers.

In another more specific embodiment, a compound of this invention is represented by

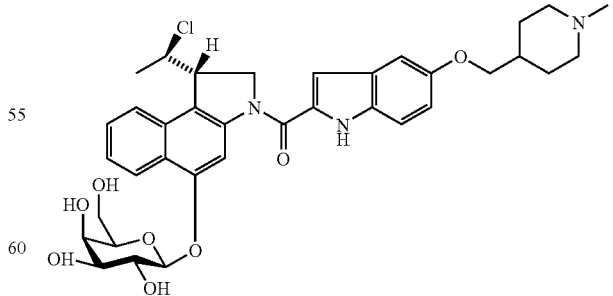

or by its (1R,10S) isomer, its (1R,10R) isomer, its (1S,10S) isomer, or by a mixture of two or more of said isomers.

In another more specific embodiment, a compound of this invention is represented by

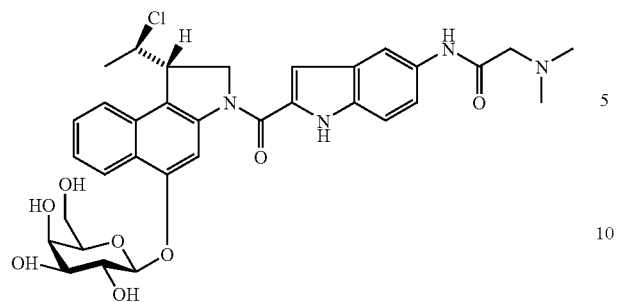

or by its (1R,10S) isomer, its (1R,10R) isomer, its (1S,10S) isomer, or by a mixture of two or more of said isomers.

In one embodiment, a compound of this invention is represented by

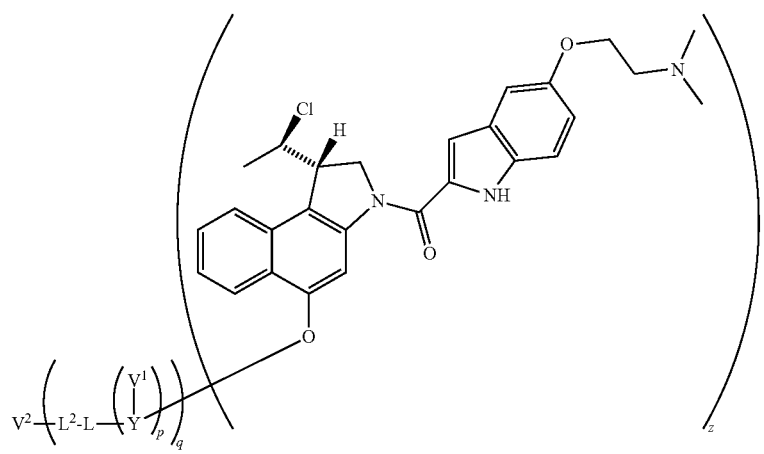

or by its (1R,10S) isomer, its (1R,10R) isomer, its (1S,10S) isomer, or by a mixture of two or more of said isomers.

In another embodiment, a compound of this invention is represented by

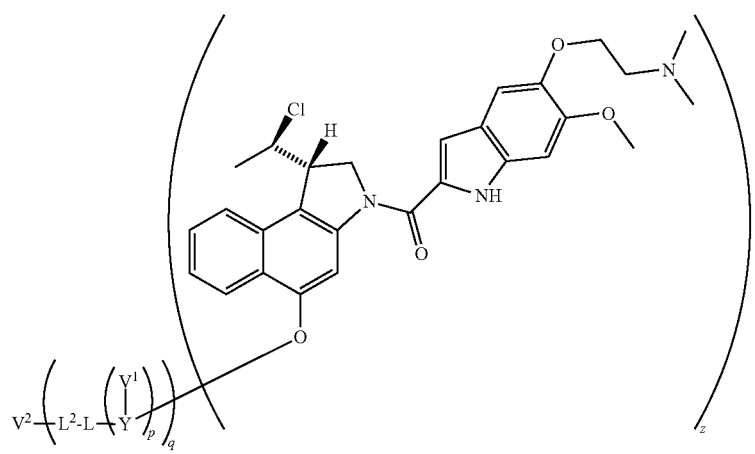

or by its (1R,10S) isomer, its (1R,10R) isomer, its (1S,10S) isomer, or by a mixture of two or more of said isomers.

In another embodiment, a compound of this invention is represented by

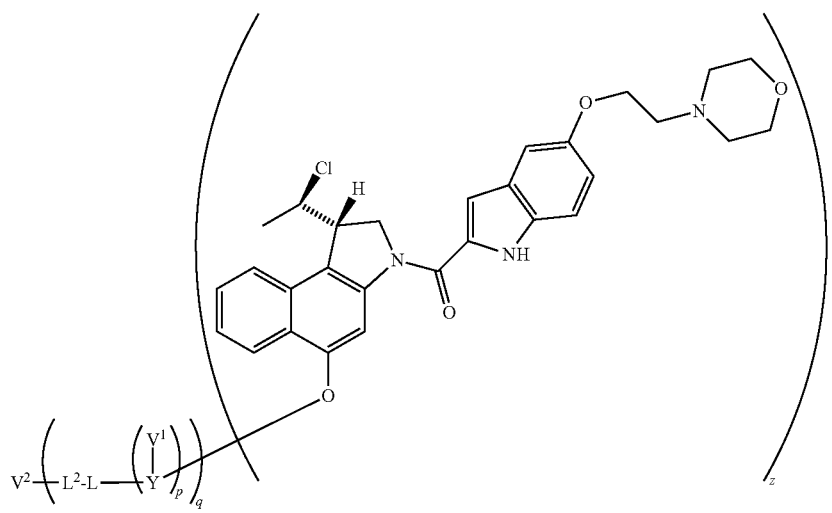

or by its (1R,10S) isomer, its (1R,10R) isomer, its (1S,10S) isomer, or by a mixture of two or more of said isomers.

In another embodiment, a compound of this invention is represented by

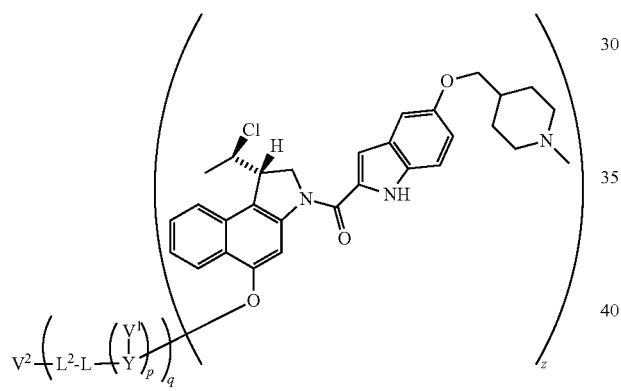

or by its (1R,10S) isomer, its (1R,10R) isomer, its (1S,10S) isomer, or by a mixture of two or more of said isomers.

In another embodiment, a compound of this invention is represented by

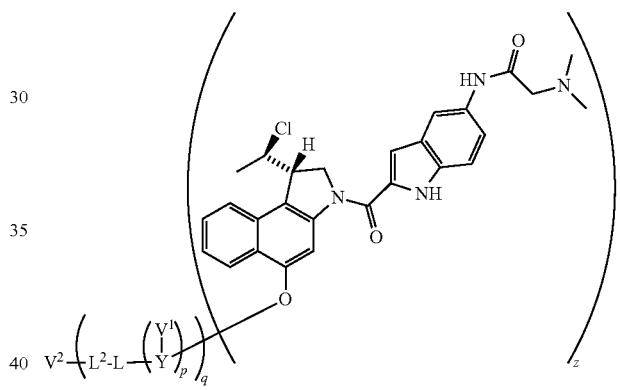

or by its (1R,10S) isomer, its (1R,10R) isomer, its (1S,10S) isomer, or by a mixture of two or more of said isomers.

In another embodiment, a compound of this invention is represented by

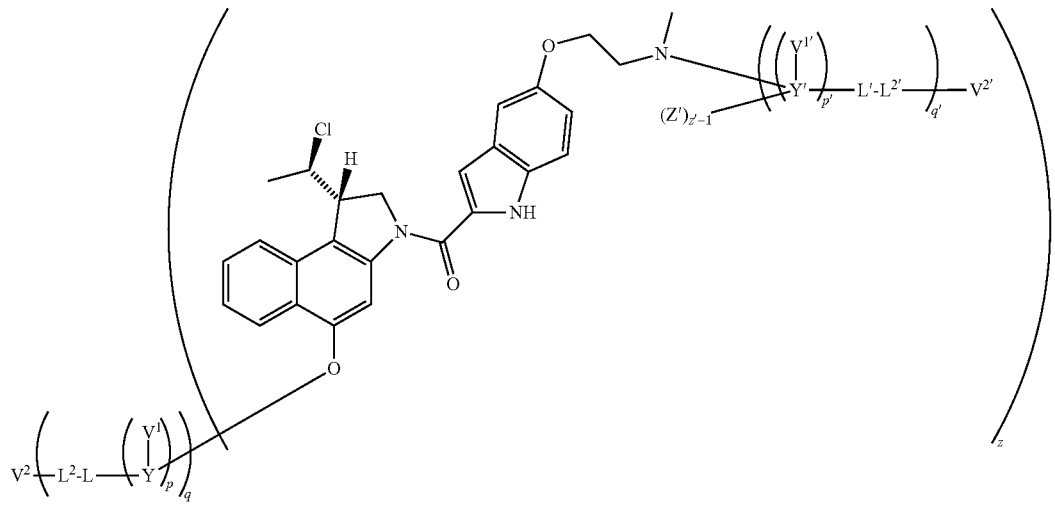

or by its (1R,10S) isomer, its (1R,10R) isomer, its (1S,10S) isomer, or by a mixture of two or more of said isomers.

In another embodiment, a compound of this invention is represented by

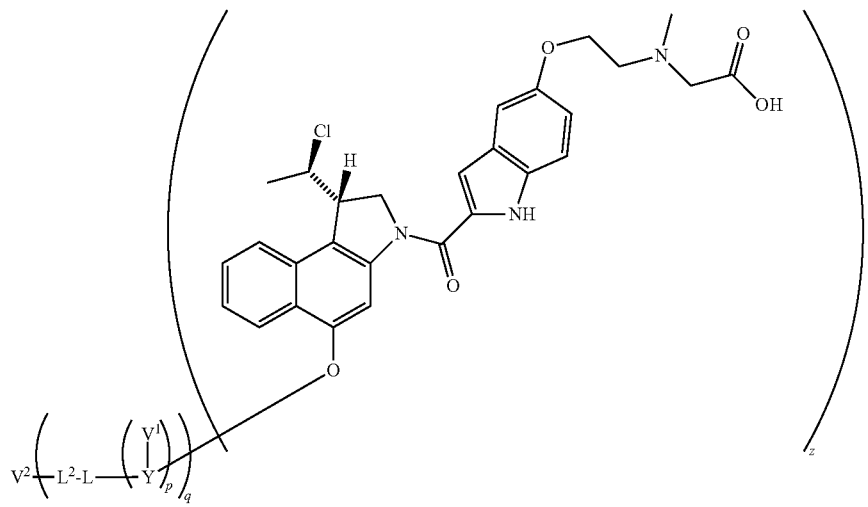

or by its (1R,10S) isomer, its (1R,10R) isomer, its (1S,10S) isomer, or by a mixture of two or more of said isomers.

In another embodiment, a compound of this invention is represented by

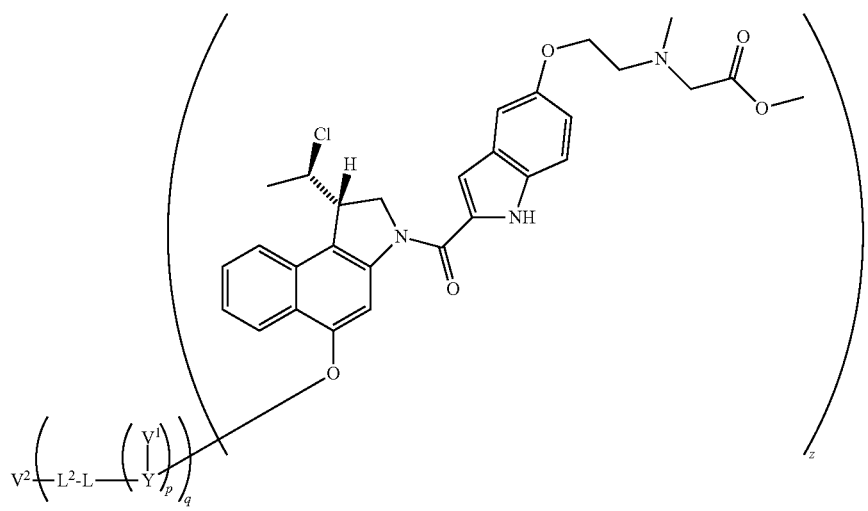

or by its (1R,10S) isomer, its (1R,10R) isomer, its (1S,10S) isomer, or by a mixture of two or more of said isomers.

In another embodiment, a compound of this invention is represented by

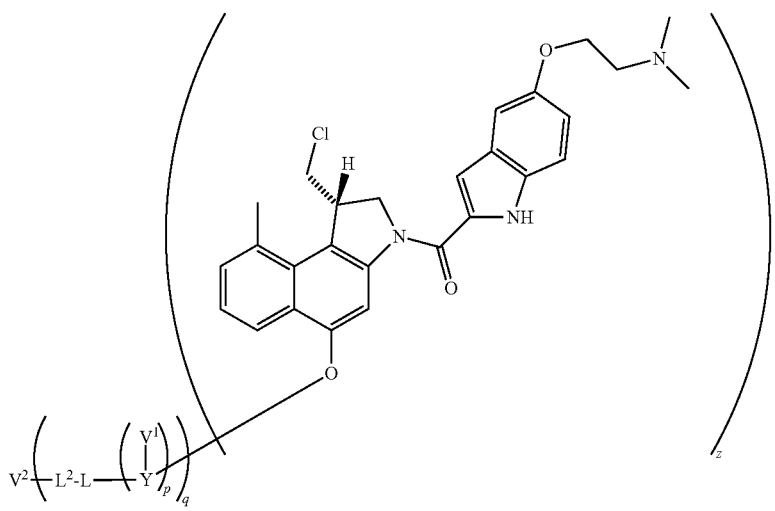

or by its (1R) isomer or by a mixture of the two isomers.

Synthesis, In Vitro Cytotoxicity, and Biological Evaluation of Compounds of the Invention As described in more detail below, compounds of formulae (I), (II), and (III), as well as compounds of formula (IV), can be conveniently prepared in a way for some part analogous to compounds reported in for example WO 01/83448, DE 4415463, WO 2004/043493, and WO 02/083180.

In one embodiment, a compound of formula (I) or (II) is used to prepare a compound of formula (III). In another embodiment, a compound of formula (I) or (II) is used to prepare a compound of formula (IV). In another embodiment, a compound of formula (IV) is used to prepare a compound of formula (III). In another embodiment, a compound of formula (III) wherein $V^1$ is a protecting group is used to prepare another compound of formula (III) wherein $V^1$ is an in vivo removable moiety.

Figure 4:
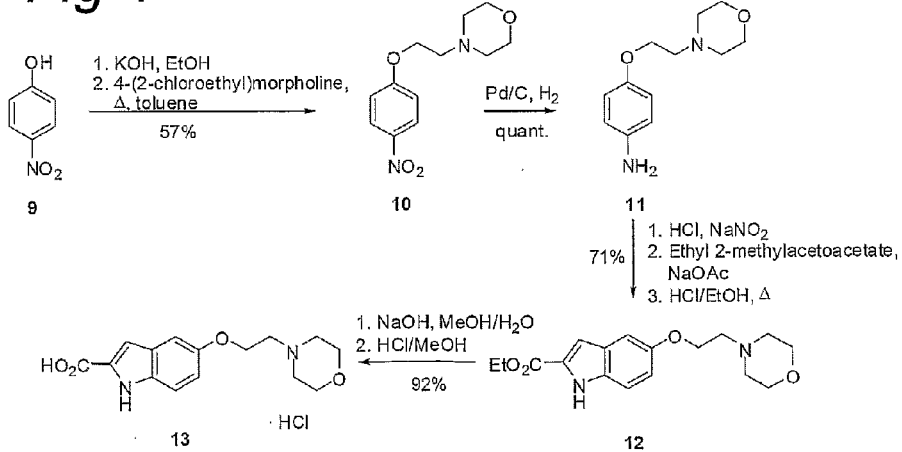
FIG. 4 depicts the preparation of DNA binder 13.

Several DNA binding units containing a water-soluble group were prepared with good yields. FIG. 4 describes the synthesis of DNA binder 13, carrying a 5-(2-(morpholin-4-yl)ethoxy) group. 4-Nitrophenol 9 was alkylated with 4-(2-chloroethyl)morpholine to give 10. Reduction of the nitro group to give 11 and subsequent Fisher indole synthesis afforded indole 12. Saponification finally afforded compound 13 in 37% overall yield.

Figure 5:
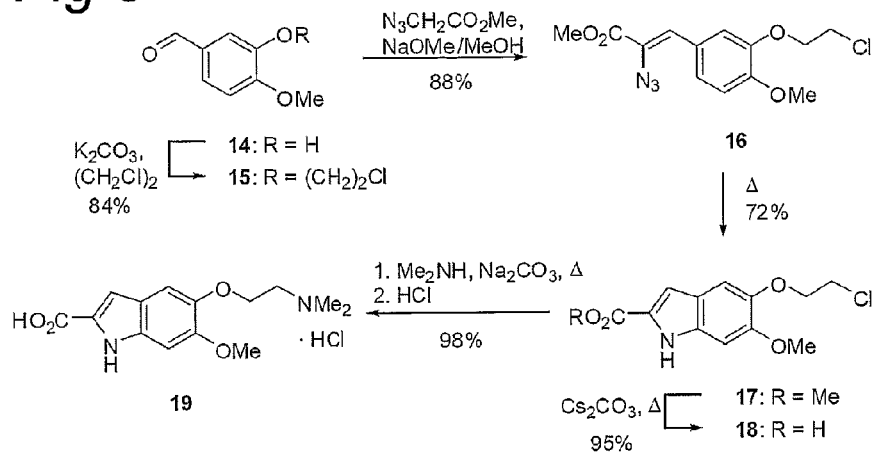
FIG. 5 illustrates the preparation of DNA binder 19.

FIG. 5 describes the synthesis of DNA binder 19. Starting from aldehyde 14, alkylation to give 15 and subsequent aldol condensation afforded azide 16. Ring closure gave indole 17, which was saponificated to give 18. Substitution of chloride by dimethylamine finally afforded 19 in 50% overall yield.

Figure 6:
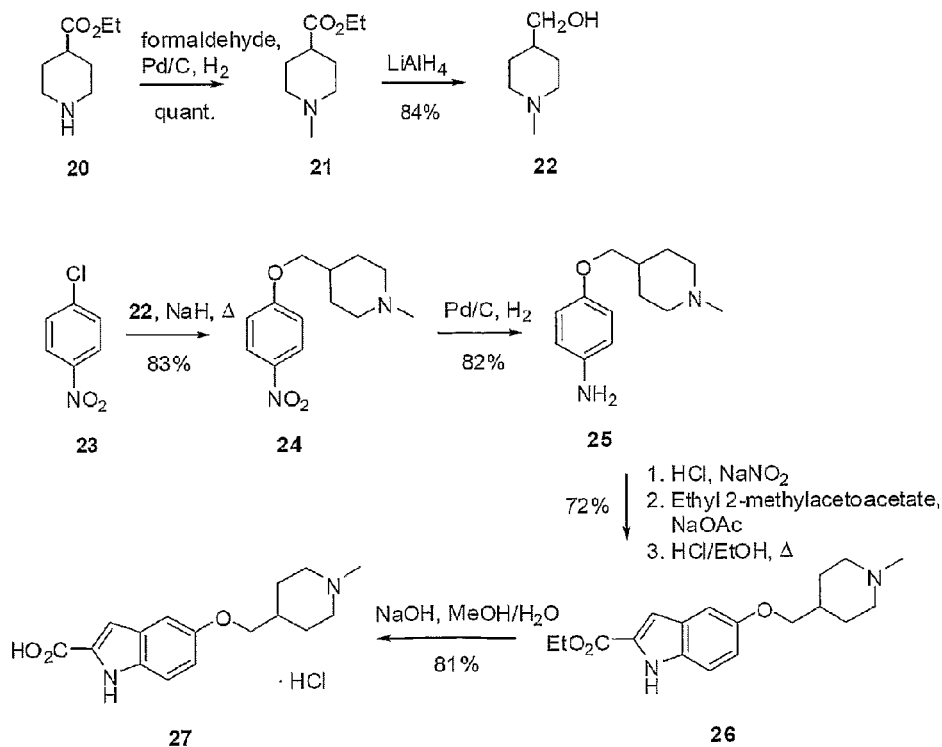
FIG. 6 describes the preparation of DNA binder 27.

FIG. 6 describes the synthesis of DNA binder 27 starting from ethyl isonipecotate (20). Methylation to give 21 was followed by reduction of the ester group to give 22. This was coupled to 1-chloro-4-nitrobenzene (23) to give 24. Reduction of the nitro group afforded 25. Fisher indole synthesis afforded 26; saponification finally gave 27 in 40% overall yield.

Figure 7:
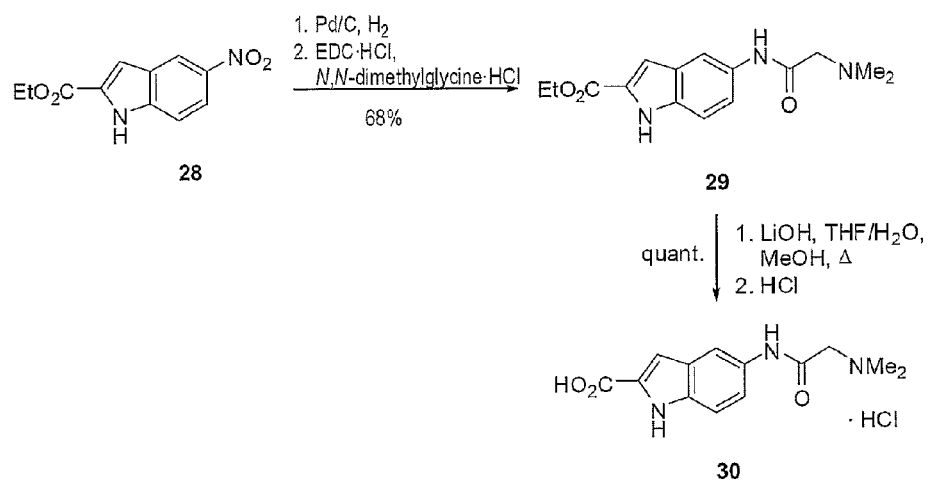
FIG. 7 illustrates the preparation of DNA binder 30.

The preparation of DNA binder 30 is depicted in FIG. 7. Starting from ester 28, reduction of the nitro group and subsequent coupling with N,N-dimethylglycine gave 29. Saponification of the ester group finally gave 30 in 68% yield.

Figure 8:
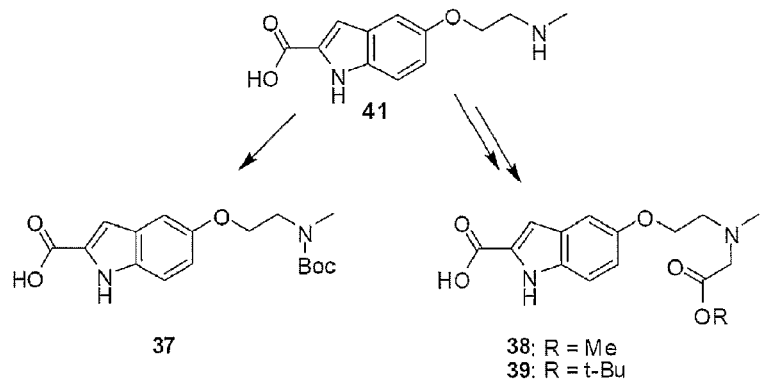
FIG. 8 illustrates the preparation of compounds 37-39 from DNA binder 41.

FIG. 8 depicts DNA binder 41 and its use for the preparation of Boc-protected DNA binder 37, DNA binder 38, and tert-butyl-protected DNA binder 39.

Figure 2:
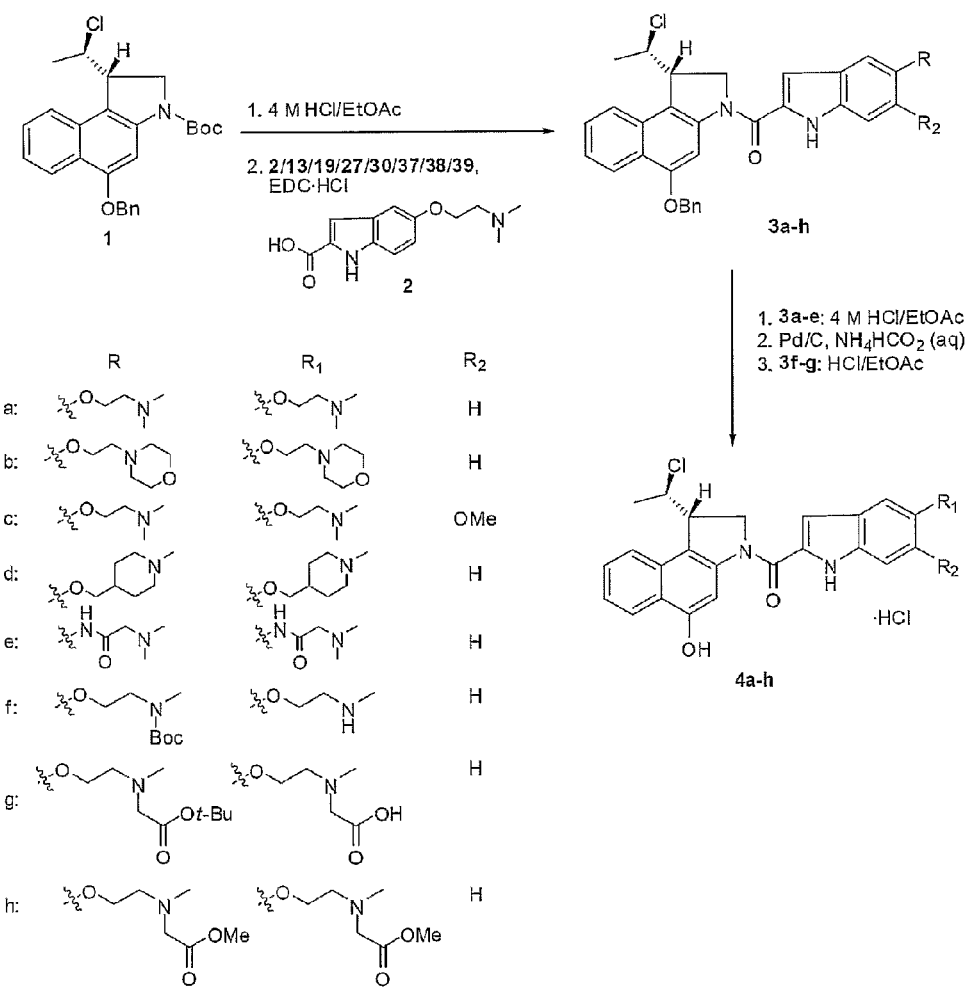
FIG. 2 illustrates the preparation of some agents by coupling a DNA-alkylating unit to a DNA-binding unit.

FIG. 2 depicts the partial deprotection of doubly protected DNA alkylator 1 followed by coupling of the amino group with DNA binders 2, 13, 19, 27, 30, 37, 38, and 39, respectively. This provided protected compounds 3a-h, which were deprotected to provide agents 4a-h.

Figure 9:
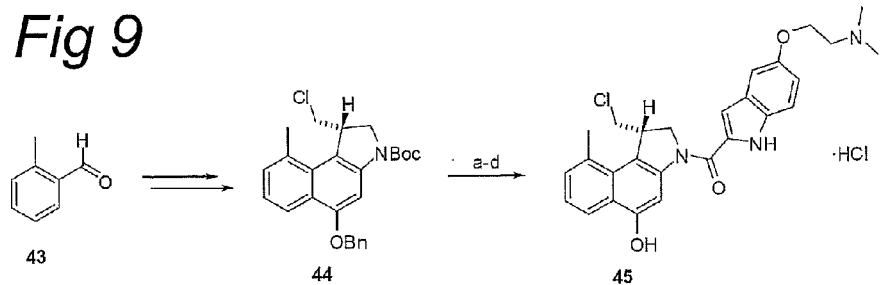
FIG. 9 illustrates the synthesis of agent 45.

FIG. 9 depicts the synthesis of agent 45 from compound 44 and DNA binder 2 following a similar protocol as for the preparation of agents 4a-h. Compound 44 was prepared analogously to the preparation of compound $1^{10}$, o-tolualdehyde instead of benzaldehyde being used as a starting material.

Figure 10:
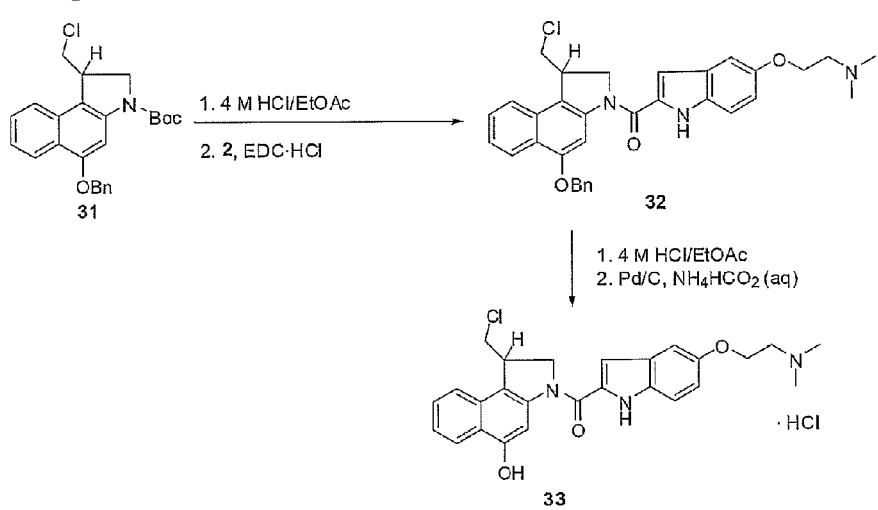
FIG. 10 describes the synthesis of agent 33.

Similarly, FIG. 10 depicts the synthesis of agent 33. Starting from 31, partial deprotection followed by coupling with DNA binder 2 gave 32. Final deprotection afforded agent 33.

Figure 3:
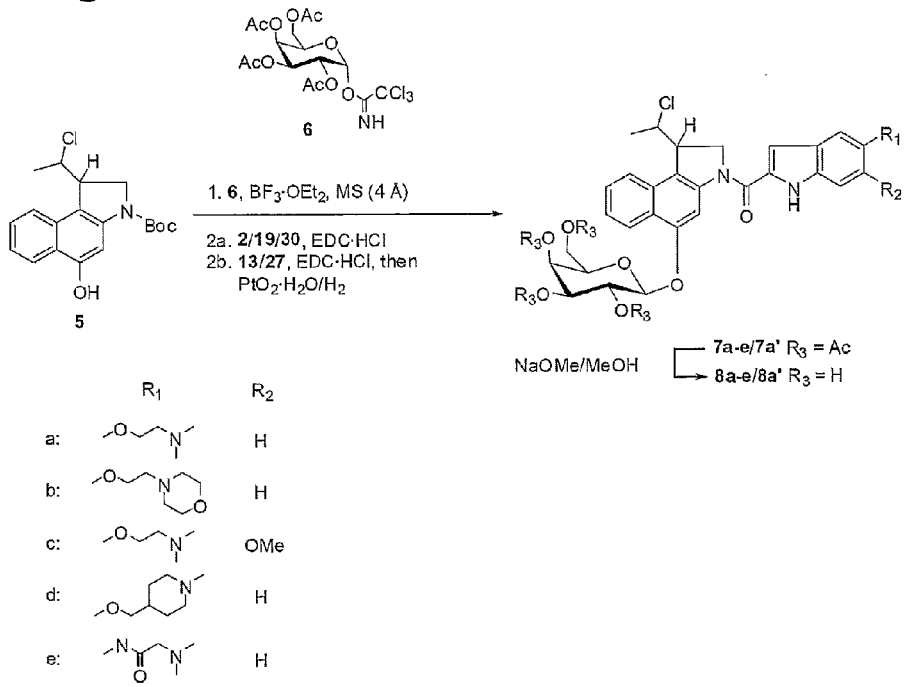
FIG. 3 illustrates the preparation of some β-galactopyranose conjugates of this invention.

FIG. 3 depicts the synthesis of several galactose conjugates. Starting from partially protected alkylating unit 5, coupling of O-(2,3,4,6-tetra-O-acetyl-α-D-galactopyranosyl) trichloracetimidate (6), subsequent deprotection, and coupling with a DNA binder moiety provided protected conjugates 7a-e. The synthesis of conjugates 7b and 7d required an additional reduction step using $PtO_2.H_2O/H_2$. Final deprotection provided galactose conjugates (1S,10R)-8a-e/(1R,10S)-8a'.

Figure 11:
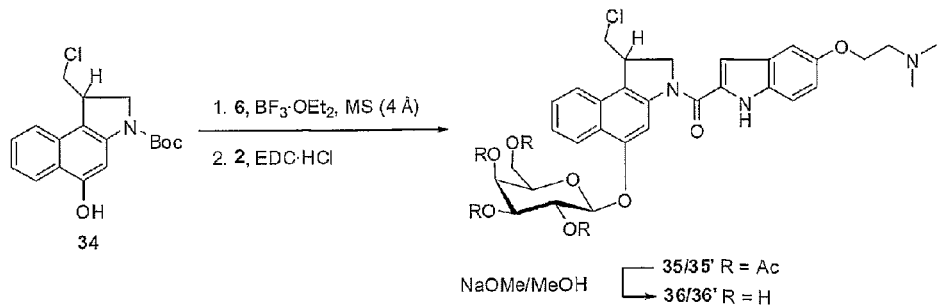
FIG. 11 illustrates the preparation of conjugate 36.

Similarly, FIG. 11 depicts the synthesis of conjugate 36. Starting from 34, coupling with 6, deprotection, and coupling with DNA binder 2 gave (1S,10R)-35/(1R,10S)-35', which were converted to 36/36' by methanolysis.

Figure 15:
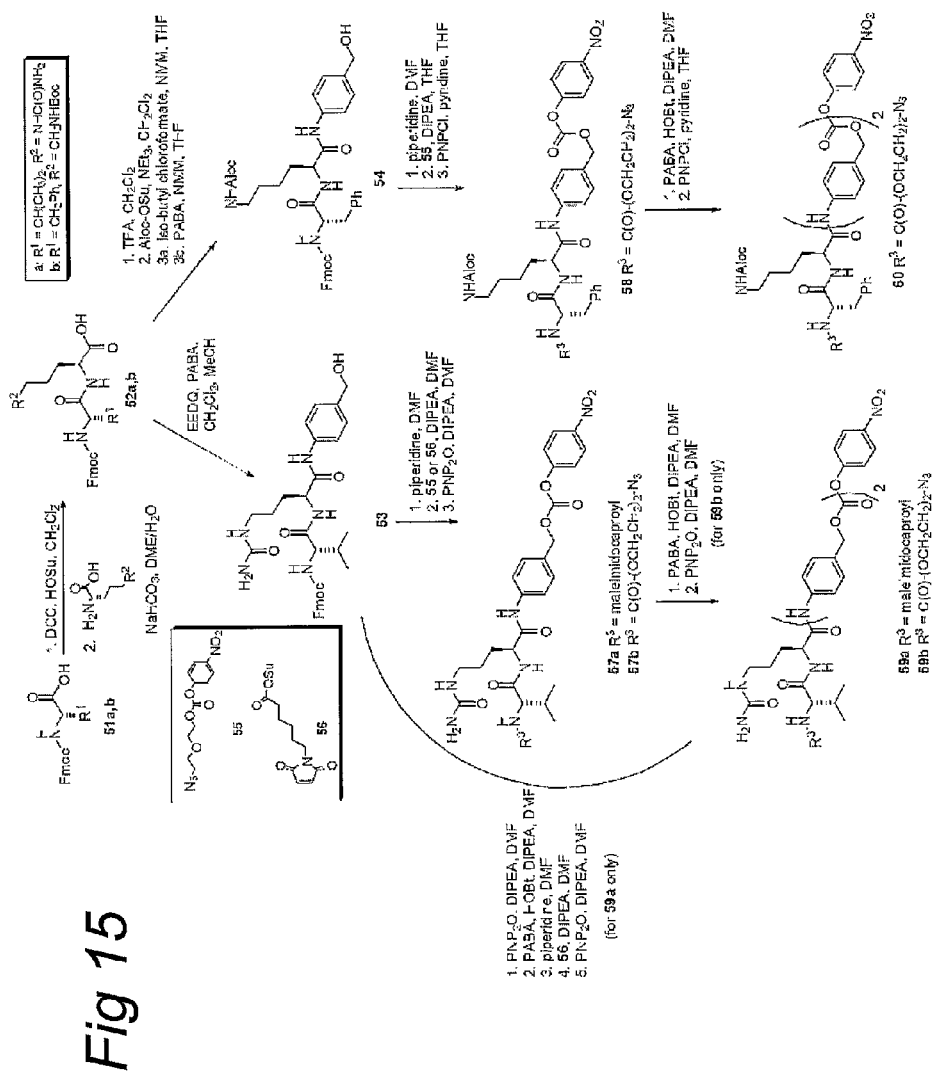
FIG. 15 describes the synthesis of activated linkers 57-60.

FIG. 12 depicts the synthesis of linker-agent conjugates 47a-47f. Starting from agent 4a, activation of the phenolic hydroxyl group, coupling with Boc-protected N,N'-dimethylethylenediamine or piperazine, and deprotection of the amino group provided compounds 46a and 46b. Coupling to p-nitrophenyl carbonate-activated linker constructs 57a, 57b, and 58 provided compounds 47a-47d and protected 47e-47f. Compounds 47e-47f were obtained after subsequent palladium-catalyzed deprotection. The activated linker constructs were prepared according to the scheme in FIG. 15. In short, coupling between 51a and citrulline or between 51b and Boc-protected lysine gave 52a or 52b, respectively. Coupling of p-aminobenzyl alcohol to 52a gave 53, which was converted to 57a and 57b by deprotection with piperidine, subsequent coupling with 55 and 56, respectively, and activation of the hydroxyl group with bis(p-nitrophenyl) carbonate. Exchange of the Boc group for an Aloc group in 52b followed by coupling of p-aminobenzyl alcohol gave 54, which was converted to 58 similarly as 53 to 57b. Compounds 59b and 60 were prepared from 57b and 58 by coupling of p-aminobenzyl alcohol and activation of the hydroxyl group. Compound 59a was prepared in 5 steps from 53.

Figure 13:
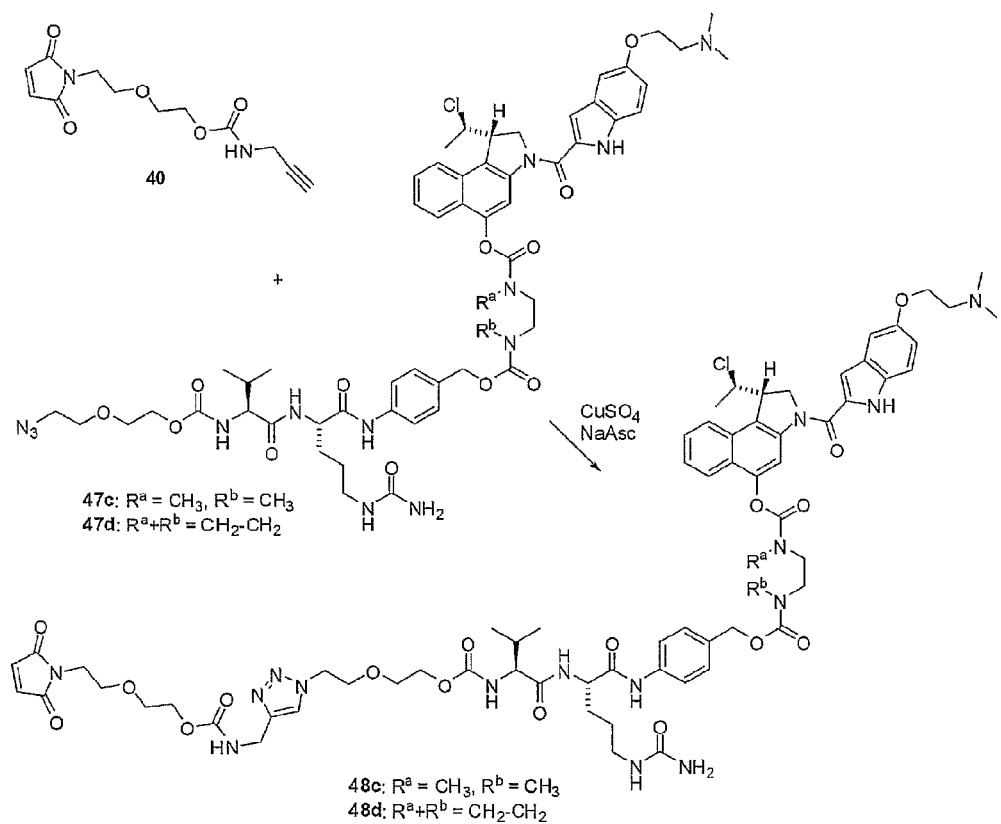
FIG. 13 depicts the synthesis of linker-agent conjugates 48c-d.

FIG. 13 describes the synthesis of linker-agent conjugates 48c and 48d from 47c and 47d, respectively, by means of a Cu(I)-catalyzed reaction with a maleimide-containing acetylene.

Figure 14:
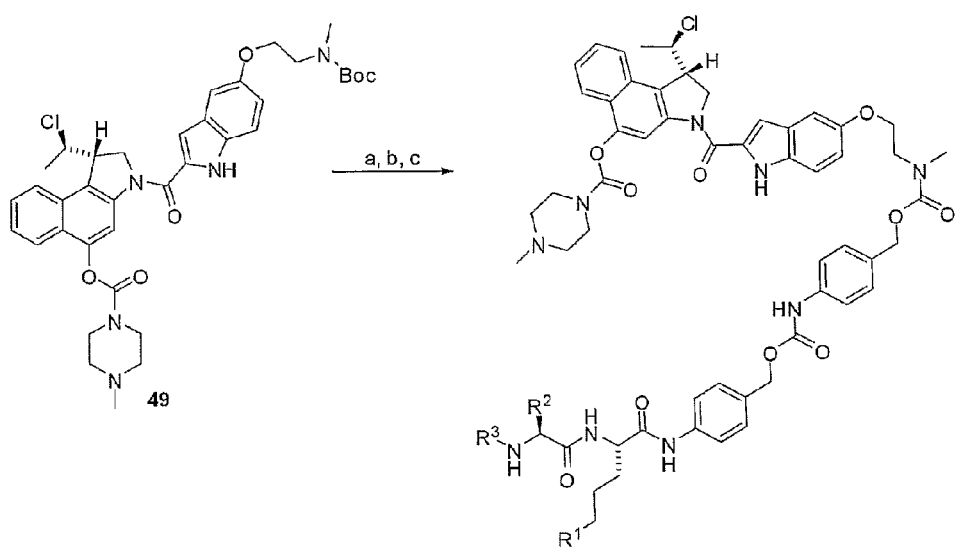
FIG. 14 illustrates the preparation of linker-agent conjugates 50a-c.
Figure 16:
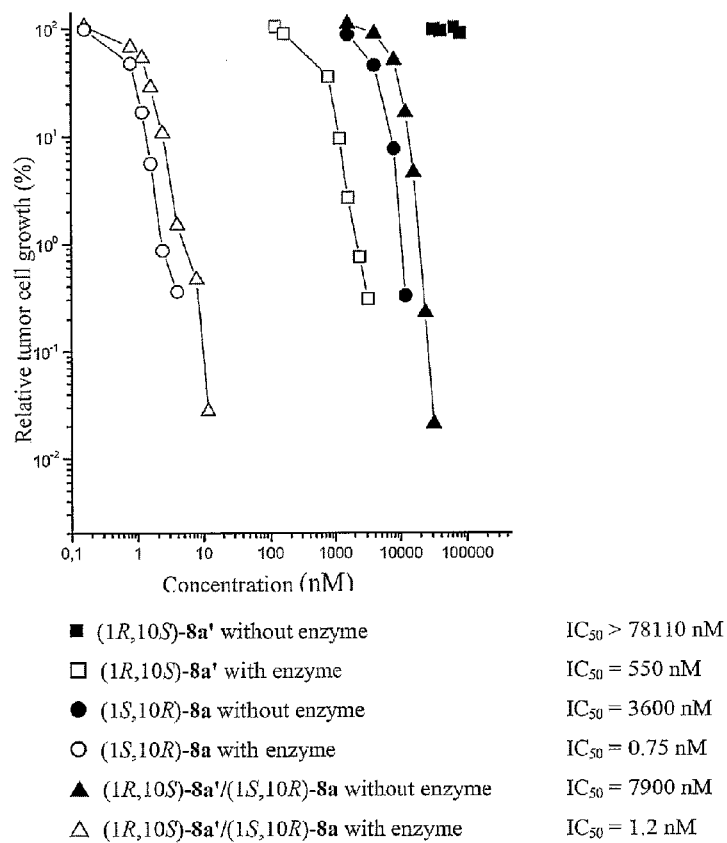
FIG. 16 depicts the in vitro cytotoxicity of conjugates 8a and 8a' against the human lung carcinoma cell line A549.

FIG. 14 describes the synthesis of linker-agent conjugates 50a-50c starting from 49. Compound 49 was prepared from 5 by first introducing the methylpiperazine moiety analogously to the route depicted in FIG. 12, followed by coupling to DNA binder 37 according to the scheme depicted in FIG. 2. Deprotection of 49 followed by coupling with p-nitrophenyl carbonate-activated linker constructs 59a, 59b, and 60 provided compounds 50a-50b and protected 50c. Compound 50c was obtained after subsequent palladium-catalyzed deprotection. Compounds 47e, 47f, 50b, and 50c can be converted to compounds similar to 48c by Cu(I)-catalyzed cycloaddition with acetylene 40. Conjugates (1S,10R)-8a and (1R,10S)-8a' were tested in an in vitro cytotoxicity assay against the human lung carcinoma cell line A549 (FIG. 16). The diastereomeric mixture of (1S,10R)-8a and (1R,10S)-8a' showed an $IC_{50}$ against A549 cells of 7900 nM in the absence of the enzyme β-D-galactosidase, whereas the $IC_{50}$ in the presence of the enzyme proved 1.2 nM. This means that the cytotoxicity quotient, the $IC_{50}$ in the absence of enzyme divided by the $IC_{50}$ in the presence of enzyme, amounts to 6583. Conjugate (1S,10R)-8a showed an $IC_{50}$ in the absence of enzyme of 3600, whereas the $IC_{50}$ decreased to 0.75 nM in the presence of the enzyme β-D-galactosidase, the cytotoxicity quotient amounting to 4800. Conjugates 8b-e were tested in the same cell line and shown to have a cytotoxicity quotient similar to or substantially greater than the ones reported before (cf. ref. 10), agents 4b-e showing nanomolar or subnanomolar activity.

Figure 17:
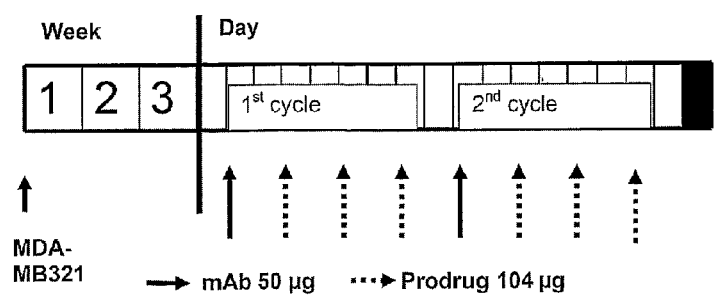
FIG. 17 depicts the treatment schedule for an ADEPT in vivo experiment.
Figure 18:
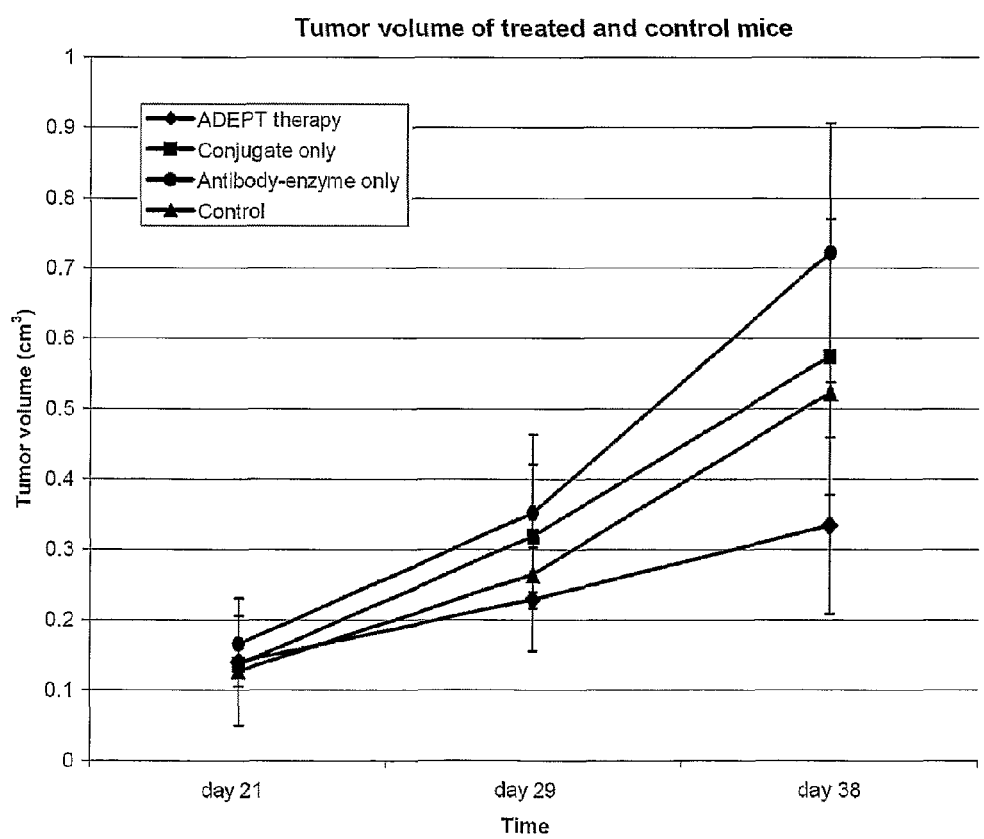
FIG. 18 depicts the tumor volume of treated and control mice in an ADEPT in vivo experiment.

Compound (+)-8a was evaluated in an orthotopic breast tumor SCID mouse model using the ADEPT concept. Female SCID mice were inoculated with $1\times10^6$ MDA-MB-231 cells (estrogen-independent human breast cancer cell line) suspended in 25 μl sterile PBS in the mammary fad pat of the $4^{th}$ mammary complex. Tumors were allowed to grow and ADEPT therapy was started after tumor volumes reached a detectable size. Mice were treated according to the treatment schedule in FIG. 17 and received two treatment cycles of a monoclonal anti-human urokinase plasminogen activator receptor (uPAR) antibody conjugated with β-Galactosidase, uPAR*β-Gal, in PBS followed by three injections with conjugate (+)-8a in 1% DMSO/NaCl solution. Control groups received either antibody-enzyme and 1% DMSO/NaCl solution (antibody-enzyme only group), PBS and conjugate (conjugate only group), or PBS and 1% DMSO/NaCl solution (control group). After one treatment cycle, primary tumors in ADEPT-treated mice reached an average volume of 0.23±0.07 $cm^3$, while the average primary tumor volume of vehicle-treated mice was 0.27±0.10 $cm^3$. After two treatment cycles, mean tumor volumes of 0.33±0.13 $cm^3$ and 0.52±0.29 $cm^3$ were found for the ADEPT-treated group and the control group, respectively (FIG. 18). The inhibitory effect of the ADEPT concept on the tumor growth rate seems thus somewhat more prominent after the second cycle of therapy. An increased inhibitory effect on tumor growth was seen in mice that had relatively small tumors at the start of therapy (data not shown). Furthermore, tumors treated with ADEPT therapy showed more necrotic tissue within tumors than tumors from vehicle-treated mice. Treatment with either uPAR*β-Gal or conjugate alone showed no inhibitory effect on tumor growth with respect to vehicle control. ADEPT therapy was well tolerated in all animals. The general condition of the animals at the day of sacrifice was similar to the mice receiving vehicle only. Blood parameters were not altered in treated mice compared to controls.

An equivalent in vivo experiment was performed in a syngenic mice model using A20 lymphoma cells and an anti-CD19 monoclonal antibody. Following the same treatment procedure as described above, lymphomas treated with ADEPT therapy showed an inhibition of tumor growth.

Uses, Methods, and Compositions

In one aspect, this invention relates to use of a compound of formula (I) or (II) for the preparation of a compound of formula (III).

In another aspect, this invention relates to use of a compound of formula (IV) for the preparation of a compound of formula (III).

In yet another aspect, this invention relates to use of a compound of formula (I) or (II) for the preparation of a compound of formula (IV).

In yet another aspect, this invention relates to use of a compound of formula (III) wherein $V^1$ is a protecting group for the preparation of another compound of formula (III) wherein $V^1$ is an in vivo removable moiety.

In yet another aspect, the invention relates to the use of any of the compounds defined above for the manufacture of a pharmaceutical composition for the treatment of a mammal being in need thereof.

In one embodiment, the invention relates to the use of any of the compounds defined above for the manufacture of a pharmaceutical composition for the treatment of a tumor in a mammal.

The invention also relates to any of the compounds defined above as a medicament or an active component or active substance in a medicament.

In a further aspect the invention relates to a process for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one embodiment, a compound of the invention is used to treat an illness characterized by undesired proliferation. In another embodiment, a compound of the invention is used to treat an illness characterized by undesired cell proliferation. In another embodiment, a compound of the invention is used to treat a tumor. In yet another embodiment, a compound of the invention is used to treat an inflammatory disease. In yet another embodiment a compound of the invention is used to treat an autoimmune disease. In yet another embodiment a compound of the invention is used to treat a bacterial or microbial infection.

In a further embodiment, this invention relates to a method of treating a mammal having an illness characterized by undesired (cell) proliferation with a compound of this invention. In another embodiment this invention relates to a method of treating a mammal carrying a tumor with a compound of this invention. In yet another embodiment this invention relates to a method of treating a mammal having an inflammatory disease with a compound of this invention. In yet another embodiment this invention relates to a method of treating a mammal having an autoimmune disease with a compound of this invention. In yet another embodiment this invention relates to a method of treating a mammal having a bacterial or microbial infection with a compound of this invention.

In a further embodiment, the invention relates to a method of treating a mammal being in need thereof, whereby the method comprises the administration of a pharmaceutical composition comprising a compound of this invention to the mammal in a therapeutically effective dose.

In one embodiment, the invention relates to a method of treating or preventing a tumor in a mammal, whereby the method comprises the administration of a pharmaceutical composition comprising a compound of this invention to the mammal in a therapeutically effective dose.

In another embodiment, the invention relates to a method of treating or preventing an inflammatory disease in a mammal, whereby the method comprises the administration of a pharmaceutical composition comprising a compound of this invention to the mammal in a therapeutically effective dose.

In another embodiment, the invention relates to a method of treating or preventing an autoimmune disease in a mammal, whereby the method comprises the administration of a pharmaceutical composition comprising a compound of this invention to the mammal in a therapeutically effective dose.

In another embodiment, the invention relates to a method of treating or preventing a bacterial or microbial infection in a mammal, whereby the method comprises the administration of a pharmaceutical composition comprising a compound of this invention to the mammal in a therapeutically effective dose.

The invention also relates to pharmaceutical compositions comprising the compounds of the invention as defined above. A compound of the invention may be administered in purified form together with a pharmaceutical carrier as a pharmaceutical composition. The preferred form depends on the intended mode of administration and therapeutic application. The pharmaceutical carrier can be any compatible, nontoxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds of the invention. Such physiologically acceptable compounds include, for example, carbohydrates, such as glucose, sucrose or dextrans, antioxidants, such as ascorbic acid or glutathione, chelating agents, low molecular weight proteins, or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion, or other known desirable features are red iron oxide, silica gel, sodium lauryl sulfate, titanium dioxide, edible white ink, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compounds of the invention are however preferably administered parenterally. Preparations of the compounds of the invention for parenteral administration must be sterile. Sterilization is readily accomplished by filtration through sterile filtration membranes, optionally prior to or following lyophilization and reconstitution. The parenteral route for administration of compounds of the invention is in accord with known methods, e.g. injection or infusion by intravenous, intraperitoneal, intramuscular, intraarterial, or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally administrable compositions are well known in the art and described in more detail in various sources, including, for example, Remington's Pharmaceutical Science[19].

The invention is further exemplified by the following examples. These examples are for illustrative purposes only and are not intended to limit the scope of the invention.

EXAMPLES

Example 1 rac-{(1,10)-anti-5-Benzyloxy-3-[(5-(2-(N,N-dimethylamino)ethoxy)-indol-2-yl)carbonyl]-1-(10-chloroethyl)-1,2-dihydro-3H-benz[e]indole} (rac-3a): Racemic 1 (100 mg, 228 µmol) was suspended in 4 M HCl/EtOAc and stirred at room temperature for 3 h. The reaction mixture was concentrated and dried in vacuo for 1 h. The residue was dissolved in DMF (10 mL). The solution was cooled to 0° C. and EDC.HCl (131 mg, 684 µmol, 3.0 equiv.) and 2 (82.0 mg, 288 µmol, 1.3 equiv.) were added. The reaction mixture was stirred at room temperature for 2 d, diluted with ethyl acetate (50 mL), water (50 mL), and saturated aqueous $NaHCO_3$, and extracted with ethyl acetate (3×100 mL). The combined organic layers were washed with brine (4×100 mL), dried over $MgSO_4$, filtered, and concentrated in vacuo. Column chromatography ($CH_2Cl_2$/MeOH=10:1) gave racemic 3 as a pale brown solid (81 mg, 143 µmol, 63%). $^1$H-NMR (300 MHz, $CDCl_3$): δ=1.65 (d, J=6.8 Hz, 3 H, 11-$CH_3$), 2.37 (s, 6 H, $NMe_2$), 2.78 (t, J=5.8 Hz, 2 H, 2"-$H_2$), 3.96-4.03 (m, 1 H, 1-H), 4.12 (t, J=5.8 Hz, 2 H, 1"-$H_2$), 4.51-4.66 (m, 2 H, 2-$H_a$, 10-H), 4.88 ($m_c$, 1 H, 2-$H_b$), 5.29 ($m_c$, 2 H, $OCH_2$Ph), 7.06 (d, J=2.3 Hz, 1 H, 3'-H), 7.07 (dd, J=8.5, 2.4 Hz, 1 H, 6'-H), 7.15 (d, J=2.4 Hz, 1 H, 4'-H), 7.31-7.46, 7.50-7.57 (m, 8 H, 7-H, 7'-H, 8-H, 5×Ph-H), 7.71 (d, J=8.3 Hz, 1 H, 9-H), 8.17 ($s_{br}$, 1 H, 4-H), 8.36 (d, J=8.5 Hz, 1 H, 6-H), 9.51 ($s_{br}$, 1H, NH); $^{13}$C-NMR (75 MHz, $CDCl_3$): δ=24.0 (11-$CH_3$), 46.0 ($NMe_2$), 47.6 (C-1), 53.7 (C-2), 58.5 (C-2"), 59.9 (C-10), 66.6 (C-1"), 70.3 ($OCH_2$Ph), 98.2 (C-4), 103.5 (C-4'), 105.9 (C-3'), 112.7 (C-7'), 117.2 (C-6', C-5a), 122.6, 123.7, 123.7, 123.9 (C-6, C-7, C-9, C-9b), 127.5, 127.6, 128.0, 128.2, 128.6 (C-3a', C-8, 5×Bn-$\underline{C}$H), 130.0, 130.8, 131.3 (C-2', C-7a', C-9a), 136.8 (Bn-C), 142.4 (C-3a), 153.9 (C-5'), 155.6

(C-5), 160.4 (C=O); MS (EI, 70 eV): m/z (%)=567.4 (1) [M]$^+$, 531.5 (5) [M-Cl]$^+$; C$_{34}$H$_{34}$ClN$_3$O$_3$ (568.11): calcd. 567.2289, found 567.2289 (EI-HRMS).

Example 2 rac-{(1,10)-anti-1-(10-Chloroethyl)-5-hydroxy-3-[(5-(2-(N,N-dimethylamino)ethoxy)indol-2-yl)carbonyl]-1,2-dihydro-3H-benz[e]indole-hydrochloride} (rac-4a): Racemic 3a (200 mg, 352 μmol) was dissolved 4 M HCl/ethyl acetate (15 mL) and stirred for 2 h at room temperature. The solution was concentrated. The residue was dried in vacuo for 1 h and then suspended in THF (15 mL). 10% Palladium on activated carbon (75 mg) and ammonium formate (25% aqueous solution, 0.75 mL) were then added at room temperature. The reaction mixture was stirred for 2 h at 40° C. and filtered over Celite, which was thoroughly rinsed with methanol (200 mL). The filtrate was concentrated in vacuo and the residue was purified by column chromatography (CH$_2$Cl$_2$/MeOH=5:1, 1% conc. HCl) to give rac-4a as a green-yellow powder (146 mg, 284 μmol, 81%). $^1$H-NMR (300 MHz, DMSO-d$_6$): δ=1.62 (d, J=6.7 Hz, 3 H, 11-CH$_3$), 2.84 (s, 6 H, NMe$_2$), 3.51 (t, J=5.0 Hz, 2 H, 2''-H$_2$), 4.16 (m$_c$, 1 H, 1-H), 4.39 (t, J=5.0 Hz, 2 H, 1''-H$_2$), 4.57 (m$_c$, 1 H, 2-H$_a$), 4.66-4.80 (m, 2 H, 2-H$_b$, 10-H), 6.99 (dd, J=8.9, 2.4 Hz, 1 H, 6'-H), 7.16 (d, J=1.6 Hz, 1 H, 3'-H), 7.25 (d, J=2.4 Hz, 1 H, 4'-H), 7.35 (t, J=7.6 Hz, 1 H, 7-H), 7.44 (d, J=8.9 Hz, 1 H, 7'-H), 7.50 (t, J=7.6 Hz, 1 H, 8-H), 7.88 (d, J=8.4 Hz, 1 H, 9-H), 7.96 (s$_{br}$, 1 H, 4-H), 8.13 (d, J=8.4 Hz, 1 H, 6-H), 10.39 (s, 1 H, OH), 10.87 (s$_{br}$, 1 H, NH$^+$), 11.64 (s$_{br}$, 1 H, NH); $^{13}$C-NMR (75 MHz, DMSO-d$_6$): δ=23.4 (11-CH$_3$), 42.7 (NMe$_2$), 45.8 (C-1), 52.1 (C-2), 55.4 (C-2''), 61.5 (C-10), 63.0 (C-1''), 100.3 (C-4), 104.2 (C-4'), 105.2 (C-3'), 113.2 (C-7'), 115.5, 115.8 (C-6', C-5a), 122.1, 122.8, 122.9, 123.1 (C-6, C-7, C-9, C-9b), 126.9, 127.4 (C-3a', C-8), 129.8, 131.3, 131.9 (C-2', C-7a', C-9a), 142.1 (C-3a), 152.0 (C-5'), 153.8 (C-5), 159.8 (C=O); MS (ESI): m/z (%)=478.4 (100) [M-Cl+H]$^+$; C$_{27}$H$_{29}$Cl$_2$N$_3$O$_3$ (514.44): calcd. 478.1892, found 478.1892, [M-Cl]$^+$ (ESI-HRMS).

Example 3

[(1,10)-anti-1-(10-Chloroethyl)-3-[(5-(2-(N,N-dimethylamino)ethoxy)indol-2-yl)carbonyl]-1,2-dihydro-3H-benz[e]indol-5-yl]-2,3,4,6-tetra-O-acetyl-β-D-gatactopyranoside ((+)-7a/(−)-7a'): A solution of rac-5 (381 mg, 1.10 mmol) in dry CH$_2$Cl$_2$ (50 mL) and molecular sieves 4 Å (1.5 g) was stirred for 30 min at room temperature. After addition of O-(2,3,4,6-tetra-O-acetyl-α-D-galactopyranosyl)-trichloracetimidate (6) (564 mg, 1.15 mmol, 1.05 equiv.), the mixture was cooled to −10° C. and a solution of BF$_3$.OEt$_2$ (69.0 μL, 548 μmol, 0.5 equiv.) in dry CH$_2$Cl$_2$ (5.5 mL) was slowly added. After 3 h at −10° C., additional BF$_3$.OEt$_2$ (0.42 mL, 3.29 mmol, 3.0 equiv.) in dry CH$_2$Cl$_2$ (5.0 mL) was added and the mixture was warmed to room temperature. After 5 h, the solution was separated from the molecular sieves, the molecular sieves were thoroughly rinsed with CH$_2$Cl$_2$ (2×20 mL), and the combined organics were concentrated in vacuo. The residue was dried in vacuo for 1 h and then dissolved in dry DMF (60 mL). The solution was cooled to 0° C., and EDC.HCl (630 mg, 3.29 mmol, 3.0 equiv.) and 2 (468 mg, 1.64 mmol, 1.5 equiv.) were added. After 20 h at room temperature, the reaction mixture was diluted with ethyl acetate (50 mL), water (50 mL), and saturated aqueous NaHCO$_3$ (50 mL), and then extracted with ethyl acetate (4×100 mL). The combined organic layers were washed with brine (4×100 mL), dried over MgSO$_4$, filtered, and concentrated in vacuo. Column chromatography (CH$_2$Cl$_2$/MeOH=10:1) gave a mixture of diastereomers 7a and 7a' as a yellow solid (475 mg, 588 μmol, 54%). MS (ESI): m/z (%)=1637 (52) [2M+Na]$^+$, 830.3 (66) [M+Na]$^+$, 808.3 (100) [M+H]$^+$.

Example 4

[(1,10)-anti-1-(10-Chloroethyl)-3-[(5-(2-(N,N-dimethylamino)ethoxy)-indol-2-yl)carbonyl]-1,2-dihydro-3H-benz[e]indol-5-yl]-β-D-galactopyranoside ((+)-8a/(−)-8a'): To a solution of 7a/7a' (473 mg, 585 μmol) in dry MeOH (20 mL) was added NaOMe in methanol (0.22 mL of a ca. 5.4 M solution, 1.17 mmol, 2.0 equiv.). The reaction mixture was stirred at room temperature for 2 h and diluted with water (5 mL). Ion exchange resin (Amberlite-IR 120) was added until the solution reached neutral pH. The solution was concentrated in vacuo and the residue was purified by column chromatography (CH$_2$Cl$_2$/MeOH=1:1), which gave a mixture of 8a and 8a' as a pale yellow solid (307 mg, 480 μmol, 82%). $^1$H-NMR (600 MHz, DMSO-d$_6$): δ=1.65 (d, J=6.7 Hz, 3 H, 11-CH$_3$), 2.24 (s, 6 H, NMe$_2$), 2.66 (t, J=5.7 Hz, 2 H, 2''-H$_2$), 3.41-3.73 (m, 4 H, 2'''-H*, 4'''-H*, 6'''-H$_2$), 3.75-3.86 (m, 2 H, 3'''-H*, 5'''-H*), 4.07 (t, J=5.7 Hz, 2 H, 1''-H$_2$), 4.21-4.28 (m, 1 H, 1-H), 4.49-4.67 (m, 3 H, 2×OH, 2-H$_a$), 4.68-5.00 (m, 4 H, 1'''-H, 2-H$_b$, 10-H, OH), 5.30 (s$_{br}$, 1 H, OH), 6.92 (dd, J=8.8, 2.4 Hz, 1 H, 6'-H), 7.13-7.20 (m, 2 H, 3'-H, 4'-H), 7.38-7.45 (m, 2 H, 7-H, 7'-H), 7.57 (m$_c$, 1 H, 8-H), 7.96 (m$_c$, 1 H, 9-H), 8.23 (s$_{br}$, 1 H, 4-H), 8.32-8.38 (m, 1 H, 6-H), 11.62 (s$_{br}$, 1 H, NH); $^{13}$C-NMR (150 MHz, DMSO-d$_6$): δ=23.4 (11-CH$_3$), 45.5 (NMe$_2$), 45.9/46.0 (C-1), 52.1 (2 signals)(C-2), 57.8 (C-2''), 59.7/59.8 (C-6'''), 61.3 (2 signals)(C-10), 66.3 (C-1''), 67.6/67.7, 70.5/70.6, 73.2 (2 signals), 75.2 (2 signals) (C-2''', C-3''', C-4''', C-5'''), 101.9 (C-4), 102.1/102.3 (C-1'''), 103.3 (2 signals)(C-4'), 105.4 (C-3'), 113.2 (C-7'), 115.9 (2 signals)(C-6'), 118.9 (2 signals)(C-5a), 122.90, 123.0, 123.3/123.4, 123.6/123.6 (C-6, C-7, C-9, C-9b), 127.3 (C-8), 127.5 (C-3a'), 129.5 (2 signals), 130.9, 131.7 (2 signals)(C-2', C-7a', C-9a), 141.9/142.0 (C-3a), 153.0 (2 signals)(C-5'), 153.6 (2 signals)(C-5), 160.1/160.2 (C=O); MS (ESI): m/z (%)=1301.0 (100) [2M+2H]$^+$, 662.3 (82) [M+Na]$^+$, 640.3 (76) [M+H]$^+$; C$_{33}$H$_{38}$ClN$_3$O$_8$ (640.12): calcd. 640.2420, found 640.2420, [M+H]$^+$ (ESI-HRMS).

Both diastereomers were obtained separately according to similar procedures starting from (+)-5 and (−)-5, respectively.

Example 5

4-[2-(4-Nitrophenoxy)ethyl]morpholine (10): A solution of KOH (3.3 g, 58 mmol) in EtOH (15 mL) was added dropwise to a solution of 4-nitrophenol (9) (7.0 g, 50 mmol) in EtOH (10 mL). After stirring for 30 min at room temperature the salt was collected by filtration, washed with cold EtOH and dried in vacuo to give the potassium salt of 9 as a yellow solid (7.1 g, 40 mmol).

The salt (7.1 g, 40 mmol) was dissolved in toluene (100 mL), a solution of 4-(2-chloroethyl)-morpholine (6.5 g, 43 mmol) in toluene (100 mL) was added and the mixture was heated at reflux for 24 h. After cooling to room temperature the precipitate was separated by filtration, washed thoroughly with toluene, and the filtrate was concentrated in vacuo to give 10 as a pale yellow solid (7.2 g, 57% overall yield), which was used for the next step without further purification. $^1$H NMR (200 MHz, CDCl$_3$): δ=2.54-2.64 (m, 4 H, 3-H$_2$, 5-H$_2$), 2.84 (t, J=5.5 Hz, 2 H, 1'-H$_2$), 3.69-3.78 (m, 4 H, 2-H$_2$, 6-H$_2$), 4.20 (t, J=5.5 Hz, 2 H, 2'-H$_2$), 6.92-7.01 (m, 2 H, 2''-H, 6''-H), 8.16-8.25 (m, 2 H, 3''-H, 5''-H) ppm; $^{13}$C NMR (50.3 MHz, CDCl$_3$): δ=54.1 (C-3, C-5), 57.3 (C-1'), 66.7 (C-2'), 66.9

(C-2, C-6), 114.5 (C-2", C-6"), 125.9 (C-3", C-5"), 141.6 (C-4"), 163.7 (C-1") ppm; MS (70 eV, EI): m/z (%)=252 (8) [M]$^+$, 100 (100) [M−CH$_2$OC$_6$H$_4$—NO$_2$]$^+$.

Example 6

4-(2-(Morpholin-4-yl)ethoxy)phenylamine (11): A solution of 10 (6.00 g, 23.8 mmol) in 95% EtOH (40 mL) was hydrogenated over Pd/C (10%, 350 mg) at 58 psi H$_2$ for 1 h at room temperature. The formed solid was removed by filtration through Celite, which was washed thoroughly with EtOH (100 mL) and MeOH (50 mL); the filtrate was concentrated in vacuo to give 11 (5.29 g, quant.) as a reddish brown oil, which was used for the next step without further purification.

$^1$H NMR (300 MHz, CDCl$_3$): δ 2.57 (m$_c$, 4 H, 3"-H$_2$, 5"-H$_2$), 2.76 (t, J=5.8 Hz, 2 H, 2'-H$_2$), 3.40 (s$_{br}$, 2 H, NH$_2$), 3.73 (m$_c$, 4 H, 2"-H$_2$, 6"-H$_2$), 4.03 (t, J=5.8 Hz, 2 H, 1'-H$_2$), 6.59-6.66 (m 2 H, 2-H, 6-H), 6.71-6.78 (m, 2 H, 3-H, 5-H) ppm; $^{13}$C NMR (50.3 MHz, CDCl$_3$): δ=54.0 (C-3", C-5"), 57.7 (C-2'), 66.3 (C-1'), 66.8 (C-2", C-6"), 115.7 (C-3, C-5), 116.2 (C-2, C-6), 140.2 (C-1), 151.7 (C-4) ppm; MS (70 eV, EI): m/z (%) 222 (17) [M]$^+$, 100 (100) [M-CH$_2$OC$_6$H$_4$—NH$_2$]$^+$.

Example 7

5-(2-(Morpholin-4-yl)ethoxy)-1H-indole-2-carboxylic acid ethyl ester (12): A stirred solution of 4-(2-(morpholin-4-yl)ethoxy)phenylamine (11) (4.00 g, 18.0 mmol) in water (38 mL) and concentrated HCl (12 mL) was treated dropwise at 0° C. with a solution of NaNO$_2$ (1.36 g, 19.8 mmol) in water (3.8 mL) and the resulting mixture was stirred for 30 min at 0° C. (solution A). Ethyl 2-methylacetoacetate (2.75 mL, 18.9 mmol) was added dropwise to a suspension of NaOAc (15.3 g) in EtOH (29 mL) at 0° C. After stirring for 30 min at this temperature, ice (18 g) was added (solution B). Then, solution A was added to solution B by a transfer cannula at 0° C., the mixture was allowed to warm to room temperature and was stirred for a further 2.5 h. After that, the reaction mixture was basified by slow addition of a saturated aqueous solution of Na$_2$CO$_3$ at 0° C. and extracted with CH$_2$Cl$_2$ (3×200 mL). The combined organic layers were washed with water (300 mL), dried (MgSO$_4$), and the solvent was removed in vacuo. The residue was then dissolved in absolute EtOH (15 mL), treated with a freshly prepared saturated solution of HCl in absolute EtOH (15 mL) and heated at reflux for 40 min. After cooling to room temperature the solvent was removed under reduced pressure and the residue was partitioned between water (50 mL) and CH$_2$Cl$_2$ (100 mL). The aqueous layer was basified using a saturated aqueous solution of Na$_2$CO$_3$ and extracted with CH$_2$Cl$_2$ (3×100 mL). The combined organic layers were washed with brine (200 mL), dried (MgSO$_4$), and concentrated in vacuo. Purification by crystallization from iPr$_2$O and column chromatography (CH$_2$Cl$_2$/MeOH, 20:1) of the residue after evaporation of the mother liquor provided 12 (4.07 g, 71% overall yield) as a yellow solid. $^1$H NMR (300 MHz, CDCl$_3$): δ 1.41 (t, J=7.1 Hz, 3 H, OCH$_2$C$\underline{H}_3$), 2.61 (m$_c$, 4 H, 3"-H$_2$, 5"-H$_2$), 2.84 (t, J=5.7 Hz, 2 H, 2'-H$_2$), 3.76 (m$_c$, 4 H, 2"-H$_2$, 6"-H$_2$), 4.15 (t, J=5.7 Hz, 2 H, 1'-H$_2$), 4.40 (q, J=7.1 Hz, 2 H, OC$\underline{H}_2$CH$_3$), 6.99 (dd, J=9.0, 2.4 Hz, 1 H, 6-H), 7.08 (d, J=2.4 Hz, 1 H, 4-H), 7.13 (d, J=1.3 Hz, 1 H, 3-H), 7.30 (d, J=9.0 Hz, 1 H, 7-H), 9.13 (s$_{br}$, 1 H, NH) ppm; $^{13}$C NMR (50.3 MHz, CDCl$_3$): δ=14.4 (OCH$_2$$\underline{C}$H$_3$), 54.1 (C-3", C-5"), 57.7 (C-2'), 60.9 (O$\underline{C}$H$_2$CH$_3$) 66.2 (C-1'), 66.9 (C-2", C-6"), 103.7 (C-4), 108.1 (C-3), 112.7 (C-7), 117.3 (C-6), 127.7, 127.9 (C-2, C-3a), 132.3 (C-7a), 153.7 (C-5), 162.0 (C=O) ppm;

MS (70 eV, EI): m/z (%)=318 (14) [M]$^+$, 100 (100) [CH$_2$N(CH$_2$)$_4$O]$^+$; C$_{17}$H$_{22}$N$_2$O$_4$ (318.37): calcd. C, 64.13; H, 6.97; found C, 63.85; H, 7.12.

Example 8

5-(2-(Morpholin-4-yl)ethoxy)-1H-indole-2-carboxylic acid hydrochloride (13): A suspension of ester 12 (1.02 g, 3.20 mmol) in MeOH (8 mL) was treated with a solution of NaOH (150 mg, 3.75 mmol) in water (4 mL) and heated at reflux for 3 h. After cooling to room temperature, the solution was adjusted to pH 6 with 1 M HCl and the solvent was removed under reduced pressure. The residue was dissolved in MeOH, 1 M HCl was added dropwise and the formed precipitate was collected by filtration to give 13 (727 mg, 70%) as a brown solid. Purification of the residue obtained by evaporation of the mother liquor using column filtration on silica gel (MeOH, 1% conc. HCl) provided a second batch of 13 (232 mg, 22%). $^1$H NMR (300 MHz, DMSO-d$_6$): δ=3.07-3.61 (m, 6 H, 2'-H$_2$, 3"-H$_2$, 5"-H$_2$), 3.76-4.06 (m, 4 H, 2"-H$_2$, 6"-H$_2$), 4.43 (t, J=5.0 Hz, 2 H, 1'-H$_2$), 6.98 (dd, J=8.9, 2.3 Hz, 1 H, 6-H), 7.01 (d, J=1.8 Hz, 1 H, 3-H), 7.20 (d, J=2.3 Hz, 1 H, 4-H), 7.37 (d, J=8.9 Hz, 1 H, 7-H), 11.39 (s$_{br}$, 1 H, NH$^+$), 11.65 (s, 1 H, NH), 12.85 (s$_{br}$, 1 H, CO$_2$H) ppm; $^{13}$C NMR (50.3 MHz, DMSO-d$_6$): δ=51.6 (C-3", C-5"), 54.9 (C-2'), 62.8 (C-1'), 63.1 (C-2", C-6"), 103.9 (C-4), 106.9 (C-3), 113.5 (C-7), 115.9 (C-6), 127.0 (C-2), 129.0 (C-3a), 133.0 (C-7a), 152.0 (C-5), 162.6 (C=O) ppm; MS (70 eV, EI): m/z (%)=290 (6) [M-Cl]$^+$, 100 (100) [CH$_2$N(CH$_2$)$_4$O]$^+$; C$_{15}$H$_{19}$ClN$_2$O$_4$ (326.78): calcd. C, 55.13; H, 5.86; found C, 54.96; H, 5.81.

Example 9

(+)-{(1,10)-anti-5-Benzyloxy-3-[(5-(2-(morpholin-4-yl)ethoxy)indol-2-yl)carbonyl]-1-(10-chloroethyl)-1,2-dihydro-3H-benz[e]indole} ((+)-3b): (+)-1 (150 mg, 342 μmol) was suspended in 4 M HCl/ethyl acetate (14 mL) and stirred at room temperature for 3 h. The mixture was then concentrated and dried in vacuo for 1 h. The residue was dissolved in DMF (10 mL), the solution was cooled to 0° C., and EDC.HCl (197 mg, 1.03 mmol, 3.0 equiv.) and 13 (146 mg, 445 μmol, 1.3 equiv.) were added. After 21 h at room temperature, ethyl acetate (50 mL), water (50 mL), and saturated aqueous NaHCO$_3$ (50 mL) were added and the mixture was extracted with ethyl acetate (4×50 mL). The combined organic layers were dried with brine (4×100 mL), dried over MgSO$_4$, filtered, and concentrated. Column chromatography (CH$_2$Cl$_2$/MeOH=30:1) gave (+)-3b as a pale brown solid (156 mg, 256 μmol, 75%). $^1$H-NMR (300 MHz, CDCl$_3$): δ=1.62 (d, J=6.7 Hz, 3 H, 11-CH$_3$), 2.61 (m$_c$, 4 H, 3'''-H$_2$, 5'''-H$_2$), 2.83 (t, J=5.8 Hz, 2 H, 2"-H$_2$), 3.76 (m$_c$, 4 H, 2'''-H$_2$, 6'''-H$_2$), 3.89-3.98 (m, 1 H, 1-H), 4.15 (t, J=5.8 Hz, 2 H, 1"-H$_2$), 4.47-4.61 (m, 2 H, 2-H$_a$, 10-H), 4.85 (m, 1 H, 2-H$_b$), 5.25 (m$_c$, 2 H, OC$\underline{H}_2$Ph), 6.94-7.02 (m, 2 H, 3'-H, 6'-H), 7.12 (d, J=2.3 Hz, 1 H, 4'-H), 7.29-7.57 (m, 8 H, 7-H, 7'-H, 8-H, 5×Ph-H), 7.68 (d, J=8.2 Hz, 1 H, 9-H), 8.19 (s$_{br}$, 1 H, 4-H), 8.34 (d, J=8.2 Hz, 1 H, 6-H), 9.88 (s$_{br}$, 1 H, NH); $^{13}$C-NMR (75 MHz, CDCl$_3$): δ=24.0 (11-CH$_3$), 47.5 (C-1), 53.6 (C-2), 54.1 (C-3''', C-5'''), 57.8 (C-2"), 59.9 (C-10), 66.3 (C-1"), 66.9 (C-2''', C-6'''), 70.3 (O$\underline{C}$H$_2$Ph), 98.2 (C-4), 103.7 (C-4'), 105.8 (C-3'), 112.8 (C-7'), 117.0, 117.2 (C-6', C-5a), 122.6 (C-9), 123.7, 123.7, 123.9 (C-6, C-7, C-9b), 127.4, 127.6, 127.9, 128.1, 128.5 (C-3a', C-8, 5×Bn-$\underline{C}$H), 130.0, 130.8, 131.5 (C-2', C-7a', C-9a), 136.7 (Bn-C), 142.4 (C-3a), 153.7 (C-5'), 155.6 (C-5), 160.5 (C=O); MS (EI, 70 eV): m/z (%)=609.2 (1) [M]$^+$, 573.1 (3) [M-Cl—H]⁺, 100.0 (100) [CH₂(CH₂)₄O]⁺. C₃₆H₃₆ClN₃O₄ (610.14): calcd. 609.2394, found 609.2394 (EI-HRMS).

Example 10

(+)-{(1,10)-anti-1-(10-Chloroethyl)-5-hydroxy-3-[(5-(2-(morpholin-4-yl)ethoxy)indol-2-yl)carbonyl]-1,2-dihydro-3H-benz[e]indole-hydrochloride} ((+)-4b): A solution of (+)-3b (80 mg, 131 µmol) in 4 M HCl/ethyl acetate (10 mL) was stirred at room temperature for 2 h. The mixture was then concentrated and dried in vacuo for 1 h. The residue was suspended in THF (8 mL), 10% palladium on active carbon (28 mg) and ammonium formate (25% aqueous solution, 0.28 mL) were added, the reaction mixture was stirred at 40° C. for 1 h and then filtered through Celite, which was rinsed with methanol (150 mL). The filtrate was concentrated and the residue was purified by column chromatography (CH₂Cl₂/MeOH=5:1, 0.1% conc. HCl) to give (+)-4b as a yellow solid (67 mg, 120 µmol, 92%). ¹H-NMR (300 MHz, DMSO-d₆): δ=1.62 (d, J=6.5 Hz, 3 H, 11-CH₃), 3.14-3.63 (m, 6 H, 2"-H₂, 3'''-H₂, 5'''-H₂), 3.83-4.03 (m, 4 H, 2'''-H₂, 6'''-H₂), 4.12-4.21 (m, 1 H, 1-H), 4.41-4.64 (m, 3 H, 1''-H₂, 2-H_a), 4.64-4.82 (m, 2 H, 2-H_b, 10-H), 7.00 (dd, J=9.0, 1.8 Hz, 1 H, 6'-H), 7.16 (s_br, 1 H, 3'-H), 7.25 (m_c, 1 H, 4'-H), 7.35 (m_c, 1 H, 7-H), 7.41-7.55 (m, 2 H, 7'-H, 8-H), 7.88 (d, J=8.4 Hz, 1 H, 9-H), 7.98 (s_br, 1 H, 4-H), 8.14 (d, J=8.3 Hz, 1 H, 6-H), 10.42 (s, 1 H, OH), 11.65 (s, 1 H, NH), 11.93 (s_br, 1 H, NH⁺); ¹³C-NMR (75 MHz, DMSO-d₆): δ=23.4 (11-CH₃), 45.9 (C-1), 51.6 (C-3''', C-5'''), 52.1 (C-2), 54.9 (C-2''), 61.5 (C-10), 62.8 (C-1''), 63.0 (C-2''', C-6'''), 100.4 (C-4), 104.0 (C-4'), 105.2 (C-3'), 113.2 (C-7'), 115.6, 115.9 (C-6', C-5a), 122.2 (C-9b), 122.8, 122.9, 123.1 (C-6, C-7, C-9), 126.9 (C-8), 127.4 (C-3a'), 129.8, 131.3, 131.9 (C-2', C-7a', C-9a), 142.1 (C-3a), 151.9 (C-5'), 153.9 (C-5), 159.8 (C=O); MS (ESI): m/z (%)=520.1 (100) [M-Cl]⁺; C₂₉H₃₁Cl₂N₃O₄ (556.48): calcd. 520.2003, found 520.1998, [M-Cl]⁺ (ESI-HRMS).

Example 11

[(+)-(1,10)-anti-1-(10-Chloroethyl)-3-[(5-(2-(morpholin-4-yl)ethoxy)indol-2-yl)carbonyl]-1,2-dihydro-3H-benz[e]indol-5-yl]-2,3,4,6-tetra-O-acetyl-β-D-galactopyranoside ((+)-7b): A solution of (+)-5 (142 mg, 408 µmol) in dry CH₂Cl₂ (18 mL) and molecular sieves 4 Å (0.8 g) was stirred for 30 min at room temperature. After addition of O-(2,3,4,6-tetra-O-acetyl-α-D-galactopyranosyl)-trichloracetimidate (6) (207 mg, 0.420 mmol, 1.03 equiv.), the mixture was cooled to −10° C. and a solution of BF₃.OEt₂ (26 µL, 205 µmol, 0.5 equiv.) in dry CH₂CO₂ (2.0 mL) was slowly added. After 4 h at −10° C., additional BF₃.OEt₂ (0.155 mL, 1.22 mmol, 3.0 equiv.) in dry CH₂Cl₂ (1.9 mL) was added and the mixture was warmed to room temperature. After 5 h, the solution was separated from the molecular sieves, the molecular sieves were thoroughly rinsed with CH₂Cl₂ (2×10 mL), and the combined organics were concentrated in vacuo. The residue was dried in vacuo for 1 h and then dissolved in dry DMF (19 mL). The solution was cooled to 0° C., and EDC.HCl (235 mg, 1.23 mmol, 3.0 equiv.) and 13 (200 mg, 0.612 mmol, 1.5 equiv.) were added. After 20 h at room temperature, the reaction mixture was diluted with ethyl acetate (50 mL), water (50 mL), and saturated aqueous NaHCO₃ (50 mL), and then extracted with ethyl acetate (4×50 mL). The combined organic layers were washed with brine (4×100 mL), dried over MgSO₄, filtered, and concentrated in vacuo. Column chromatography (CH₂Cl₂/MeOH=10:1) gave the N-oxide of (+)-7b as a pale brown solid (142 mg, 164 µmol, 40%).

To a solution of the N-oxide (67 mg, 77 µmol) in dry ethanol (15 mL), PtO₂.H₂O (6 mg, 21 µmol, 0.3 equiv.) was added. Hydrogen was then bubbled through the reaction mixture for 5 h. The reaction mixture was filtered over Celite, and the Celite was thoroughly rinsed with methanol (50 mL). The filtrate was concentrated in vacuo and the residue was purified by column chromatography (CH₂Cl₂/MeOH=10:1) to give (+)-7b as a yellow solid (53 mg, 62 µmol, 81%). C₄₃H₄₈ClN₃O₁₃ (850.31): calcd. 850.2954, found 850.2948, [M+H]⁺ (ESI-HRMS).

Example 12

[(+)-(1,10)-anti-1-(10-Chloroethyl)-3-[(5-(2-(morpholin-4-yl)ethoxy)-indol-2-yl)carbonyl]-1,2-dihydro-3H-benz[e]indol-5-yl]-β-D-galactopyranoside ((+)-8b): To a solution of 7a (51 mg, 60 µmol) in dry MeOH (6 mL) was added NaOMe in methanol (22 µL of a ca. 5.4 M solution, 120 µmol, 2.0 equiv.). The reaction mixture was stirred at room temperature for 20 min and diluted with water (2 mL) and methanol (2 mL). Ion exchange resin (Amberlite-IR 120) was added until the solution reached neutral pH. The resin was removed and rinsed with methanol (10 mL). The combined organics were concentrated in vacuo and the residue was purified by column chromatography (gradient: CH₂Cl₂/MeOH=10:1//CH₂Cl₂/MeOH=4:1). The obtained solid was washed with pentane (4×15 mL), which gave 8b as a yellow solid (37 mg, 54 µmol, 90%).

¹H-NMR (600 MHz, DMSO-d₆): δ=1.65 (d, J=6.6 Hz, 3 H, 11-CH₃), 2.48-2.52 (m, 4 H, 3'''-H₂, 5'''-H₂), 2.73 (t, J=5.8 Hz, 2 H, 2''-H₂), 3.45-3.70 (m, 8 H, 2''''-H₂, 6''''-H₂, 3''''-H, 5''''-H, 6''''-H₂), 3.76-3.85 (m, 2 H, 2''''-H, 4''''-H), 4.11 (t, J=5.8 Hz, 2 H, 1''-H₂), 4.25 (m, 1H, 1-H), 4.52-4.65 (m, 3 H, 2-H_a, 2×OH), 4.72-4.79 (m, 1 H, 2-H_b), 4.79-4.88 (1, 2 H, 10-H, OH), 4.92 (m_c, 1 H, 1'''-H), 5.30 (s_br, 1 H, OH), 6.92 (dd, J=8.9, 2.4 Hz, 1 H, 6'-H), 7.14-7.20 (m, 2 H, 3'-H, 4'-H), 7.40 (d, J=8.8 Hz, 1 H, 7'-H), 7.43 (m_c, 1 H, 7-H), 7.57 (m, 1 H, 8-H), 7.96 (d, J=8.4 Hz, 1 H, 9-H), 8.22 (s_br, 1 H, 4-H), 8.36 (d, J=8.5 Hz, 1 H, 6-H), 11.63 (s, 1 H, NH);

¹³C-NMR (150 MHz, DMSO-d₆): δ=23.4 (11-CH₃), 46.0 (C-1), 52.1 (C-2), 53.6 (C-3''', C-5'''), 57.1 (C-2''), 59.5 (C-6''''), 61.3 (C-10), 65.9 (C-1''), 66.2 (C-2''', C-6'''), 67.5 (C-4''''), 70.6 (C-2''''), 73.2 (C-3''''), 75.1 (C-5''''), 101.9 (C-4), 102.3 (C-1''''), 103.4 (C-4'), 105.4 (C-3'), 113.2 (C-7'), 115.9 (C-6'), 118.9 (C-5a), 122.9, 123.0, 123.4, 123.7 (C-6, C-7, C-9, C-9b), 127.3, 127.5 (C-3a', C-8), 129.5, 130.9, 131.7 (C-2', C-7a', C-9a), 142.0 (C-3a), 152.9 (C-5'), 153.6 (C-5), 160.1 (C=O); MS (ESI): m/z (%)=1385.1 (13) [2M+Na]⁺, 704.3 (100) [M+Na]⁺, 682.3 (32) [M+H]⁺; C₃₅H₄₀ClN₃O₉ (682.16): calcd. 682.2531, found 682.2526, [M+H]⁺ (ESI-HRMS).

Example 13

3-(2-Chloroethoxy)-4-methoxybenzaldehyde (15): A mixture of 3-hydroxy-4-methoxybenzaldehyde (14) (10.0 g, 65.7 mmol), K₂CO₃ (45.4 g, 329 mmol), 1,2-dichloroethane (104 mL, 1.31 mol), and DMF (300 mL) was stirred at 65-70° C. for 16 h. After cooling, 1,2-dichloroethane was removed under reduced pressure, the remaining slurry was poured onto ice and the mixture was extracted with Et₂O (3×250 mL) and EtOAc (4×250 mL). The combined organic layers were washed with water (4×400 mL) and brine (2×400 mL), dried (MgSO₄), and the solvent was removed in vacuo. Crystallization from EtOAc/hexane provided 15 (11.9 g, 84%) as colorless needles. $^1$H NMR (200 MHz, CDCl$_3$): δ=3.88 (t, J=6.1 Hz, 2 H, 2'-H$_2$), 3.97 (s, 3 H, OMe), 4.35 (t, J=6.1 Hz, 2 H, 1'-H$_2$), 7.01 (d, J=8.1 Hz, 1 H, 5-H), 7.43 (d, J=1.8 Hz, 1 H, 2-H), 7.51 (dd, J=8.1, 1.8 Hz, 1 H, 6-H), 9.86 (s, 1 H, CHO) ppm; $^{13}$C NMR (50.3 MHz, CDCl$_3$): δ=41.5 (C-2'), 56.2 (OMe), 68.9 (C-1'), 111.0, 111.3 (C-2, C-5), 127.4 (C-6), 129.9 (C-1), 148.1 (C-3), 154.9 (C-4), 190.7 (CHO) ppm; MS (70 eV, EI): m/z (%)=214 (100) [M]$^+$, 151 (57) [M-CH$_2$)$_2$Cl]$^+$; C$_{10}$H$_{11}$ClO$_3$ (214.65): calcd. C, 55.96; H, 5.17; found C, 56.04; H, 4.97.

Example 14

2-Azido-3-[3-(2-chloroethoxy)-4-methoxyphenyl]acrylic acid methyl ester (16): NaN$_3$ (22.2 g, 341 mmol) was added slowly to a solution of methyl chloroacetate (20.0 mL, 227 mmol) in DMSO (100 mL). After stirring at room temperature for 24 h, water (150 mL) was added and the mixture was extracted with Et$_2$O (3×100 mL). The combined organic fractions were dried (MgSO$_4$) and concentrated in vacuo to 50 mL. Then, a solution of aldehyde 15 (5.37 g, 25.0 mmol) in MeOH (50 mL) was added and the mixture was cooled to −30° C. After that, the reaction mixture was treated with 5.4 M NaOMe/MeOH (35.0 mL, 189 mmol) within 30 min at −30° C., warmed to 0° C. and diluted with MeOH (50 mL). After stirring for 16 h at 0° C., water (200 mL) was added and the mixture was extracted with CH$_2$Cl$_2$ (3×200 mL). The combined organic fractions were washed with brine (200 mL), dried (MgSO$_4$), and the solvent was removed in vacuo to give 16 (6.84 g, 88% from 15) as a pale yellow solid that was used for the next step without further purification. $^1$H NMR (300 MHz, CDCl$_3$): δ=3.84 (t, J=6.1 Hz, 2 H, 2"-H$_2$), 3.87, 3.88 (2×s, 6 H, OMe, CO$_2$Me), 4.29 (t, J=6.1 Hz, 2 H, 1"-H$_2$), 6.83 (s, 1 H, 1'-H), 6.87 (d, J=8.5 Hz, 1 H, 5-H), 7.36 (dd, J=8.5, 2.1 Hz, 1 H, 6-H), 7.53 (d, J=2.1 Hz, 1 H, 2-H) ppm; $^{13}$C NMR (50.3 MHz, CDCl$_3$): δ=41.6 (C-2"), 52.8 (CO$_2$Me), 56.0 (OMe), 69.3 (C-1"), 111.5 (C-2), 116.2 (C-5), 123.4 (C-2'), 125.4, 126.0, 126.2 (C-1, C-1', C-6), 147.1, 150.9 (C-3, C-4), 164.1 (C=O) ppm.

Example 15

5-(2-Chloroethoxy)-6-methoxy-1H-indole-2-carboxylic acid methyl ester (17): A solution of 16 (6.81 g, 21.8 mmol) in toluene (200 mL) was heated at reflux for 4 h. After cooling to room temperature the reaction mixture was concentrated in vacuo. The formed precipitate was isolated by filtration and dried in vacuo to give 17 (4.48 g, 72%) as a pale yellow solid. $^1$H NMR (300 MHz, DMSO-d$_6$): δ=3.82, 3.84 (2×s, 6 H, OMe, CO$_2$Me), 3.93 (t, J=5.3 Hz, 2 H, 2'-H$_2$), 4.21 (t, J=5.3 Hz, 2 H, 1'-H$_2$), 6.92 (s, 1 H, 7-H), 7.02 (d, J=1.5 Hz, 1 H, 3-H), 7.15 (s, 1 H, 4-H), 11.62 (s$_{br}$, 1 H, NH) ppm. —$^{13}$C NMR (50.3 MHz, DMSO-d$_6$): δ=42.9 (C-2'), 51.3 (CO$_2$Me), 55.5 (OMe), 69.4 (C-1'), 94.8 (C-7), 105.6 (C-4), 107.9 (C-3), 119.7 (C-3a), 125.4 (C-2), 133.2 (C-7a), 144.1 (C-5), 149.8 (C-6), 161.4 (C=O) ppm. –MS (70 eV, EI): m/z (%)=283 (100) [M]$^+$, 220 (50) [M-CH$_2$)$_2$Cl]$^+$. —C$_{13}$H$_{14}$ClNO$_4$ (283.71): calcd. C, 55.04; H, 4.97; found C, 54.86; H, 5.06.

Example 16

5-(2-Chloroethoxy)-6-methoxy-1H-indole-2-carboxylic acid (18): A suspension of ester 17 (2.00 g, 7.05 mmol), Cs$_2$CO$_3$ (3.45 g, 10.6 mmol), 95% EtOH (40 mL), and water (20 mL) was heated at reflux for 8 h. After cooling to room temperature the solvent was removed in vacuo, the residue was treated with water (50 µL), and the resulting solution was acidified with 2 M HCl. The formed precipitate was isolated by filtration, washed with water (100 mL), and dried in vacuo to give 18 (1.80 g, 95%) as a beige solid. $^1$H NMR (300 MHz, DMSO-d$_6$): δ=3.81 (s, 3 H, OMe), 3.93 (t, J=5.3 Hz, 2 H, 2'-H$_2$), 4.21 (t, J=5.3 Hz, 2 H, 1'-H$_2$), 6.91 (s, 1 H, 7-H), 6.96 (d, J=2.1 Hz, 1 H, 3-H), 7.15 (s, 1 H, 4-H), 11.44 (s$_{br}$, 1 H, NH), 12.57 (s$_{br}$, 1 H, CO$_2$H) ppm; $^{13}$C NMR (50.3 MHz, DMSO-d$_6$): δ=43.0 (C-2'), 55.6 (OMe), 69.5 (C-1'), 94.9 (C-7), 105.8 (C-4), 107.5 (C-3), 119.8 (C-3a), 126.8 (C-2), 133.0 (C-7a), 143.9 (C-5), 149.5 (C-6), 162.4 (C=O) ppm; MS (70 eV, EI): m/z (%)=269 (100) [M]$^+$, 206 (58) [M-(CH$_2$)$_2$Cl]$^+$; C$_{12}$H$_{12}$ClNO$_4$ (269.68): calcd. C, 53.44; H, 4.49; found C, 53.54; H, 4.29.

Example 17

5-(2-(N,N-Dimethylamino)ethoxy)-6-methoxy-1H-indole-2-carboxylic acid hydrochloride (19): A mixture of acid 18 (300 mg, 1.11 mmol), 40% aqueous Me$_2$NH (2.81 mL, 22.2 mmol), Na$_2$CO$_3$ (295 mg, 2.78 mmol), and water (20 mL) was stirred at 100° C. for 1.5 h. After cooling to room temperature the solvent was removed in vacuo, the residue was dissolved in water (15 mL), and the resulting solution was acidified with 2 M HCl. Then, the solution was evaporated to dryness and the resulting crude product was purified by column chromatography on silica gel (MeOH/CH$_2$Cl$_2$, 10:1, 1% conc. HCl) to provide a green solid which was dissolved in water. Insoluble silica gel was removed by filtration, the water was removed under reduced pressure and the residue was dried in vacuo to give 19 (343 mg, 98%) as a grey-green solid. $^1$H NMR (300 MHz, DMSO-d$_6$): δ=2.87 (s, 6 H, NMe$_2$), 3.49 (t, J=5.0 Hz, 2 H, 2'-H$_2$), 3.82 (s, 3 H, OMe), 4.34 (t, J=5.0 Hz, 2 H, 1'-H$_2$), 6.94 (s, 1 H, 7-H), 6.97 (d, J=1.8 Hz, 1 H, 3-H), 7.23 (s, 1 H, 4-H), 10.99 (s$_{br}$, 1 H, NH$^+$), 11.50 (s$_{br}$, 1 H, NH), 12.60 (s$_{br}$, 1 H, CO$_2$H) ppm; $^{13}$C NMR (50.3 MHz, DMSO-d$_6$): δ=42.7 (NMe$_2$), 55.2 (C-2'), 55.6 (OMe), 64.5 (C-1'), 94.8 (C-7), 106.2 (C-4), 107.5 (C-3), 119.7 (C-3a), 127.0 (C-2), 133.2 (C-7a), 143.4 (C-5), 149.4 (C-6), 162.4 (C=O) ppm; MS (70 eV, EI): m/z (%)=278 (7) [M−HCl]$^+$, 58 (100) [CH$_2$NMe$_2$]$^+$; C$_{14}$H$_{19}$ClN$_2$O$_4$ (314.76): calcd. 278.1267 [M−HCl]$^+$, found 278.1267.

Example 18

(+)-{(1,10)-anti-5-Benzyloxy-3-[(5-(2-(N,N-dimethylamino)ethoxy)-6-methoxy-indol-2-yl)carbonyl]-1-(10-chloroethyl)-1,2-dihydro-3H-benz[e]indole} ((+)-3c): (+)-1 (150 mg, 342 µmol) was suspended in 4 M HCl/EtOAc and stirred at room temperature for 3 h. The reaction mixture was concentrated and dried in vacuo for 1.5 h. The residue was dissolved in DMF (10 mL). The solution was cooled to 0° C. and EDC.HCl (197 mg, 1.03 mmol, 3.0 equiv.) and 19 (140 mg, 445 µmol, 1.3 equiv.) were added. The reaction mixture was stirred at room temperature for 20 h, diluted with ethyl acetate (50 mL), water (50 mL), and saturated aqueous NaHCO$_3$ (50 mL), and extracted with ethyl acetate (4×50 mL). The combined organic layers were washed with brine (4×100 mL), dried over MgSO$_4$, filtered, and concentrated in vacuo. Column chromatography (CH$_2$Cl$_2$/MeOH=10:1) gave (+)-3c as a pale brown solid (134 mg, 224 µmol, 66%). $^1$H-NMR (300 MHz, CDCl$_3$): δ=1.60 (d, J=6.7 Hz, 3 H, 11-CH$_3$), 2.35 (s, 6 H, NMe$_2$), 2.80 (t, J=6.1 Hz, 2 H, 2"-H$_2$), 3.28 (s, 3 H, OCH$_3$), 3.89-3.98 (m, 1 H, 1-H), 4.09 (t, J=6.1 Hz, 2 H, 1"-H$_2$), 4.48-4.65 (m, 2 H, 2-H$_a$, 10-H), 4.78-4.88 (m, 1 H, 2-H$_b$), 5.26 (m$_c$, 2 H, OCH$_2$Ph), 6.71 (s, 1 H, 7'-H), 6.98 (d, J=1.5 Hz, 1 H, 3'-H), 7.07 (s, 1 H, 4'-H), 7.22-7.43, 7.45-7.56 (2×m, 7 H, 7-H, 8-H, 5×Ph-H), 7.67 (d, J=8.2 Hz, 1 H, 9-H), 8.35 (d, J=8.3 Hz, 1 H, 6-H), 8.39 ($s_{br}$, 1 H, 4-H), 10.68 ($s_{br}$, 1 H, NM); $^{13}$C-NMR (75 MHz, CDCl$_3$): δ=23.8 (11-CH$_3$), 45.8 (NMe$_2$), 47.4 (C-1), 53.5 (C-2), 55.2 (OCH$_3$), 58.0 (C-2"), 59.7 (C-10), 67.4 (C-1"), 70.4 (OCH$_2$Ph), 93.9 (C-7'), 98.5 (C-4), 104.8 (C-4'), 106.5 (C-3'), 117.3 (C-5a), 120.5 (C-3a'), 122.4 (C-9), 123.5, 123.6, 123.9 (C-6, C-7, C-9b), 127.5 (2 signals), 127.9, 128.5, (C-8, 5×Bn-CH), 128.7, 129.9, 132.3 (C-2', C-7a', C-9a), 136.6 (Bn-C), 142.7 (C-3a), 145.0 (C-5'), 150.4 (C-6'), 155.5 (C-5), 160.5 (C=O); MS (ESI): m/z (%)=1217.0 (19) [2M+Na]$^+$, 598.2 (100) [M+H]$^+$; C$_{35}$H$_{36}$ClN$_3$O$_4$ (598.13): calcd. 598.2473, found 598.2467, [M+H]$^+$ (ESI-HRMS).

Example 19

(+)-{(1,10)-anti-1-(10-Chloroethyl)-5-hydroxy-3-[(5-(2-(N,N-dimethylamino)ethoxy)-6-methoxy-indol-2-yl)carbonyl]-1,2-dihydro-3H-benz[e]indole-hydrochloride} ((+)-4c): Compound (+)-3c (80 mg, 134 μmol) was dissolved 4 M HCl/ethyl acetate (15 mL) and stirred for 2 h at room temperature. The solution was concentrated. The residue was dried in vacuo for 1 h and then suspended in THF (8 mL). 10% Palladium on activated carbon (29 mg) and ammonium formate (25% aqueous solution, 0.29 mL) were then added at room temperature. The reaction mixture was stirred for 20 min at 40° C. and filtered over Celite, which was thoroughly rinsed with methanol (150 mL). The filtrate was concentrated in vacuo and the residue was purified by column chromatography (CH$_2$Cl$_2$/MeOH=5:1, 0.1% conc. HCl) to give (+)-4c as a green-yellow powder (63 mg, 116 μmol, 86%). $^1$H-NMR (300 MHz, DMSO-d$_6$): δ=1.63 (d, J=6.6 Hz, 3 H, 11-CH$_3$), 2.89 (s, 6 H, NMe$_2$), 3.51 (m$_c$, 2 H, 2"-H$_2$), 3.84 (s, 3 H, OCH$_3$), 4.11-4.20 (m$_c$, 1 H, 1-H), 4.39 (m$_c$, 2 H, 1"-H$_2$), 4.50-4.82 (m, 3 H, 2-H$_2$, 10-H), 7.04 (s, 1 H, 7'-H), 7.14 (d, J=1.5 Hz, 1 H, 3'-H), 7.30 (s, 1 H, 4'-H), 7.34 (m$_c$, 1 H, 7-H), 7.50 (m, 1 H, 8-H), 7.87 (d, J=8.2 Hz, 1 H, 9-H), 7.99 (s, 1 H, 4-H), 8.13 (d, J=8.2 Hz, 1 H, 6-H), 10.40 (s, 1 H, OH), 11.18 ($s_{br}$, 1 H, NH$^+$), 11.51 ($s_{br}$, 1 H, NH); $^{13}$C-NMR (75 MHz, DMSO-d$_6$): δ=23.4 (11-CH$_3$), 42.8 (NMe$_2$), 45.9 (C-1), 52.1 (C-2), 55.3 (C-2"), 55.6 (OCH$_3$), 61.5 (C-10), 64.6 (C-1"), 94.7 (C-7'), 100.4 (C-4), 105.9 (C-3'), 106.6 (C-4'), 115.6 (C-5a), 120.1 (C-3a'), 122.1 (C-9b), 122.7, 122.8 (C-7, C-9), 123.1 (C-6), 126.9 (C-8), 129.4, 129.8 (C-2', C-9a), 132.3 (C-7a'), 142.3 (C-3a), 143.4 (C-5'), 149.3 (C-6'), 153.8 (C-5), 159.7 (C=O); MS (ESI): m/z (%)=508.2 (100) [M-Cl]$^+$; C$_{29}$H$_3$Cl$_2$N$_3$O$_4$ (544.47): calcd. 508.2003, found 508.1998, [M-Cl]$^+$ (ESI-HRMS).

Example 20

[(+)-(1S,10R)-1-(10-Chloroethyl)-3-[(5-(2-(N,N-dimethylamino)ethoxy)-6-methoxy-indol-2-yl)carbonyl]-1,2-dihydro-3H-benz[e]indol-5-yl]-2,3,4,6-tetra-O-acetyl-β-D-galactopyranoside ((+)-7c): A solution of (+)-5 (106 mg, 305 μmol) in dry CH$_2$Cl$_2$ (14 mL) and molecular sieves 4 Å (0.8 g) was stirred for 30 min at room temperature. After addition of O-(2,3,4,6-tetra-O-acetyl-α-D-galactopyranosyl)-trichloracetimidate (6) (155 mg, 314 μmol, 1.03 equiv.), the mixture was cooled to −10° C. and a solution of BF$_3$.OEt$_2$ (19 μL, 152 μmol, 0.5 equiv.) in dry CH$_2$Cl$_2$ (1.5 mL) was slowly added. After 4 h at −10° C., additional BF$_3$.OEt$_2$ (116 μL, 914 μmol, 3.0 equiv.) in dry CH$_2$Cl$_2$ (1.4 mL) was added and the mixture was warmed to room temperature. After 5 h, the solution was separated from the molecular sieves, the molecular sieves were thoroughly rinsed with CH$_2$Cl$_2$ (2×10 mL), and the combined organics were concentrated in vacuo. The residue was dried in vacuo for 1 h and then dissolved in dry DMF (14 μL). The solution was cooled to 0° C., and EDC.HCl (175 mg, 914 μmol, 3.0 equiv.) and 19 (144 mg, 457 μmol, 1.5 equiv.) were added. After 22 h at room temperature, the reaction mixture was diluted with ethyl acetate (50 mL), water (50 mL), and saturated aqueous NaHCO$_3$ (50 mL), and then extracted with ethyl acetate (4×50 mL). The combined organic layers were washed with brine (4×100 mL), dried over MgSO$_4$, filtered, and concentrated in vacuo. Column chromatography (CH$_2$Cl$_2$/MeOH=10:1) gave (+)-7c as a pale brown solid (128 mg, 153 μmol, 50%). C$_{42}$H$_{49}$ClN$_3$O$_{13}$ (838.30): calcd. 838.2957, found 838.2948, [M+H]$^+$ (ESI-HRMS).

Example 21

[(+)-(1S,10R)-1-(10-Chloroethyl)-3-[(5-(2-(N,N-dimethylamino)ethoxy)-6-methoxy-indol-2-yl)carbonyl]-1,2-dihydro-3H-benz[e]indol-5-yl]-β-D-galactopyranoside ((+)-8c): To a solution of compound (+)-7c (125 mg, 149 μmol) in dry MeOH (7 mL) was added NaOMe in methanol (55 μL of a ca. 5.4 M solution, 298 μmol, 2.0 equiv.). The reaction mixture was stirred at room temperature for 30 min and diluted with methanol (9 mL) and water (5 mL). Ion exchange resin (Amberlite-IR 120) was added until the solution reached neutral pH. The solution was concentrated in vacuo and the residue was purified by column chromatography (CH$_2$Cl$_2$/MeOH=1:1), which gave (+)-8c as a pale yellow solid (86 mg, 128 μmol, 86%). $^1$H-NMR (600 MHz, DMSO-d$_6$): δ=1.66 (d, J=6.7 Hz, 3 H, 11-CH$_3$), 2.25 (s, 6 H, NMe$_2$), 2.66 (t, J=6.0 Hz, 2 H, 2"-H$_2$), 3.47 (m$_c$, 1 H, 3'''-H), 3.53-3.59 (m, 2 H, 5'''-H, 6'''-H$_a$), 3.67 (m$_c$, 1-H, 6'''-H$_b$), 3.77-3.83 (m, 5 H, 2'''-H, 4'''-H, OCH$_3$), 4.05 (t, J=6.0 Hz, 2 H, 1"-H$_2$), 4.24 (m$_c$, 1 H, 1-H), 4.54-4.77 (m, 4 H, 2×OH, 2-H$_2$), 4.82 (m$_c$, 1 H, 10-H), 4.85-4.99 (m, 2 H, 1'''-H, OH), 5.32 ($s_{br}$, 1 H, OH), 6.98 (s, 1 H, 7'-H), 7.14 ($s_{br}$, 1 H, 3'-H), 7.18 (s, 1 H, 4'-H), 7.42 (t, J=7.7 Hz, 1 H, 7-H), 7.56 (t, J=7.6 Hz, 1 H, 8-H), 7.95 (d, J=8.6 Hz, 1 H, 9-H), 8.23 ($s_{br}$, 1 H, 4-H), 8.35 (d, J=8.6 Hz, 1 H, 6-H), 11.48 (s, 1 H, NH); $^{13}$C-NMR (150 MHz, DMSO-d$_6$): δ=23.4 (11-CH$_3$), 45.6 (NMe$_2$), 46.0 (C-1), 52.0 (C-2), 55.6 (OCH$_3$), 57.8 (C-2"), 59.6 (C-6'''), 61.3 (C-10), 67.2 (C-1"), 67.5 (C-4'''), 70.6 (C-2'''), 73.3 (C-3'''), 75.2 (C-5'''), 94.7 (C-7'), 101.9 (C-4), 102.3 (C-1'''), 104.7 (C-4'), 106.1 (C-3'), 118.6 (C-5a), 120.3 (C-3a'), 122.8 (C-9), 122.9 (C-9b), 123.4 (C-6), 123.5 (C-7), 127.2 (C-8), 128.9, 129.5 (C-2', C-9a), 131.8 (C-7a'), 142.2 (C-3a), 144.6 (C-5'), 149.4 (C-6'), 153.6 (C-5), 160.1 (C=O); MS (ESI): m/z (%)=670.3 (100) [M+H]$^+$; C$_{34}$H$_{40}$ClN$_3$O$_9$ (670.15): calcd. 670.2531. found 670.2526, [M+H]$^+$ (ESI-HRMS).

Example 22

1-Methylpiperidine-4-carboxylic acid ethyl ester (21): Ethyl isonipecotate (20) (5.00 g, 31.8 mmol) was dissolved in an ice-cold mixture of glacial acetic acid (3.80 g, 63.6 mmol) and water (11 mL). Then, a 37% aqueous formaldehyde solution (2.85 mL, 38.2 mmol) was added and the reaction mixture was hydrogenated over Pd/C (10%, 338 mg) at 58 psi H$_2$ for 3.5 h at room temperature. The solid was removed by filtration through Celite, which was washed thoroughly with water (50 mL) and the filtrate was adjusted to pH 11 with 1 M NaOH under cooling. The resulting solution was extracted with Et$_2$O (5×100 mL), the combined organic fractions were dried (MgSO$_4$), and the solvent was removed under reduced pressure to provide 21 (5.44 g, quant.) as a colorless liquid that was used for the next step without further purification. $^1$H NMR (300 MHz, CDCl$_3$): δ=1.25 (t, J=7.1 Hz, 3 H, OCH$_2$CH$_3$), 1.69-2.06 (m, 6 H, 2-H$_{ax}$, 3-H$_2$, 5-H$_2$, 6-H$_{ax}$), 2.18-2.32

(m, 1 H, 4-H), 2.27 (s, 3 H, NMe), 2.75-2.87 (m, 2 H, 2-$H_{eq}$, 6-$H_{eq}$), 4.13 (q, J=7.1 Hz, 2 H, OC$\underline{H}_2$CH$_3$) ppm. —$^{13}$C NMR (75.5 MHz, CDCl$_3$): δ=14.1 (OCH$_2\underline{C}$H$_3$), 28.2 (C-3, C-5), 40.5 (C-4), 46.3 (NMe), 54.9 (C-2, C-6), 60.2 (O$\underline{C}$H$_2$CH$_3$), 175.0 (C=O) ppm. –MS (70 eV, EI): m/z (%)=171 (31) [M]$^+$, 142 (59) [M–CH$_2$CH$_3$]$^+$, 126 (40) [M–OCH$_2$CH$_3$]$^+$, 98 (56) [M–CO$_2$Et]$^+$. —C$_9$H$_{17}$NO$_2$ (171.24).

Example 23

(1-Methylpiperidin-4-yl)methanol (22): A solution of ester 21 (10.1 g, 59.0 mmol) in Et$_2$O (40 mL) was added dropwise to a suspension of LiAlH$_4$ (2.46 g, 64.9 mmol) in Et$_2$O (200 mL) at 0° C. Then, the reaction mixture was allowed to warm to room temperature and was then stirred for 4 h at this temperature. Water (10 mL) was added slowly and stirring was continued for a further 30 min. The formed white precipitate was separated by filtration and washed thoroughly with Et$_2$O (250 mL). After removal of the solvent under reduced pressure the resulting oil was purified by distillation (bp. 108° C., 14 mbar) to give alcohol 22 (6.40 g, 84%) as a colorless oil. –R$_f$=0.53 (CH$_2$Cl$_2$/MeOH, 5:1, 5% NEt$_3$, PMA: dark blue). $^1$H NMR (300 MHz, CDCl$_3$): δ=1.28 (dq, J=12.2, 3.7 Hz, 2 H, 3-$H_{ax}$, 5-$H_{ax}$), 1.38-1.55 (m, 1 H, 4-H), 1.68-1.79 (m, 2 H, 3-$H_{eq}$, 5-$H_{eq}$), 1.93 (dt, J=11.8, 2.3 Hz, 2 H, 2-$H_{ax}$, 6-$H_{ax}$), 2.26 (s, 3 H, NMe), 2.82-2.92 (m, 2 H, 2-$H_{eq}$, 6-$H_{eq}$), 3.12 (s$_{br}$, 1 H, OH), 3.46 (d, J=6.4 Hz, 2 H, CH$_2$OH) ppm. —$^{13}$C NMR (75.5 MHz, CDCl$_3$): δ=28.8 (C-3, C-5), 37.9 (C-4), 46.3 (NMe), 55.5 (C-2, C-6), 67.4 (CH$_2$OH) ppm. –MS (70 eV, EI): m/z (%)=129 (55) [M]$^+$, 128 (100) [M–H]$^+$, 112 (10) [M–OH]$^+$, 98 (21) [M–CH$_2$OH]$^+$. —C$_7$H$_{15}$NO (129.20).

Example 24

1-Methyl-4-(4-nitrophenoxymethyl)piperidine (24): A mixture of 1-chloro-4-nitrobenzene (23) (2.37 g, 15.0 mmol), alcohol 22 (1.94 g, 15.0 mmol), and DMSO (25 mL) was treated portionwise with NaH (60% in mineral oil, 660 mg, 16.5 mmol) at 40° C. The mixture was stirred at 70° C. for 3 h, poured into water (150 mL), and extracted with Et$_2$O (5×100 mL). The combined organic fractions were washed with water (250 mL) and brine (250 mL), dried (MgSO$_4$), and the solvent was removed in vacuo. The resulting solid was recrystallized from Et$_2$O to give 24 (3.12 g, 83%) as yellow needles. $^1$H NMR (300 MHz, CDCl$_3$): δ=1.36-1.56 (m, 2 H, 3-$H_{ax}$, 5-$H_{ax}$), 1.75-1.91 (m, 3 H, 3-$H_{eq}$, 4-H, 5-$H_{eq}$), 1.98 (dt, J=11.9, 1.9 Hz, 2 H, 2-$H_{ax}$, 6-$H_{ax}$), 2.30 (s, 3 H, NMe), 2.85-2.98 (m, 2 H, 2-$H_{eq}$, 6-$H_{eq}$), 3.90 (d, J=5.8 Hz, 2 H, OCH$_2$), 6.94 (m$_c$, 2 H, 2'-H, 6'-H), 8.19 (m$_c$, 2 H, 3'-H, 5'-H) ppm. —$^{13}$C NMR (50.3 MHz, CDCl$_3$): δ=28.9 (C-3, C-5), 35.1 (C-4), 46.4 (NMe), 55.3 (C-2, C-6), 73.3 (OCH$_2$), 114.3 (C-2', C-6'), 125.8 (C-3', C-5'), 141.3 (C-4'), 164.1 (C-1') ppm. –MS (70 eV, EI): m/z (%)=250 (79) [M]$^+$, 249 (100) [M–H]$^+$. —C$_{13}$H$_{18}$N$_2$O$_3$ (250.29): calcd. C, 62.38; H, 7.25; found C, 62.25; H, 7.40.

Example 25

4-((1-Methylpiperidin-4-yl)methoxy)phenylamine (25): A solution of 1-methyl-4-(4-nitrophenoxymethyl)piperidine (24) (1.0 g, 4.0 mmol), MeOH (20 mL), and concentrated HCl (1 mL) was hydrogenated over Pd/C (10%, 100 mg) at 58 psi H$_2$ for 1 h at room temperature. Then, the solid was removed by filtration through Celite, which was washed thoroughly with MeOH (200 mL), and the filtrate was concentrated in vacuo. The residue was dissolved in water (50 mL) and the resulting solution was adjusted to pH 10 with a saturated aqueous solution of NaHCO$_3$ and 2 M NaOH. The mixture was extracted with CH$_2$Cl$_2$ (3×100 mL), dried (MgSO$_4$), and the solvent was removed in vacuo. Purification by column chromatography (CH$_2$Cl$_2$/MeOH, 10:1, 2% NEt$_3$) gave 25 (0.72 g, 82%) as a reddish brown solid. $^1$H NMR (300 MHz, CDCl$_3$): δ=1.31-1.48 (m, 2 H, 3'-$H_{ax}$, 5'-$H_{ax}$), 1.66-1.89 (m, 3 H, 3'-$H_{eq}$, 4'-H, 5'-$H_{eq}$), 1.96 (dt, J=11.9, 2.3 Hz, 2 H, 2'-$H_{ax}$, 6'-$H_{ax}$), 2.28 (s, 3 H, NMe), 2.84-2.93 (m, 2 H, 2'-$H_{eq}$, 6'-$H_{eq}$), 3.41 (s$_{br}$, 2 H, NH$_2$), 3.73 (d, J=6.4 Hz, 2 H, OCH$_2$), 6.60-6.67 (m, 2 H, 3-H, 5-H), 6.70-6.76 (m, 2 H, 2-H, 6-H) ppm. —$^{13}$C NMR (75.5 MHz, CDCl$_3$): δ=29.1 (C-3', C-5'), 35.3 (C-4'), 46.4 (NMe), 55.4 (C-2', C-6'), 73.2 (OCH$_2$), 115.4 (C-3, C-5), 116.3 (C-2, C-6), 139.8 (C-1), 152.2 (C-4) ppm. –MS (70 eV, EI): m/z (%)=220 (3) [M]$^+$, 112 (100) [C$_7$H$_{14}$N]$^+$. —C$_{13}$H$_{20}$N$_2$O (220.31): calcd. C, 70.87; H, 9.15; found C, 70.50; H, 8.94.

Example 26

5-((1-Methylpiperidin-4-yl)methoxy)-1H-indole-2-carboxylic acid ethyl ester (26): To a stirred solution of 4-((1-methylpiperidin-4-yl)methoxy)phenylamine (25) (2.00 g, 9.08 mmol) in water (19 mL) and concentrated HCl (6 mL) was added dropwise a solution of NaNO$_2$ (689 mg, 9.99 mmol) in water (2 mL) at 0° C., and stirring was continued for 50 min at 0° C. (solution A). Ethyl 2-methylacetoacetate (1.39 mL, 9.53 mmol) was added dropwise to a stirred suspension of NaOAc (7.8 g) in EtOH (15 mL) at 0° C. and stirring was continued for 30 min at this temperature; then ice (9 g) was added (solution B). Solution A was added to solution B by a transfer cannula at 0° C. and the mixture was allowed to warm to room temperature. After 2.5 h the reaction mixture was basified by slow addition of a saturated aqueous solution of Na$_2$CO$_3$ at 0° C. and extracted with CH$_2$Cl$_2$ (3×100 mL). The combined organic layers were washed with water (200 mL), dried (MgSO$_4$), and the solvent was removed in vacuo. The residue was then dissolved in absolute EtOH (10 mL), treated with a freshly prepared saturated solution of HCl in absolute EtOH (10 mL) and heated at reflux for 50 min. After cooling to room temperature the solvent was removed under reduced pressure and the residue was partitioned between water (50 mL) and CH$_2$Cl$_2$ (100 mL). The aqueous layer was basified using a saturated aqueous solution of Na$_2$CO$_3$ and extracted with CH$_2$Cl$_2$ (3×100 mL). The combined organic layers were washed with brine (200 mL), dried (MgSO$_4$), and concentrated in vacuo. Purification by crystallization from iPr$_2$O and column chromatography (CH$_2$Cl$_2$/MeOH, 30:1, 2% NEt$_3$) of the residue obtained after evaporation of the mother liquor provided 26 (2.06 g, 72% overall yield) as a yellow solid. $^1$H NMR (300 MHz, CDCl$_3$): δ=1.36-1.54 (m, 5 H, OCH$_2$C$\underline{H}_3$, 3'-$H_{ax}$, 5'-$H_{ax}$), 1.73-2.06 (m, 5 H, 2-$H_{ax}$, 3'-$H_{eq}$, 4'-H, 5'-$H_{eq}$, 6'-$H_{ax}$), 2.30 (s, 3 H, NMe), 2.87-2.97 (m, 2 H, 2'-$H_{eq}$, 6'-$H_{eq}$), 3.83 (d, J=6.2 Hz, 2 H, ArOC$\underline{H}_2$), 4.40 (q, J=7.2 Hz, 2H, OC$\underline{H}_2$CH$_3$), 6.98 (dd, J=8.9, 2.4 Hz, 1 H, 6-H), 7.05 (d, J=2.0 Hz, 1 H, 3-H), 7.12 (m$_c$, 1 H, 4-H), 7.30 (d, J=8.9 Hz, 1 H, 7-H), 9.11 (s$_{br}$, 1 H, NH) ppm. —$^{13}$C NMR (50.3 MHz, CDCl$_3$): δ=14.4 (OCH$_2\underline{C}$H$_3$), 29.2 (C-3', C-5), 35.3 (C-4'), 46.4 (NMe), 55.5 (C-2', C-6'), 60.9 (O$\underline{C}$H$_2$CH$_3$), 73.2 (ArO$\underline{C}$H$_2$), 103.4 (C-4), 108.1 (C-3), 112.7 (C-7), 117.2 (C-6), 127.8 (C-2, C-3a), 132.2 (C-7a), 154.1 (C-5), 162.0 (C=O) ppm. –MS (70 eV, EI): m/z (%)=316 (6) [M]$^+$, 112 (100) [C$_7$H$_{14}$N]$^+$. —C$_{18}$H$_{24}$N$_2$O$_3$ (316.39): calcd. C, 68.33; H, 7.65; found C, 68.03; H, 7.84.

Example 27

5-((1-Methylpiperidin-4-yl)methoxy)-1H-indole-2-carboxylic acid hydrochloride (27): A suspension of ester 26

(1.00 g, 3.16 mmol) in MeOH (8 mL) was treated with a solution of NaOH (155 mg, 3.88 mmol) in water (4 mL) and heated at reflux for 3.5 h. After cooling to room temperature, the solution was adjusted to pH 6 with 2 M HCl and the solvent was removed under reduced pressure. The residue was dissolved in MeOH, 2 M HCl was added dropwise, and the formed precipitate was collected by filtration to give 27 (712 mg, 69%) as a brown solid. The residue obtained after evaporation of the mother liquor was purified by column chromatography ($CH_2Cl_2$/MeOH, 6:1, 1% conc. HCl) to provide a second batch of 27 (226 mg, 22%). $^1$H NMR (300 MHz, DMSO-$d_6$): δ=1.56-1.77 (m, 2 H, 3'-$H_{ax}$, 5'-$H_{ax}$), 1.89-2.09 (m, 3 H, 3'-$H_{eq}$, 4l-H, 5'-$H_{eq}$), 2.69 (s, 3 H, NMe), 2.87-3.05 (m, 2 H, 2'-$H_{ax}$, 6'-$H_{ax}$) 3.24-3.48 (m, 2 H, 2'-$H_{eq}$, 6'-$H_{eq}$), 3.79-3.92 (m, 2 H, ArOC$\underline{H}_9$), 6.90 (dd, J=9.0, 2.2 Hz, 1 H, 6-H), 6.98 (d, J=1.7 Hz, 1 H, 3-H), 7.12 (d, J=2.2 Hz, 1 H, 4-H), 7.34 (d, J=9.0 Hz, 1 H, 7-H), 10.84 ($s_{br}$, 1H, NH$^+$), 11.59 (s, 1H, NH), 12.74 ($s_{br}$, 1 H, $CO_2$H) ppm. —$^{13}$C NMR (75.5 MHz, DMSO-$d_6$): δ=25.8 (C-3', C-5'), 32.8 (C-4'), 42.5 (NMe), 52.8 (C-2', C-6'), 71.6 (OC$H_2$), 103.4 (C-4), 106.8 (C-3), 113.3 (C-7), 116.0 (C-6), 127.1 (C-2), 128.7 (C-3a), 132.6 (C-7a), 152.9 (C-5), 162.5 (C=O) ppm. –MS (70 eV, EI): m/z (%)=288 (14) [M–HCl]$^+$, 112 (100) [$C_7H_{14}N$]$^+$. —$C_{16}H_{21}ClN_2O_3$ (324.80): calcd. 288.1474 [M–HCl]$^+$; found 288.1474.

Example 28

(+)-{(1,10)-anti-5-Benzyloxy-3-[(5-((1-methylpiperidin-4-yl)methoxy)indol-2-yl)carbonyl]-(10-chloroethyl)-1,2-dihydro-3H-benz[e]indole} ((+)-3d)

Compound (+)-1 (150 mg, 342 μmol) was suspended in 4 M HCl/EtOAc and stirred at room temperature for 3.5 h. The reaction mixture was concentrated and dried in vacuo for 1 h. The residue was dissolved in DMF (10 mL). The solution was cooled to 0° C. and EDC.HCl (197 mg, 1.03 mmol, 3.0 equiv.) and 27 (144 mg, 445 μmol, 1.3 equiv.) were added. The reaction mixture was stirred at room temperature for 23 h, diluted with ethyl acetate (50 mL), water (50 mL), and saturated aqueous $NaHCO_3$ (50 mL), and extracted with ethyl acetate (4×50 mL). The combined organic layers were washed with brine (4×100 mL), dried over $MgSO_4$, filtered, and concentrated in vacuo. Column chromatography ($CH_2Cl_2$/MeOH=10:1) gave (+)-3d as a cream-colored solid (158 mg, 260 μmol, 76%). $^1$H-NMR (300 MHz, DMSO-$d_6$): δ=1.32-1.51 (m, 2 H, 3'''-$H_{ax}$, 5'''-$H_{ax}$), 1.63 (d, J=6.7 Hz, 3 H, 11-$CH_3$), 1.71-1.88 (m, 3 H, 3'''-$H_{eq}$, 4'''-H, 5'''-$H_{eq}$), 2.07-2.22 (m, 2 H, 2'''-$H_{ax}$, 6'''-$H_{ax}$), 2.30 (s, 3H, $NCH_3$), 2.85-3.01 (m, 2 H, 2'''-$H_{eq}$, 6'''-$H_{eq}$), 3.85 (d, J=5.7 Hz, 2 H, 1''-$H_2$), 4.16-4.27 (m, 1 H, 1-H), 4.56-4.86 (m, 3 H, 2-$H_2$, 10-H), 5.30 ($m_c$, 2 H, OC$\underline{H}_2$Ph), 6.93 (d, J=8.9, 2.3 Hz, 1 H, 6'-H), 7.13-7.20 (m, 2 H, 3'-H, 4'-H), 7.32-7.49, 7.51-7.62 (2×m, 8 H, 7-H, 7'-H, 8-H, 5×Ph-H), 7.96 (d, J=8.3 Hz, 1 H, 9-H), 8.12 ($s_{br}$, 1 H, 4-H), 8.23 (d, J=8.4 Hz, 1 H, 6-H), 11.62 ($s_{br}$, 1H, NH); $^{13}$C-NMR (75 MHz, DMSO-$d_6$): δ=23.3 (11-$CH_3$), 27.8 (C-3''', C-5'''), 34.2 (C-4'''), 45.1 ($NCH_3$), 45.9 (C-1), 52.0 (C-2), 54.3 (C-2''', C-6'''), 61.3 (C-10), 69.6 (OC$\underline{H}_2$Ph), 72.3 (C-1''), 98.4 (C-4), 103.4 (C-4'), 105.3 (C-3'), 113.1 (C-7'), 115.8 (C-6'), 117.5 (C-5a), 122.6 (2 signals) 123.0, 123.7 (C-6, C-7, C-9, C-9b), 127.3, 127.4, 127.5, 127.8, 128.4 (C-3a', C-8, 5×Bn-$\underline{C}$H), 129.6, 130.9, 131.6 (C-2', C-7a', C-9a), 136.8 (Bn-C), 142.1 (C-3a), 153.1 (C-5'), 154.2 (C-5), 160.1 (C=O); MS (EI, 70 eV): m/z (%)=607.0 (4) [M]$^+$, 571.0 (23) [M-Cl—H]$^+$; $C_{37}H_{38}ClN_3O_3$ (608.17): calcd. 608.2680, found 608.2675, [M+H]$^+$ (ESI-HRMS).

Example 29

(+)-{(1,10)-anti-1-(10-Chloroethyl)-5-hydroxy-3-[(5-((1-methylpiperidin-4-yl)methoxy)indol-2-yl)carbonyl]-1,2-dihydro-3H-benz[e]indole-hydrochloride} ((+)-4d): Compound (+)-3d (90 mg, 148 μmol) was dissolved in 4 M HCl/ethyl acetate (15 mL) and stirred for 2 h at room temperature. The solution was concentrated. The residue was dried in vacuo for 1 h and then suspended in THF (9 mL). 10% Palladium on activated carbon (32 mg) and ammonium formate (25% aqueous solution, 0.32 mL) were then added at room temperature. The reaction mixture was stirred for 75 min at 40° C. and filtered over Celite, which was thoroughly rinsed with methanol (150 mL). The filtrate was concentrated in vacuo and the residue was purified by column chromatography ($CH_2Cl_2$/MeOH=5:1, 0.1% conc. HCl) to give (+)-4d as a yellow solid (67 mg, 121 μmol, 82%). $^1$H-NMR (300 MHz, DMSO-$d_6$): δ=1.60 (d, J=6.5 Hz, 3 H, 11-$CH_3$), 1.64-1.82 (m, 2 H, 3'''-$H_{ax}$, 5'''-$H_{ax}$), 1.87-2.09 (m, 3 H, 3'''-$H_{eq}$, 4'''-H, 5'''-$H_{eq}$), 2.67 (s, 3 H, $NCH_3$), 2.85-3.04 (m, 2 H, 2'''-$H_{ax}$, 6'''-$H_{ax}$), 3.26-3.45 (m, 2 H, 2'''-$H_{eq}$, 6'''-$H_{eq}$), 3.85 ($m_c$, 2 H, 1''-$H_2$), 4.14 ($m_c$, 1 H, 1-H), 4.47-4.79 (m, 3 H, 2-$H_2$, 10-H), 6.91 ($m_c$, 1 H, 6'-H), 7.11, 7.16 (2×$s_{br}$, 2 H, 3'-H, 4'-H), 7.28-7.44 (m, 2 H, 7-H, 7'-H), 7.48 ($m_c$, 1 H, 8-H), 7.86 (d, J=8.3 Hz, 1 H, 9-H), 7.96 ($s_{br}$, 1 H, 4-H), 8.12 (d, J=8.3 Hz, 1 H, 6-H), 10.43 (s, 1 H, OH), 10.97 ($s_{br}$, 1 H, NH$^+$), 11.59 (s, 1 H, NH); $^{13}$C-NMR (75 MHz, DMSO-$d_6$): δ=23.4 (11-$CH_3$), 25.8 (C-3''', C-5'''), 32.8 (C-4'''), 42.5 ($NCH_3$), 45.8 (C-1), 52.1 (C-2), 52.8 (C-2''', C-6'''), 61.5 (C-10), 71.7 (C-1''), 100.4 (C-4), 103.6, 105.2 (C-3', C-4'), 113.1 (C-7'), 115.6, 115.8 (C-6', C-5a), 122.2, 122.8, 122.9, 123.1 (C-6, C-7, C-9, C-9b), 126.9 (C-8), 127.5 (C-3a'), 129.8, 131.1, 131.7 (C-2', C-7a', C-9a), 142.1 (C-3a), 152.9 (C-5'), 153.9 (C-5), 159.8 (C=O); MS (ESI): m/z (%)=518.0 (100) [M-Cl]$^+$; $C_{30}H_{33}Cl_2N_3O_3$ (554.51): calcd. 518.2210, found 518.2205, [M-Cl]$^+$ (ESI-HRMS).

Example 30

[(+)-(1,10)-anti-1-(10-Chloroethyl)-3-[(5-((1-methylpiperidin-4-yl)methoxy)indol-2-yl)carbonyl]-1,2-dihydro-3H-benz[e]indol-5-yl]-2,3,4,6-tetra-O-acetyl-β-D-galactopyranoside ((+)-7d): A solution of (+)-5 (134 mg, 385 μmol) in dry $CH_2Cl_2$ (17 mL) and molecular sieves 4 Å (0.8 g) was stirred for 30 min at room temperature. After addition of O-(2,3,4,6-tetra-O-acetyl-α-D-galactopyranosyl)-trichloracetimidate (6) (196 mg, 398 μmol, 1.03 equiv.), the mixture was cooled to −10° C. and a solution of $BF_3.OEt_2$ (25 μL, 197 μmol, 0.5 equiv.) in dry $CH_2Cl_2$ (1.9 mL) was slowly added. After 4 h at −10° C., additional $BF_3$—$OEt_2$ (0.146 mL, 1.15 mmol, 3.0 equiv.) in dry $CH_2Cl_2$ (1.8 mL) was added and the mixture was warmed to room temperature. After 5 h, the solution was separated from the molecular sieves, the molecular sieves were thoroughly rinsed with $CH_2Cl_2$ (2×10 mL), and the combined organics were concentrated in vacuo. The residue was dried in vacuo for 1 h and then dissolved in dry DMF (18 mL). The solution was cooled to 0° C., and EDC.HCl (222 mg, 1.16 mmol, 3.0 equiv.) and 27 (188 mg, 0.579 mmol, 1.5 equiv.) were added. After 22 h at room temperature, the reaction mixture was diluted with ethyl acetate (50 mL), water (50 mL), and saturated aqueous $NaHCO_3$ (50 mL), and then extracted with ethyl acetate (4×50 mL). The combined organic layers were washed with brine (4×100 mL), dried over $MgSO_4$, filtered, and concentrated in vacuo. Column chromatography (gradient: $CH_2Cl_2$/MeOH=10:1//$CH_2Cl_2$/MeOH=5:1) gave (+)-7d (65 mg, 77 μmol, 20%) and its N-oxide (110 mg, 127 μmol, 33%), both as pale brown solids.

To a solution of the N-oxide (40 mg, 46 μmol) in dry ethanol (6 mL), $PtO_2·H_2O$ (6 mg, 21 μmol, 0.5 equiv.) was added. Hydrogen was then bubbled through the reaction mixture for 16 h. The reaction mixture was filtered over Celite, and the Celite was thoroughly rinsed with methanol (50 mL) and ethanol (100 mL). The filtrate was concentrated in vacuo and the residue was purified by column chromatography ($CH_2Cl_2$/MeOH=10:1) to give (+)-7d as a yellow solid (24 mg, 28 μmol, 61%). $C_{44}H_{50}ClN_3O_{12}$ (848.33): calcd. 848.3161, found 848.3156, $[M+H]^+$ (ESI-HRMS).

Example 31

[(+)-(1,10)-anti-1-(10-Chloroethyl)-3-[(5-((1-methylpiperidin-4-yl)methoxy)-indol-2-yl)carbonyl]-1,2-dihydro-3H-benz[e]indol-5-yl]-β-D-galactopyranoside ((+)-8d): To a solution of 7d (74 mg, 87 μmol) in dry MeOH (6 mL) was added NaOMe in methanol (32 μL of a ca. 5.4 M solution, 173 μmol, 2.0 equiv.). The reaction mixture was stirred at room temperature for 30 min and diluted with water (2 mL) and methanol (2 mL). Ion exchange resin (Amberlite-IR 120) was added until the solution reached neutral pH. The resin was removed and rinsed with methanol (10 mL). The combined organics were concentrated in vacuo and the residue was purified by column chromatography (gradient: $CH_2Cl_2$/MeOH=5:1//$CH_2Cl_2$/MeOH=7:1, 0.5% $NEt_3$//$CH_2Cl_2$/MeOH=5:1, 0.5% $NEt_3$). The obtained solid was washed with pentane (5×15 mL), which gave 8d as a pale yellow solid (53 mg, 78 μmol, 90%). $^1$H-NMR (600 MHz, DMSO-$d_6$, 100° C.): δ=1.40-1.50 (m, 2 H, 3'''-$H_{ax}$, 5'''-$H_{ax}$), 1.65 (d, J=6.7 Hz, 3 H, 11-$CH_3$), 1.77-1.86 (m, 3 H, 3'''-$H_{eq}$, 4'''-H, 5'''-$H_{eq}$), 2.14 ($m_c$, 2 H, 2'''-$H_{ax}$, 6'''-$H_{ax}$), 2.29 (s, 3 H, $NCH_3$), 2.87-2.93 (m, 2 H, 2'''-$H_{eq}$, 6'''-$H_{eq}$), 3.15 ($s_{br}$, $H_2O$, 4×OH), 3.47-3.51, 3.52-3.56, 3.60-3.64, 3.68-3.73 (4×m, 4 H, 3''''-H, 5''''-H, 6''''-$H_2$), 3.81-3.92 (m, 4 H, 1''-$H_2$, 2''''-H, 4''''-H), 4.22 ($m_c$, 1 H, 1-H), 4.63-4.73 (m, 2 H, 2-$H_2$), 4.81 ($m_c$, 1 H, 10-H), 4.92 (d, J=7.6 Hz, 1 H, 1''''-H), 6.93 ($m_c$, 1 H, 6'-H), 7.09, 7.18 (2×$s_{br}$, 2 H, 3'-H, 4'-H), 7.40-7.45 (m, 2 H, 7-H, 7'-H), 7.56 ($m_c$, 1 H, 8-H), 7.93 (d, J=8.4 Hz, 1 H, 9-H), 8.17 ($s_{br}$, 1 H, 4-H), 8.37 (d, J=8.6 Hz, 1 H, 6-H), 11.31 (s, 1 H, NH); $^{13}$C-NMR (150 MHz, DMSO-$d_6$): δ=23.4 (11-$CH_3$), 28.1 (C-3'''), C-5'''), 34.5 (C-4'''), 45.5 ($NCH_3$), 46.0 (C-1), 52.1 (C-2), 54.5 (C-2''', C-6'''), 59.6 (C-6''''), 61.3 (C-10), 67.5 (C-4''''), 70.6 (C-2''''), 72.5 (C-1''), 73.3 (C-3''''), 75.2 (C-5''''), 101.9 (C-4), 102.3 (C-1''''), 103.4 (C-4'), 105.4 (C-3'), 113.2 (C-7'), 115.8 (C-6'), 118.9 (C-5a), 122.9, 123.0, 123.4, 123.7 (C-6, C-7, C-9, C-9b), 127.3, 127.5 (C-3a', C-8), 129.5, 130.9, 131.7 (C-2', C-7a', C-9a), 142.0 (C-3a), 153.2 (C-5'), 153.6 (C-5), 160.2 (C=O); MS (ESI): m/z (%)=702.3 (12) $[M+Na]^+$, 680.3 (100) $[M+H]^+$; $C_{36}H_{42}ClN_3O_8$ (680.19): calcd. 680.2739, found 680.2733, $[M+H]^+$ (ESI-HRMS).

Example 32

5-(2-(N,N-Dimethylamino)acetylamino)-1H-indole-2-carboxylic acid ethyl ester (29): A solution of 5-nitro-1H-indole-2-carboxylic acid ethyl ester (28) (750 mg, 3.20 mmol) in EtOAc (125 mL) was hydrogenated over Pd/C (10%, 300 mg) at 60 psi $H_2$ for 5 h at room temperature. Then, the solid was removed by filtration through Celite, which was washed thoroughly with $CH_2Cl_2$ (400 mL) and MeOH (400 mL), and the filtrate was concentrated in vacuo. The residue was dissolved in DMF (30 mL) and the solution was cooled to 0° C. EDC.HCl (1.84 g, 9.60 mmol) and N,N-dimethylglycine hydrochloride (670 mg, 4.80 mmol) were added and the reaction mixture was allowed to warm to room temperature. After stirring for 21 h at this temperature, the solution was diluted with EtOAc (100 mL) and water (100 mL). The mixture was adjusted to pH 9 with a saturated aqueous solution of $NaHCO_3$ and extracted with EtOAc (4×150 mL). The combined organic fractions were washed with water (4×200 mL) and brine (300 mL), dried ($MgSO_4$), and the solvent was removed in vacuo. Purification by column chromatography ($CH_2Cl_2$/MeOH, 10:1) gave 29 (626 mg, 68% overall yield) as a pale brown solid. $^1$H NMR (200 MHz, $CDCl_3$): δ=1.42 (t, J=7.1 Hz, 3 H, $OCH_2CH_3$), 2.40 (s, 6 H, $NMe_2$), 3.11 (s, 2 H, 1'-$H_2$), 4.41 (q, J=7.1 Hz, 2 H, $OCH_2CH_3$), 7.18 (d, J=1.8 Hz, 1 H, 3-H), 7.36 (d, J=8.8 Hz, 1 H, 7-H), 7.43 (dd, J=8.8, 1.8 Hz, 1 H, 6-H), 8.04 ($s_{br}$, 1 H, 4-H), 9.04 ($s_{br}$, 1 H, NH), 9.13 ($s_{br}$, 1 H, NH) ppm; $^{13}$C NMR (50.3 MHz, $CDCl_3$): δ=14.3 ($OCH_2CH_3$), 46.0 ($NMe_2$), 61.0 ($OCH_2CH_3$), 63.6 (C-1'), 108.5 (C-3), 112.2, 112.8 (C-4, C-7), 119.2 (C-6), 127.5, 128.2 (C-2, C-3a), 131.1 (C-5), 134.1 (C-7a), 162.0 (NHCO), 168.6 ($CO_2Et$) ppm; MS (70 eV, EI): m/z (%)=289 (25) $[M]^+$, 58 (100) $[CH_2NMe_2]^+$; $C_{15}H_{19}N_3O_3$ (289.33): calcd. 289.1426, found 289.1426.

Example 33

5-(2-(N,N-Dimethylamino)acetylamino)-1H-indole-2-carboxylic acid hydrochloride (30): A mixture of ester 29 (0.200 g, 0.691 mmol), THF (6 mL), MeOH (2 mL), and water (2 mL) was treated with LiOH.$H_2O$ (0.035 g, 0.830 mmol) and stirred at 60° C. for 4 h. After that, the solvent was removed in vacuo and the residue dissolved in water. The resulting solution was acidified with 2 M HCl, water was then evaporated under reduced pressure, and the residue was taken up in acetone/EtOH (1:1). The remaining precipitate (LiCl) was separated by filtration and the filtrate was concentrated under reduced pressure. Purification of the crude product by column chromatography ($CH_2Cl_2$/MeOH, 5:1, 0.5% conc. HCl) provided acid 30 (0.205 g, quant.) as a pale yellow solid. $^1$H NMR (300 MHz, DMSO-$d_6$): δ=2.89 (s, 6 H, $NMe_2$), 4.16 (s, 2 H, 1'-$H_2$), 7.07 (d, —2.1 Hz, 1 H, 3-H), 7.38-7.46 (m, 2 H, 6-H, 7-H), 8.01 ($s_{br}$, 1 H, 4-H), 10.11 ($s_{br}$, 1 H, $NH^+$), 10.80 ($s_{br}$, 1 H, NH), 11.74 ($s_{br}$, 1 H, NH), 12.90 ($s_{br}$, 1 H, $CO_2H$) ppm; $^{13}$C NMR (50.3 MHz, DMSO-$d_6$): δ=43.1 ($NMe_2$), 57.8 (C-1'), 107.3 (C-3), 112.1, 112.6 (C-4, C-7), 118.4 (C-6), 126.6, 129.2 (C-2, C-3a), 130.9 (C-5), 134.4 (C-7a), 162.4, 162.5 (2×C=O) ppm. –MS (70 eV, EI): m/z (%)=261 (7) $[M-HCl]^+$, 58 (100) $[C_3H_8N]^+$; $C_{13}H_{16}ClN_3O_3$ (297.74): calcd. 261.1113 $[M-HCl]^+$, found 261.1113.

Example 34

(+)-{(1,10)-anti-5-Benzyloxy-3-[(5-(2-(N,N-Dimethylamino)acetylamino)indol-2-yl)carbonyl]-1-(10-chloroethyl)-1,2-dihydro-3H-benz[e]indole} ((+)-3e): Compound (+)-1 (150 mg, 342 μmol) was suspended in 4 M HCl/EtOAc (14 mL) and stirred at room temperature for 3.5 h. The reaction mixture was concentrated and dried in vacuo for 1 h. The residue was dissolved in DMF (10 mL). The solution was cooled to 0° C. and EDC.HCl (197 mg, 1.03 mmol, 3.0 equiv.) and 30 (133 mg, 445 μmol, 1.3 equiv.) were added. The reaction mixture was stirred at room temperature for 24 h, diluted with ethyl acetate (50 mL), water (50 mL), and saturated aqueous $NaHCO_3$ (50 mL), and extracted with ethyl acetate (4×50 mL). The combined organic layers were washed with brine (4×100 mL), dried over $MgSO_4$, filtered, and concentrated in vacuo. Column chromatography (CH$_2$Cl$_2$/MeOH=30:1) gave (+)-3e as a pale green foam (155 mg, 267 µmol, 78%). $^1$H-NMR (300 MHz, CDCl$_3$): δ=1.63 (d, J=6.8 Hz, 3 H, 11-CH$_3$), 2.39 (s, 6 H, NMe$_2$), 3.11 (s, 2 H, 1"-H$_2$), 3.88-4.02 (m, 1 H, 1-H), 4.47-4.63 (m, 2 H, 2-H$_a$, 10-H), 4.84 (dd, J=10.8, 1.5 Hz, 1 H, 2-H$_b$), 5.24 (m$_c$, 2 H, OCH$_2$Ph), 7.06 (d, J=1.4 Hz, 1 H, 3'-H), 7.20 (dd, J=8.8, 1.9 Hz, 1 H, 6'-H), 7.28-7.56 (m, 8 H, 7-H, 7'-H, 8-H, 5×Ph-H), 7.68 (d, J=8.2 Hz, 1 H, 9-H), 8.13-8.28 (m, 2 H, 4-H, 4'-H), 8.35 (d, J=8.3 Hz, 1 H, 6-H), 9.11 (s, 1 H, NH), 10.03 (s, 1 H, NH); $^{13}$C-NMR (75 MHz, CDCl$_3$): δ=23.9 (11-CH$_3$), 46.0 (NMe$_2$), 47.4 (C-1), 53.5 (C-2), 59.9 (C-10), 63.6 (C-1"), 70.3 (OCH$_2$Ph), 98.2 (C-4), 106.4 (C-3'), 112.1 (C-7'), 112.6 (C-4'), 117.3 (C-5a), 118.8 (C-6'), 122.5 (C-9), 123.7, 123.8, 123.9 (C-6, C-7, C-9b), 127.4, 127.6, 127.9, 128.0, 128.5 (C-3a', C-8, 5×Bn-CH), 129.9 (C-5'), 131.1, 131.2, 133.2 (C-2', C-7a', C-9a), 136.7 (Bn-C), 142.3 (C-3a), 155.5 (C-5), 160.4 (C=O), 168.6 (C=O); MS (EI, 70 eV): m/z (%)=580.0 (10) [M]$^+$, 544.0 (7) [M-Cl-H]$^+$; C$_{34}$H$_{33}$ClN$_4$O$_3$ (581.10): calcd. 580.2319, found 581.2314, [M+H]$^+$ (ESI-HRMS).

Example 35

(+)-{(1,10)-anti-1-(10-Chloroethyl)-5-hydroxy-3-[(5-(2-(2-(N,N-Dimethylamino)acetylamino)-indol-2-yl)carbonyl]-1,2-dihydro-3H-benz[e]indole-hydrochloride} ((+)-4e): Compound (+)-3e (80 mg, 138 µmol) was dissolved in 4 M HCl/ethyl acetate (10 mL) and stirred for 2 h at room temperature. The solution was concentrated. The residue was dried in vacuo for 1 h and then suspended in THF (8 mL). 10% Palladium on activated carbon (30 mg) and ammonium formate (25% aqueous solution, 0.30 mL) were then added at room temperature. The reaction mixture was stirred for 40 min at 40° C. and filtered over Celite, which was thoroughly rinsed with methanol (150 mL). The filtrate was concentrated in vacuo and the residue was purified by column chromatography (MeOH, 0.1% conc. HCl). The product was then dissolved in a bit CH$_2$Cl$_2$/MeOH, 0.1% conc. HCl. The solution was filtered and the filtrate was concentrated to give (+)-4e as a green solid (78 mg, 152 µmol, 86%). $^1$H-NMR (300 MHz, DMSO-d$_6$): δ=1.63 (d, J=6.3 Hz, 3 H, 11-CH$_3$), 2.90 (s, 6 H, NMe$_2$), 4.11-4.25 (m, 3 H, 1-H, 1"-H$_2$), 4.53-4.64 (m, 1 H, 2-H$_a$), 4.65-4.81 (m, 2 H, 2-H$_b$, 10-H), 7.21-7.55 (m, 5 H, 3'-H, 6'-H, 7-H, 7'-H, 8-H), 7.88 (d, J=8.3 Hz, 1 H, 9-H), 7.99 (s$_{br}$, 1 H, 4-H), 8.07-8.19 (m, 2 H, 4'-H, 6-H), 10.30 (s$_{br}$, 1 H, OH), 10.43, 11.03, 11.73 (3×s, 3 H, 2×NH, NH$^+$); $^{13}$C-NMR (75 MHz, DMSO-d$_6$): δ=23.3 (11-CH$_3$), 43.1 (NMe$_2$), 45.8 (C-1), 52.1 (C-2), 57.9 (C-1"), 61.5 (C-10), 100.3 (C-4), 105.6 (C-3'), 112.1, 112.3 (C-4', C-7'), 115.9 (C-5a), 118.0 (C-6'), 122.2, 122.9 (2 Signals), 123.1 (C-6, C-7, C-9, C-9b), 126.9, 127.0 (C-3a', C-8), 129.7, 130.8, 131.4, 133.3 (C-2', C-5', C-7a', C-9a), 142.1 (C-3a), 153.8 (C-5), 159.7 (C=O), 162.4 (C=O); MS (ESI): m/z (%)=981.0 (11) [2M+H]$^+$, 491.1 (100) [M-Cl]$^+$; C$_{27}$H$_{28}$Cl$_2$N$_4$O$_3$ (527.44): calcd. 491.1850, found 491.1844, [M-Cl]$^+$ (ESI-HRMS).

Example 36

[(+)-(1S,10R)-1-(10-Chloroethyl)-3-[(5-(2-(N,N-Dimethylamino)acetylamino)indol-2-yl)carbonyl]-1,2-dihydro-3H-benz[e]indol-5-yl]-2,3,4,6-tetra-O-acetyl-β-D-galactopyranoside ((+)-7e): A solution of (+)-5 (137 mg, 394 µmol) in dry CH$_2$Cl$_2$ (17 mL) and molecular sieves 4 Å (0.8 g) was stirred for 30 min at room temperature. After addition of O-(2,3,4,6-tetra-O-acetyl-α-D-galactopyranosyl)-trichloracetimidate (6) (200 mg, 406 µmol, 1.03 equiv.), the mixture was cooled to −10° C. and a solution of BF$_3$.OEt$_2$ (25 µL, 197 µmol, 0.5 equiv.) in dry CH$_2$Cl$_2$ (1.9 mL) was slowly added. After 4 h at −10° C., additional BF$_3$—OEt$_2$ (150 µL, 1.18 mmol, 3.0 equiv.) in dry CH$_2$Cl$_2$ (1.8 mL) was added and the mixture was warmed to room temperature. After 5 h, the solution was separated from the molecular sieves, the molecular sieves were thoroughly rinsed with CH$_2$Cl$_2$ (2×10 mL), and the combined organics were concentrated in vacuo. The residue was dried in vacuo for 1 h and then dissolved in dry DMF (18 mL). The solution was cooled to 0° C., and EDC.HCl (227 mg, 1.18 mmol, 3.0 equiv.) and 30 (176 mg, 591 µmol, 1.5 equiv.) were added. After 21 h at room temperature, the reaction mixture was diluted with ethyl acetate (50 mL), water (50 mL), and saturated aqueous NaHCO$_3$ (50 mL), and then extracted with ethyl acetate (4×50 mL). The combined organic layers were washed with brine (4×100 mL), dried over MgSO$_4$, filtered, and concentrated in vacuo. Column chromatography (CH$_2$Cl$_2$/MeOH=25:1) gave (+)-7e as a pale brown solid (155 mg, 189 µmol, 48%). C$_{41}$H$_{45}$ClN$_4$O$_{12}$ (821.27): calcd. 821.2801, found 821.2795, [M+H]$^+$ (ESI-HRMS).

Example 37

[(+)-(1S,10R)-1-(10-Chloroethyl)-3-[(5-(2-(N,N-Dimethylamino)acetylamino)carbonyl]-1,2-dihydro-3H-benz[e]indol-5-yl]-β-D-galactopyranoside ((+)-8e): To a solution of (+)-7e (142 mg, 173 µmol) in dry MeOH (6 mL) was added NaOMe in methanol (64 µL of a ca. 5.4 M solution, 346 µmol, 2.0 equiv.). The reaction mixture was stirred at room temperature for 30 min and diluted with methanol (2 mL) and water (2 mL). Ion exchange resin (Amberlite-IR 120) was added until the solution reached neutral pH. The resin was separated from the solution and rinsed with methanol (10 mL). The combined organic fractions were concentrated in vacuo and the residue was purified by column chromatography (gradient: CH$_2$Cl$_2$/MeOH=7:1//CH$_2$Cl$_2$/MeOH=3:1). The crude product was washed with pentane (5×15 mL), which gave (+)-8e as a yellow solid (93 mg, 142 µmol, 82%). $^1$H-NMR (600 MHz, DMSO-d$_6$): δ=1.65 (d, J=6.7 Hz, 3 H, 11-CH$_3$), 2.31 (s, 6 H, NMe$_2$), 3.08 (s, 2 H, 1"-H$_2$), 3.45-3.52 (m, 1 H, 3'''-H), 3.53-3.61 (m, 2 H, 5'''-H, 6'''-H$_a$), 3.64-3.71 (m, 1 H, 6'''-H$_b$), 3.77-3.85 (m, 2 H, 2'''-H, 4'''-H), 4.25 (m$_c$, 1 H, 1-H), 4.55-4.66 (m, 3 H, 2-H$_a$, 2×OH), 4.72-4.90 (m, 3 H, 2-H$_b$, 10-H, OH), 4.93 (m$_c$, 1 H, 1'''-H), 5.31 (s$_{br}$, 1 H, OH), 7.25 (s$_{br}$, 1 H, 3'-H), 7.37-7.46 (m, 3 H, 6'-H, 7'-H, 7-H), 7.57 (m$_c$, 1 H, 8-H), 7.96 (d, J=8.4 Hz, 1 H, 9-H), 8.13 (s$_{br}$, 1 H, 4'-H), 8.24 (s$_{br}$, 1 H, 4-H), 8.36 (d, J=8.6 Hz, 1 H, 6-H), 9.60 (s, 1 H, NH), 11.70 (s, 1 H, NH); $^{13}$C-NMR (150 MHz, DMSO-d$_6$): δ=23.4 (11-CH$_3$), 45.3 (NMe$_2$), 46.0 (C-1), 52.1 (C-2), 59.6 (C-6'''), 61.4 (C-10), 63.2 (C-1"), 67.5 (C-4'''), 70.6 (C-2'''), 73.3 (C-3'''), 75.2 (C-5'''), 101.9 (C-4), 102.3 (C-1'''), 105.8 (C-3'), 112.1 (C-4'), 112.2 (C-7'), 118.6 (C-6'), 119.0 (C-5a), 122.9, 123.1, 123.4, 123.7 (C-6, C-7, C-9, C-9b), 127.1 (C-3a'), 127.3 (C-8), 129.5, 131.1, 131.5, 133.3 (C-2', C-5', C-7a', C-9a), 142.0 (C-3a), 153.6 (C-5), 160.1 (C=O), 168.2 (C=O); MS (ESI): m/z (%)=653.2 (100) [M+H]$^+$; C$_{33}$H$_{37}$ClN$_4$O$_8$ (653.12): calcd. 653.2378, found 653.2373, [M+H]$^+$ (ESI-HRMS).

Example 38

5-Benzyloxy-3-[(5-(2-(N,N-Dimethylamino)acetylamino)indol-2-yl)carbonyl]-1-(10-chloromethyl)-1,2-dihydro-3H-benz[e]indole} (rac-32): Compound rac-31 (300 mg, 708 µmol) was suspended in 4 M HCl/EtOAc (30 mL) and stirred at room temperature for 3 h. The reaction mixture was concentrated and dried in vacuo for 2 h. The residue was dissolved in DMF (25 mL). The solution was cooled to 0° C. and EDC.HCl (407 mg, 2.12 mmol, 3.0 equiv.) and 2 (302 mg, 1.06 mmol, 1.5 equiv.) were added. The reaction mixture was stirred at room temperature for 2.5 d, diluted with ethyl acetate (100 mL), water (100 mL), and saturated aqueous NaHCO$_3$ (100 mL), and extracted with ethyl acetate (3×200 mL). The combined organic layers were washed with brine (4×200 mL), dried over MgSO$_4$, filtered, and concentrated in vacuo. Column chromatography (CH$_2$Cl$_2$/MeOH=10:1) gave rac-32 as a yellow-brown solid (229 mg, 413 μmol, 58%). $^1$H-NMR (300 MHz, CDCl$_3$): δ=2.37 (s, 6 H, NMe$_2$), 2.78 (t, J=5.7 Hz, 2 H, 2"-H$_2$), 3.44 (t, J=10.9 Hz, 1 H, 10-H$_a$), 3.95 (dd, J=11.2, 2.9 Hz, 1 H, 10-H$_b$), 4.04-4.15 (m, 3 H, 1-H, 1"-H$_2$), 4.58-4.67 (m, 1 H, 2-H$_a$), 4.78 (dd, J=11.0, 1.6 Hz, 1 H, 2-H$_b$) 5.25 (m$_c$, 2 H, OCH$_2$Ph), 6.97-7.03 (m, 2 H, 3'-H, 6'-H), 7.11 (d, J=2.3 Hz, 1 H, 4'-H), 7.28-7.43, 7.46-7.57 (2×m, 8 H, 7-H, 7'-H, 8-H, 5×Ph-H), 7.69 (d, J=8.3 Hz, 1 H, 9-H), 8.19 (s$_{br}$, 1 H, 4-H), 8.34 (d, J=8.3 Hz, 1 H, 6-H), 9.75 (s$_{br}$, 1 H, NH); $^{13}$C-NMR (50 MHz, CDCl$_3$): δ=43.1 (C-1), 45.8 (NMe$_2$), 46.0 (C-10), 55.2 (C-2), 58.3 (C-2"), 66.4 (C-1"), 70.3 (OCH$_2$Ph), 98.3 (C-4), 103.5 (C-4'), 106.1 (C-3'), 112.7 (C-7'*), 116.4 (C-5a), 117.3 (C-6'*), 122.1, 123.6, 123.7, 124.1 (C-6, C-7, C-9, C-9b), 127.6, 127.8, 128.0, 128.2, 128.5 (C-3a', C-8, 5×Bn-CH), 129.7, 130.5, 131.4 (C-2', C-7a', C-9a), 136.7 (Bn-C), 142.1 (C-3a), 153.8 (C-5'), 155.8 (C-5), 160.7 (C=O); MS (EI, 70 eV): m/z (%)=553.3 (33) [M]$^+$, 517.3 (7) [M-Cl]$^+$; C$_{33}$H$_{32}$ClN$_3$O$_3$ (554.08): calc. 553.2132, found 553.2132 (EI-HRMS).

Example 39

1-(10-Chloromethyl)-5-hydroxy-3-[(5-(2-(2-(N,N-Dimethylamino)acetylamino)indol-2-yl)carbonyl]-1,2-dihydro-3H-benz[e]indole-hydrochloride} (rac-33): Compound rac-32 (100 mg, 180 μmol) was dissolved in 4 M HCl/ethyl acetate (10 mL) and stirred for 2 h at room temperature. The solution was concentrated. The residue was dried in vacuo for 1 h and then suspended in THF (15 mL). 10% Palladium on activated carbon (38 mg) and ammonium formate (25% aqueous solution, 0.38 mL) were then added at room temperature. The reaction mixture was stirred for 4 h at 40° C. and filtered over Celite, which was thoroughly rinsed with methanol (300 mL). The filtrate was concentrated in vacuo and the residue was purified by column chromatography (CH$_2$Cl$_2$/MeOH=5:1, 0.1% conc. HCl) to give rac-33 as a yellow solid (73 mg, 146 μmol, 81%). $^1$H-NMR (300 MHz, MeOH-d$_4$): δ=2.98 (s, 6 H, NMe$_2$), 3.51-3.65 (m, 3 H, 2"-H$_2$, 10-H$_a$), 3.93 (dd, J=11.2, 3.0 Hz, 1 H, 10-H$_b$), 4.03-4.13 (m, 1 H, 1-H), 4.32 (t, J=4.8 Hz, 2 H, 1"-H$_2$), 4.52-4.66 (m, 2 H, 2-H$_2$), 6.99-7.06 (m, 2 H, 3'-H, 6'-H), 7.24 (d, J=2.4 Hz, 1 H, 4'-H), 7.33 (t, J=7.6 Hz, 1 H, 7-H), 7.43 (d, J=8.9 Hz, 1 H, 7'-H), 7.49 (t, J=7.6 Hz, 1 H, 8-H), 7.72 (d, J=8.4 Hz, 1 H, 9-H), 7.81 (s$_{br}$, 1 H, 4-H), 8.18 (d, J=8.4 Hz, 1 H, 6-H); $^{13}$C-NMR (75 MHz, MeOH-d$_4$): δ=43.5 (C-1), 43.9 (NMe$_2$), 47.5 (C-10), 56.8 (C-2), 57.8 (C-2"), 63.7 (C-1"), 101.4 (C-4), 105.2 (C-4'), 107.2 (C-3'), 114.2 (C-7'), 117.1, 117.2 (C-5a, C-6), 123.5 (C-9), 124.3, 124.5, 124.6 (C-6, C-7, C-9a), 128.6 (C-8), 129.2, 131.5, 132.5, 133.9 (C-2, C-3a', C-7a, C-9b), 143.1 (C-3a), 153.8 (C-5'), 155.8 (C-5), 162.6 (C=O); MS (ESI): m/z (%)=928.9 (35) [2M-2Cl]$^+$, 464.2 (100) [M-Cl]$^+$; C$_{26}$H$_{27}$Cl$_2$N$_3$O$_3$ (500.42): calcd. 464.1741, found 464.1736, [M-Cl]$^+$ (ESI-HRMS).

Example 40

[1-(10-Chloromethyl)-3-[(5-(2-(N,N-Dimethylamino)acetylamino)indol-2-yl)carbonyl]-1,2-dihydro-3H-benz[e]indol-5-yl]-2,3,4,6-tetra-O-acetyl-β-D-galactopyranoside (35/35'): A solution of rac-34 (136 mg, 407 μmol) in dry CH$_2$Cl$_2$ (18 mL) and molecular sieves 4 Å (0.8 g) was stirred for 30 min at room temperature. After addition of O-(2,3,4,6-tetra-O-acetyl-α-D-galactopyranosyl)-trichloracetimidate (6) (211 mg, 428 μmol, 1.05 equiv.), the mixture was cooled to −10° C. and a solution of BF$_3$ OEt$_2$ (26 μL, 205 μmol, 0.5 equiv.) in dry CH$_2$Cl$_2$ (2.1 mL) was slowly added. After 4 h at −10° C., additional BF$_3$.OEt$_2$ (155 μL, 1.22 mmol, 3.0 equiv.) in dry CH$_2$Cl$_2$ (1.8 mL) was added and the mixture was warmed to room temperature. After 5 h, the solution was separated from the molecular sieves, the molecular sieves were thoroughly rinsed with CH$_2$Cl$_2$ (2×10 mL), and the combined organics were concentrated in vacuo. The residue was dried in vacuo for 1 h and then dissolved in dry DMF (19 mL). The solution was cooled to 0° C., and EDC.HCl (234 mg, 1.22 mmol, 3.0 equiv.) and 2 (174 mg, 611 μmol, 1.5 equiv.) were added. After 20 h at room temperature, the reaction mixture was diluted with ethyl acetate (25 mL), water (25 mL), and saturated aqueous NaHCO$_3$ (25 mL), and then extracted with ethyl acetate (4×50 mL). The combined organic layers were washed with brine (4×100 mL), dried over MgSO$_4$, filtered, and concentrated in vacuo. Column chromatography (CH$_2$Cl$_2$/MeOH=10:1) gave a mixture of both diastereomers 35 and 35' as a yellow solid (173 mg, 218 μmol, 54%). (−)-35: C$_{40}$H$_{44}$ClN$_3$O$_{12}$ (794.24): calcd. 794.2692, found 794.2686, [M+H]$^+$ (ESI-HRMS).

Example 41

[1-(10-Chloromethyl)-3-[(5-(2-(N,N-Dimethylamino)acetylamino)carbonyl]-1,2-dihydro-3H-benz[e]indol-5-yl]-β-D-galactopyranoside (36/36'): To a solution of 35/35' (170 mg, 214 μmol) in dry MeOH (9 mL) was added NaOMe in methanol (79 μL of a ca. 5.4 M solution, 428 μmol, 2.0 equiv.). The reaction mixture was stirred at room temperature for 2 h and diluted with methanol (2 mL) and water (2 mL). Ion exchange resin (Amberlite-IR 120) was added until the solution reached neutral pH. The resin was separated from the solution and rinsed with methanol (10 mL). The combined organic fractions were concentrated in vacuo and the residue was purified by column chromatography (CH$_2$Cl$_2$/MeOH=1:1) to give diastereomers 36/36' as a pale yellow solid (94 mg, 150 μmol, 70%). $^1$H-NMR (600 MHz, DMSO-d$_6$): δ=2.24 (s, 6 H, NMe$_2$), 2.66 (t, J=5.9 Hz, 2 H, 2"-H$_2$), 3.35-3.86 (m, 6 H, 2'"-H, 3'"-H, 4'"-H, 5'"-H, 6'"-H$_2$), 3.89-3.95 (m, 1 H, 10-H$_a$), 4.02-4.09 (m, 3 H, 1"-H$_2$, 10-H$_b$), 4.25-4.32 (m, 1 H, 1-H), 4.53-4.63 (m, 3 H, 2-H$_2$, OH), 4.71-4.97 (m, 3 H, 1'"-H, 2×OH), 5.27-5.36 (m, 1 H, OH), 6.91 (dd, J=8.9, 2.3 Hz, 1 H, 6'-H), 7.06-7.11 (m, 1 H, 3'-H), 7.17-7.19 (m, 1 H, 4'-H), 7.38-7.45 (m, 2 H, 7-H, 7'-H), 7.57 (m, 1 H, 8-H), 7.91 (d, J=8.6 Hz, 1 H, 9-H), 7.98-8.28 (m, 1 H, 4-H), 8.33, 8.35 (2×d, J=8.6 Hz, 1 H, 6-H), 11.62, 11.64 (2×s$_{br}$, 1 H, NH); $^{13}$C-NMR (150 MHz, DMSO-d$_6$): δ=41.0/41.2 (C-1), 45.5 (NMe$_2$), 47.5 (C-10), 54.9/55.0 (C-2), 57.8 (C-2"), 59.6/59.7 (C-6'"), 66.3 (C-1"), 67.5/67.7, 70.4/70.5, 73.2 (2 signals), 75.2 (C-2'", C-3'", C-4'", C-5'"), 101.8 (C-4), 102.1/102.3 (C-1'"), 103.2/103.3 (C-4'), 105.2/105.3 (C-3'), 113.1/113.2 (C-7'), 115.8/115.9 (C-6'), 117.9/118.0 (C-5a), 122.70 (C-9), 122.9/123.0 (C-9b), 123.3/123.4 (C-6), 123.7/123.8 (C-7), 127.5 (C-3a', C-8), 129.5 (2 signals) (C-9a), 130.9 (2 signals), 131.6/131.7 (C-2', C-7a'), 142.1 (C-3a), 153.0 (2 signals) (C-5'), 153.7 (2 signals) (C-5), 160.3 (2 signals) (C=O); MS (ESI): m/z (%)=1252.0 (11) [2M+2H]$^+$, 626.4 (100) [M+H]$^+$; C$_{32}$H$_{36}$ClN$_3$O$_8$ (626.10): calcd. 626.2269, found 626.2264, [M+H]$^+$ (ESI-HRMS).

Example 42

(1S,10R)-1-(10-Chloroethyl)-5-hydroxy-3-[(5-(2-(N-methylamino)ethoxy)indol-2-yl)carbonyl]-1,2-dihydro-3H-benz[e]indole-hydrochloride (4f): Compound 3f (12 mg, 18.3 μmol) was dissolved in THF (2 mL). 10% Palladium on activated carbon (4 mg) and ammonium formate (25% aqueous solution, 40 μL) were then added at room temperature. The reaction mixture was stirred for 2 h at 45° C. and filtered over Celite, which was thoroughly rinsed with methanol (3×5 mL). The filtrate was concentrated in vacuo. The residue was dissolved in 4 N HCl in ethyl acetate (10 mL). The reaction mixture was stirred at room temperature for 1 h, after which the reaction mixture was concentrated. Ethyl acetate was added to the residue and the suspension was concentrated. The residue was purified by column chromatography ($CH_2Cl_2$/MeOH=5:1, 0.1% conc. HCl) to afford 4f (5.6 mg, 11.2 μmol, 61%) as a pale green solid. $^1$H-NMR (400 MHz, $CDCl_3$/$CD_3OD$): δ=1.65 (d, 3 H, 10-$CH_3$), 2.81 (s, 3 H, N—$CH_3$), 3.45 (t, 2 H, 2"-H), 4.03 (m, 1 H, 1-H), 4.38 (t, 2 H, 1"-H), 4.59-4.65 (in 2 H, 10-H, 2-H), 4.79 (d, 1 H, 2-H), 7.07 (d, 1 H, 6'-H), 7.09 (s, 1 H, 3'-H), 7.24 (s, 1 H, 4'-H), 7.38 (t, 1 H, 7-H), 7.47 (d, 1 H, 7'-H), 7.52 (t, 1 H, 8-H), 7.75 (d, 1 H, 9-H), 7.79 (br. s, 1 H, 4-H), 8.23 (d, 1 H, 6-H).

Example 43

(1S,10R)-1-(10-Chloroethyl)-5-hydroxy-3-[(5-(2-(N-methyl-N-(carboxymethyl)-amino)ethoxy)indol-2-yl)carbonyl]-1,2-dihydro-3H-benz[e]indole-hydrochloride (4g): Compound 4g was prepared from 3g according to the procedure given for the conversion of 3f to 4f. Compound 4g was obtained as a pale green solid in 50% yield. $^1$H-NMR (400 MHz, DMSO-$d_6$): δ=1.61 (m, 3 H, 10-$CH_3$), 2.93 (s, 3 H, $NCH_3$), 3.14-3.18 (m, 2 H, $OCH_2CH_2N$), 3.61 (s, 2 H, $CH_2CO_2H$), 3.82 (m, 1 H, 1-H), 4.17-4.74 (m, 5 H, $OCH_2CH_2N$, 2×2-H, 10-H), 6.93-8.12 (m, 9 H, 6'-H, 3'-H, 4'-H, 7'-H, 7-H, 8-H, 9-H, 4-H, 6-H), 10.42 (s, 1 H, NH), 11.67 (s, 1 H, OH); MS (ESI): m/z=522 $[M+H]^+$, 1043 $[2M+H]^+$.

Example 44

(1S,10R)-1-(10-Chloroethyl)-5-hydroxy-3-[(5-(2-(N-methyl-N-(2-methoxy-2-oxoethyl)amino)-ethoxy)indol-2-yl)carbonyl]-1,2-dihydro-3H-benz[e]indole-hydrochloride (4h): Compound 4h was prepared from 3h according to the procedure given for the conversion of 3a to 4a except that the acidification step with HCl in ethyl acetate was omitted. Compound 4h was obtained as a pale green solid in 87% yield. $^1$H-NMR (300 MHz, $CDCl_3$/$CD_3OD$): δ=1.57 (d, 3 H, 10-$CH_3$), 2.67 (s, 3 H, $NCH_3$), 3.21 (t, 2 H, $OCH_2CH_2N$), 3.65 (s, 2 H, $CH_2CO_2Me$), 3.70 (s, 3 H, $OCH_3$), 3.82 (m, 1 H, 1-H), 4.15 (t, 2 H, $OCH_2CH_2N$), 4.38 (m, 1 H, 2-H), 4.48 (m, 1 H, 10-H), 4.70 (m, 1 H, 2-H), 6.85-6.90 (m, 2 H, 6'-H, 3'-H), 7.06 (d, 1 H, 4'-H), 7.27-7.38 (m, 2 H, 7'-H, 7-H), 7.46 (m, 1 H, 8-H), 7.60 (d, 1 H, 9-H), 7.89 (br. s, 1 H, 4-H), 8.28 (d, 1 H, 6-H), 10.21 (s, 1 H, NH); MS (ESI): m/z=536 $[M+H]^+$, 1093 $[2M+Na]^+$.

Example 45

(1S)-1-Chloromethyl-5-hydroxy-3-[(5-(2-(2-(N,N-dimethylamino)ethoxy)indol-2-yl)carbonyl]-9-methyl-1,2-dihydro-3H-benz[e]indole-hydrochloride (45): Compound 45 was prepared from 44 in 4 consecutive steps according to the procedure described for the synthesis of 4a from 1. Compound 45 was obtained as a pale green solid in a 4-step yield of 20%. $^1$H-NMR (300 MHz, $CD_3OD$): δ=2.78 (s, 3 H, 9-$CH_3$), 2.98 (s, 6 H, $N(CH_3)_2$), 3.25 (t, 1 H, 2-H), 3.58 (t, 2 H, 2"-H), 3.68 (d, 1 H, 2-H), 4.25 (dd, 1 H, 1-H), 4.33 (t, 2 H, 1"-H), 4.50 (t, 1 H, 10-H), 4.64 (d, 1 H, 10-H), 7.00-7.08 & 7.18-7.31 (2×m, 5 H, 7-H, 3'-H, 4'-H, 6'-H, 7'-H), 7.43 (d, 1 H, 8-H), 7.85 (s, 1 H, 4-H), 8.11 (d, 1 H, 6-H); MS (ESI): m/z=478 $[M+H]^+$.

Example 46

Compound 46a: Compound (+)-4a (36 mg, 71 μmol) was suspended in acetonitrile (10 mL) and the mixture was cooled to 0° C. p-Nitrophenyl chloroformate (28.4 mg, 0.141 mmol) and DIPEA (58.3 μL, 0.353 mmol) were added and the reaction mixture was warmed to room temperature. After 1 h, the reaction mixture was concentrated to dryness. The residue was washed with toluene (2×5 mL) and dried in vacuo. The residue was dissolved in acetonitrile (10 mL) and N-Boc-N,N'-dimethylethylenediamine (133 mg, 0.706 mmol) was added. After 1 h, the reaction mixture was concentrated in vacuo. The residue was dissolved in dichloromethane; the solution was washed with water, dried over $Na_2SO_4$, filtered, and concentrated. The crude residue was dissolved in TFA. After 30 minutes, the reaction mixture was concentrated in vacuo to afford crude 46a quantitatively as an off-white solid.

Compound 46b: Compound 46b was prepared from (+)-4a according to the procedure used for 46a, except that N-Boc-piperazine was used instead of N-Boc-N,N'-dimethylethylenediamine. Compound 46b was obtained quantitatively as an off-white solid.

Example 47

Generalized procedure for the preparation of 47a-47f from 46a/46b: A solution of crude 46a or 46b (71 μmol) in DMF (1 mL) was cooled to 0° C. p-Nitrophenyl carbonate-activated linker 57a, 57b, or 58 (0.142 mmol) and DIPEA (29 μL, 0.177 mmol) were added and the reaction temperature was subsequently increased to room temperature. After 1 h, the reaction mixture was concentrated to dryness. The residue was purified by column chromatography ($CH_2Cl_2$/MeOH=5:1) to afford the product as an off-white solid. Compounds 47e and 47f were prepared from their Aloc-protected analogs by dissolution in dichloromethane and addition of $Pd(PPh_3)_4$ (0.1 equiv.) and morpholine (10 equiv.). After 1 h, the reaction mixture was concentrated, the residue was redissolved in dichloromethane, and the solution was acidified (H 3) with trifluoroacetic acid. The solution was concentrated and the residue purified by preparative HPLC (acetonitrile/aqueous ammonium formate) to afford the product as a white solid.

Compound 47a: 38% yield; $^1$H-NMR (400 MHz, $CDCl_3$/$CD_3OD$): δ=0.94 (d, J=6.4 Hz, 6 H, $H_{val}$), 1.26-135 (m, 2 H, 2×$H_{capr}$), 1.49-1.74 (m, 10 H, 10-$CH_3$, 7×$H_{cit}$/$H_{capr}$), 1.87 (m, 1 H, $H_{cit}$), 2.06 (m, 1 H, $H_{val}$), 2.26 (t, J=7.6 Hz, 2 H, $CH_2C(O)$), 2.49 (s, 6 H, $N(CH_3)_2$), 2.90-3.22 (m, 10 H, $NCH_{2,cit}$, 2×$NCH_3$, $OCH_2CH_2N$), 3.46-3.83 (m, 6 H, $NCH_2CH_2N$, $CH_{2,capr}$), 4.09 (m, 1H, 1-H), 4.15-4.21 (m, 3 H, $OCH_2CH_2N$, α-$H_{val}$), 4.53-4.69 (m, 3 H, 2a-H, 10-H, α-$H_{cit}$), 4.86 (m, 1 H, 2b-H), 5.06-5.14 (m, 2 H, $CH_2OC(O)$), 6.72 (s, 2 H, CH=CH), 7.00-7.06 (m, 2 H, 6'-H, 3'-H), 7.17 (m, 1 H, 4'-H), 7.23-7.61 & 7.79-7.93 (m, 9 H, 7'-H, 7-H, 8-H, 6-H, 9-H, 4×$H_{Ar,PABA}$), 8.22 (br. s, 1 H, 4-H).

Compound 47b: 72% yield; $^1$H-NMR (400 MHz, $CDCl_3$/$CD_3OD$, TFA salt): δ=0.94 (d, J=6.8 Hz, 3 H, $CH_{3,val}$), 0.95 (d, J=6.8 Hz, 3 H, $CH_{3,val}$), 1.28-1.34 (m, 2 H, 2×$H_{capr}$), 1.50-1.77 (m, 10 H, 10-$CH_3$, 7×$H_{cit}$/$H_{capr}$), 1.89 (m, 1 H, H$_{cit}$), 2.05 (m, 1 H, H$_{val}$), 2.25 (t, J=7.6 Hz, 2 H, CH$_2$C(O)), 2.98 (s, 6 H, N(CH$_3$)$_2$), 3.09-3.25 (m, 2 H, NCH$_{2,cit}$), 3.50 (t, J=7.6 Hz, 2 H, CH$_{2,capr}$), 3.54 (m, 2 H, OCH$_2$CH$_2$N), 3.57-3.71 (m, 6 H, H$_{piperazine}$), 3.78-3.91 (m, 2 H, H$_{piperazine}$), 4.05 (m, 1 H, 1-H), 4.16 (d, J=7.6 Hz, 1 H, α-H$_{val}$), 4.40 (m, 2 H, OCH$_2$CH$_2$N), 4.54-4.65 (m, 3 H, 2a-H, 10-H, α-H$_{cit}$), 4.85 (dd, 1 H, 2b-H), 5.13 (s, 2 H, CH$_2$OC(O)), 6.70 (s, 2 H, CH=CH), 6.98 (dd, J=2.4 Hz, J=9.2 Hz, 1 H, 6'-H), 7.03 (s, 1 H, 3'-H), 7.17 (d, J=2.4 Hz, 1 H, 4'-H), 7.34 (d, 2H, H$_{Ar,PABA}$), 7.41 (d, J=9.2 Hz, 1 H, 7'-H), 7.45 (t, J=7.2 Hz, 1 H, 7-H), 7.52 (t, J=7.2 Hz, 1 H, 8-H), 7.61 (d, J=8.4 Hz, 2 H, H$_{Ar,PABA}$), 7.77 (d, J=8.4 Hz, 1 H, 9-H), 7.87 (d, J=8.0 Hz, 1 H, 6-H), 8.25 (br. s, 1 H, 4-H).

Compound 47c: 64% yield; $^1$H-NMR (400 MHz, CDCl$_3$/CD$_3$OD): δ=0.94 (d, J=6.7 Hz, 3 H, CH$_{3,val}$), 0.98 (d, J=6.7 Hz, 3 H, CH$_{3,val}$), 1.48-1.60 (m, 2 H, H$_{cit}$), 1.65-1.78 (m, 3 H, 10-CH$_3$, H$_{cit}$), 1.89 (m, 1 H, H$_{cit}$), 2.10 (m, 1 H, H$_{val}$), 2.65 (s, 6 H, N(CH$_3$)$_2$), 2.95-3.40 (m, 12 H, 2×H$_3$CNC(O), 2×H$_{cit}$, CH$_2$N$_3$, CH$_2$NMe$_2$), 3.50-4.10 (m, 10 H, CH$_2$OCH$_2$, NCH$_2$CH$_2$N, α-H$_{val}$, 1-H), 4.18-4.30 (m, 4 H, OCH$_2$CH$_2$N, CH$_2$CH$_2$OC(O)), 4.53-4.68 (m, 3 H, 2a-H, 10-H, α-H$_{cit}$), 4.80 (m, 1 H, 2b-H), 5.05-5.18 (m, 2 H, CH$_2$OC(O)), 6.94-7.04 (m, 2 H, 6'-H, 3'-H), 7.16 (br. s, 1 H, 4'-H), 7.20-7.95 (m, 9 H, 4×H$_{Ar,PABA}$, 7'-H, 7-H, 8-H, 9-H, 6-H), 8.23 (br. s, 1 H, 4-H).

Compound 47d: 85% yield; $^1$H-NMR (400 MHz, CDCl$_3$/CD$_3$OD, TFA salt): δ=0.95 (d, J=6.8 Hz, 3 H, CH$_{3,val}$), 0.99 (d, J=6.8 Hz, 3 H, CH$_{3,val}$), 1.50-1.67 (m, 2 H, H$_{cit}$), 1.69 (d, J=6.9 Hz, 3 H, 10-CH$_3$), 1.73 (m, 1 H, H$_{cit}$), 1.92 (m, 1 H, H$_{cit}$), 2.12 (m, 1 H, H$_{val}$), 2.94 (s, 6 H, N(CH$_3$)$_2$), 3.10-3.28 (m, 2 H, H$_{cit}$), 3.40 (t, J=5.0 Hz, 2 H, CH$_2$N$_3$), 3.50 (br. t, 2 H, OCH$_2$CH$_2$N), 3.56-3.74 (m, 10 H, 6×H$_{piperazine}$, CH$_2$OCH$_2$), 3.80-3.94 (m, 2 H, H$_{piperazine}$), 4.01 (m, 1 H, 1-H), 4.11 (m, 1 H, α-H$_{val}$), 4.24 (m, 2 H, CH$_2$CH$_2$OC(O)), 4.36 (t, J=4.9 Hz, 2 H, OCH$_2$CH$_2$N), 4.54-4.72 (m, 3 H, 2a-H, 10-H, α-H$_{cit}$), 4.86 (d, 1 H, 2b-H), 5.15 (s, 2 H, CH$_2$OC(O)), 7.03 (dd, J=2.4 Hz, J=8.9 Hz, 1 H, 6'-H), 7.07 (d, J=0.7 Hz, 1 H, 3'-H), 7.21 (d, J=2.2 Hz, 1 H, 4'-H), 7.36 (d, J=8.6 Hz, 2 H, H$_{Ar,PABA}$), 7.46 (d, J=8.9 Hz, 1 H, 7'-H), 7.48 (t, 1 H, 7-H), 7.58 (t, J=6.8 Hz, 1 H, 8-H), 7.62 (d, J=8.7 Hz, 2 H, H$_{Ar,PABA}$), 7.83 (d, J=8.4 Hz, 1 H, 9-H), 7.88 (d, J=8.7 Hz, 1 H, 6-H), 8.23 (br. s, 1 H, 4-H).

Compound 47e: 63% yield; MS (ESI): m/z=587 [M+H]$^{2+}$, 1173 [M+H]$^+$, 1195 [M+Na]$^+$.

Compound 47f: 84% yield; $^1$H-NMR (300 MHz, CDCl$_3$/CD$_3$OD): δ=1.33-1.48 (m, 2 H, H$_{lys}$), 1.60-1.79 (m, 6 H, 3×H$_{lys}$, 10-CH$_3$), 1.87 (m, 1 H, H$_{lys}$), 2.53 (s, 6 H, N(CH$_3$)$_2$), 2.83-3.05 (m, 5 H, CH$_2$NH$_2$, OCH$_2$CH$_2$N, H$_{phe}$), 3.13 (dd, J=6.0 Hz, J=14.1 Hz, 1 H, H$_{phe}$), 3.35 (m, 1 H, CH$_2$N$_3$), 3.52-3.75 (m 10 H, 6×H$_{piperazine}$, CH$_2$OCH$_2$), 3.75-3.98 (br. s, 2 H, H$_{piperazine}$), 4.02 (br. d, 1 H, 1-H), 4.09-4.23 (m, 4 H, CH$_2$CH$_2$OC(O), OCH$_2$CH$_2$N), 4.41 (t, 1 H, α-H$_{phe}$), 4.47 (dd, 1 H, α-H$_{lys}$), 4.52-4.68 (m, 2 H, 2a-H, 10-H), 4.82 (d, J=10.5 Hz, 1 H, 2b-H), 5.15 (s, 2 H, CH$_2$OC(O)), 6.99 (dd, 1 H, 6'-H), 7.01 (br. s, 1 H, 3'-H), 7.15 (m, 1 H, 4'-H), 7.20 (br. s, 1 H, H$_{phenyl}$), 7.36 (d, 2 H, H$_{Ar,PABA}$), 7.44 (t, J=7.7 Hz, 1 H, 7-H), 7.52 (t, J=7.5 Hz, 1 H, 8-H), 7.60 (d, J=8.5 Hz, 2 H, H$_{Ar,PABA}$), 7.75 (d, J=8.0 Hz, 1 H, 9-H), 7.86 (d, J=7.9 Hz, 1 H, 6-H), 8.28 (br. s, 1 H, 4-H).

Example 48

Generalized procedure for the preparation of 48c-48d from 47c-47d: A solution of 47c or 47d (25 µmol), sodium ascorbate (3.0 mg, 15 µmol), 40 (10.1 mg, 38 µmol), and CuSO$_4$ (1.9 mg, 7.5 µmol) in THF/water was stirred at room temperature. The reaction was followed by HPLC. Upon completion of the reaction, the reaction mixture was diluted with THF/water and the product was purified by preparative HPLC (acetonitrile/aqueous ammonium formate) to afford the product as an off-white solid after freeze-drying.

Compound 48c: 31% yield; $^1$H-NMR (400 MHz, CDCl$_3$/CD$_3$OD, TFA salt): δ=0.98 (m, 6 H, H$_{val}$), 1.26-135 (m, 2 H, 2×H$_{capr}$), 1.49-1.61 (m, 2 H, H$_{cit}$), 1.62-1.75 (m, 4 H, 10-CH$_3$, H$_{cit}$), 1.89 (m, 1 H, H$_{cit}$), 2.13 (m, 1 H, H$_{val}$), 2.93-3.25 (m, 13 H, N(CH$_3$)$_2$, 2×NCH$_3$, CH$_{2,cit}$), 3.50-4.88 (m, 30 H, 2×OCH$_2$CH$_2$O, 3×OCH$_2$CH$_2$N, NCH$_2$CH$_2$N, HNCH$_2$, α-H$_{val}$, α-H$_{cit}$, 2a-H, 2b-H, 1-H, 10-H), 5.02-5.20 (m, 2 H, C$_{6l H4}$CH$_2$OC(O)), 6.74 (s, 2 H, HC=CH), 6.94-8.25 (m, 14 H, 6'-H, 3'-H, 4'-H, 7-H, 8-H, 7'-H, 4×H$_{Ar,PABA}$, 9-H, 6-H, H$_{thiazole}$, 4-H).

Compound 48d: 48% yield; $^1$H-NMR (300 MHz, CDCl$_3$/CD$_3$OD): δ=0.92 (d, J=6.9 Hz, 3 H, H$_{val}$), 0.95 (d, J=6.8 Hz, 3 H, H$_{val}$), 1.46-1.58 (m, 2 H, H$_{cit}$), 1.64 (d, J=6.8 Hz, 3 H, 10-CH$_3$), 1.70 (m, 1 H, Hit), 1.87 (m, 1 H, H$_{cit}$), 2.09 (m, 1 H, H$_{val}$), 2.50 (br. s, 6 H, N(CH$_3$)$_2$), 2.97 (br. s, 2 H, CH$_2$NMe$_2$), 3.09 (m, 1 H, Hit), 3.18 (m, 1 H, Hat), 3.52-3.72 & 3.78-3.90 & 3.95 & 4.04-4.24 & 4.35 & 4.48-4.70 (m, 33 H, 2×OCH$_2$CH$_2$O, 2×NCH$_2$CH$_2$O, OCH$_2$CH$_2$NMe$_2$, 8×H$_{piperazine}$, α-H$_{val}$, α-H$_{cit}$, 2a-H, 1-H, 10-H, HNCH$_2$), 4.82 (d, 1 H, 2b-H), 5.11 (s, 2 H, C$_6$H$_4$CH$_2$OC(O)), 6.69 (s, 2 H, HC=CH), 6.96-7.04 (m, 2 H, 6'-H, 3'-H), 7.15 (br. s, 1 H, 4'-H), 7.32 (d, J=8.5 Hz, 2 H, H$_{Ar,PABA}$), 7.37-7.45 (m, 2 H, 7'-H, 7-H), 7.53 (t, 1 H, 8-H), 7.57 (d, J=8.4 Hz, 2 H, H$_{Ar,PABA}$), 7.78-7.85 (m, 3 H, 6-H, 9-H, H$_{triazole}$), 8.21 (br. s, 1 H, 4-H).

Example 49

Generalized procedure for the preparation of 50a-50c from 49: A solution of compound 49 (78 mg, 0.11 mmol) in 4 N HCl in ethyl acetate (15 mL) was stirred for 1 h at room temperature. The reaction mixture was concentrated and the residue was suspended in ethyl acetate (15 mL). The resultant mixture was concentrated and the residue dried in vacuo for 1 h. The residue was dissolved in DMF (2 mL) and the solution was cooled to 0° C. p-Nitrophenyl carbonate-activated linker 59a, 59b, or 60 (0.12 mmol) and triethylamine (38 µL, 0.272 mmol) were added and the reaction mixture was subsequently warmed to room temperature. After 1.5 h, the reaction mixture was concentrated in vacuo and the crude product was purified by column chromatography (CH$_2$Cl$_2$/MeOH=9:1) to afford the product as an off-white solid. Compound 50c was prepared from its Aloc-protected analog according to the procedure used for the preparation of 47e and 47f.

Compound 50a: 44% yield; $^1$H-NMR (400 MHz, CDCl$_3$/CD$_3$OD, TFA salt): δ=0.92 (d, J=6.7 Hz, 3 H, H$_{val}$), 0.93 (d, J=6.7 Hz, 3 H, H$_{val}$), 1.24-134 (m, 2 H, 2×H$_{capr}$), 1.48-1.75 (m, 10 H, 10-CH$_3$, 7×H$_{cit}$/H$_{capr}$), 1.86 (m, 1 H, H$_{cit}$), 2.06 (m, 1 H, H$_{val}$), 2.23 (t, J=7.4 Hz, 2 H, CH$_2$C(O)), 2.91 (s, 1 H, NCH$_3$), 3.06 (s, 3 H, H$_3$CNC(O)), 3.08-3.20 (m, 2 H, NCH$_{2,cit}$), 3.24-3.42 (m, 4 H, H$_{piperazine}$), 3.47 (t, 2 H, CH$_{2,capr}$), 3.60-4.25 (m, 10 H, 1-H, OCH$_2$CH$_2$N, OCH$_2$CH$_2$N, α-H$_{val}$, 4×H$_{piperazine}$), 4.49-4.67 (m, 3 H, 2a-H, 10-H, α-H$_{cit}$), 4.83 (m, 1 H, 2b-H), 5.05-5.13 (m, 4 H, 2×CH$_2$OC(O)), 6.68 (s, 2 H, CH=CH), 6.88-7.59 (m, 14 H, 6'-H, 3'-H, 4'-H, 7'-H, 7-H, 8-H, 8×H$_{Ar,PABA}$), 7.79 (d, J=8.2 Hz, 1 H, 9-H), 7.85 (d, J=8.0 Hz, 1 H, 6-H), 8.25 (br. s, 1 H, 4-H).

Compound 50b: 74% yield; $^1$H-NMR (300 MHz, CDCl$_3$/CD$_3$OD): δ=0.93 (d, J=6.8 Hz, 3 H, H$_{val}$), 0.97 (d, J=6.8 Hz, 3 H, H$_{val}$), 1.49-1.61 (m, 2 H, H, it), 1.63 (d, J=6.7 Hz, 3 H, 10-CH$_3$), 1.72 (m, 1 H, H$_{cit}$), 1.90 (m, 1 H, H$_{cit}$), 2.11 (m, 1 H, H$_{val}$), 2.41 (s, 3 H, N(CH$_3$)), 2.53-2.67 (m, 4 H, H$_{piperazine}$), 3.07 (s, 3 H, $H_3CNC(O)$), 3.09 (m, 1 H, $H_{cit}$), 3.21 (m, 1 H, $H_{cit}$), 3.36 (m, 2 H, $CH_2N_3$), 3.59-3.72 (m, 8 H, $CH_2OCH_2$, $OCH_2CH_2N$, 2×$H_{piperazine}$), 3.90 (m, 2 H, $H_{piperazine}$), 3.97 (m, 1 H, 1-H), 4.02 (d, J=6.2 Hz, 1 H, α-$H_{val}$), 4.08-4.27 (m, 4 H, $CH_2CH_2OC(O)$, $OCH_2CH_2N$), 4.50-4.62 (m, 3 H, 2a-H, 10-H, α-$H_{cit}$), 4.75 (dd, 1 H, 2b-H), 5.07-5.13 (m, 4 H, 2×$CH_2OC(O)$), 6.88 (m, 1 H, 6'-H), 6.97 (m, 1 H, 3'-H), 7.06 & 7.11 (2×br. s, 1 H, 4'-H), 7.25-7.38 & 7.40-7.61 (2×m, 11 H, 7-H, 8-H, 7'-H, 8×$H_{Ar,PABA}$), 7.73 (d, J=8.3 Hz, 1-H, 9-H), 7.86 (d, J=8.1 Hz, 1 H, 6-H), 8.28 (br. s, 1 H, 4-H).

Example 50

Conjugation of linker-agent conjugate 47a to Herceptin antibody: Herceptin antibody (40 mg) was treated with 1.5 molar equivalents of dithiothreitol (DTT) in 0.025 M sodium borate pH 8, 0.025 M NaCl, 1 mM DTPA for 2 h at 37° C. Excess DTT was removed using a Sephadex G-25 column (0.025 M sodium borate pH 8, 0.025 M NaCl, 1 mM DTPA). Thiol determination with Ellman's reagent indicated that there were approximately three thiol groups per Herceptin. Compound 47a (1.13 mg, 1.1 equiv./SH group) was dissolved in approximately 100 µl of DMSO and added dropwise to the reduced Herceptin solution in reaction buffer (0.025 M sodium borate pH 8, 0.025 M NaCl, 1 mM DTPA). The mixture was incubated for 30 minutes at 4° C. Excess 47a was removed using gel filtration (G-25, PBS). Protein concentration and drug loading were determined by spectral analysis at 280 and 320 nm, respectively. It was found that on average 2.5 drugs were conjugated per Herceptin. Size-exclusion FPLC showed no sign of aggregation of the antibody-drug conjugate.

Example 51

In vitro cytotoxicity of compounds (+)-8a-e and (+)-4a-e: Adherent cells of line A549 were sown in triplicate in 6 multiwell plates at concentrations of $10^2$, $10^3$, $10^4$, and $10^5$ cells per cavity. Culture medium was removed after 24 h and cells were washed hi the incubation medium Ultraculture (UC, serum-free special medium, purchased from BioWhittaker Europe, Verviers, Belgium). Incubation with compounds (+)-8a-e and (+)-4a-e was then performed in Ultraculture medium at various concentrations for 24 h. All substances were used as freshly prepared solutions in DMSO (Merck, Darmstadt, Germany) diluted with incubation medium to a final concentration of 1% DMSO in the wells. After 24 h of exposure the test substance was removed and the cells were washed with fresh medium. Cultivation was done at 37° C. and 7.5% $CO_2$ in air for 12 days. The medium was removed and the clones were dried and stained with Löffler's methylene blue (Merck, Darmstadt, Germany). They were then counted macroscopically.

The $IC_{50}$ values are based on the relative clone forming rate, which was determined according to the following formula: relative clone forming rate [%]=100×(number of clones counted after exposure)/(number of clones counted in the control).

Liberation of the drugs from their glycosidic prodrugs was achieved by addition of 4.0 U·mL$^{-1}$ β-D-galactosidase (EC 3.2.1.23, Grade X, purchased from Sigma Germany, Deisenhofen, Germany) to the cells during incubation with the substances.

The $IC_{50}$ values are given in the table below.

| Compound | Addition of β-D-galactosidase | $IC_{50}$ [nM] | $QIC_{50}$ |
|---|---|---|---|
| (+)-8a | − | $3.6 \times 10^3$ | 4800 |
| (+)-8a | + | 0.75 | |
| (+)-4a | − | 0.75 | |
| (+)-8b | − | $1.5 \times 10^3$ | 600 |
| (+)-8b | + | 2.5 | |
| (+)-4b | − | 3.7 | |
| (+)-8c | − | $9.4 \times 10^2$ | 4300 |
| (+)-8c | + | 0.22 | |
| (+)-4c | − | 0.20 | |
| (+)-8d | − | $8.3 \times 10^2$ | 1100 |
| (+)-8d | + | 0.75 | |
| (+)-4d | − | 0.80 | |
| (+)-8e | − | $7.7 \times 10^3$ | 1300 |
| (+)-8e | + | 5.9 | |
| (+)-4e | − | 3.8 | |

Example 52

In vivo evaluation of compound (+)-8a in an orthotopic breast tumor SCID mouse model using the ADEPT concept: Before tumor cell implantation, female SCID mice were anesthetized by peritoneal injection of 75 mg/kg ketamine hydrochloride with 15 mg/kg xylazine. 1×10$^6$ MDA-MB-231 cells (estrogen-independent human breast cancer cell line) suspended in 25 µl sterile phosphate-buffered saline (PBS) were then implanted into the mammary fad pat of the 4$^{th}$ mammary complex. After implantation, mice were inspected daily for body weight loss, general condition, and tumor formation. On day 21, animals were randomized in groups of 5-12 mice (control, antibody-enzyme only, prodrug only, and ADEPT therapy). On days 22 and 30, mice were injected intravenously with PBS (control, prodrug only groups) or 50 µg of a monoclonal anti-human urokinase plasminogen activator receptor (uPAR) antibody conjugated with β-Galactosidase, uPAR*β-Gal, in PBS (antibody-enzyme only, ADEPT therapy groups). On days 24, 26, 28, 32, 34, and 36, mice were injected intravenously with 1% DMSO/NaCl solution (control, antibody-enzyme only groups) or 104 µg of (+)-8a in 1% DMSO/NaCl solution (prodrug only, ADEPT therapy groups). Mice were sacrificed on day 38 and tumors were excised, weighed, placed in phosphate-buffered 4% formalin for 16 hours at room temperature, and embedded in paraffin. Tissue sections (2.5 µm) were obtained, stained with hematoxylin and eosin (H & E), and inspected by routine microscopic examinations. For immunohistochemistry, 2.5 µm sections from formalin-fixed and paraffin-embedded tissues, were mounted on slides, deparaffinized in xylene and rehydrated in ethanol/water dilutions. Slides for Ki67 staining were pretreated by boiling in a microwave oven (5×5 min) in citrate buffer (pH 6.0) for antigen retrieval. Endogenous peroxidases were inactivated by treatment with 3% hydrogen peroxide for 10 min. Tris-buffered 10% rabbit serum solution (Dako, Hamburg, Germany, No. X 0902) was then added to block nonspecific protein binding and slides were incubated with murine anti-human Ki67 (Dianova, Hamburg, Germany, No. dia 505) for 60 min (2 µg/ml) followed by exposure to biotinylated rabbit anti-mouse F(ab')$_2$-fragment (Dako, No. E 0413, 16.8 µg/ml) for 30 min. Sections were then incubated with avidin-peroxidase solution (Dako, No. P 364), stained with aminoethylcarbazole (AEC substrate solution, Sigma), rinsed in water, and finally counterstained with hematoxylin. The average number of Ki67 positive nuclei was counted in the three most cellular fields in the tumors containing subjectively the highest density of mitotic figures and was defined as a proportion of the total amount of nuclei stained with H & E in the same areas.

Tumor size was determined at distinct time points during the therapy experiment (days 21, 29, and 38) with a flat panel volume computer tomograph prototype (fpVCT GE Global Research, Niskayuna N.Y., US). Mice were anesthetized with vaporized isoflurane at 0.8-1% concentration throughout the imaging session, centered on the fpVCT gantry axis of rotation, and placed perpendicular to the z-axis of the system, so that it was possible to scan the whole mouse with one rotation. Contrast medium, 150 µl Isovist© 300 (Schering, Berlin, Germany), was applied intravenously 20 seconds before scanning. All data sets were acquired with the same protocol: 1000 views per rotation, 8 seconds rotation time, 360 used detector rows, 80 kVp, and 100 mA. A modified Feldkamp algorithm was used for image reconstruction resulting in an isotropic high-resolution volume data set (512×512 matrix, resolution about 200 µm).

REFERENCES

1 Boger, D. L.; Johnson, D. S.; Wrasidlo, W. *Bioorg. Med. Chem. Lett.* 1994, 4, 631-636.
2 McGovren, J. P., Clarke, G. L., Pratt, E. A., DeKoning, T. F. *J. Antibiot.* 1984, 37, 63-70.
3 Carter, P.; Smith, L.; Ryan, M. *Endocr.-Relat. Cancer* 2004, 11, 659-687.
4 Bagshawe, K. D. *Drug Dev. Res.* 1995, 34, 220-230.
5 Melton, R.; Connors, T.; Knox, R. J. *S.T.P. Pharma Sciences*, 1999, 13-33.
6 Huber, B. E.; Richards, C. A.; Krenitsky, T. A. *Proc. Natl. Acad. Sci. USA,* 1991, 88, 8039-8043.
7 Bagshawe, K. D.; Springer, C. J.; Searle, F.; Antoniw, P.; Sharma, S. K.; Melton, R. G.; Sherwood, R. F. *Br. J. Cancer,* 1988, 58, 700-703.
8 Duncan, R. *Nat. Rev. Drug Discov.* 2003, 2, 347-360.
9 Tietze, L. F.; Lieb, M.; Herzig, T.; Haunert, F.; Schuberth, I. *Bioorg. Med. Chem.* 2001, 9, 1929-1939.
10 Tietze, L. F., Herzig, T.; Fecher, A.; Haunert, F., Schuberth, I. *Chem Bio Chem* 2001, 758-765.
11 Toki, B. E.; Cerveny, C. G.; Wahl, A. F.; Senter, P. D. *J. Org. Chem.,* 2002, 67, 1866-1872.
12 See for some recently disclosed cyclization spacers for example WO 2005/079398, WO 2005/105154, and WO 2006/012527.
13 Greenwald, R. B., Choe, Y. H., McGuire, J., Conover, C. D. *Adv. Drug Delivery Rev.* 2003, 55, 217-250.
14 Kingsbury, W. D.; Boehm; J. C.; Mehta, R. J.; Grappel, S. F.; Gilvarg, C. *J. Med. Chem.* 1984, 27, 1447-1451.
15 Greenwald, R. B.; Zhao, H.; Yang, K.; Reddy, P.; Martinez, A. *J. Med. Chem.* 2004, 47, 726-734.
16 (a) Franke, A. E.; Sievers, E. L.; and Scheinberg, D. A. *Cancer Biother. Radiopharm.* 2000, 15, 459-476. (b) Murray, J. L. *Semin. Oncol.* 2000, 27, 2564-2570 (c) Breitling, F., and Dubel, S., Recombinant Antibodies, John Wiley and Sons, New York, 1998.
17 Ringsdorf, H. *J. Polym. Sci., Polym. Symp.* 1975, 51, 135-153.
18 Elvira, C.; Gallardo, A.; San Roman, J.; Cifuentes, A. *Molecules* 2005, 10, 114-125.
19 Remington's Pharmaceutical Science (15th ed., Mack Publishing, Easton, Pa., 1980) (incorporated by reference in its entirety for all purposes)

The invention claimed is:
1. A compound which is

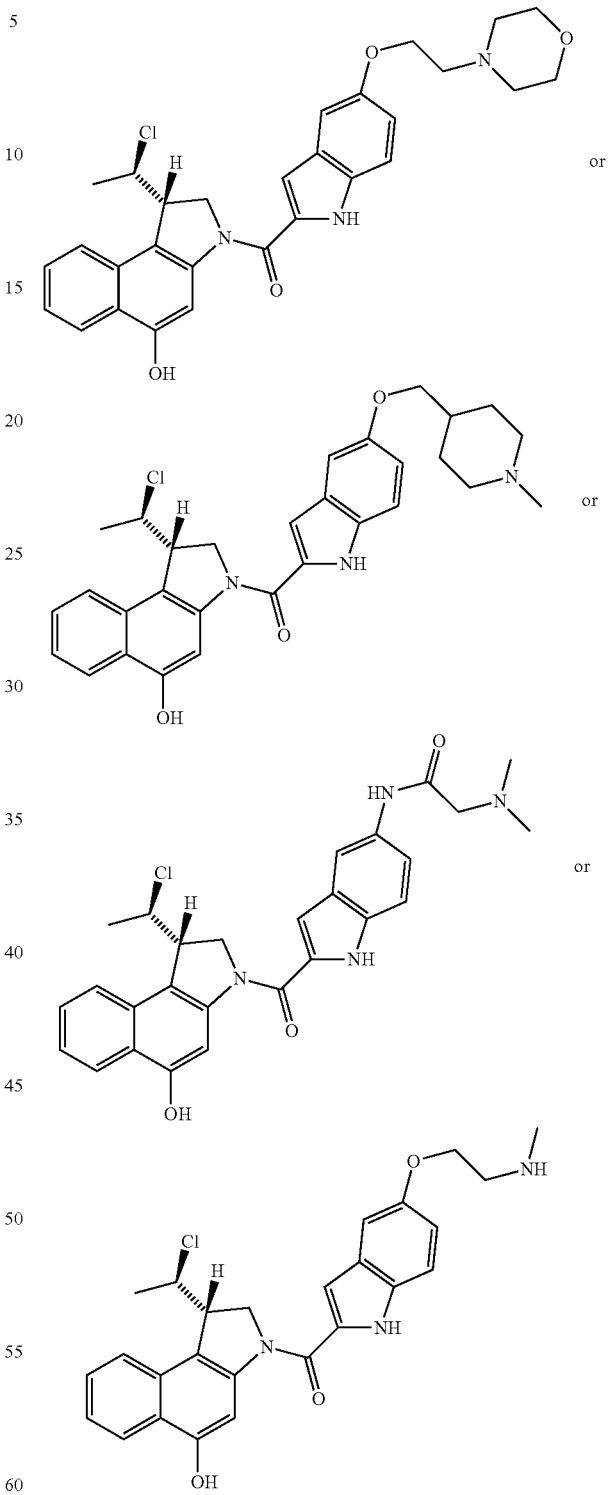

or the (1R,10S) isomer, the (1R,10R) isomer, or the (1S,10S) isomer of one of these, or a mixture of two or more of said isomers.

2. A compound which is:
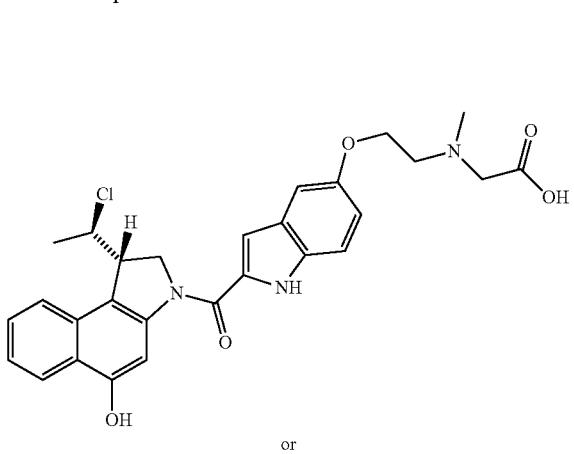
or
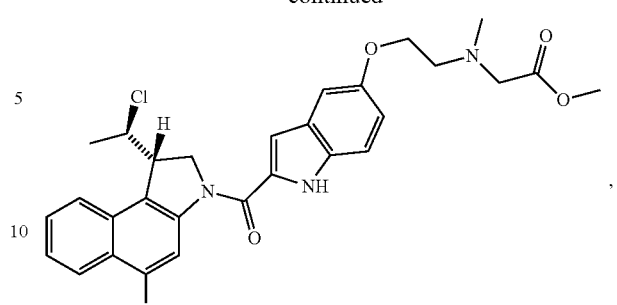
or the (1R,10S) isomer, the (1R,10R) isomer, or the (1S,10S) isomer of one of these, or a mixture of two or more of said isomers.
* * * * *

UNITED STATES PATENT AND TRADEMARK OFFICE
CERTIFICATE OF CORRECTION

PATENT NO. : 8,940,784 B2
APPLICATION NO. : 12/223682
DATED : January 27, 2015
INVENTOR(S) : P Beusker Page 1 of 1

It is certified that error appears in the above-identified patent and that said Letters Patent is hereby corrected as shown below:

On the Title Page

Identify the second assignee as GEORG-AUGUST-UNIVERSITAT GOTTINGEN STIFTUNG OFFENTILICHEN RECHTS (OHNE BEREICH HUMANMEDIZIN), Gottingen (DE)

Signed and Sealed this
Twenty-seventh Day of October, 2020

Andrei Iancu
*Director of the United States Patent and Trademark Office*